US009623415B2

(12) United States Patent
Andreyev et al.

(10) Patent No.: US 9,623,415 B2
(45) Date of Patent: Apr. 18, 2017

(54) DEVICES AND METHODS FOR MOLECULAR DIAGNOSTIC TESTING

(71) Applicant: Click Diagnostics, Inc., Menlo Park, CA (US)

(72) Inventors: Boris Andreyev, Foster City, CA (US); Keith E. Moravick, Mountain View, CA (US); Brian Ciopyk, Pleasanton, CA (US); Victor Briones, Gilroy, CA (US); Gregory Loney, Los Altos, CA (US); Adam de la Zerda, Palo Alto, CA (US); Jesus Ching, Saratoga, CA (US); Colin Kelly, San Francisco, CA (US); Steven Chu, Menlo Park, CA (US); David Swenson, Santa Clara, CA (US); Helen Huang, San Pablo, CA (US)

(73) Assignee: Click Diagnostics, Inc., Menlo Park, CA (US)

( * ) Notice: Subject to any disclaimer, the term of this patent is extended or adjusted under 35 U.S.C. 154(b) by 0 days.

(21) Appl. No.: 14/984,573

(22) Filed: Dec. 30, 2015

(65) Prior Publication Data

US 2016/0186240 A1 Jun. 30, 2016

Related U.S. Application Data

(60) Provisional application No. 62/098,769, filed on Dec. 31, 2014, provisional application No. 62/213,291, filed on Sep. 2, 2015.

(51) Int. Cl.

| | |
|---|---|
| ***B01L 7/00*** | (2006.01) |
| ***C12Q 1/68*** | (2006.01) |
| *B01L 3/00* | (2006.01) |

(52) U.S. Cl.

CPC .............. *B01L 7/52* (2013.01); *B01L 3/5027* (2013.01); *B01L 3/5029* (2013.01); *B01L 3/527* (2013.01);

(Continued)

(58) Field of Classification Search

CPC .... B01L 7/52; B01L 2200/10; B01L 2300/18; B01L 2300/0627; B01L 2300/0883;

(Continued)

(56) References Cited

U.S. PATENT DOCUMENTS 3,697,227 A 10/1972 Goldstein et al.
4,710,355 A 12/1987 Ushikubo (Continued)

FOREIGN PATENT DOCUMENTS

EP 1347833 B1 10/2011
WO WO-0149416 A1 7/2001

(Continued)

OTHER PUBLICATIONS

BioFire Online Demo FilmArray. http://filmarray.com/the-evidence/online-demo. 2014, 6 pages.

(Continued)

*Primary Examiner* — Michael Hobbs
*Assistant Examiner* — Liban Hassan
(74) *Attorney, Agent, or Firm* — ReavesColey PLLC

(57) ABSTRACT

A hand-held molecular diagnostic test device includes a housing, an amplification (or PCR) module, and a detection module. The amplification module is configured to receive an input sample, and defines a reaction volume. The amplification module includes a heater such that the amplification module can perform a polymerase chain reaction (PCR) on the input sample. The detection module is configured to receive an output from the amplification module and a reagent formulated to produce a signal that indicates a (Continued)

presence of a target amplicon within the input sample. The amplification module and the detection module are integrated within the housing.

17 Claims, 61 Drawing Sheets

(52) U.S. Cl.
CPC ... *B01L 2200/025* (2013.01); *B01L 2200/028* (2013.01); *B01L 2200/0647* (2013.01); *B01L 2200/0689* (2013.01); *B01L 2200/10* (2013.01); *B01L 2300/0627* (2013.01); *B01L 2300/0672* (2013.01); *B01L 2300/0681* (2013.01); *B01L 2300/0867* (2013.01); *B01L 2300/0883* (2013.01); *B01L 2300/18* (2013.01); *B01L 2300/1844* (2013.01); *B01L 2400/0457* (2013.01); *B01L 2400/0478* (2013.01); *B01L 2400/0487* (2013.01); *B01L 2400/0605* (2013.01)

(58) Field of Classification Search
CPC ....... B01L 2400/0487; B01L 2200/028; B01L 2400/0478; B01L 2400/0457; B01L 2300/1844; B01L 2300/0867; B01L 3/5027; B01L 3/5029; B01L 3/527; B01L 2200/025; B01L 2400/0605; B01L 2200/0647; B01L 2200/0689; B01L 2300/0672; C12Q 1/686
See application file for complete search history.

(56) References Cited

U.S. PATENT DOCUMENTS 4,889,692 A 12/1989 Holtzman
RE33,858 E 3/1992 Gropper et al.
5,164,159 A 11/1992 Hayashi et al.
5,229,297 A 7/1993 Schnipelsky et al.
5,270,183 A 12/1993 Corbett et al.
5,273,905 A 12/1993 Muller et al.
5,405,585 A 4/1995 Coassin
5,429,807 A 7/1995 Matson et al.
5,631,165 A 5/1997 Chupp et al.
5,633,168 A 5/1997 Glasscock et al.
5,660,993 A 8/1997 Cathey et al.
5,882,903 A 3/1999 Andrevski et al.
5,922,591 A 7/1999 Anderson et al.
5,952,664 A 9/1999 Wake et al.
5,976,470 A 11/1999 Maiefski et al.
6,039,924 A 3/2000 Horn
6,126,804 A 10/2000 Andresen
6,146,591 A 11/2000 Miller
6,153,425 A 11/2000 Kozwich et al.
6,168,760 B1 1/2001 Horn
6,261,431 B1 7/2001 Mathies et al.
6,303,081 B1 10/2001 Mink et al.
6,313,471 B1 11/2001 Giebeler et al.
6,365,378 B1 4/2002 Hirota et al.
6,374,684 B1 4/2002 Dority
6,416,718 B1 7/2002 Maiefski et al.
6,426,215 B1 7/2002 Sandell
6,514,750 B2 2/2003 Bordenkircher et al.
6,610,499 B1 8/2003 Fulwyler et al.
6,649,378 B1 11/2003 Kozwich et al.
6,656,744 B2 12/2003 Pronovost et al.
6,677,151 B2 1/2004 Sandell
6,680,617 B2 1/2004 Moreland et al.
6,780,380 B2 8/2004 Hunnell et al.
6,780,617 B2 8/2004 Chen
6,781,056 B1 8/2004 O'Rourke et al.
6,813,568 B2 11/2004 Powell et al.
6,821,771 B2 11/2004 Festoc
6,875,403 B2 4/2005 Liu et al.
6,893,879 B2 5/2005 Petersen et al.
6,901,217 B2 5/2005 Gamboa et al.
6,911,181 B1 6/2005 McNeil
6,964,862 B2 11/2005 Chen
6,990,290 B2 1/2006 Kylberg et al.
7,041,481 B2 5/2006 Anderson et al.
7,144,742 B2 12/2006 Boehringer et al.
7,179,639 B2 2/2007 Pottathil et al.
7,189,522 B2 3/2007 Esfandiari
7,192,721 B1 3/2007 Esfandiari
7,235,216 B2 6/2007 Kiselev et al.
7,297,313 B1 11/2007 Northrup et al.
7,341,697 B2 3/2008 Takeuchi et al.
7,377,291 B2 5/2008 Moon et al.
7,378,285 B2 5/2008 Lambotte et al.
7,384,782 B2 6/2008 Nakatani et al.
7,438,852 B2 10/2008 Tung et al.
7,459,302 B2 12/2008 Reid et al.
7,491,551 B2 2/2009 Boehringer et al.
7,517,495 B2 4/2009 Wu et al.
7,544,324 B2 6/2009 Tung et al.
7,550,112 B2 6/2009 Gou et al.
7,553,675 B2 6/2009 Jerome et al.
7,569,382 B2 8/2009 Li
7,579,172 B2 8/2009 Cho et al.
7,592,139 B2 9/2009 West et al.
7,632,687 B2 12/2009 Gokhan
7,648,835 B2 1/2010 Breidford et al.
7,682,801 B2 3/2010 Esfandiari
7,691,644 B2 4/2010 Lambotte et al.
7,705,339 B2 4/2010 Smith et al.
7,709,250 B2 5/2010 Corbett et al.
7,754,452 B2 7/2010 Kim et al.
7,767,439 B2 8/2010 Oh et al.
7,794,656 B2 9/2010 Liang et al.
7,837,939 B2 11/2010 Tung et al.
7,858,396 B2 12/2010 Corstjens et al.
7,871,568 B2 1/2011 Liang et al.
7,879,293 B2 2/2011 Niedbala et al.
7,914,986 B2 3/2011 Nunn
7,915,013 B2 3/2011 Cho et al.
7,935,504 B2 5/2011 Chen
7,943,348 B2 5/2011 Cho et al.
7,959,877 B2 6/2011 Esfandiari
7,985,716 B2 7/2011 Yershov et al.
7,988,915 B2 8/2011 Lee et al.
7,998,757 B2 8/2011 Darrigrand et al.
8,008,046 B2 8/2011 Maltezos et al.
8,008,080 B2 8/2011 Tokhtuev et al.
8,012,427 B2 9/2011 Bommarito et al.
8,018,593 B2 9/2011 Tan et al.
8,048,386 B2 11/2011 Dority et al.
8,062,883 B2 11/2011 Woudenberg et al.
8,075,854 B2 12/2011 Yang et al.
8,076,129 B2 12/2011 Hanafusa et al.
8,088,616 B2 1/2012 Handique
8,110,148 B2 2/2012 Ball et al.
8,133,671 B2 3/2012 Williams et al.
8,133,703 B2 3/2012 Ching et al.
8,148,116 B2 4/2012 Chen
8,163,535 B2 4/2012 Reed et al.
8,169,610 B2 5/2012 Oldham et al.
8,173,077 B2 5/2012 Korampally et al.
8,187,557 B2 5/2012 Van Atta et al.
8,198,074 B2 6/2012 Moriwaki et al.
8,222,023 B2 7/2012 Battrell et al.
8,231,844 B2 7/2012 Gorfinkel et al.
8,232,091 B2 7/2012 Maltezos et al.
8,232,094 B2 7/2012 Hasson et al.
8,247,221 B2 8/2012 Fawcett
8,263,392 B2 9/2012 Gale et al.
8,277,763 B2 10/2012 Steinmann et al.
8,278,091 B2 10/2012 Rutter et al.
8,298,763 B2 10/2012 Regan
8,323,583 B2 12/2012 Gou et al.
8,343,442 B2 1/2013 McBride et al.
8,343,754 B2 1/2013 Wittwer et al.
8,357,490 B2 1/2013 Froehlich et al.

(56) References Cited

U.S. PATENT DOCUMENTS 8,372,340 B2 2/2013 Bird et al.
8,389,960 B2 3/2013 Pieprzyk et al.
8,394,322 B2 3/2013 Windeyer et al.
8,394,608 B2 3/2013 Ririe et al.
8,394,626 B2 3/2013 Ramsey et al.
8,431,413 B2 4/2013 Dority et al.
8,435,461 B2 5/2013 Kirby et al.
8,448,824 B2 5/2013 DiPerna
8,492,136 B2 7/2013 Carlisle et al.
8,507,259 B2 8/2013 Esfandiari
8,580,575 B2 11/2013 Hanafusa
8,597,937 B2 12/2013 Ward et al.
8,603,835 B2 12/2013 Esfandiari
8,617,486 B2 12/2013 Kirby et al.
8,629,264 B2 1/2014 Reed et al.
8,637,250 B2 1/2014 Jenison
8,663,976 B2 3/2014 Chung et al.
8,673,238 B2 3/2014 Dority et al.
8,673,239 B2 3/2014 Niedbala et al.
8,691,561 B2 4/2014 Igata
8,722,426 B2 5/2014 Lambotte et al.
8,728,765 B2 5/2014 Ching et al.
8,735,103 B2 5/2014 Chung et al.
8,758,701 B2 6/2014 Van Atta et al.
8,765,454 B2 7/2014 Zhou et al.
8,772,017 B2 7/2014 Battrell et al.
8,795,592 B2 8/2014 Eiriksson
8,859,199 B2 10/2014 Hellyer et al.
8,865,458 B2 10/2014 Ramsey et al.
8,871,155 B2 10/2014 Wu et al.
8,877,450 B2 11/2014 Esfandiari
8,894,946 B2 11/2014 Nielsen et al.
8,900,828 B2 12/2014 Smith et al.
8,900,853 B2 12/2014 Verhaar et al.
8,911,941 B2 12/2014 Michlitsch
8,911,949 B2 12/2014 Bertrand et al.
8,916,375 B2 12/2014 Landers et al.
8,945,843 B2 2/2015 Alvino et al.
8,975,027 B2 3/2015 Gale et al.
8,980,177 B2 3/2015 Carlisle et al.
8,986,927 B2 3/2015 Lee et al.
8,992,854 B2 3/2015 Brewster et al.
9,011,770 B2 4/2015 Wu et al.
9,012,236 B2 4/2015 Jovanovich et al.
9,023,639 B2 5/2015 Kim et al.
9,044,729 B2 6/2015 Rengifo et al.
9,207,241 B2 12/2015 Lambotte et al.
9,243,288 B2 1/2016 Colston, Jr. et al.
2001/0055799 A1 12/2001 Baunoch et al.
2002/0086417 A1 7/2002 Chen
2003/0027244 A1 2/2003 Colston et al.
2004/0110141 A1 6/2004 Pusey et al.
2004/0209331 A1 10/2004 Ririe
2004/0224317 A1 11/2004 Kordunsky et al.
2004/0251426 A1 12/2004 Birk et al.
2005/0019875 A1 1/2005 Chen
2005/0227275 A1 10/2005 Jung et al.
2006/0088931 A1 4/2006 Ririe
2006/0154341 A1 7/2006 Chen
2007/0026391 A1 2/2007 Stoughton et al.
2007/0154922 A1 7/2007 Collier et al.
2007/0292941 A1* 12/2007 Handique ............. B01L 3/5027 435/288.7
2008/0026451 A1 1/2008 Braman et al.
2008/0038737 A1 2/2008 Smith et al.
2008/0043235 A1 2/2008 Oldham et al.
2008/0050735 A1 2/2008 Pushnova
2008/0145852 A1 6/2008 Shuber
2008/0153078 A1 6/2008 Braman et al.
2008/0220468 A1 9/2008 Windeyer et al.
2008/0280285 A1 11/2008 Chen et al.
2009/0029422 A1 1/2009 Hanafusa et al.
2009/0042256 A1 2/2009 Hanafusa et al.
2009/0215072 A1* 8/2009 McDevitt ........... G01N 21/6428 435/7.1
2009/0325276 A1 12/2009 Battrell et al.
2010/0113762 A1 5/2010 Ball et al.
2010/0173393 A1 7/2010 Handique et al.
2010/0210038 A1 8/2010 Blatt et al.
2010/0297640 A1 11/2010 Kumar et al.
2011/0207121 A1 8/2011 Chen
2011/0211331 A1 9/2011 Alkjaer et al.
2011/0227551 A1 9/2011 Black
2011/0269191 A1 11/2011 Belgrader et al.
2011/0313148 A1 12/2011 Christ et al.
2012/0021454 A1 1/2012 Bikker et al.
2012/0088294 A1 4/2012 Sun et al.
2012/0135511 A1 5/2012 Battrell et al.
2012/0141337 A1 6/2012 Maltezos et al.
2012/0237939 A1 9/2012 Reed et al.
2012/0264202 A1 10/2012 Walker et al.
2012/0276532 A1 11/2012 Chen
2012/0288897 A1 11/2012 Ching et al.
2013/0053255 A1* 2/2013 Vangbo ............ G01N 27/44791 506/2
2013/0078736 A1* 3/2013 Grover .................... B01L 3/502 436/180
2013/0115712 A1 5/2013 Yu et al.
2013/0118900 A1* 5/2013 Reimitz ........... G01N 27/44782 204/450
2013/0149710 A1 6/2013 Yoon et al.
2013/0171640 A1 7/2013 Kwon et al.
2013/0210080 A1 8/2013 Rajagopal et al.
2013/0217026 A1* 8/2013 Egan .................... C12Q 1/6844 435/6.12
2013/0220781 A1 8/2013 Czarnecki
2014/0045191 A1 2/2014 DeJohn et al.
2014/0051159 A1 2/2014 Bergstedt et al.
2014/0098252 A1 4/2014 Chang et al.
2014/0120539 A1 5/2014 Tanner et al.
2014/0199685 A1 7/2014 Lambotte et al.
2015/0031087 A1 1/2015 Nagai et al.
2015/0176057 A1 6/2015 Smith et al.
2015/0182966 A1 7/2015 Coursey et al.
2016/0310948 A1 10/2016 Nowakowski et al.

FOREIGN PATENT DOCUMENTS

WO WO-2009047804 A2 4/2009
WO WO-2014144548 A2 9/2014
WO WO-2015138343 A1 9/2015
WO WO-2015138648 A1 9/2015
WO WO2015/164770 A1 10/2015
WO WO-2016040523 A1 3/2016
WO WO-2016109691 A1 7/2016

OTHER PUBLICATIONS

PCT Patent Application No. PCT/US2015/019497 International Search Report and Written Opinion dated Jun. 8, 2015.
PCT Patent Application No. PCT/US2015/049247 International Search Report and Written Opinion mailed Jan. 12, 2016.
PCT Patent Application No. PCT/US2015/068101 International Search Report and Written Opinion dated May 5, 2016.
Schwerdt. Application of ferrofluid as a valve/pump for polycarbonate microfluidic devices. Johns Hopkins University. NSF Summer Undergraduate Fellowship in Sensor Technologies 2006, 17 pages.
Tanriverdi, et al. A rapid and automated sample-to-result HIV load test for near-patient application. J Infect Dis., 201 Suppl 1:S52-S58, 2010.
Kopp et al., "Chemical Amplification: Continuous-Flow PCR on a Chip", Science (1998); 280(5366): 1046-1048.

* cited by examiner

DEVICES AND METHODS FOR MOLECULAR DIAGNOSTIC TESTING

CROSS-REFERENCE TO RELATED APPLICATIONS

This application claims priority to, and the benefit of, U.S. Provisional Application No. 62/098,769, entitled "Molecular Diagnostic Device," filed Dec. 31, 2014 and U.S. Provisional Application No. 62/213,291, entitled "Devices and Methods for Molecular Diagnostic Testing," filed Sep. 2, 2015, the entire disclosure of each of which is incorporated herein by reference in its entirety.

BACKGROUND

The embodiments described herein relate to methods and devices for molecular diagnostic testing. More particularly, the embodiments described herein relate to disposable, self-contained devices and methods for molecular diagnostic testing.

There are over one billion infections in the U.S. each year, many of which are treated incorrectly due to inaccurate or delayed diagnostic results. Many known point of care (POC) tests have poor sensitivity (30-70%), while the more highly sensitive tests, such as those involving the specific detection of nucleic acids or molecular testing associated with a pathogenic target, are only available in laboratories. Thus, approximately ninety percent of the current molecular diagnostics testing is practiced in centralized laboratories. Known devices and methods for conducting laboratory-based molecular diagnostics testing, however, require trained personnel, regulated infrastructure, and expensive, high throughput instrumentation. Known laboratory instrumentation is often purchased as a capital investment along with a regular supply of consumable tests or cartridges. Known high throughput laboratory equipment generally processes many (96 to 384 and more) samples at a time, therefore central lab testing is done in batches. Known methods for processing typically include processing all samples collected during a time period (e.g., a day) in one large run, with a turn-around time of hours to days after the sample is collected. Moreover, such known instrumentation and methods are designed to perform certain operations under the guidance of a skilled technician who adds reagents, oversees processing, and moves sample from step to step. Thus, although known laboratory tests and methods are very accurate, they often take considerable time, and are very expensive.

There are limited testing options available for testing done at the point of care ("POC"), or in other locations outside of a laboratory. Known POC testing options tend to be single analyte tests with low analytical quality. These tests are used alongside clinical algorithms to assist in diagnosis, but are frequently verified by higher quality, laboratory tests for the definitive diagnosis. Thus, neither consumers nor physicians are enabled to achieve a rapid, accurate test result in the time frame required to "test and treat" in one visit. As a result doctors and patients often determine a course of treatment before they know the diagnosis. This has tremendous ramifications: antibiotics are either not prescribed when needed, leading to infections; or antibiotics are prescribed when not needed, leading to new antibiotic-resistant strains in the community. Moreover, known systems and methods often result in diagnosis of severe viral infections, such as H1N1 swine flu, too late, limiting containment efforts. In addition, patients lose much time in unnecessary, repeated doctor visits.

Thus, a need exists for improved devices and methods for molecular diagnostic testing. In particular, a need exists for an affordable, easy-to-use test that will allow healthcare providers and patients at home to diagnose infections accurately and quickly so they can make better healthcare decisions.

SUMMARY

A molecular diagnostic test device includes a housing, an amplification module and a detection module. The amplification module is configured to receive an input sample, and defines a reaction volume. The amplification module includes a heater such that the amplification module can perform a polymerase chain reaction (PCR) on the input sample. The detection module is configured to receive an output from the amplification module and a reagent formulated to produce a signal that indicates a presence of a target amplicon within the input sample. The amplification module and the detection module are integrated within the housing such that the molecular diagnostic test device is a handheld device.

DETAILED DESCRIPTION

Figure 1:
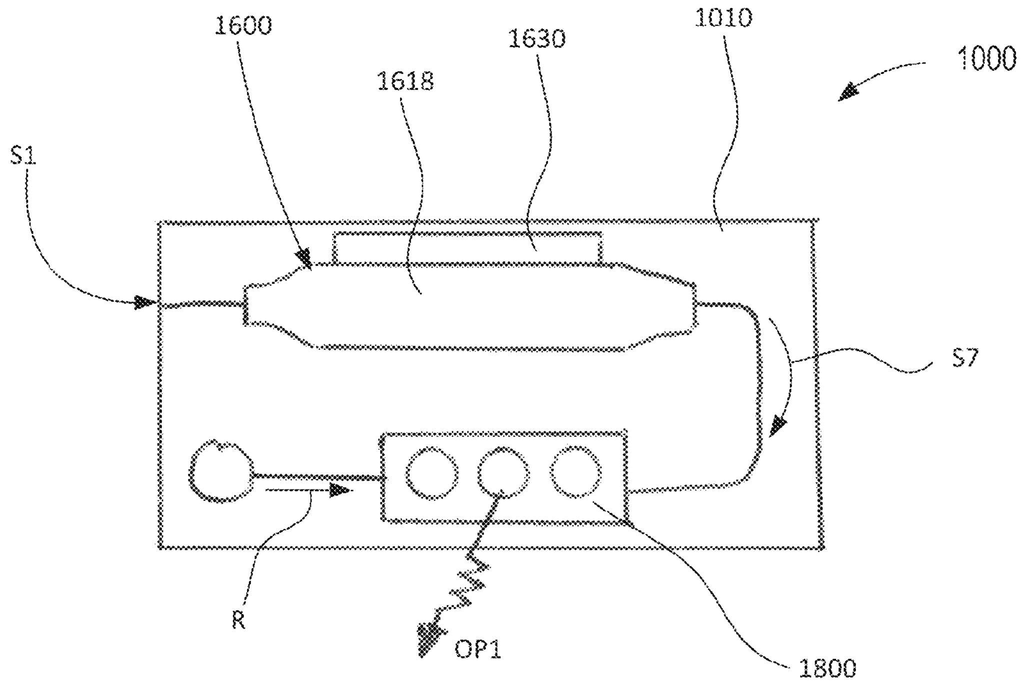
FIG. 1 is a schematic illustration of a molecular diagnostic test device, according to an embodiment.

In some embodiments, an apparatus is configured for a disposable, portable, single-use, inexpensive, molecular diagnostic approach. The apparatus can include one or more modules configured to perform high quality molecular diagnostic tests, including, but not limited to, sample preparation, nucleic acid amplification (e.g., via polymerase chain reaction or PCR), and detection. In some embodiments, sample preparation can be performed by isolating the target pathogen/entity and removing unwanted PCR inhibitors. The target entity can be subsequently lysed to release target nucleic acid for PCR amplification. A target nucleic acid in the target entity can be amplified with a polymerase undergoing temperature cycling to yield a greater number of copies of the target nucleic acid sequence for detection.

Detection can occur, in some embodiments, through a colorimetric reaction in a read lane. Multiple nucleic acid targets can be read in the lane, permitting for multiplexed detection/testing. The apparatus can also contain on-board reagent storage, fluidic pumping, valving and electronics to properly sequence test steps and control operation. Further, the apparatus can be battery powered, allowing the diagnostic test(s) to be run without A/C power, and at any suitable location (e.g., outside of a laboratory and/or at any suitable "point of care").

In some embodiments, the apparatus can be configured to detect pathogens commonly associated with sexually transmitted infections (STI) including, but not limited to, *Chlamydia trachomatis* (CT), *Neisseria gonorrhea* (NG) and *Trichomonas vaginalis* (TV), through nucleic acid detection. In some embodiments, the apparatus includes on-board positive and negative controls to ensure that the diagnostic test(s) are functioning properly.

In some embodiments, the apparatus is optimized for disposable and portable operation. For example, in some embodiments, the power module can be operated by a small battery (e.g., a 9V battery), and can include a controller to control the timing and/or magnitude of power draw to accommodate the capacity of the battery. In other embodiments, the apparatus can include any number of features, such as safety locks, configured to minimize the chances of user error.

In some embodiments, a hand-held molecular diagnostic test device includes a housing, an amplification (or PCR) module, and a detection module. The amplification module is configured to receive an input sample, and defines a reaction volume. The amplification module includes a heater such that the amplification module can perform a polymerase chain reaction (PCR) on the input sample. The detection module is configured to receive an output from the amplification module and a reagent formulated to produce a signal that indicates a presence of a target amplicon within the input sample. The amplification module and the detection module are integrated within the housing.

In some embodiments, an apparatus includes a housing, a sample preparation module, an amplification (or PCR) module, and a detection module. The sample preparation module is disposed within the housing and is configured to receive an input sample. The amplification module is disposed within the housing and is configured to receive an output from the sample preparation module. The amplification module includes a flow member and a heater, with the flow member defining a serpentine flow path. The heater is coupled to the flow member. The amplification module is configured perform a polymerase chain reaction (PCR) on the output from the sample preparation module. The detection module is disposed within the housing and is configured to receive an output from the amplification module. The detection module is configured to receive a reagent formulated to produce a colorimetric signal that indicates a presence of a target organism in said input sample. The sample preparation module, amplification (or PCR) module, and detection module are collectively configured for one-time use. In some embodiments, the apparatus is disposable via standard waste procedures after use.

In some embodiments, an apparatus includes an amplification (or PCR) module, and a detection module. The amplification module is configured to receive an input sample, and defines a reaction volume. The amplification module includes a heater such that the amplification module can perform a polymerase chain reaction (PCR) on the input sample. The detection module is configured to receive an output from the amplification module and a reagent formulated to produce a signal that indicates a presence of a target organism within the input sample. The apparatus is configured to produce the signal in a time of less than about 25 minutes.

In some embodiments, an apparatus includes a housing, an amplification (or PCR) module, and a detection module. The amplification module is configured to receive an input sample, and defines a reaction volume. The amplification module includes a heater such that the amplification module can perform a polymerase chain reaction (PCR) on the input sample. The detection module is configured to receive an output from the amplification module and a reagent formulated to produce a signal that indicates a presence of a target organism within the input sample. The target organism is associated with a disease. The amplification module and the detection module are integrated within the housing and collectively have a sensitivity of at least about 93 percent and a specificity of at least about 95 percent for the detection of the disease.

In some embodiments, an apparatus includes a housing, an amplification (or "PCR") module, a reagent module, and a detection module. The housing includes a sample input port and defines a detection opening. The PCR module is disposed within the housing, and includes a flow member and a heater. The flow member defines a PCR flow path having an inlet portion in fluid communication with the sample input port. The heater is fixedly coupled to the flow member such that the heater and the PCR flow path intersect at multiple locations. The reagent module is disposed within the housing, and contains a substrate formulated to catalyze the production of an optical signal by a signal molecule associated with a target amplicon. The detection module defines a detection channel in fluid communication with an outlet portion of the PCR flow path and the reagent module. The detection module includes a detection surface within the detection channel that is configured to retain the target amplicon. The detection module is disposed within the housing such that the detection surface is visible via the detection opening of the housing In some embodiments, the detection channel has a width of at least about 4 mm. In some embodiments, the housing includes a mask portion configured to surround at least a portion of the detection surface. The mask portion can be configured to enhance visibility of the detection surface through the detection opening.

In some embodiments, an apparatus includes a housing, an amplification module, a reagent module, and a detection module. The amplification module is disposed within the housing and is configured to receive an input sample. The amplification module defines a reaction volume and includes a heater such that the amplification module can perform a polymerase chain reaction (PCR) on the input sample. The reagent module is disposed within the housing, and defines a reagent volume within which at least one of a sample wash, an elution buffer, a PCR reagent, a detection reagent or a substrate is contained. The reagent module is actuated by a reagent actuator configured to convey the reagent from the volume when the reagent actuator is moved from a first position to a second position. The reagent actuator is configured to remain locked in the second position. The detection module is disposed within the housing and is configured to receive an output from the amplification module. The detection module is configured to receive the detection reagent from the reagent module, the detection reagent being formulated to produce a colorimetric signal that indicates a presence of a target organism in the input.

In some embodiments, the apparatus also includes a power source disposed within the housing. In some embodiments, the power source has a nominal voltage of about 9V and a capacity of less than about 1200 mAh. In some embodiments, the apparatus also includes a controller disposed within the housing, where the controller is implemented in at least one of a memory or a processor. In some embodiments, the controller includes at least a thermal control module configured to produce a thermal control signal to adjust an output of the heater.

In some embodiments, an apparatus includes a housing, an amplification module, a reagent module, a detection module, and a power source. The amplification module is disposed within the housing and is configured to receive an input sample. The amplification module includes a flow member defining a reaction volume. The amplification module includes a heater coupled to the flow member such that the amplification module can perform a polymerase chain reaction (PCR) on the input sample. The reagent module is disposed within the housing and defines a reagent volume within which at least one of a sample wash, an elution buffer, a PCR reagent, a detection reagent or a substrate is contained. The reagent module includes a reagent actuator configured to convey the reagent from the volume when the reagent actuator is moved from a first position to a second position. The detection module is configured to receive an output from the amplification module and the detection reagent. The detection reagent is formulated to produce a signal that indicates a presence of a target amplicon within the input sample. The detection module includes a detection surface from which the signal is produced, and which is visible via the detection opening. The power source is electrically isolated from at least one of a processor or the amplification module when the reagent actuator is in the first position. The power source is electrically coupled to at least one of the processor or the amplification module when the reagent actuator is in the second position.

In some embodiments, an apparatus includes a flow member and a heater assembly. The flow member defines a serpentine flow path having at least 30 amplification flow channels. The heater assembly is coupled to the flow member to define three heating zones within each amplification flow channel. The heater assembly and the flow member are collectively configured to maintain a temperature of a first portion of the flow member associated with the first heating zone at a first temperature. The heater assembly and the flow member are collectively configured to maintain a temperature of a second portion of the flow member associated with the second heating zone at a second temperature. The heater assembly and the flow member are collectively configured to maintain a temperature of a third portion of the flow member associated with the third heating zone at the first temperature. The heater assembly is coupled to of a first side the flow member via an adhesive bond.

In some embodiments, a method includes conveying a sample into a sample preparation module of a diagnostic device. The sample preparation module is disposed within a housing of the diagnostic device. The method also includes actuating the diagnostic device to extract, within the sample preparation module, a target molecule. The method also includes actuating the diagnostic device to flow a PCR solution containing the target molecule within a PCR flow path defined by a PCR module, such that the PCR solution is thermally cycled by a heater coupled to the PCR module. The method also includes actuating the diagnostic device to convey the PCR solution from an outlet of the PCR module into a detection channel of a detection module. The detection module includes a detection surface within the detection channel, the detection surface configured to retain the target molecule. The method also includes actuating the diagnostic device to convey a reagent into the detection channel, such that when the reagent reacts with a signal molecule associated with a target amplicon, a visible optical signal associated with the detection surface is produced. The method also includes viewing the detection surface via a detection opening of the housing.

As used herein, the term "about" when used in connection with a referenced numeric indication means the referenced numeric indication plus or minus up to 10% of that referenced numeric indication. For example, the language "about 50" covers the range of 45 to 55.

As used in this specification and the appended claims, the words "proximal" and "distal" refer to direction closer to and away from, respectively, an operator of the diagnostic device. Thus, for example, the end of an actuator depressed by a user that is furthest away from the user would be the distal end of the actuator, while the end opposite the distal end (i.e., the end manipulated by the user) would be the proximal end of the actuator.

As used in this specification and the appended claims, the term "reagent" includes any substance that is used in connection with any of the reactions described herein. For example, a reagent can include an elution buffer, a PCR reagent, an enzyme, a substrate, a wash solution, or the like. A reagent can include a mixture of one or more constituents. A reagent can include such constituents regardless of their state of matter (e.g., solid, liquid or gas). Moreover, a reagent can include the multiple constituents that can be included in a substance in a mixed state, in an unmixed state and/or in a partially mixed state. A reagent can include both active constituents and inert constituents. Accordingly, as used herein, a reagent can include non-active and/or inert constituents such as, water, colorant or the like.

The term "fluid-tight" is understood to encompass hermetic sealing (i.e., a seal that is gas-impervious) as well as a seal that is only liquid-impervious. The term "substantially" when used in connection with "fluid-tight," "gas-impervious," and/or "liquid-impervious" is intended to convey that, while total fluid imperviousness is desirable, some minimal leakage due to manufacturing tolerances, or other practical considerations (such as, for example, the pressure applied to the seal and/or within the fluid), can occur even in a "substantially fluid-tight" seal. Thus, a "substantially fluid-tight" seal includes a seal that prevents the passage of a fluid (including gases, liquids and/or slurries) therethrough when the seal is maintained at pressures of less than about 5 psig, less than about 10 psig, less than about 20 psig, less than about 30 psig, less than about 50 psig, less than about 75 psig, less than about 100 psig, and all values in between. Any residual fluid layer that may be present on a portion of a wall of a container after component defining a "substantially-fluid tight" seal are moved past the portion of the wall are not considered as leakage.

The term "opaque" is understood to include structures (such as portions of a device housing) that are not transparent and/or that do not permit an object to be clearly or distinctly seen through the structure. The term "opaque" or "substantially opaque" or "semi-opaque" when used in connection with the description of a device housing or any other structure described herein is intended to convey that objects cannot be clearly seen through the housing. A housing (or portion thereof) described as being "opaque" or "substantially opaque" or "semi-opaque" is understood to include structures that may have a blocking color, or that may not have a color, but that are otherwise hazy, blurry, smeared, textured or the like.

Unless indicated otherwise, the terms apparatus, diagnostic apparatus, diagnostic system, diagnostic test, diagnostic test system, test unit, and variants thereof, can be interchangeably used.

FIG. 1 is a schematic illustration of a handheld molecular diagnostic test device 1000 (also referred to as a "test device") according to an embodiment. The test device 1000 includes a housing 1010, an amplification module 1600 and a detection module 1800. The housing 1010 can be any structure within which the amplification module 1600 and the detection module 1800 are contained to form a handheld device. Similarly stated, the molecular diagnostic test device 1000 has a size, shape and/or weight such that the device can be carried, held, used and/or manipulated in a user's hands. In this manner, the user can conduct a molecular diagnostics test for rapid, accurate detection of disease without a large, expensive instrument. Moreover, this arrangement portable, self-contained molecular diagnostics test for rapid, accurate detection of disease. In some embodiments, the test device 1000 (and any of the test devices described herein) can have an overall volume of less than about 260 $cm^3$ (or about 16 cubic inches; e.g., a length of about 10.2 cm, a width of about 10.2 cm and a thickness of about 2.5 cm). In some embodiments, the test device 1000 (and any of the test devices described herein) can have an overall volume of less than about 200 $cm^3$ (or about 12.25 cubic inches; e.g., a length of about 8.9 cm, a width of about 8.9 cm and a thickness of about 2.5 cm). In some embodiments, the test device 1000 (and any of the test devices described herein) can have an overall volume of less than about 147 $cm^3$ (or about 9 cubic inches; e.g., a length of about 7.6 cm, a width of about 7.6 cm and a thickness of about 2.5 cm). In some embodiments, the test device 1000 (and any of the test devices described herein) can have an overall volume of about 207 $cm^3$ (or about 12.6 cubic inches; e.g., a length of about 9.0 cm, a width of about 7.7 cm and a thickness of about 3.0 cm).

The amplification module 1600 is configured to receive an input sample S1 that may contain a target organism associated with a disease state. The sample S1 (and any of the input samples described herein) can be, for example, blood, urine, male urethral specimens, vaginal specimens, cervical swab specimens, and/or nasal swab specimens gathered using a commercially available sample collection kit. The sample collection kit can be a urine collection kit or swab collection kit. Non-limiting examples of such sample collection kits include Copan Mswab or BD ProbeTec Urine Preservative Transport Kit, Cat #440928, neat urine. In some embodiments, the sample S1 can be a raw sample obtained from the source, and upon which limited preparation (filtering, washing, or the like) has been performed. In some embodiments, for example, the device 1000 can include a sample input module and/or a sample preparation module of the types shown and described herein.

The amplification module 1600 defines a reaction volume 1618 and includes a heater 1630 such that the amplification module 1600 can perform a polymerase chain reaction (PCR) on the input sample S1. In some embodiments, the reaction volume 1618 can be a central volume within which the sample S1 is maintained while the heater 1630 repeatedly cycles the sample S1 through a series of temperature set points to amplify the target organism and/or portions of the DNA of the organism. In other embodiments, the reaction volume 1618 can be a volume through which the sample S1 is flowed, and that has various portions maintained at different temperatures by the heater 1630. In this manner, the amplification module 1600 can perform a "flow through" PCR. In some embodiments, the reaction volume can have a curved, "switchback," and/or serpentine shape to allow for a high flow length while maintaining the overall size of the device within the desired limits.

The heater 1630 can be any suitable heater or collection of heaters that can perform the functions described herein to amplify the sample S1. For example, in some embodiments, the heater 1630 can be single heater that is thermally coupled to the reaction volume 1618 and that can cycle through multiple temperatures set points (e.g., between about 60 C and about 90 C). In other embodiments, the heater 1630 can be a set of heaters, each of which is thermally coupled to the reaction volume 1618 and that is maintained at a substantially constant set point. In this manner, the heater 1630 and the reaction volume 1618 can establish multiple temperature zones through which the sample S1 flows and/or can define a desired number of amplification cycles to ensure the desired test sensitivity (e.g., at least 30 cycles, at least 34 cycles, at least 36 cycles, at least 38 cycles, or at least 40 cycles). The heater 1630 (and any of the heaters described herein) can be of any suitable design. For example, in some embodiments, the heater 1630 can be a resistance heater, a thermoelectric device (e.g. a Peltier device), or the like.

The detection module 1800 receives an output S7 from the amplification module 1800 and a reagent R. The reagent R is formulated to produce a signal OP1 that indicates a presence of a target amplicon and/or organism within the input sample S1. In this manner, the stand-alone device 1000 can provide reliable molecular diagnosis within a point-of-care setting (e.g., doctor's office, pharmacy or the like) or at the user's home. The signal OP1 can be any suitable signal that alerts the user regarding whether or not the target organism is present. Similarly stated, the signal OP1 can be any suitable signal to detect a disease associated with the target amplicon and/or organism. The signal OP1 can be, for example, a visual signal, an audible signal, a radio frequency signal or the like.

In some embodiments, the signal OP1 is a visual signal that can viewed by the user through a detection opening (not shown in FIG. 1) defined by the housing. The visual signal can be, for example, a non-fluorescent signal. This arrangement allows the device 1000 to be devoid of a light source (e.g., lasers, light-emitting diodes or the like) and/or any light detectors (photomultiplier tube, photodiodes, CCD devices, or the like) to detect and/or amplify the signal OP1. In some embodiments, the signal OP1 is a visible signal characterized by a color associated with the presence of the target amplicon and/or organism. Said another way, in some embodiments, the device 1000 can produce a colormetric output signal that is visible to the user. In such embodiments, the detection module 1800 (and any of the detection modules described herein) can produce a chemiluminescent signal that results from the introduction of the reagent R and/or any other substances (e.g., a substrate to catalyze the production of the signal OP1, and the like). In some embodiments, the reagent is formulated such that the visible signal OP1 remains present for at least about 30 minutes. The reagent R and any other compositions formulated to produce the signal OP1 can be any suitable compositions as described herein. In some embodiments, the reagent R can be stored within the housing 1010 in any manner as described herein (e.g., in a sealed container, a lyophilized form or the like).

In some embodiments, the device 1000 (and any of the other devices shown and described herein) can be configured to produce the signal OP1 in a time of less than about 25 minutes from when the sample S1 is received. In other embodiments, the device 1000 (and any of the other devices shown and described herein) can be configured to produce the signal OP1 in a time of less than about 20 minutes from when the sample S1 is input, less than about 18 minutes from when the sample S1 is input, less than about 16 minutes from when the sample S1 is input, less than about 14 minutes from when the sample S1 is input, and all ranges therebetween.

Similarly stated, the device 1000 and the components therein can be configured to conduct a "rapid" PCR (e.g., completing at least 30 cycles in less than about 10 minutes), and rapid production of the signal OP1. Similarly stated, the device 1000 (and any of the other devices shown and described herein) can be configured to process volumes, to have dimensional sizes and/or be constructed from materials that facilitates a rapid PCR or amplification in less than about 10 minutes, less than about 9 minutes, less than about 8 minutes, less than about 7 minutes, less than about 6 minutes, or any range therebetween, as described herein.

In some embodiments, the device 1000 (and any of the other devices shown and described herein) can be disposable and/or configured for a single use. Similarly stated, the device 1000 (and any of the other devices shown and described herein) can be configured for one and only one use. For example, in some embodiments, the amount of the reagent R can be sufficient for only one use. In other embodiments, the device 1000 can include an on-board power source (e.g., a DC battery) to power the amplification module 1600 and/or any sample preparation or fluid transfer modules that may be present (not shown in FIG. 1) that has a capacity sufficient for only one test. In some embodiments, the device 1000 can include a power source (not shown in FIG. 1) having a capacity of less than about 1200 mAh.

Figure 2:
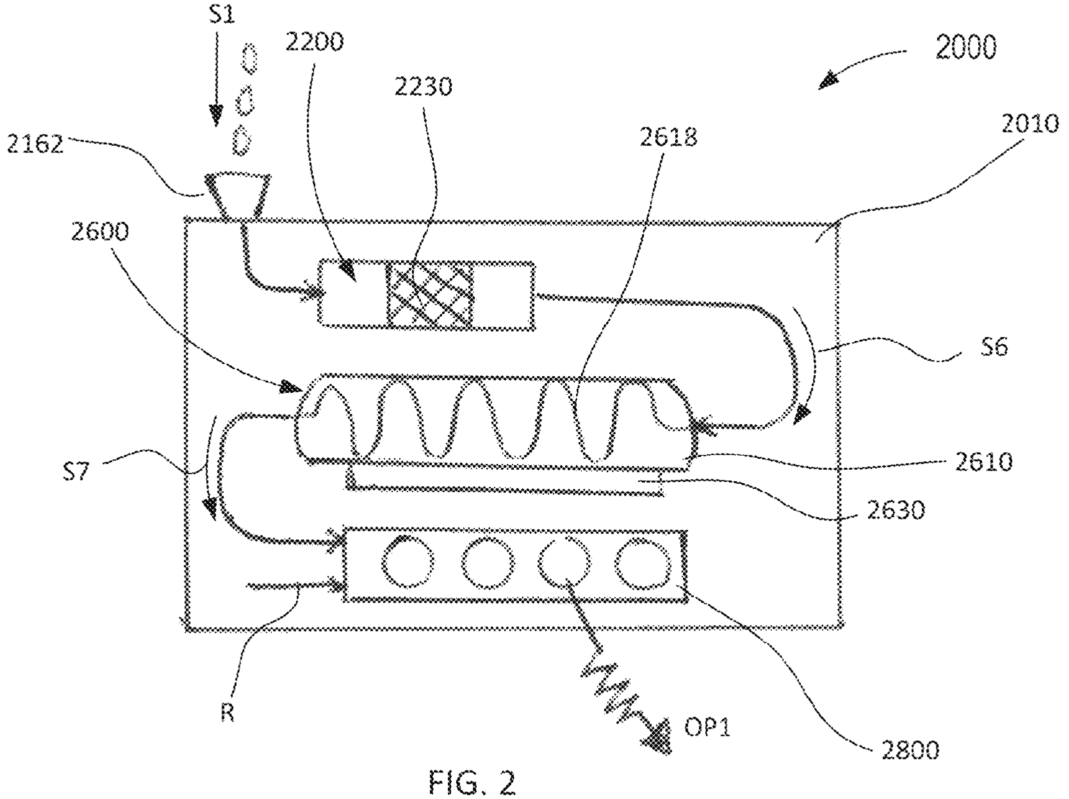
FIG. 2 is a schematic illustration of a molecular diagnostic test device, according to an embodiment.

Another example of a device configured for a single use is shown in FIG. 2, which shows a molecular diagnostic test device 2000 (also referred to as a "test device" or "device"), according to an embodiment. The test device 2000 includes a housing 2010, a sample preparation module 2200, an amplification module 2600 and a detection module 2800. The housing 2010 can be any structure within which the sample preparation module 2200, the amplification module 2600 and the detection module 2800 are contained. In some embodiments, the test device 2000 have a size, shape and/or weight such that the device can be carried, held, used and/or manipulated in a user's hands (i.e., it can be a "handheld" device). In other embodiments, the test device 2000 can be a self-contained, single-use device that has an overall volume greater than about 260 $cm^3$ (or about 16 cubic inches). In some embodiments, the test device 2000 (and any of the test devices described herein) can have an overall volume of about 207 $cm^3$ (or about 12.6 cubic inches; e.g., a length of about 9.0 cm, a width of about 7.7 cm and a thickness of about 3.0 cm).

The sample preparation module 2200 is disposed within the housing 2010, and is configured receive an input sample S1 via an input portion 2162 of the housing 2010. As described herein, the sample preparation module 2200 is configured to process the sample S1 to facilitate detection of an organism therein that is associated with a disease. For example, in some embodiments, the sample preparation module 2200 can be configured to concentrate and lyse cells in the sample S1, thereby allowing subsequent extraction of DNA to facilitate amplification and/or detection. In some embodiments, the processed/lysed sample is pushed and/or otherwise transferred from the sample preparation module 2200 to other modules within the device 2000 (e.g., the amplification module 2600, a mixing module (not shown), or the like). By eliminating the need for external sample preparation and a cumbersome instrument, the device 2000 is suitable for use within a point-of-care setting (e.g., doctor's office, pharmacy or the like) or at the user's home, and can receive any suitable sample S1. The sample S1 (and any of the input samples described herein) can be, for example, blood, urine, male urethral specimens, vaginal specimens, cervical swab specimens, and/or nasal swab specimens gathered using a commercially available sample collection kit.

The sample preparation module 2200 includes a filter assembly 2230 through which the sample S1 flows during a "dispense" or "sample actuation" operation. Although not shown in FIG. 2, in some embodiments, the sample preparation module 2200 includes a waste reservoir to which the waste product from the filtering operation is conveyed. In some embodiments, the sample preparation module 2200 includes components and/or substances to follow the "sample dispense" operation with a wash operation. In some embodiments, the sample preparation module 2200 is configured for a back-flow elution operation to deliver captured particles from the filter membrane and deliver the eluted volume to the target destination (e.g., towards the amplification module 2600). In some embodiments, the sample preparation module 2200 is configured so as not cause the output solution to be contaminated by previous reagents (e.g., like the sample or wash).

The amplification module 2600 includes a flow member 2610 and a heater 2630, and is configured to perform a polymerase chain reaction (PCR) on the input sample S6 that is output by the sample preparation module 2200. The flow member 2610 defines a "switchback" or serpentine flow path 2618 through which the prepared sample S6 flows. Similarly stated, the flow member 2610 defines a flow path 2618 that is curved such that the flow path 2618 intersects the heater 2630 at multiple locations. In this manner, the amplification module 2600 can perform a "flow through" PCR where the sample S6 flows through multiple different temperature regions.

The heater 2630 can be any suitable heater or collection of heaters that can perform the functions described herein to amplify the sample S6. Specifically, the heater 2630 is coupled to the flow member 2610, and is configured to establish multiple temperature zones through which the sample S6 flows and/or can define a desired number of amplification cycles to ensure the desired test sensitivity (e.g., at least 30 cycles, at least 34 cycles, at least 36 cycles, at least 38 cycles, or at least 40 cycles). The heater 2630 (and any of the heaters described herein) can be of any suitable design. For example, in some embodiments, the heater 2630 can be a resistance heater, a thermoelectric device (e.g. a Peltier device), or the like. In some embodiments, the heater 2630 can be one or more linear "strip heaters" arranged such that the flow path 2618 crosses the heaters at multiple different points. In other embodiments, the heater 2630 can be one or more curved heaters having a geometry that corresponds to that of the flow member 2610 to produce multiple different temperature zones in the flow path 2618.

The detection module 2800 receives an output S7 from the amplification module 2800 and a reagent R. The reagent R is formulated to produce a signal OP1 that indicates a presence of a target amplicon and/or organism within the input sample S1. In this manner, the stand-alone device 2000 can provide reliable molecular diagnosis within a point-of-care setting (e.g., doctor's office, pharmacy or the like) or at the user's home. The signal OP1 can be any suitable signal that alerts the user regarding whether or not the target organism is present. Similarly stated, the signal OP1 can be any suitable signal to detect a disease associated with the target amplicon and/or organism. The signal OP1 can be, for example, a visual signal, an audible signal, a radio frequency signal or the like.

In some embodiments, the signal OP1 is a visual signal that can viewed by the user through a detection opening (not shown in FIG. 2) defined by the housing. The visual signal can be, for example, a non-fluorescent signal. This arrangement allows the device 2000 to be devoid of a light source (e.g., lasers, light-emitting diodes or the like) and/or any light detectors (photomultiplier tube, photodiodes, CCD devices, or the like) to detect and/or amplify the signal OP1. In some embodiments, the signal OP1 is a visible signal characterized by a color associated with the presence of the target amplicon and/or organism. Said another way, in some embodiments, the device 2000 can produce a colormetric output signal that is visible to the user. In such embodiments, the detection module 2800 (and any of the detection modules described herein) can produce a chemiluminescent signal that results from the introduction of the reagent R and/or any other substances (e.g., a substrate to catalyze the production of the signal OP1, and the like). In some embodiments, the reagent is formulated such that the visible signal OP1 remains present for at least about 30 minutes. The reagent R and any other compositions formulated to produce the signal OP1 can be any suitable compositions as described herein. In some embodiments, the reagent R can be stored within the housing 2010 in any manner as described herein (e.g., in a sealed container, a lyophilized form or the like).

In some embodiments, the device 2000 (and any of the other devices shown and described herein) can be configured to produce the signal OP1 in a time of less than about 25 minutes from when the sample S1 is received. In other embodiments, the device 2000 (and any of the other devices shown and described herein) can be configured to produce the signal OP1 in a time of less than about 20 minutes from when the sample S1 is input, less than about 18 minutes from when the sample S1 is input, less than about 16 minutes from when the sample S1 is input, less than about 14 minutes from when the sample S1 is input, and all ranges therebetween.

Similarly stated, the device 2000 and the components therein can be configured to conduct a "rapid" PCR (e.g., completing at least 30 cycles in less than about 20 minutes), and rapid production of the signal OP1. Similarly stated, the device 2000 (and any of the other devices shown and described herein) can be configured to process volumes, to have dimensional sizes and/or be constructed from materials that facilitates a rapid PCR or amplification in less than about 10 minutes, less than about 9 minutes, less than about 8 minutes, less than about 7 minutes, less than about 6 minutes, or any range therebetween, as described herein.

As described above, the device 2000 is configured as a single-use device that can be used in a point-of-care setting and/or in a user's home. Similarly stated, in some embodiments, the device 2000 (and any of the other devices shown and described herein) can be configured for use in a decentralized test facility. Further, in some embodiments, the device 2000 (and any of the other devices shown and described herein) can be a CLIA-waived device and/or can operate in accordance with methods that are CLIA waived. Similarly stated, in some embodiments, the device 2000 (and any of the other devices shown and described herein) is configured to be operated in a sufficiently simple manner, and can produce results with sufficient accuracy to pose a limited likelihood of misuse and/or to pose a limited risk of harm if used improperly. In some embodiments, the device 2000 (and any of the other devices shown and described herein), can be operated by a user with minimal (or no) scientific training, in accordance with methods that require little judgment of the user, and/or in which certain operational steps are easily and/or automatically controlled.

For example, in some embodiments, the sample preparation module 2200 of the single-use molecular diagnostic test device 2000 can be fixedly coupled within the housing 2010. In this manner, the risk of improperly positioning a removable cartridge within the housing (such risk being present with known cartridge-based systems) is eliminated. More particularly, in some embodiments, the device 2000 can include a sample transfer module (not shown in FIG. 2) configured to generate fluid pressure, fluid flow and/or otherwise convey the input sample S1 through the modules of the device. Such a sample transfer module, can be a single-use module that is configured to contact and/or receive the sample flow. The single-use arrangement eliminates the likelihood that contamination of the fluid transfer module and/or the sample preparation module 2200 will become contaminated from previous runs, thereby negatively impacting the accuracy of the results.

As another example, in some embodiments, the device 2000 (and any of the other devices shown and described herein), can include a variety of lock-out devices that prevent the user from conducting certain operational steps out of the desired order. Moreover, the device 2000 (and any of the other devices shown and described herein), can include a variety of lock-out devices that prevent the user from reusing the device after an initial use has been attempted and/or completed. In this manner, the device 2000 (and any of the other devices shown and described herein), can be specifically configured for a single-use operation and can pose a limited risk of misuse. For example, in some embodiments, the device 2000 can include a sample actuator (not shown in FIG. 2) configured to produce a force to convey the input sample S1 through the filter assembly 2230 when the sample actuator is moved relative to the housing 2010. The sample actuator can further be configured with protrusions, recesses and/or other features such that the sample actuator will remain locked in the actuated position after a single use.

Figure 4:
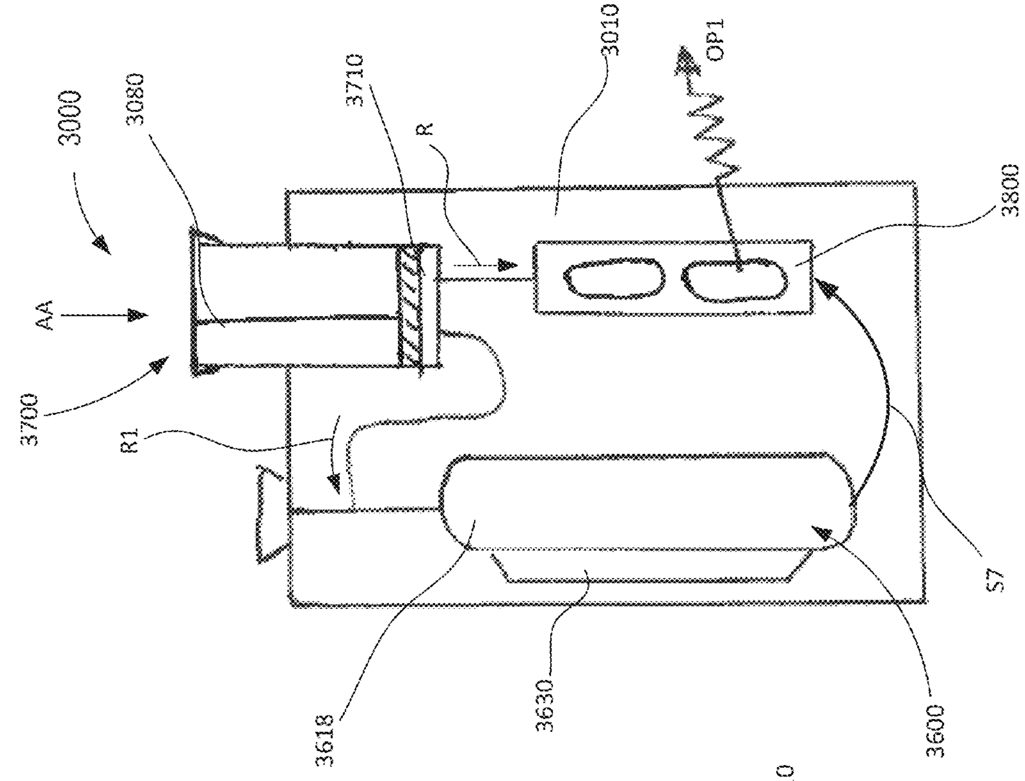
FIGS. 3 and 4 are schematic illustrations of a molecular diagnostic test device, according to an embodiment in a first configuration and a second configuration, respectively.
Figure 3:
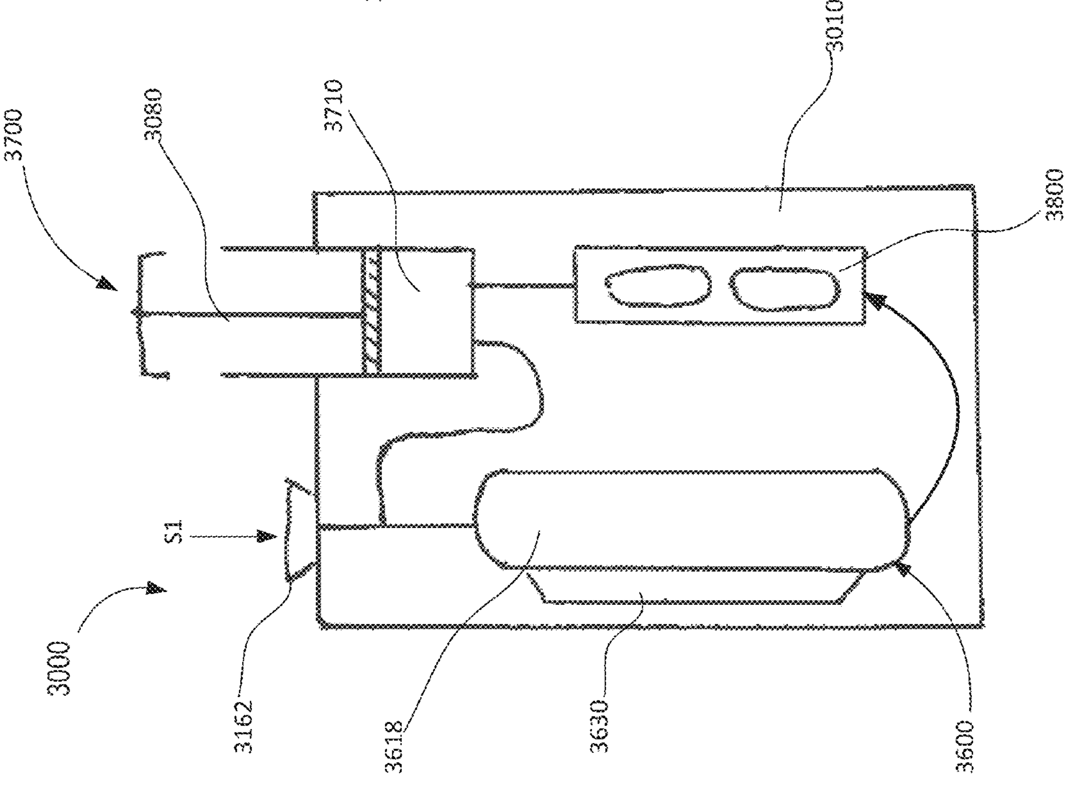

As yet another example, in some embodiments, a device can include on board reagents and a single-use reagent module configured to dispense the reagents in a manner that can be operated by a user with minimal (or no) scientific training, in accordance with methods that require little judgment of the user. In some embodiments, a device including a reagent module can include a lock-out device that prevents the user from actuating the module out of the desired order and/or prevents the user from reusing the device after an initial use has been attempted and/or completed. For example, FIGS. 3 and 4 show a molecular diagnostic test device 3000 (also referred to as a "test device" or "device"), according to an embodiment. The test device 3000 includes a housing 3010, a reagent module 3700, an amplification module 3600 and a detection module 3800. The housing 3010 can be any structure within which the reagent module 3700, the amplification module 3600 and the detection module 3800 are contained. In some embodiments, the test device 3000 have a size, shape and/or weight such that the device can be carried, held, used and/or manipulated in a user's hands (i.e., it can be a "handheld" device). In other embodiments, the test device 3000 can be a self-contained, single-use device that has an overall volume greater than about 260 $cm^3$ (or about 16 cubic inches). In some embodiments, the test device 3000 (and any of the test devices described herein) can have an overall volume of about 207 $cm^3$ (or about 12.6 cubic inches; e.g., a length of about 9.0 cm, a width of about 7.7 cm and a thickness of about 3.0 cm).

The reagent module 3700 is disposed within the housing 3010, and defines a reagent volume 3710 within which at least one reagent is contained. Although FIGS. 3 and 4 show the reagent volume 3710 containing a reagent R and a reagent R1, and being fluidically coupled to the amplification module 3600 and the detection module 3800, in other embodiments, a reagent module can contain any suitable reagents and can be fluidically coupled to and/or can convey such reagents to any suitable module within the device. For example, in some embodiments, the reagent volume can contain any of a sample wash, an elution buffer, one or more PCR reagents, a detection reagent and/or a substrate.

As shown by the arrow AA in FIG. 4, the reagent module 3700 is actuated by a reagent actuator 3080 to convey the reagent (indicated as reagent R and reagent R1) from the reagent volume 3710. Specifically, the reagent actuator 3080 is moved from a first position (FIG. 3) to a second position (FIG. 4) to convey the reagent(s) from the reagent volume 3710. The reagent actuator 3080 is configured to remain locked in the second position to prevent reuse of the device 3000. In some embodiments, the reagent actuator 3080 can include protrusions, recesses and/or other features that interface with the housing 3010 and/or other portions of the device to maintain the actuator 3080 in the second position. Similarly stated, the reagent actuator 3080 can include any suitable structure to maintain the reagent module 3700 in its second (or actuated) configuration. In this manner, the device 3000 (and any of the other devices shown and described herein), can be specifically configured for a single-use operation and can pose a limited risk of misuse.

Although the reagent actuator 3080 is shown as being a moved in a linear direction to convey the reagents, in other embodiments, the reagent actuator 3080 can be configured to rotate to develop the pressure and/or flow of reagent(s). Moreover, in some embodiments, the reagent actuator 3080 (and any of the reagent actuators described herein) can be an automatic actuator (i.e., an electronic actuator, an actuator that is moved and/or actuated with limited human interaction, and/or an actuator that is moved and/or actuated with no direct human interaction). In other embodiments, the reagent actuator 3080 (and any of the reagent actuators described herein) can be a manual actuator (e.g., a non-electronic actuator that is manipulated directly by a user). This arrangement allows the reagent actuator 3080 to be actuated without the need for electronic power and/or before the device 3000 is powered on. In some embodiments, the movement of the actuator 3080 can also initialize a power-on sequence of the device 3000. In this manner, the device can limit any power use prior to beginning of the test, thereby limiting the likelihood of misuse and/or an inaccurate test (e.g., due to an unexpected dead battery).

The amplification module 3600 defines a reaction volume 3618, includes a heater 3630, and is configured to perform a polymerase chain reaction (PCR) on the input sample S1. The input sample S1, can be any suitable sample as described herein, and can be conveyed to the amplification module via an input portion 3162 of the housing 3010. In some embodiments, the reaction volume 3618 can be a central volume within which the sample S1 is maintained while the heater 3630 repeatedly cycles the sample S1 through a series of temperature set points to amplify the target organism and/or portions of the DNA of the organism. In other embodiments, the reaction volume 3618 can be a volume through which the sample S1 is flowed, and that has various portions maintained at different temperatures by the heater 3630. In this manner, the amplification module 3600 can perform a "flow through" PCR. In some embodiments, the reaction volume can have a curved, "switchback," and/or serpentine shape to allow for a high flow length while maintaining the overall size of the device within the desired limits.

The heater 3630 can be any suitable heater or collection of heaters that can perform the functions described herein to amplify the sample S1. For example, in some embodiments, the heater 3630 can be single heater that is thermally coupled to the reaction volume 3618 and that can cycle through multiple temperatures set points (e.g., between about 60 C and about 90 C). In other embodiments, the heater 3630 can be a set of heaters, each of which is thermally coupled to the reaction volume 3618 and that is maintained at a substantially constant set point. In this manner, the heater 3630 and the reaction volume 3618 can establish multiple temperature zones through which the sample S1 flows and/or can define a desired number of amplification cycles to ensure the desired test sensitivity (e.g., at least 30 cycles, at least 34 cycles, at least 36 cycles, at least 38 cycles, or at least 40 cycles). The heater 3630 (and any of the heaters described herein) can be of any suitable design. For example, in some embodiments, the heater 3630 can be a resistance heater, a thermoelectric device (e.g. a Peltier device), or the like.

As shown in FIG. 4, the detection module 3800 receives an output S7 from the amplification module 3800 and a reagent R from the reagent module 3700. The reagent R is a detection reagent formulated to produce and/or catalyze the production of a signal OP1 that indicates a presence of a target amplicon and/or organism within the input sample S1. In this manner, the stand-alone device 3000 can provide reliable molecular diagnosis within a point-of-care setting (e.g., doctor's office, pharmacy or the like) or at the user's home. The signal OP1 can be any suitable signal that alerts the user regarding whether or not the target organism is present. Similarly stated, the signal OP1 can be any suitable signal to detect a disease associated with the target amplicon and/or organism. The signal OP1 can be, for example, a visual signal, an audible signal, a radio frequency signal or the like.

In some embodiments, the signal OP1 is a visual signal that can viewed by the user through a detection opening (not shown in FIGS. 3 and 4) defined by the housing. The visual signal can be, for example, a non-fluorescent signal. This arrangement allows the device 3000 to be devoid of a light source (e.g., lasers, light-emitting diodes or the like) and/or any light detectors (photomultiplier tube, photodiodes, CCD devices, or the like) to detect and/or amplify the signal OP1. In some embodiments, the signal OP1 is a visible signal characterized by a color associated with the presence of the target amplicon and/or organism. Said another way, in some embodiments, the device 3000 can produce a colormetric output signal that is visible to the user. In such embodiments, the detection module 3800 (and any of the detection modules described herein) can produce a chemiluminescent signal that results from the introduction of the reagent R and/or any other substances (e.g., a substrate to catalyze the production of the signal OP1, and the like). In some embodiments, the reagent is formulated such that the visible signal OP1 remains present for at least about 30 minutes. The reagent R and any other compositions formulated to produce the signal OP1 can be any suitable compositions as described herein. In some embodiments, the reagent R can be stored within the housing 3010 in any manner as described herein (e.g., in a sealed container, a lyophilized form or the like).

In some embodiments, the device 3000 (and any of the other devices shown and described herein) can be configured to produce the signal OP1 in a time of less than about 25 minutes from when the sample S1 is received. In other embodiments, the device 3000 (and any of the other devices shown and described herein) can be configured to produce the signal OP1 in a time of less than about 20 minutes from when the sample S1 is input, less than about 18 minutes from when the sample S1 is input, less than about 16 minutes from when the sample S1 is input, less than about 14 minutes from when the sample S1 is input, and all ranges therebetween.

Similarly stated, the device 3000 and the components therein can be configured to conduct a "rapid" PCR (e.g., completing at least 30 cycles in less than about 10 minutes), and rapid production of the signal OP1. Similarly stated, the device 3000 (and any of the other devices shown and described herein) can be configured to process volumes, to have dimensional sizes and/or be constructed from materials that facilitates completion of a rapid PCR or amplification in less than about 10 minutes, less than about 9 minutes, less than about 8 minutes, less than about 7 minutes, less than about 6 minutes, or any range therebetween, as described herein.

As described above, the device 3000 is configured as a single-use device that can be used in a point-of-care setting and/or in a user's home. Similarly stated, in some embodiments, the device 3000 (and any of the other devices shown and described herein) can be configured for use in a decentralized test facility. Further, in some embodiments, the device 3000 (and any of the other devices shown and described herein) can be a CLIA-waived device and/or can operate in accordance with methods that are CLIA waived. Similarly stated, in some embodiments, the device 3000 (and any of the other devices shown and described herein) is configured to be operated in a sufficiently simple manner, and can produce results with sufficient accuracy to pose a limited likelihood of misuse and/or to pose a limited risk of harm if used improperly. In some embodiments, the device 3000 (and any of the other devices shown and described herein), can be operated by a user with minimal (or no) scientific training, in accordance with methods that require little judgment of the user, and/or in which certain operational steps are easily and/or automatically controlled.

For example, in some embodiments, the reagent module 3700 of the molecular diagnostic test device 3000 can include seals such that the reagent volume 3710 is a sealed reagent volume within which the reagent(s) are stored. In such embodiments, the reagent actuator 3080 is configured to puncture the seal that fluidically isolates the reagent volume 3710 when moved. In this manner, the molecular diagnostic test device 3000 can be configured for long term storage in a manner that poses a limited likelihood of misuse (spoilage of the reagent(s), expiration of the reagents(s), leakage of the reagent(s), or the like). In some embodiments, the reagent module 3700 and/or any area in fluid communication therewith (or any other reagent modules described herein) can include a desiccant, seals or other compositions or components to maintain stability for long term storage. In some embodiments, the molecular diagnostic test device 3000 is configured to be stored for up to about 36 months, up to about 32 months, up to about 26 months, up to about 24 months, up to about 20 months, up to about 18 months, or any values there between.

In some embodiments, the device 3000 (or any of the devices shown herein) can include an on-board power source (e.g., a DC battery, a capacitor, or the like) to power the amplification module 3600 and/or any sample preparation or fluid transfer modules that may be present (not shown in FIGS. 3 and 4). Moreover, the power source can have a capacity sufficient for only one test. In this manner, the likelihood of misuse of the device is limited. Moreover, by including a power source with a limited capacity, the risk of re-use or improper use (e.g., after an erroneous "power on" event) is limited or reduced. In some embodiments, the device 3000 can include a power source (not shown in FIG. 1) having a capacity of less than about 1200 mAh. In some embodiments, the device 3000 (or any other devices shown and described herein) can include a switch, isolation member or the like that facilitates electrically coupling of the power source to a processor (not shown in FIGS. 3 and 4), the amplification module or any other module within the device 3000 to actuation of sample preparation module, reagent module or the like.

Figure 6:
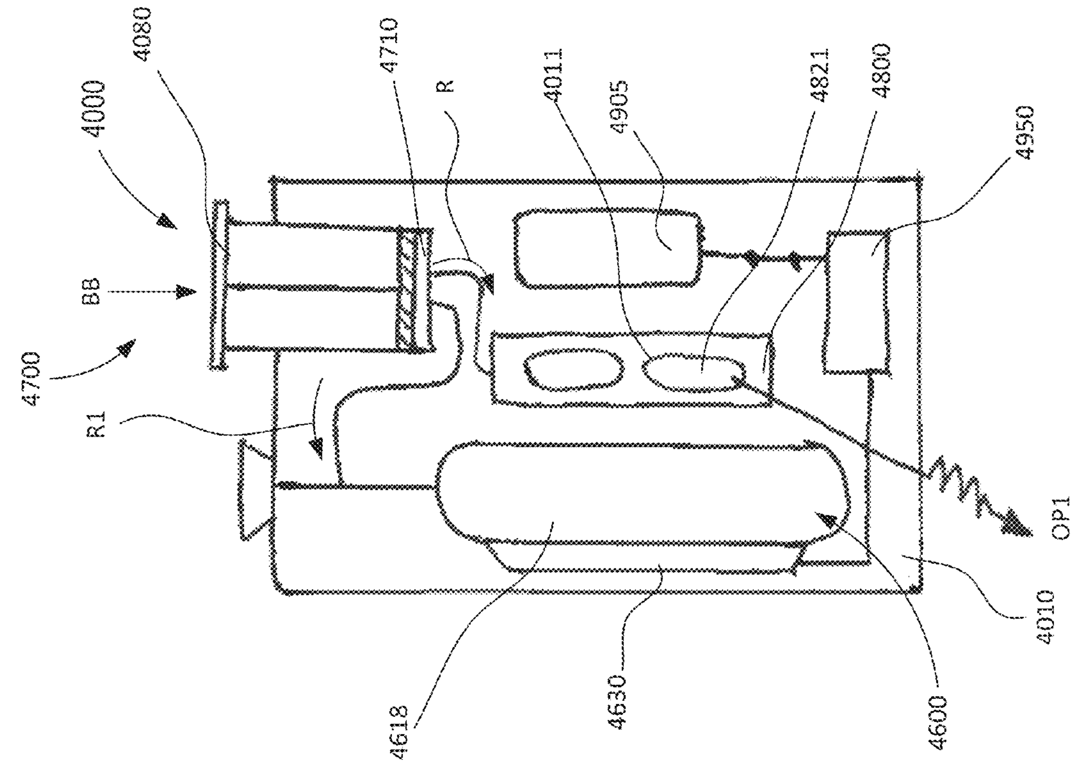
FIGS. 5 and 6 are schematic illustrations of a molecular diagnostic test device, according to an embodiment in a first configuration and a second configuration, respectively.
Figure 5:
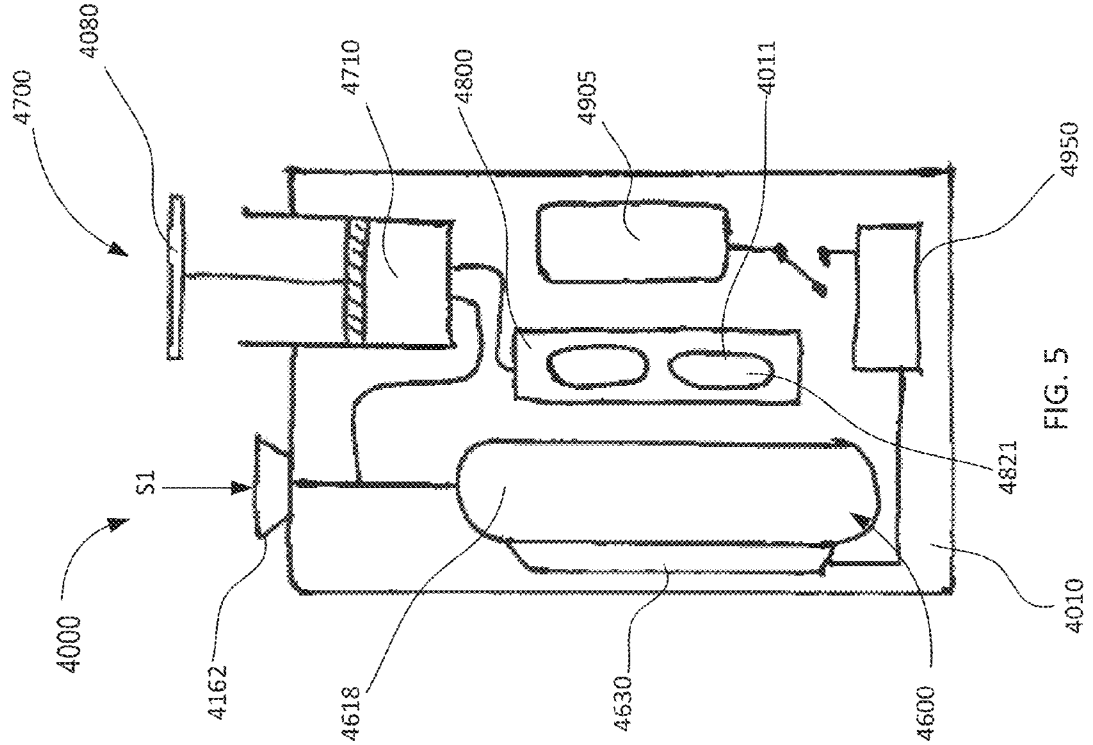

For example, FIGS. 5 and 6 show a molecular diagnostic test device 4000 (also referred to as a "test device" or "device"), according to an embodiment that includes a power source 4905. The test device 4000 also includes a housing 4010, a reagent module 4700, an amplification module 4600 and a detection module 4800. The housing 4010 can be any structure within which the reagent module 4700, the amplification module 4600, the detection module 4800, and the power source 4905 are contained. In some embodiments, the test device 4000 have a size, shape and/or weight such that the device can be carried, held, used and/or manipulated in a user's hands (i.e., it can be a "handheld" device). In other embodiments, the test device 4000 can be a self-contained, single-use device that has an overall volume greater than about 260 $cm^3$ (or about 46 cubic inches). In some embodiments, the test device 4000 (and any of the test devices described herein) can have an overall volume of about 207 $cm^3$ (or about 12.6 cubic inches; e.g., a length of about 9.0 cm, a width of about 7.7 cm and a thickness of about 3.0 cm).

The reagent module 4700 is disposed within the housing 4010, and defines a reagent volume 4710 within which at least one reagent is contained. Although FIGS. 5 and 6 show the reagent volume 4710 containing a reagent R and a reagent R1, and being fluidically coupled to the amplification module 4600 and the detection module 4800, in other embodiments, a reagent module can contain any suitable reagents and can be fluidically coupled to and/or can convey such reagents to any suitable module within the device. For example, in some embodiments, the reagent volume can contain any of a sample wash, an elution buffer, one or more PCR reagents, a detection reagent and/or a substrate.

As shown by the arrow BB in FIG. 6, the reagent module 4700 is actuated by a reagent actuator 4080 to convey the reagent (indicated as reagent R and reagent R1) from the reagent volume 4710. Specifically, the reagent actuator 4080 is moved from a first position (FIG. 4) to a second position (FIG. 4) to convey the reagent(s) from the reagent volume 4710. Although the reagent actuator 4080 is shown as being a moved in a linear direction to convey the reagents, in other embodiments, the reagent actuator 4080 can be configured to rotate to develop the pressure and/or flow of reagent(s). Moreover, the reagent actuator 4080 is a manual actuator (e.g., a non-electronic actuator that is manipulated directly by a user). This arrangement allows the reagent actuator 4080 to be actuated without the need for electronic power and/or before the device 4000 is powered on. Further, as described in more detail below, the movement of the actuator 4080 can also initialize a power-on sequence of the device 4000. In this manner, the device 4000 can limit any power use prior to beginning of the test, thereby limiting the likelihood of misuse and/or an inaccurate test (e.g., due to an unexpected dead battery).

The amplification module 4600 includes a heater 4630 and a flow member 4610 that defines a reaction volume 4618, and is configured to perform a polymerase chain reaction (PCR) on the input sample S1. The input sample S1, can be any suitable sample as described herein, and can be conveyed to the amplification module via an input portion 4162 of the housing 4010. In some embodiments, the reaction volume 4618 can be a central volume within which the sample S1 is maintained while the heater 4630 repeatedly cycles the sample S1 through a series of temperature set points to amplify the target organism and/or portions of the DNA of the organism. In other embodiments, the reaction volume 4618 can be a volume through which the sample S1 is flowed, and that has various portions maintained at different temperatures by the heater 4630. In this manner, the amplification module 4600 can perform a "flow through" PCR. In some embodiments, the reaction volume can have a curved, "switchback," and/or serpentine shape to allow for a high flow length while maintaining the overall size of the device within the desired limits.

The heater 4630 can be any suitable heater or collection of heaters that can perform the functions described herein to amplify the sample S1. For example, in some embodiments, the heater 4630 can be single heater that is thermally coupled to the reaction volume 4618 and that can cycle through multiple temperatures set points (e.g., between about 60 C and about 90 C). In other embodiments, the heater 4630 can be a set of heaters, each of which is thermally coupled to the reaction volume 4618 and that is maintained at a substantially constant set point. In this manner, the heater 4630 and the reaction volume 4618 can establish multiple temperature zones through which the sample S1 flows and/or can define a desired number of amplification cycles to ensure the desired test sensitivity (e.g., at least 30 cycles, at least 34 cycles, at least 36 cycles, at least 38 cycles, or at least 40 cycles). The heater 4630 (and any of the heaters described herein) can be of any suitable design. For example, in some embodiments, the heater 4630 can be a resistance heater, a thermoelectric device (e.g. a Peltier device), or the like.

As shown in FIG. 6, the detection module 4800 receives an output S7 from the amplification module 4800 and a reagent R from the reagent module 4700. The reagent R is a detection reagent formulated to produce and/or catalyze the production of a signal OP1 that indicates a presence of a target amplicon and/or organism within the input sample S1. In this manner, the device 4000 can provide reliable molecular diagnosis within a point-of-care setting (e.g., doctor's office, pharmacy or the like) or at the user's home. The signal OP1 can be any suitable signal that alerts the user regarding whether or not the target organism is present. Similarly stated, the signal OP1 can be any suitable signal to detect a disease associated with the target amplicon and/or organism. The signal OP1 can be, for example, a visual signal, an audible signal, a radio frequency signal or the like.

In some embodiments, the signal OP1 is a visual signal that can viewed by the user through a detection opening (not shown in FIGS. 5 and 6) defined by the housing. The visual signal can be, for example, a non-fluorescent signal. This arrangement allows the device 4000 to be devoid of a light source (e.g., lasers, light-emitting diodes or the like) and/or any light detectors (photomultiplier tube, photodiodes, CCD devices, or the like) to detect and/or amplify the signal OP1. In some embodiments, the signal OP1 is a visible signal characterized by a color associated with the presence of the target amplicon and/or organism. Said another way, in some embodiments, the device 4000 can produce a colormetric output signal that is visible to the user. In such embodiments, the detection module 4800 (and any of the detection modules described herein) can produce a chemiluminescent signal that results from the introduction of the reagent R and/or any other substances (e.g., a substrate to catalyze the production of the signal OP1, and the like). In some embodiments, the reagent is formulated such that the visible signal OP1 remains present for at least about 30 minutes. The reagent R and any other compositions formulated to produce the signal OP1 can be any suitable compositions as described herein. In some embodiments, the reagent R can be stored within the housing 4010 in any manner as described herein (e.g., in a sealed container, a lyophilized form or the like).

The device 4000 includes an electronic circuit system that includes at least a processor 4950 and the power source 4905. Although not shown in FIGS. 5 and 6, the electronic circuit system (and any of the electronic circuit systems described herein) can include any suitable electronic components, such as, for example, printed circuit boards, switches, resistors, capacitors, diodes, memory chips arranged in a manner to control the operation of the device 4000. The processor 4950 (and any of the processors shown herein) can be a commercially-available processing device dedicated to performing one or more specific tasks. For example, in some embodiments, the microprocessor 4950 can be a commercially-available microprocessor, such as an 8-bit PIC microcontroller. Alternatively, the processor 4950 can be an application-specific integrated circuit (ASIC) or a combination of ASICs, which are designed to perform one or more specific functions, in yet other embodiments, the processor 4950 can be an analog or digital circuit, or a combination of multiple circuits.

The power source 4905 can be any suitable power source that provides power to the electronic circuit system (including the processor 4950) and any of the modules within the device 4000. Specifically, the power source 4905 can provide power to the amplification module 4600 and/or the heater 4630 to facilitate the completion of the PCR on the input sample S1. In some embodiments, the power source 4905 can be one or more DC batteries, such as, for example, multiple 1.5 VDC cells (e.g., AAA or AA alkaline batteries). In other embodiments, the power source 4905 can be a 9 VDC battery having a capacity of less than about 1200 mAh. In other embodiments, the power source 4905 can be any suitable energy storage/conversion member, such as a capacitor a magnetic storage systems, a fuel cell or the like.

As shown in FIG. 5, power source 4905 is electrically isolated from the processor 4950 and/or the amplification module 4600 when the reagent actuator 4080 is in the first position. In this manner, the "power-up" event is tied to the movement of the reagent actuator 4080. This arrangement limits the likelihood of premature power drain from the power source 4905 during storage. As shown in FIG. 6, the power source 4905 is electrically coupled to the processor 4950 and/or the amplification module 4600 when the reagent actuator 4080 is in the second position. This arrangement allows for the device 4000 to be operated in a sufficiently simple manner, and reduces the judgment of the user in the operation. Specifically, no judgment is required regarding when to power-up the device 4000, and the likelihood of a user powering up the device 4000 and then delaying subsequent operation of the device 4000 (which can deplete the stored energy) is limited and/or eliminated.

The reagent actuator 4080 can actuate the power source 1905 and/or place the power source 4905 in electrical connection with the processor 4950 and/or the amplification module 4600 in any suitable manner. For example, in some embodiments, the reagent actuator 4080 can include a protrusion (not shown) that actuates a switch to place the power source 4905 in electrical connection with the processor 4950 and/or the amplification module 4600 when the reagent actuator 4080 is moved from the first position to the second position. In other embodiments, the reagent actuator 4080 can include and/or be coupled to an isolation member that, when removed, places the power source 4905 in electrical connection with the processor 4950 and/or the amplification module 4600 when the reagent actuator 4080 is moved from the first position to the second position.

In some embodiments, the device 4000 (and any of the other devices shown and described herein) can be configured to produce the signal OP1 in a time of less than about 25 minutes from when the sample S1 is received. In other embodiments, the device 4000 (and any of the other devices shown and described herein) can be configured to produce the signal OP1 in a time of less than about 20 minutes from when the sample S1 is input, less than about 18 minutes from when the sample S1 is input, less than about 16 minutes from when the sample S1 is input, less than about 14 minutes from when the sample S1 is input, and all ranges therebetween.

Similarly stated, the device 4000 and the components therein can be configured to conduct a "rapid" PCR (e.g., completing at least 40 cycles in less than about 10 minutes), and rapid production of the signal OP1. Similarly stated, the device 4000 (and any of the other devices shown and described herein) can be configured to process volumes, to have dimensional sizes and/or be constructed from materials that facilitates completion of a rapid PCR or amplification in less than about 10 minutes, less than about 9 minutes, less than about 8 minutes, less than about 7 minutes, less than about 6 minutes, or any range therebetween, as described herein.

In some embodiments, the reagent actuator 4080 is configured to remain locked in the second position to prevent reuse of the device 4000. In this manner, the device 4000 (and any of the other devices shown and described herein), can be specifically configured for a single-use operation and can pose a limited risk of misuse. For example, in some embodiments, the reagent module 4700 of the molecular diagnostic test device 4000 can include seals such that the reagent volume 4710 is a sealed reagent volume within which the reagent(s) are stored. In such embodiments, the reagent actuator 4080 is configured to puncture the seal that fluidically isolates the reagent volume 4710 when moved. In this manner, the molecular diagnostic test device 4000 can be configured for long term storage in a manner that poses a limited likelihood of misuse (spoilage of the reagent(s), expiration of the reagents(s), leakage of the reagent(s), or the like). In some embodiments, the reagent module 4700 and/or any area in fluid communication therewith (or any other reagent modules described herein) can include a desiccant, seals or other compositions or components to maintain stability for long term storage. In some embodiments, the molecular diagnostic test device 4000 is configured to be stored for up to about 46 months, up to about 42 months, up to about 26 months, up to about 24 months, up to about 20 months, up to about 18 months, or any values there between.

In some embodiments, a molecular diagnostic test device can include a set of modules to produces an integrated test device that can receive an input sample and deliver a signal indicative of whether the sample contains an organism associated with a disease. For example, in some embodiments, a molecular diagnostic test device can include a sample input and/or preparation module, an elution module, an amplification module, one or more reagent modules and a detection module. Such devices can be, for example, single-use devices that can be used in a point-of-care setting and/or in a user's home. Further, in some embodiments, such devices can be a CLIA-waived device and/or can operate in accordance with methods that are CLIA waived.

Figure 7:
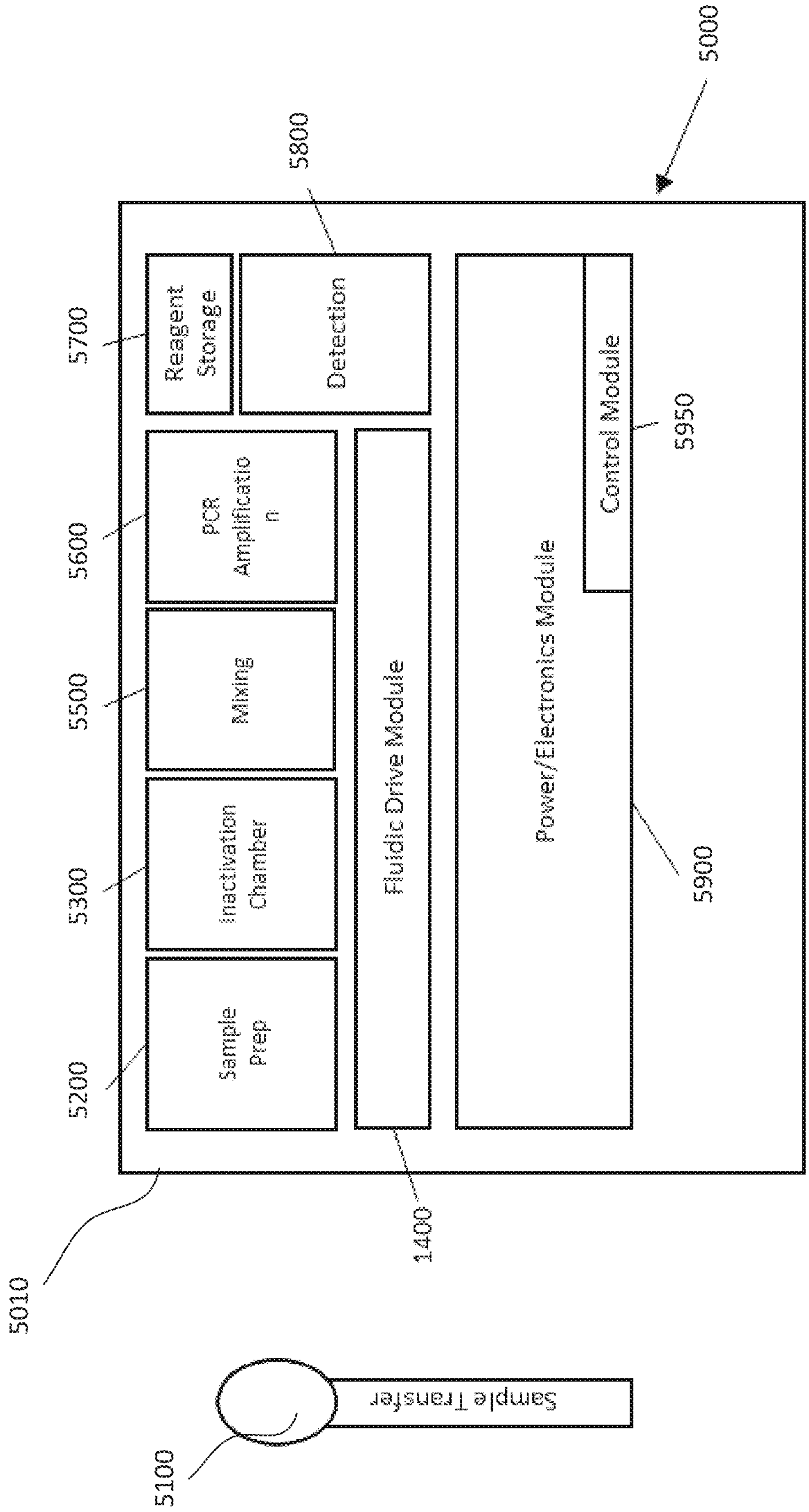
FIG. 7 is a schematic illustration of a molecular diagnostic test device, according to an embodiment.

An example of an integrated test device shown in FIG. 7, which is a schematic block diagram of a molecular diagnostic system 5000 (also referred to as "system" or "test unit"), according to an embodiment. The test unit 5000 is configured to manipulate a sample to produce an optical indication associated with a target cell according to any of the methods described herein. In some embodiments, the test unit 5000 can be a single-use, disposable device that can provide an optical output without need for any additional instrument to manipulate or otherwise condition the test unit 5000. Said another way, the test unit 5000 is an integrated cartridge/instrument, and the entire unit can be used to perform a diagnostic assay and then be disposed. The test unit 5000 includes a sample transfer device 5100, a sample preparation module 5200, an inactivation chamber 5300, a fluidic drive module 5400, a mixing chamber 5500, an amplification module 5600, a reagent storage module 5700, a detection module 5800, a power/electronics module 5900, and a control module 5950. A brief description of the major subsystems of the test unit 5000 is provided below.

The sample transfer device 5100 is configured to transport a sample such as, for example, a blood, urine, male urethral specimens, vaginal specimens, cervical swab specimens, and/or nasal swab specimens sample gathered using a commercially available sample collection kit, to the sample preparation module 5200. The sample collection kit can be a urine collection kit or swab collection kit. Non-limiting examples of such sample collection kits include Copan Mswab or BD ProbeTec Urine Preservative Transport Kit, Cat #440928, neat urine. The sample transfer device 5100 dispenses and/or otherwise transfers an amount of sample or sample/media to the sample preparation module 5200 through an input port (not shown). The input port can then be capped. In some embodiments, the sample transfer device 5100 can be locked and/or fixedly coupled to the sample preparation module 5200 as a part of the dispensing operation. In this manner, the interface between the sample transfer device 5100 and the sample preparation module 5200 can be configured to prevent reuse of the test unit 5000, transfer of additional samples, or the like. Although shown as including the sample transfer device 5100, in other embodiments, the test unit 5000 need not include a sample transfer device.

In some embodiments, through a series of user actions or in an automated/semi-automated matter, the sample preparation module 5200 is configured to process the sample. For example, the sample preparation module 5200 can be configured to concentrate and lyse cells in the sample, thereby allowing subsequent extraction of DNA. In some embodiments, the processed/lysed sample is pushed and/or otherwise transferred from the sample preparation module 5200 to the inactivation chamber 5300, which is configured to inactivate, in the lysed sample, the proteins used during lysing. In some embodiments, the fluidic drive module 5400 is configured to aspirate the sample from the inactivation chamber 5300, and is further configured to convey the sample to the amplification module 5600. The fluidic drive module 5400 is also configured to convey the sample and/or reagents (e.g., from the reagent storage module 5700) to perform any of the methods of diagnostic testing described herein. Similarly stated, the fluidic drive module 5400 is configured to generate fluid pressure, fluid flow and/or otherwise convey the input sample S1 through the modules of the device. In some embodiments, the fluidic drive module 5400, can be a single-use module that is configured to contact and/or receive the sample flow. The single-use arrangement eliminates the likelihood that contamination of the fluid transfer module and/or the other modules to which the fluidic drive module 5400 is fluidically coupled will become contaminated from previous runs, thereby negatively impacting the accuracy of the results.

The mixing chamber 5500 mixes the output of inactivation chamber 5300 with the reagents necessary to conduct a PCR reaction. In some embodiments, the mixing chamber 5500 can contain the PCR reagents in the form of one or more lyophilized reagent beads that contain the primers and enzymes necessary for PCR. In such embodiments, the mixing chamber 5500 can be configured to hydrate and/or reconstitute the lyophilized beads in a given input volume, while ensuring even local concentrations of reagents in the entirety of the volume. The mixing chamber 5500 can include any suitable mechanism for producing the desired solution, such as, for example, a continuous flow mixing channel, an active mixing element (e.g., a stir rod) and/or a vibratory mixing element. The mixed sample is then conveyed to the amplification module 5600 (e.g., by the fluidic drive module 5400).

The amplification module 5600 is configured to run polymerase chain reaction (PCR) on the sample to generate an amplified sample, in any manner as described herein. After PCR, the amplified sample is further pushed, transferred or conveyed to a detection module 5800. In some embodiments, the detection module 5800 is configured to run and/or facilitate a colorimetric enzymatic reaction on the amplified sample. In particular, a series of reagents from the reagent storage module 5700 can be conveyed by the fluidic drive module 5400 to facilitate the optical output from the test. In some embodiments, all of the various modules/subsystems of the main test unit 5000 are controlled and/or powered by the power/electronics module 5900 and the control module 5950.

In some embodiments, the control module 5950 can include one or more modules, and can automatically control the valves, pumps, power delivery and/or any other components of the test unit 5000 to facilitate the molecular testing as described herein. The control module 5950 can include a memory, a processor, an input/output module (or interface), and any other suitable modules or software to perform the functions described herein.

Figure 8:
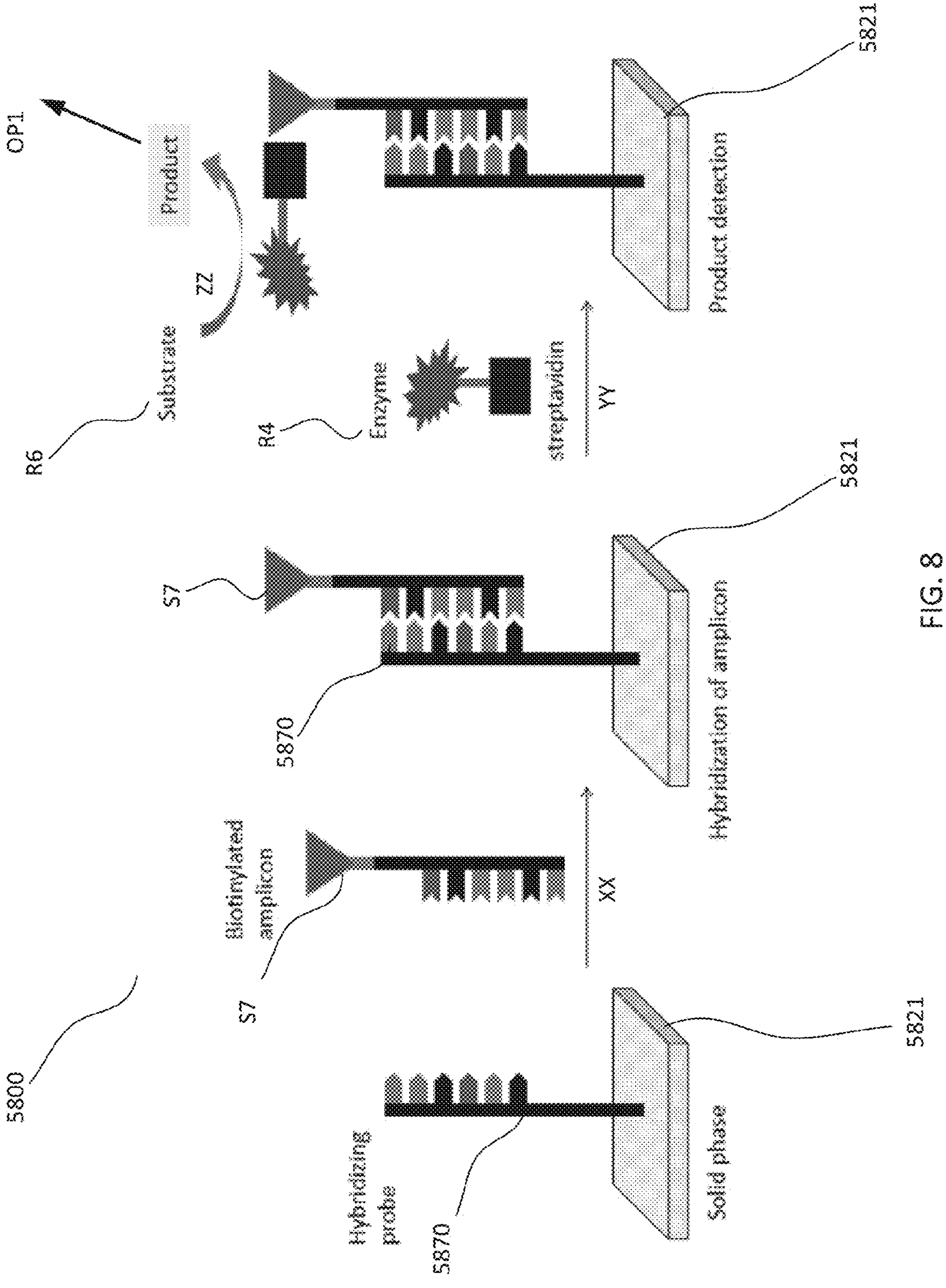
FIG. 8 is a diagram illustrating an enzyme linked reaction according to an embodiment conducted on the device of FIG. 7, resulting in the production a colorimetric result.

FIG. 8 illustrates a portion of the operations and/or features associated with an enzymatic reaction, according to an embodiment, that can be conducted by or within the detection module 5800, or any other detection module described herein (e.g., the detection module 6800 described below). In some embodiments, the enzymatic reaction can be carried out to facilitate visual detection of a molecular diagnostic test result using the device 5000, the device 6000, or any other devices or systems described herein. The reaction, the detection module 5800 and/or the remaining components within the test unit 5000 can be collectively configured such that the test unit 5000 is a single-use device that can be used in a point-of-care setting and/or in a user's home. Similarly stated, in some embodiments, the test unit 5000 (and any of the other devices shown and described herein) can be configured for use in a decentralized test facility. Further, in some embodiments, the reaction shown in FIG. 8 can facilitate the test unit 5000 (and any of the other devices shown and described herein) operating with sufficient simplicity and accuracy to be a CLIA-waived device. Similarly stated, in some embodiments, the reaction shown in FIG. 8 can provide the output signal OP1 in a manner that poses a limited likelihood of misuse and/or that poses a limited risk of harm if used improperly. In some embodiments, the reaction can be successfully completed within the test unit 5000 (or any other device described herein) upon actuation by a user with minimal (or no) scientific training, in accordance with methods that require little judgment of the user, and/or in which certain operational steps are easily and/or automatically controlled.

As shown, the detection module 5800 includes a detection surface 5821 within a read lane or flow channel. The detection surface 5821 is spotted and/or covalently bonded with a specific hybridizing probe 5870, such as an oligonucleotide. In some embodiments, the hybridizing probe 5870 is specific for a target organism and/or amplicon. The bonding of the hybridizing probe 5870 to the detection surface 5821 can be performed using any suitable procedure or mechanism. For example, in some embodiments, the hybridizing probe 5870 can be covalently bound to the detection surface 5821. Reference S7 illustrates the biotinylated amplicon that is produced from the PCR amplification step such as, for example, by the amplification module 5600 of FIG. 7 (or any other amplification modules described herein). The biotin can be incorporated within the amplification operation and/or within the amplification module 5600 in any suitable manner. As shown by the arrow XX, the output from the amplification module, including the biotinylated amplicon S7 is conveyed within the read lane and across the detection surface 5821. The hybridizing probe 5870 is formulated to hybridize to the target amplicon S7 that is present within the flow channel and/or in proximity to the detection surface 5821. The detection module 5800 and/or the detection surface 5821 is heated to incubate the biotinylated amplicon S7 in the read lane in the presence of the hybridizing probe 5870 for a few minutes allowing binding to occur. In this manner, the target amplicon S7 is captured and/or is affixed to the detection surface 5821, as shown. In some embodiments, a first wash solution (not shown in FIG. 8) can be conveyed across the detection surface 5821 and/or within the flow channel to remove unbound PCR products and/or any remaining solution.

As shown by the arrow YY, a detection reagent R4 is conveyed within the read lane and across the detection surface 5821. The detection reagent R4 can be, for example, a horseradish peroxidase (HRP) enzyme ("enzyme") with a streptavidin linker. In some embodiments, the streptavidin and the HRP are cross-linked to provide dual functionality. As shown, the detection reagent is bound to the captured amplicon S7. The detection module 5800 and/or the detection surface 5821 is heated to incubate the detection reagent R4 within the read lane in the presence of the biotinylated amplicon S7 for a few minutes to facilitate binding. In some embodiments, a second wash solution (not shown in FIG. 8) can be conveyed across the detection surface 5821 and/or within the flow channel to remove unbound detection reagent R4.

As shown by the arrow ZZ, a detection reagent R6 is conveyed within the read lane and across the detection surface 5821. The detection reagent R4 can be, for example, a substrate formulated to enhance, catalyze and/or promote the production of the signal OP1 from the detection reagent R4. Specifically, the substrate is formulated such that upon contact with the detection reagent R4 (the HRP/streptavidin) a colormetric output signal OP1 is developed where HRP attaches to the amplicon. The color of the output signal OP1 indicates the presence of bound amplicon: if the target pathogen, target amplicon and/or target organism is present, the color product is formed, and if the target pathogen, target amplicon and/or target organism is not present, the color product does not form.

Similarly stated, upon completion of the reaction, if the target pathogen, target amplicon and/or target organism is present the detection module produces a signal OP1. In accordance with the reaction described in FIG. 8, the signal OP1 is a non-fluorescent, visual signal that can viewed by the user (e.g., through a detection opening or window defined by a device housing). This arrangement allows the device to be devoid of a light source (e.g., lasers, light-emitting diodes or the like) and/or any light detectors (photomultiplier tube, photodiodes, CCD devices, or the like) to detect and/or amplify the signal OP1.

Said another way, the reaction produces a colormetric output signal that is visible to the user, and that requires little to no scientific training and/or little to know judgment to determine whether the target organism is present. In some embodiments, the reagents R4, R6 are formulated such that the visible signal OP1 remains present for at least about 30 minutes. In some embodiments, the reagents R4, R6 can be stored within a housing (not shown in FIG. 8) in any manner as described herein (e.g., in a sealed container, a lyophilized form or the like).

Figure 9:
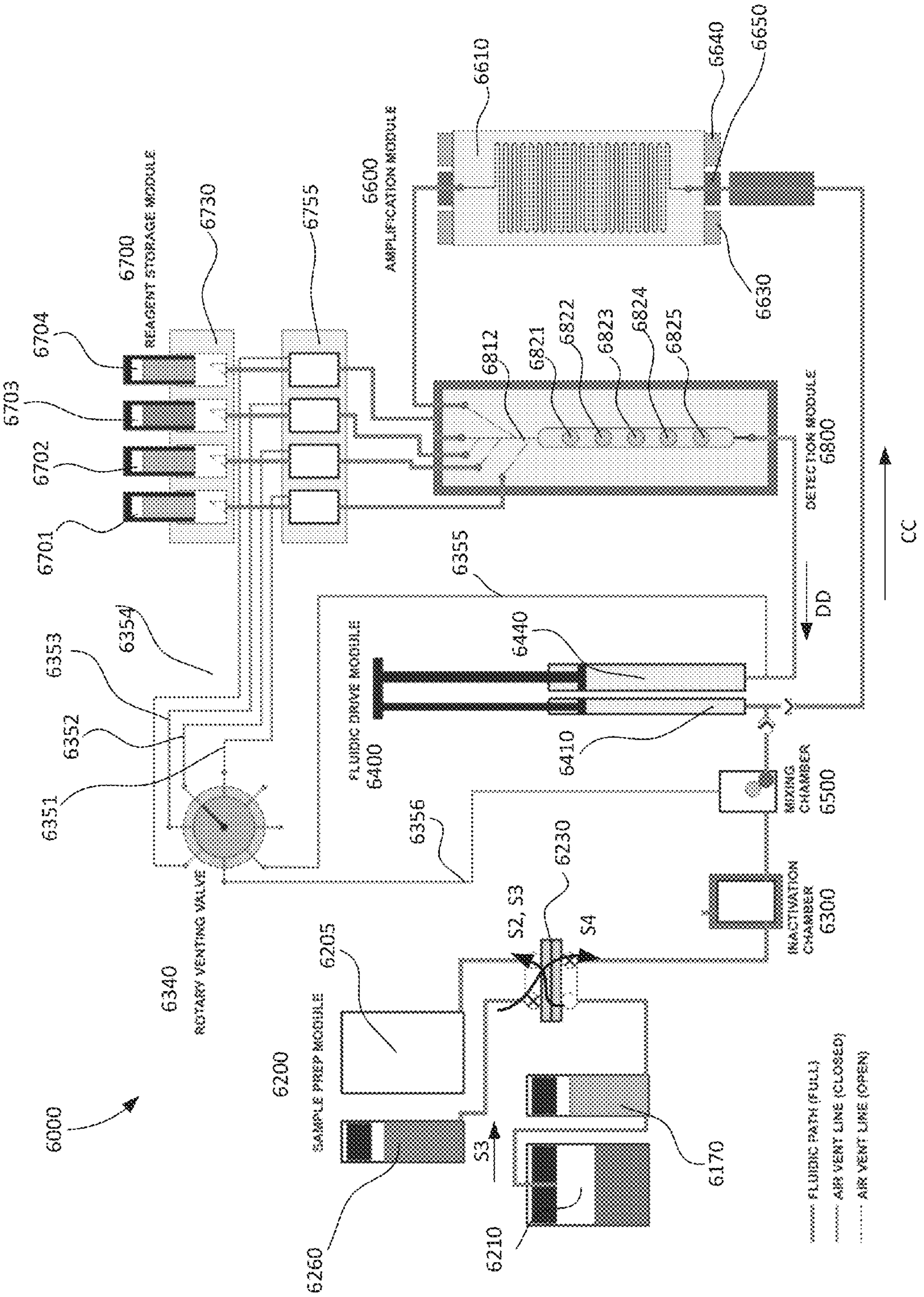
FIG. 9 is a schematic illustration of a molecular diagnostic test device, according to an embodiment.
Figure 10:
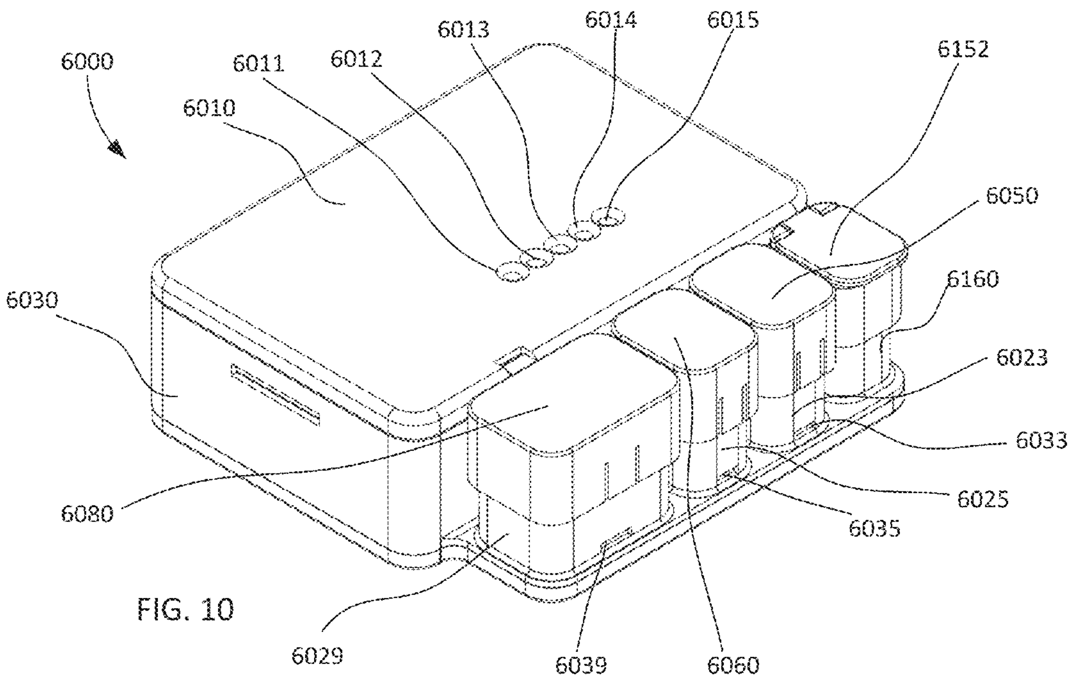
FIGS. 10 and 11 are perspective views of a molecular diagnostic test device, according to an embodiment.
Figure 66:
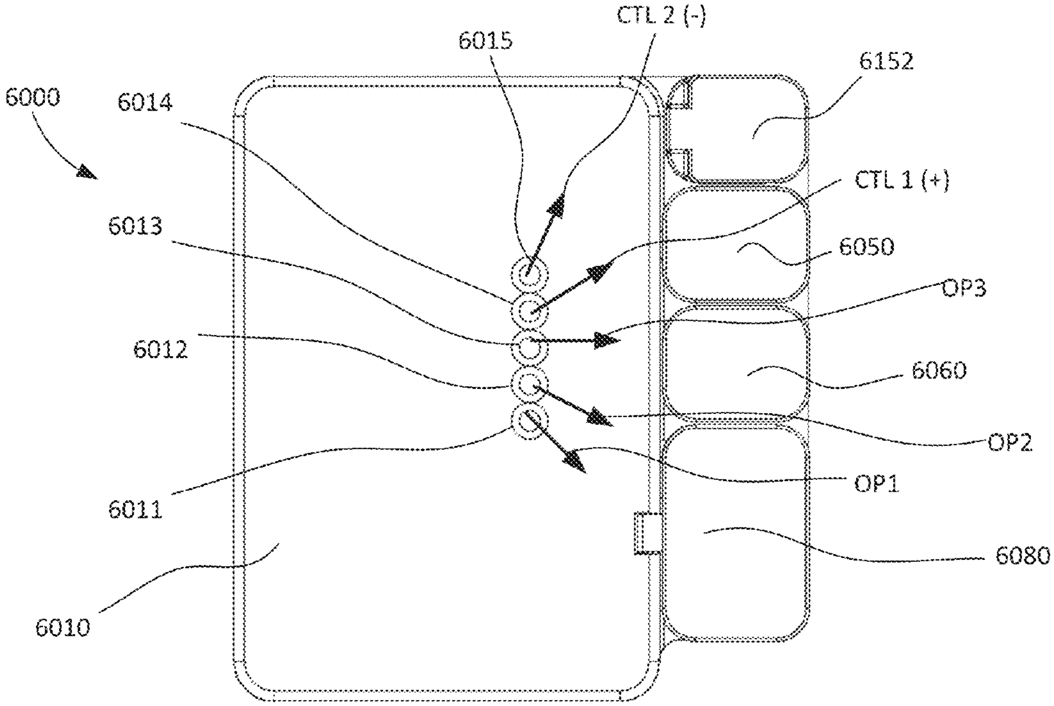
FIG. 66 is a perspective view of the molecular diagnostic test device shown in FIGS. 10 and 11 in a fifth (read) configuration.

FIG. 9 is a schematic illustration of a molecular diagnostic test device 6000 (also referred to as a "test device" or "device"), according to an embodiment. The schematic illustration describes the primary components of the test device 6000 as shown in FIGS. 10-66. As described below, the test device 6000 is an integrated device (i.e., the modules are contained within a single housing) that is suitable for use within a point-of-care setting (e.g., doctor's office, pharmacy or the like), decentralized test facility, or at the user's home. In some embodiments, the device 6000 can have a size, shape and/or weight such that the device 6000 can be carried, held, used and/or manipulated in a user's hands (i.e., it can be a "handheld" device). In other embodiments, the test device 6000 can be a self-contained, single-use device. Similarly stated, in some embodiments, the test device 6000 can be configured with lock-outs or other mechanisms to prevent re-use or attempts to re-use the device.

Figure 11:
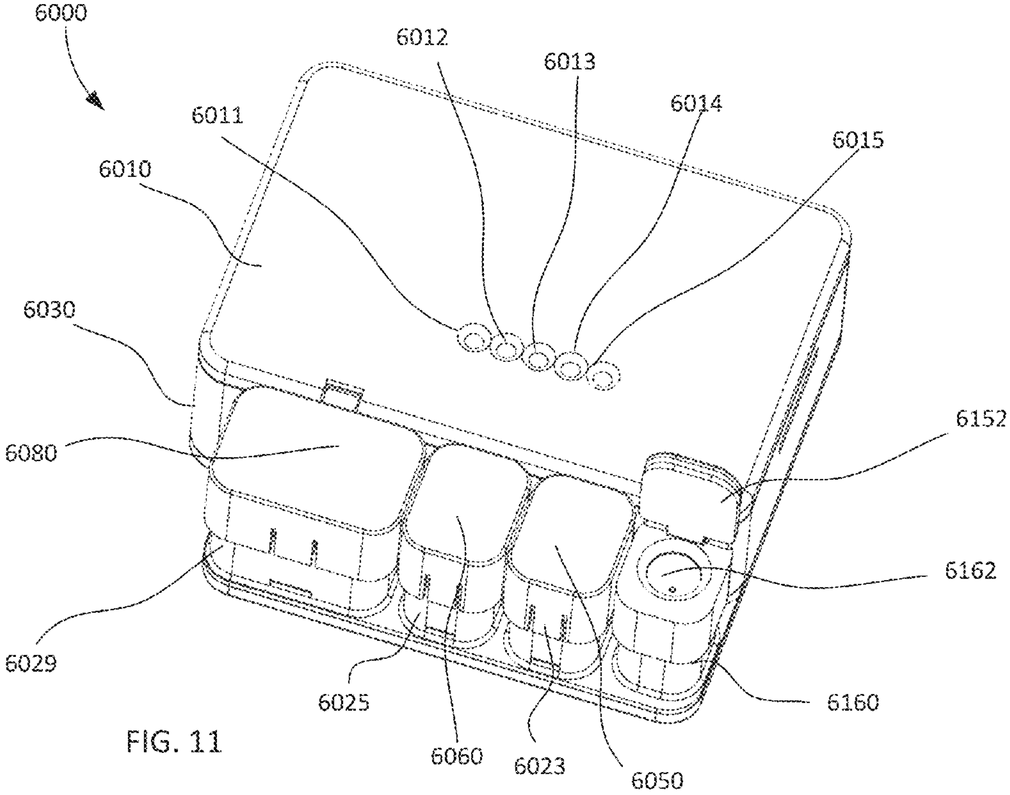

Further, in some embodiments, the device 6000 can be a CLIA-waived device and/or can operate in accordance with methods that are CLIA waived. Similarly stated, in some embodiments, the device 6000 (and any of the other devices shown and described herein) is configured to be operated in a sufficiently simple manner, and can produce results with sufficient accuracy to pose a limited likelihood of misuse and/or to pose a limited risk of harm if used improperly. In some embodiments, the device 6000 (and any of the other devices shown and described herein), can be operated by a user with minimal (or no) scientific training, in accordance with methods that require little judgment of the user, and/or in which certain operational steps are easily and/or automatically controlled. In some embodiments, the molecular diagnostic test device 6000 can be configured for long term storage in a manner that poses a limited likelihood of misuse (spoilage of the reagent(s), expiration of the reagents(s), leakage of the reagent(s), or the like). In some embodiments, the molecular diagnostic test device 6000 is configured to be stored for up to about 36 months, up to about 32 months, up to about 26 months, up to about 24 months, up to about 20 months, up to about 18 months, or any values there between The test device 6000 is configured to manipulate an input sample S1 to produce on or more output signals OP1, OP2, OP3 (see FIG. 66) associated with a target cell according to any of the methods described herein (e.g., including the enzymatic reaction described above with respect to FIG. 8). FIGS. 10 and 11 show perspective views of the molecular diagnostic test device 6000. The diagnostic test device 6000 includes a housing (including a top portion 6010 and a bottom portion 6030), within which a variety of modules are contained. Specifically, the device 6000 includes a sample preparation module 6200, an inactivation module 6300, a fluidic drive (or fluid transfer) module 6400, a mixing chamber 6500, an amplification module 6600, a detection module 6800, a reagent storage module 6700, a rotary venting valve 6340, and a power and control module 6900. A description of each module and/or subsystem follows.

Figure 12:
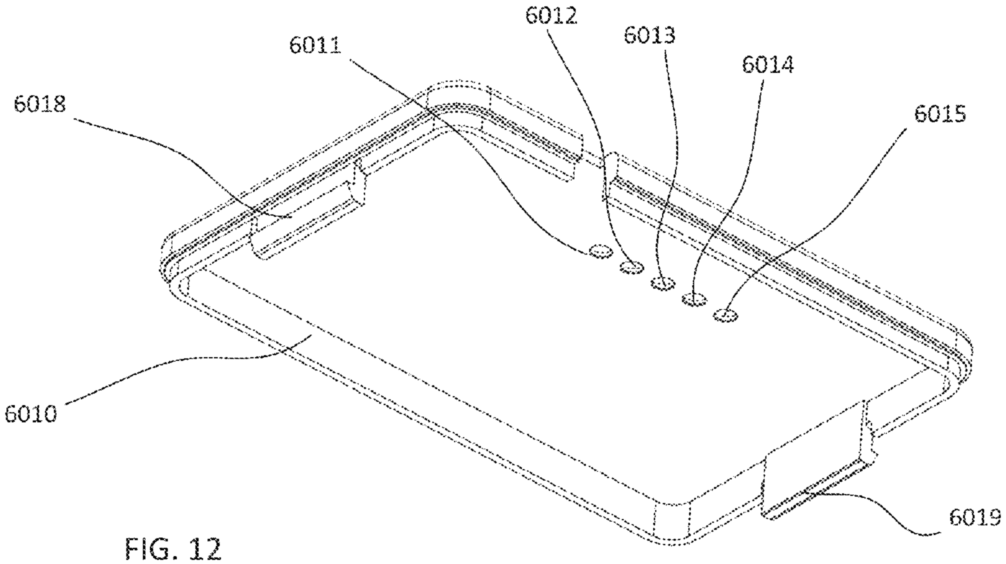
FIG. 12 is a perspective view of a top portion of a housing of the molecular diagnostic test device shown in FIGS. 10 and 11.
Figure 13:
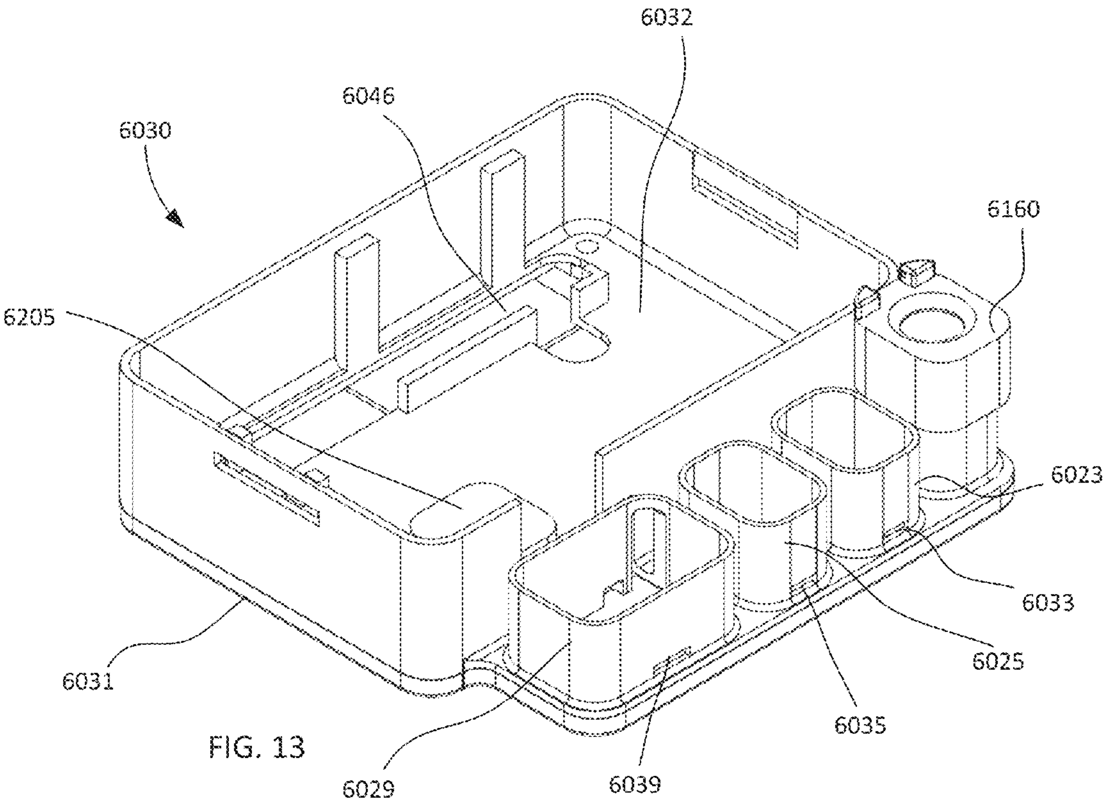
FIG. 13 is a perspective view of a bottom portion of a housing of the molecular diagnostic test device shown in FIGS. 10 and 11.
Figure 14:
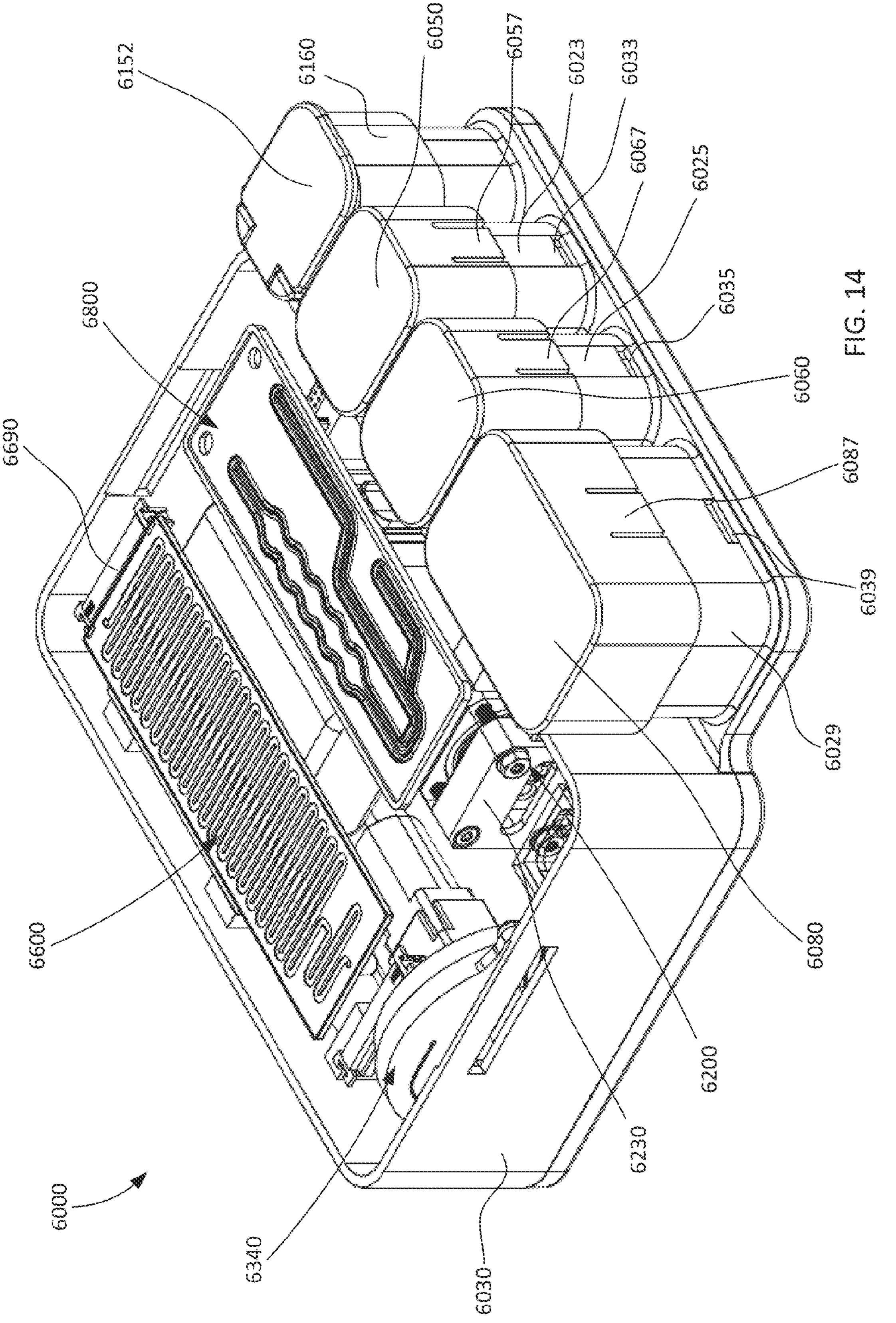
FIG. 14 is a perspective view of the molecular diagnostic test device shown in FIGS. 10 and 11, with the top portion of the housing removed to show the internal components.
Figure 15:
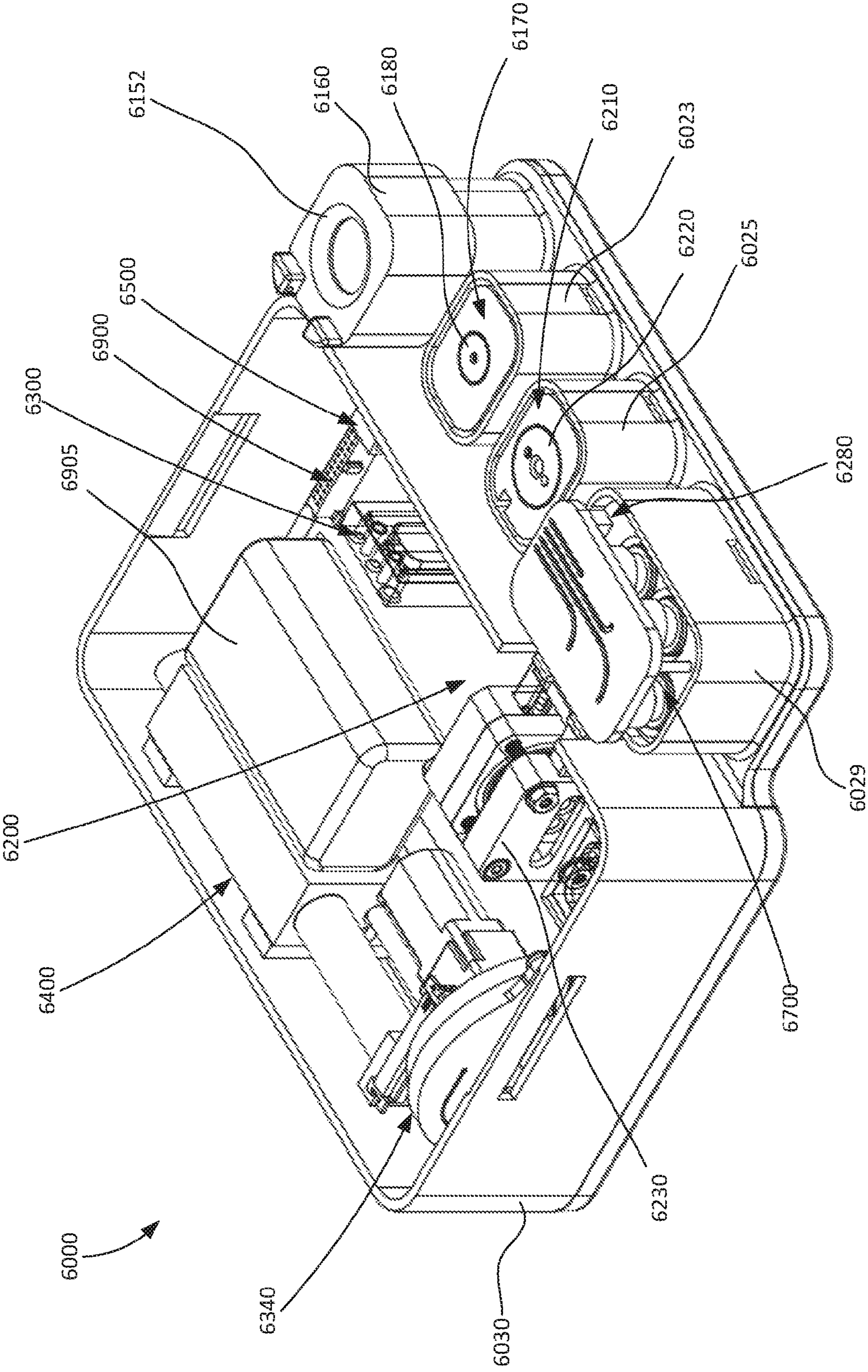
FIG. 15 is a perspective view of the molecular diagnostic test device shown in FIGS. 10, 11 and 14, with the top portion of the housing, the amplification module, and the detection module removed to show the internal components.
Figure 49:
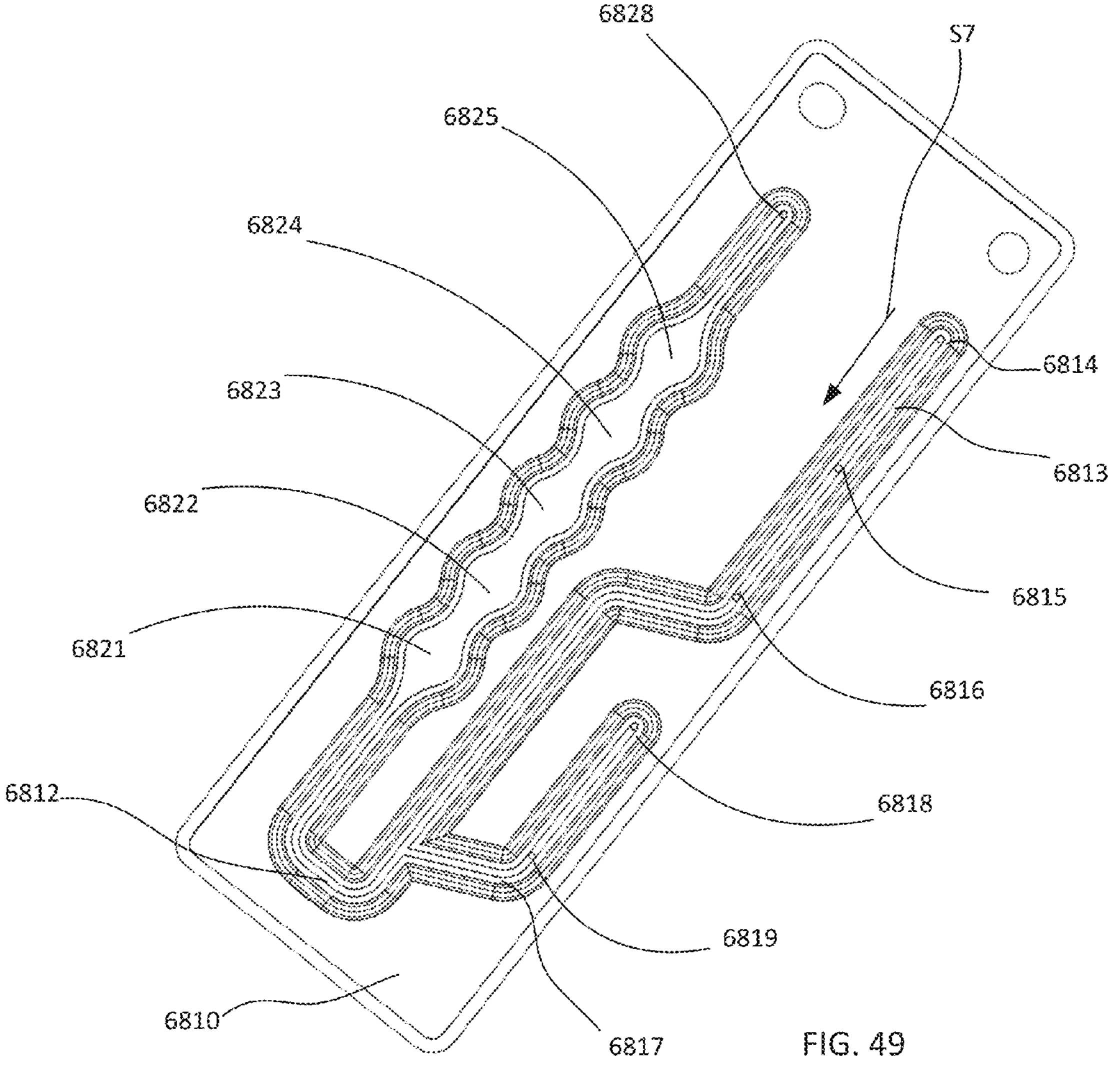
FIG. 49 is a top view of a portion of the detection module shown in FIG. 46.
Figure 50:
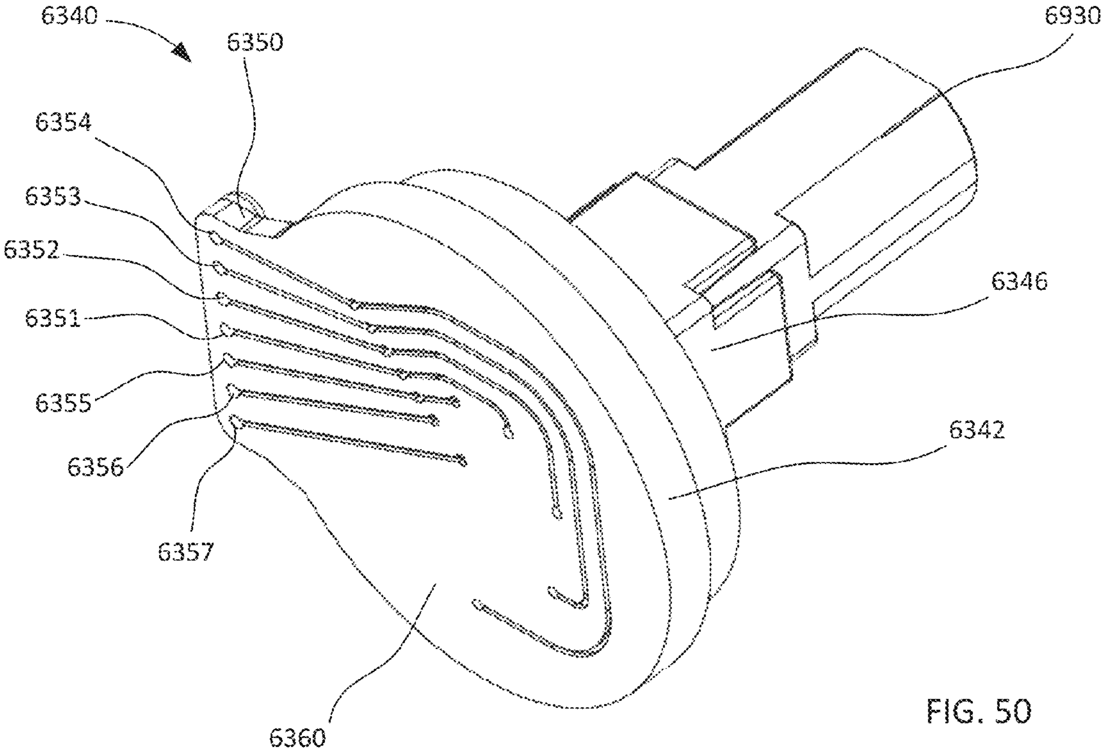
FIGS. 50 and 51 are a front perspective view and a rear perspective view, respectively, of rotary valve assembly of the molecular diagnostic test device shown in FIGS. 10 and 11.

FIG. 14 shows the device 6000 with the top housing 6010 removed so that the placement of the modules can be seen. FIG. 15 shows the device 6000 with the top housing 6010, the actuation buttons, the amplification module 6600, and the detection module 6800 removed so that underlying modules can be seen. As shown in FIGS. 12 and 13, the device 6000 is includes a top housing 6010, a lower housing 6030 and a bottom plate 6031. The top housing 6010 includes connection protrusions 6018, 6019 that correspond to notches, slots and or openings defined by the lower housing 6030 to facilitate assembly of the housing and/or the device. The top housing further defines a series of detection (or "status") openings that allow the user to visually inspect the output signal(s) produced by the device 6000. Specifically, the top housing 6010 defines a first detection opening 6011, a second detection opening 6012, a third detection opening 6013, a fourth detection opening 6014, and a fifth detection opening 6015. When the top housing 6010 is coupled to the lower housing 6030, the detection openings are aligned with the corresponding detection surfaces of the detection module 6800 such that the signal produced by and/or on each detection surface is visible through the corresponding detection opening. Specifically, the first detection opening 6011 corresponds to the first detection surface 6821 (see FIG. 49), the second detection opening 6012 corresponds to the second detection surface 6822, the third detection opening 6013 corresponds to the third detection surface 6823, the fourth detection opening 6014 corresponds to the fourth detection surface 6824, and the fifth detection opening 6015 corresponds to the fifth detection surface 6825.

In some embodiments, the top housing 6010 and/or the portion of the top housing 6010 surrounding the detection openings is opaque (or semi-opaque), thereby "framing" or accentuating the detection openings. In some embodiments, for example, the top housing 6010 can include markings (e.g., thick lines, colors or the like) to highlight the detection openings. For example, in some embodiments, the top housing 6010 can include indicia identifying the detection opening to a particular disease (e.g., *Chlamydia trachomatis* (CT), *Neisseria gonorrhea* (NG) and *Trichomonas vaginalis* (TV)) or control. In other embodiments, the top housing 6010 can include a series of color spots having a range of colors associated with a range of colors that is likely produced by the signals OP1, OP2, OP3, CTL 1 and/or CTL 2 to assist the user in determining the results of the test. In this manner, the housing design can contribute to reducing the amount of user judgment required to accurately read the test.

Figure 62:
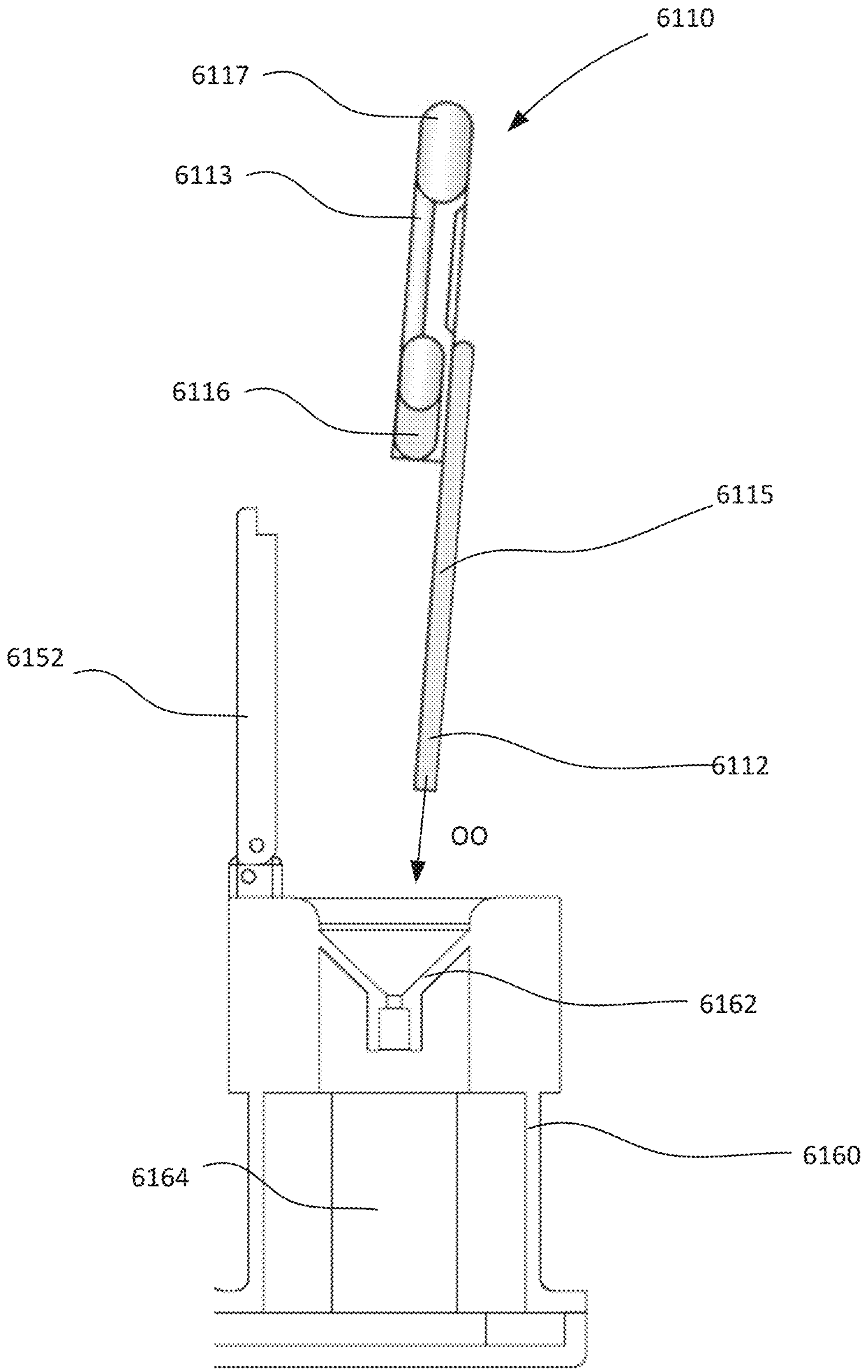
FIG. 62 is a side cross-sectional view of a sample transfer portion of the molecular diagnostic test device shown in FIGS. 10 and 11 in a first configuration, and an external transfer device according to an embodiment.

The lower housing 6030 defines a volume 6032 within which the modules and or components of the device 6000 are disposed. As shown in FIG. 13, the lower housing 6030 includes a sample input portion 6160, a sample preparation portion 6023, a wash portion 6025, and an elution/reagent portion 6029. As shown in FIG. 62, the sample input portion 6160 defines a receiving volume 6164, and includes a movable cap 6152 and an input member 6162. The movable cap 6152 can rotate about the lower housing 6030 to provide access to the input member 6162 and/or the receiving volume 6164. The cap 6152 can include seals or other locking members such that it can be securely fastened to the lower housing 6030 and/or closed during shipping, after delivery of a sample thereto, or the like. In some embodiments, the input port cap 6152 can include an irreversible lock to prevent reuse of the device 6000 and/or the addition of supplemental sample fluids. In this manner, the device 6000 can be suitably used by untrained individuals.

The input member 6162 defines a passageway through which the sample is conveyed into the receiving volume 6164. As shown, the input member 6162 has a funnel shape and is configured to minimize splash when transferring the sample from the transfer device 6110 (described below) into the receiving volume 6164. In some embodiments, the sample input member 6162 can include a filter, screen or the like.

Figure 20:
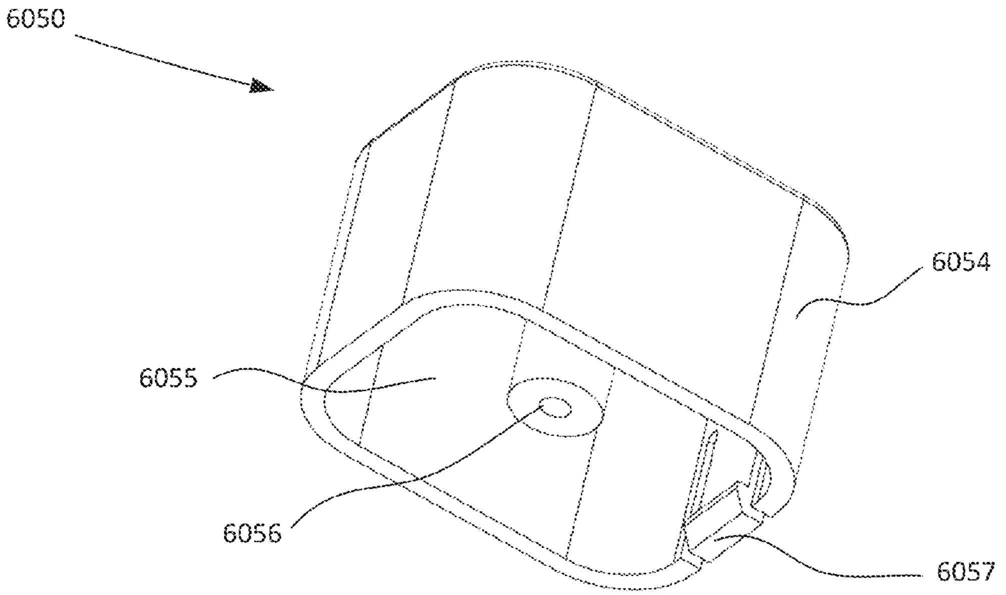
FIG. 20 is a side perspective view of a sample actuator of the molecular diagnostic test device shown in FIGS. 10 and 11.

The sample preparation portion 6023 receives at least a portion of the sample input module 6170. As described in more detail herein, the sample input module 6170 is actuated by the sample actuator (or button) 6050. The sample preparation portion 6023 defines a notch or opening 6033 that receives a lock tab 6057 of the sample actuator 6050 after the actuator 6050 has been moved to begin the sample preparation operation (see, e.g., FIGS. 20 and 21). In this manner, the sample actuator 6050 is configured to prevent the user from reusing the device after an initial use has been attempted and/or completed.

The wash portion 6025 receives at least a portion of the wash module 6210. The wash module 6210 is actuated by the wash actuator (or button) 6060. The wash portion 6025 defines a notch or opening 6035 that receives a lock tab 6067 of the wash actuator 6060 after the actuator 6060 has been moved to begin the wash operation (see, e.g., FIG. 64). In this manner, the wash actuator 6060 is configured to prevent the user from reusing the device after an initial use has been attempted and/or completed.

Figure 65:
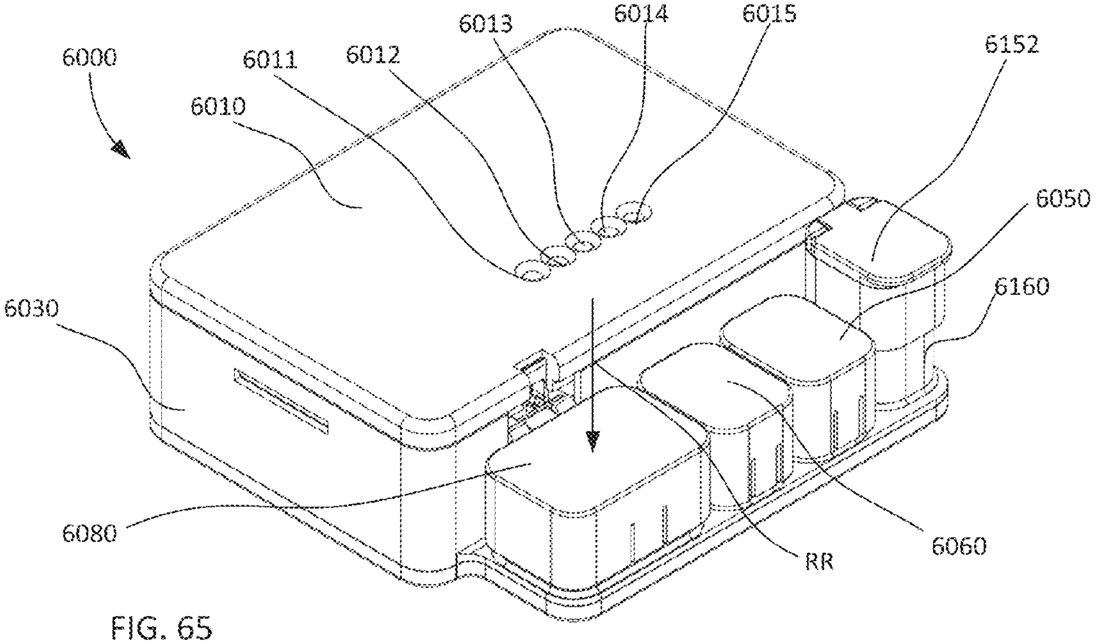
FIG. 65 is a perspective view of the molecular diagnostic test device shown in FIGS. 10 and 11 in a fourth (elution and reagent actuated) configuration.

The elution/reagent portion 6029 receives at least a portion of the elution module 6260 and a portion of the reagent module 6700. The elution/reagent portion 6029 defines a notch or opening 6039 that receives a lock tab 6087 of the reagent actuator 6080 after the actuator 6080 has been moved to begin the elution and/or reagent opening operation (see, e.g., FIG. 65). In this manner, the reagent actuator 6080 is configured to prevent the user from reusing the device after an initial use has been attempted and/or completed. By including such lock-out mechanisms, the device 6000 is specifically configured for a single-use operation, and poses a limited risk of misuse.

The lower housing 6030 of the device 6000 includes mounting structure and features to retain the modules disposed therein. For example, the lower housing 6030 includes mounting structure 6046 for retaining the fluid transfer module 6400. The lower housing 6030 also includes the waste reservoir 6205 within which waste products and/or flow is stored.

Sample Transfer Device

In some embodiments, the diagnostic test device 6000 can include and/or be packaged along with a sample transport device 6110 (see FIG. 62) configured to provide a sample into the device 6000 and/or the sample preparation module 6200. As shown in FIG. 62, the sample transfer device 6110 includes a distal end portion 6112 and a proximal end portion 6113, and can be used to aspirate or withdraw a sample from a sample cup, container or the like, and then deliver a desired amount of the sample to an input portion 6160 of the device 6000. Specifically, the distal end portion 6112 includes a dip tube portion defining a reservoir 6115 having a desired volume. The proximal end portion 6113 includes an actuator 6117 or squeeze bulb that can be manipulated by the user to draw the sample into the reservoir

6115. The sample transport device 6110 includes an overflow reservoir 6116 that receives excess flow of the sample during the aspiration step. The overflow reservoir 6116 includes a valve member that prevents the overflow amount from being conveyed out of the transfer device 6110 when the actuator 6117 is manipulated to deposit the sample into the input portion 6160 of the device 6000. This arrangement, ensures that the desired sample volume is delivered to the device 6000. Moreover, by including a "valved" overflow reservoir 6116, the likelihood of misuse during sample input is limited. This arrangement also requires minimal (or no) scientific training and/or little judgment of the user to properly deliver the sample into the device.

In some embodiments, the sample transfer device 6110, or any other sample transfer devices herein, can be used to aspirate fluid from a transfer tube or cup that is also included as part of a kit within which the device 6000 is included. In some embodiments, the sample transfer device 6110 can be any suitable, commercially available transport pipette. For example, in some embodiments, the sample transfer device 6110 can include the Alpha Industries, UK, 250 μl Dual Bulb Pastette LW4790 (Pasteur Pipette), which transfers a sample volume of 250 μl+/−10%. The test system 6000 is configured to accommodate such variation (e.g., +/−10%) in pipetted volume. Transfer pipettes holding and/or delivering 500 μl and 1000 μl can also be used with the device 6000. In some embodiments, the sample transfer device 6110 (or any of the sample transfer devices described herein) can deliver a sample volume of between about 250 and about 500 μl.

In some embodiments, the sample transfer device 6110 can include a status window or opening through which the user can visually check to see that adequate volume has been aspirated.

Although shown as being used in conjunction with and/or packaged with an external sample transfer device (i.e., the sample transfer device 6110), in other embodiments, the device 6000 can include an integrated sample transfer portion or device.

Sample Preparation Module

The sample preparation module 6200 is disposed at least partially within the sample preparation portion 6023 the lower housing 6030, and is configured receive an input sample S1 from the receiving volume 6164 of the sample input portion 6160. As described herein, the sample preparation module 6200 is configured to process the sample S1 to facilitate detection of an organism therein that is associated with a disease. By eliminating the need for external sample preparation and a cumbersome instrument, the device 6000 is suitable for use within a point-of-care setting (e.g., doctor's office, pharmacy or the like) or at the user's home, and can receive any suitable sample S1. The sample S1 (and any of the input samples described herein) can be, for example, blood, urine, male urethral specimens, vaginal specimens, cervical swab specimens, and/or nasal swab specimens gathered using a commercially available sample collection kit.

In some embodiments, the sample preparation module 6200 is configured to accept and allow for spill-proof containment of a volume of liquid from the sample input portion 6160. As described below, the sample preparation module 6200 is configured for onboard storage of wash solution, elution solution, and/or a positive control (e.g., *Aliivibrio fischeri, N. subflava*, or any other suitable organism). The positive control may be stored in liquid form in the wash solution or stored as a lyophilized bead that is subsequently hydrated by the wash solution. In some embodiments, the sample preparation module 6200 is configured for dispensing the majority of the sample liquid (e.g., about 80%) through a filter, and storing the generated waste in a secure manner (i.e., within the waste reservoir 6205). In some embodiments, the sample preparation module 6200 is configured for following the sample dispense operation with a wash dispense operation, thereby dispensing the bulk of the stored liquid (e.g., about 80%). In some embodiments, the sample preparation module 6200 is configured for backflow elution to occur to remove the desired target particles from the filter membrane and deliver the bulk (e.g., about 80%) of the eluted volume to the target destination (e.g., the inactivation module 6300, the amplification module 6600 or the like). In some embodiments, the sample preparation module 6200 is configured so as not cause the output solution to be contaminated by previous reagents (e.g., like the sample or wash). In some embodiments, the sample preparation module 6200 is configured for ease of operation by a lay user, requiring few, simple, non-empirical steps, and for a low amount of actuation force.

The sample preparation module 6200 includes a sample input module 6170 (FIGS. 16-21), a wash module 6210 (FIGS. 22-24), an elution module 6260 (FIGS. 25-28), a filter assembly 6230 (FIGS. 32-35), and various fluidic conduits (e.g., tubes, lines, valves, etc.) connecting the various components. Referring to FIGS. 16-21, the sample input module 6170 includes a housing 6172 that defines a sample volume 6174, and a piston 6180 that is movably disposed within the sample volume 6174. The housing 6172 further defines a sample input port 6175, a sample output port 6177, and a wash input port 6176. In use, the input sample is conveyed from the sample input portion 6160 into the sample volume 6174 via the sample input port 6175. The sample can be conveyed by gravity feed or any other suitable mechanism. As shown the sample input port 6175 is disposed towards the top of sample volume 6174 such that after the piston 6180 moves downward to move the sample, the sample input port 6175 is blocked to prevent backflow of the sample back towards and/or into the sample input portion 6160. In other embodiments, the sample input port 6175 can include any suitable flow control devices, such as check valves, duck-bill valves, or the like.

Figure 21:
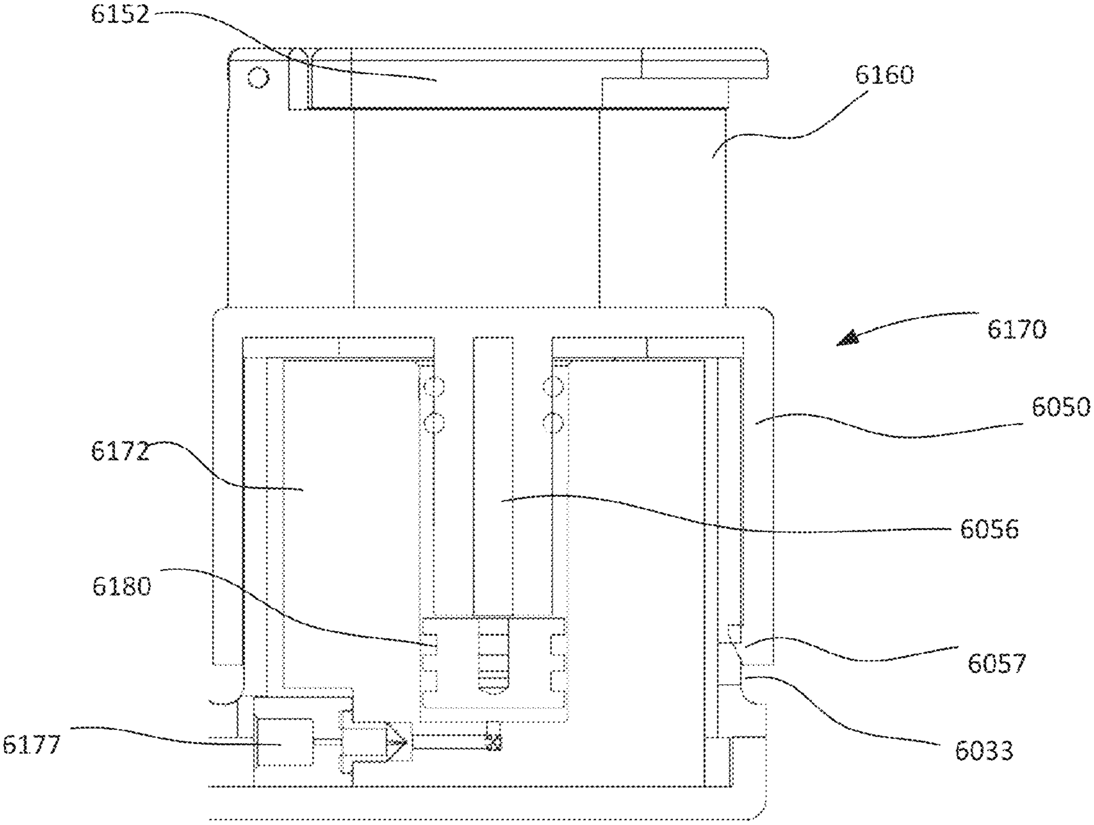
FIG. 21 is a side cross-sectional view of the sample input module shown in FIGS. 10 and 11 in an actuated configuration.

As shown in FIG. 21, when the piston 6180 is moved downward within the sample volume 6174, the sample within the sample volume 6174 is conveyed towards the filter assembly 6230 via the sample output port 6177. The flow of the input sample towards the filter assembly 6230 is shown by the arrow S2 in FIG. 9. The sample output port 6177 can include any suitable flow control devices, such as check valves, duck-bill valves, or the like, to prevent flow from the filter back into and/or towards the sample volume 6174.

The sample input module 6170 is actuated by the sample actuator (or button) 6050. The sample actuator 6050 is movably coupled to the sample preparation portion 6023 of the housing 6030, and includes a side wall 6054 that defines an inner volume 6055 that can receive a portion of the sample input module 6170. The sample actuator 6050 includes a protrusion 6056 that is aligned with and can move the piston 6180 when the sample input module 6170 is actuated. The sample actuator 6050 further includes a lock tab 6057 that is fixedly received within the notch or opening 6033 to fix the sample actuator 6050 in its second or "actuated" position, as described above.

Figure 63:
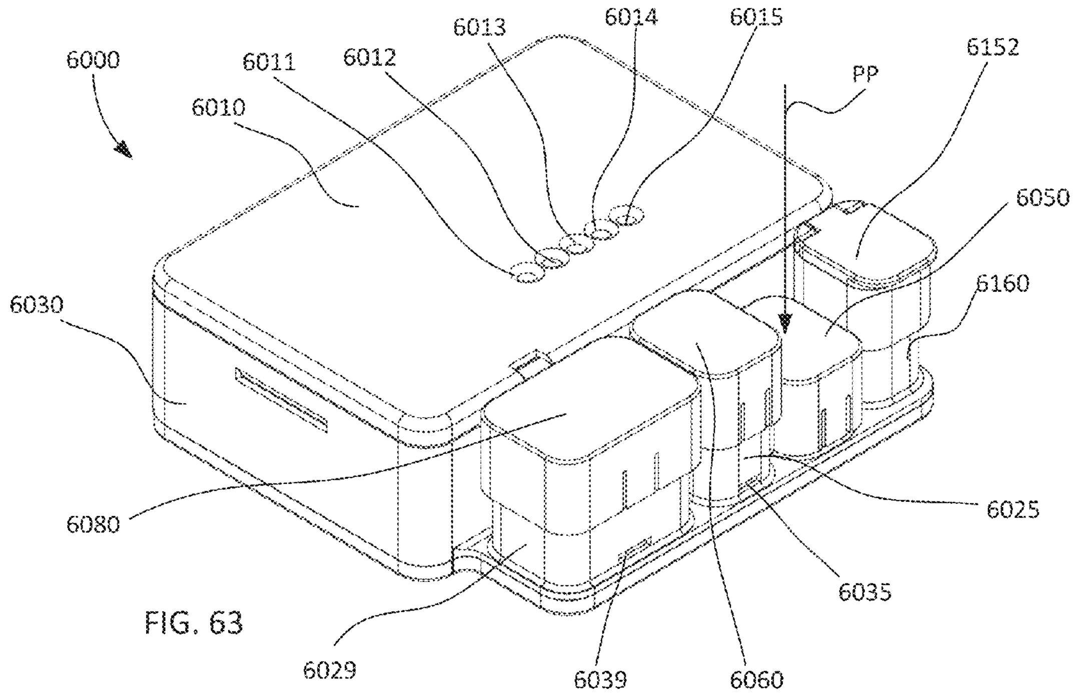
FIG. 63 is a perspective view of the molecular diagnostic test device shown in FIGS. 10 and 11 in a second (sample actuated) configuration.

In use, after the input sample S1 has been placed into the sample input portion 6160 and the desired portion of the sample has been conveyed into the volume 6174, the sample input operation can be initiated by the downward movement of the sample actuator 6050 relative to the lower housing 6030 (this is shown by the arrow PP in FIG. 63; see also FIG. 21). Movement of the piston 6180 within the volume 6174 increases the internal pressure, and thus cause the sample therein to flow through the output port 6177 towards the filter assembly 6230. The sample actuator 6050 is remains locked in its second or "actuated" position by the interface between the lock tab 6057 and the notch 6033. When the sample actuator 6050 is in the locked position, the piston 6180 is spaced apart from the bottom surface defining the sample volume 6174 to allow some amount of "dead volume" through which the wash compositions can flow.

Figure 22:
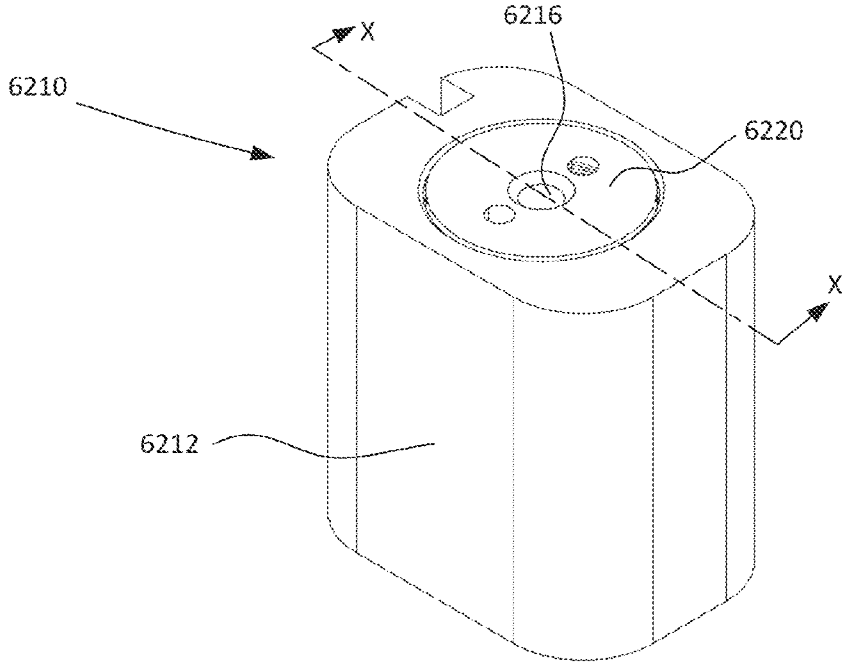
FIG. 22 is a front perspective view of a wash module of the molecular diagnostic test device shown in FIGS. 10 and 11.
Figure 23:
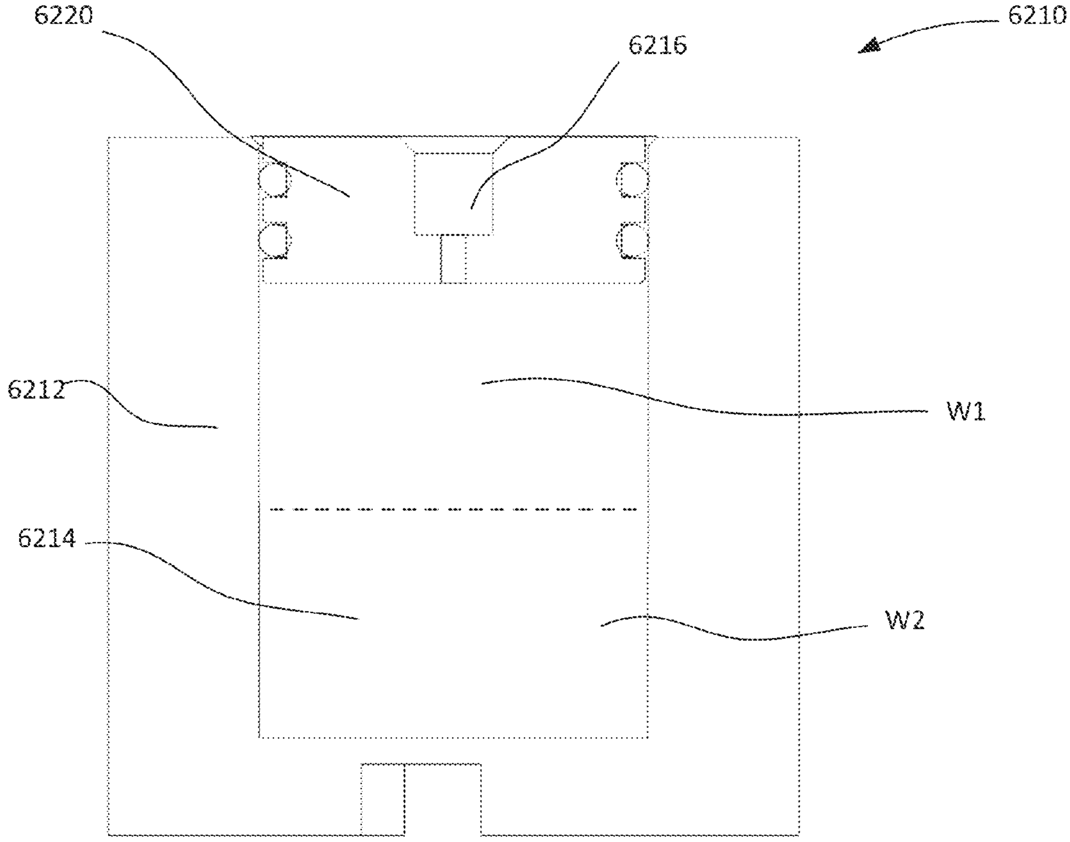
FIG. 23 is a perspective cross-sectional view of the wash module shown in FIG. 22 taken along the line X-X in FIG. 22.
Figure 24:
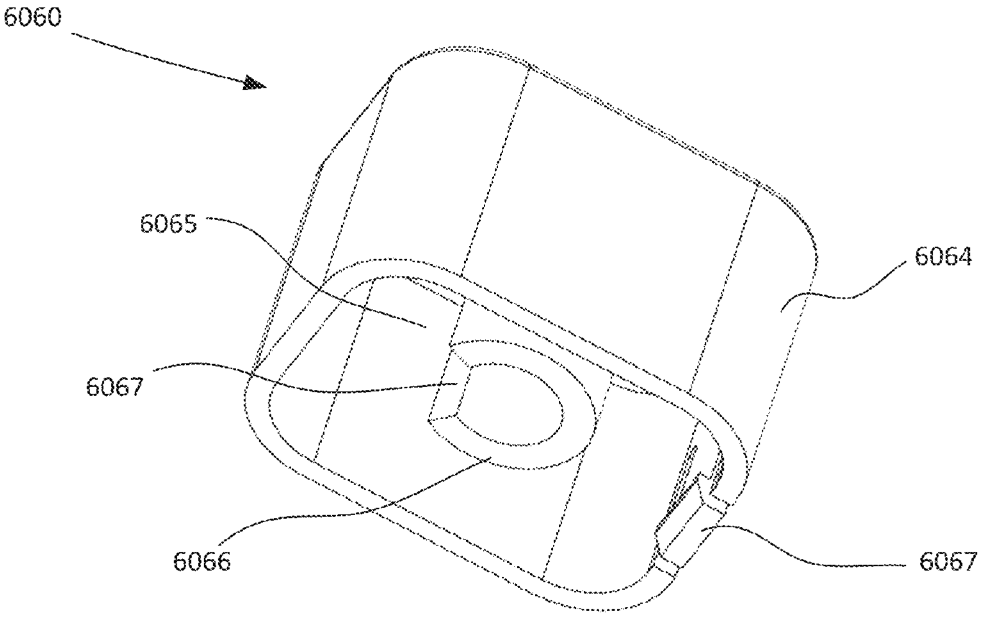
FIG. 24 is a side perspective view of a wash actuator of the molecular diagnostic test device shown in FIGS. 10 and 11.
Figure 25:
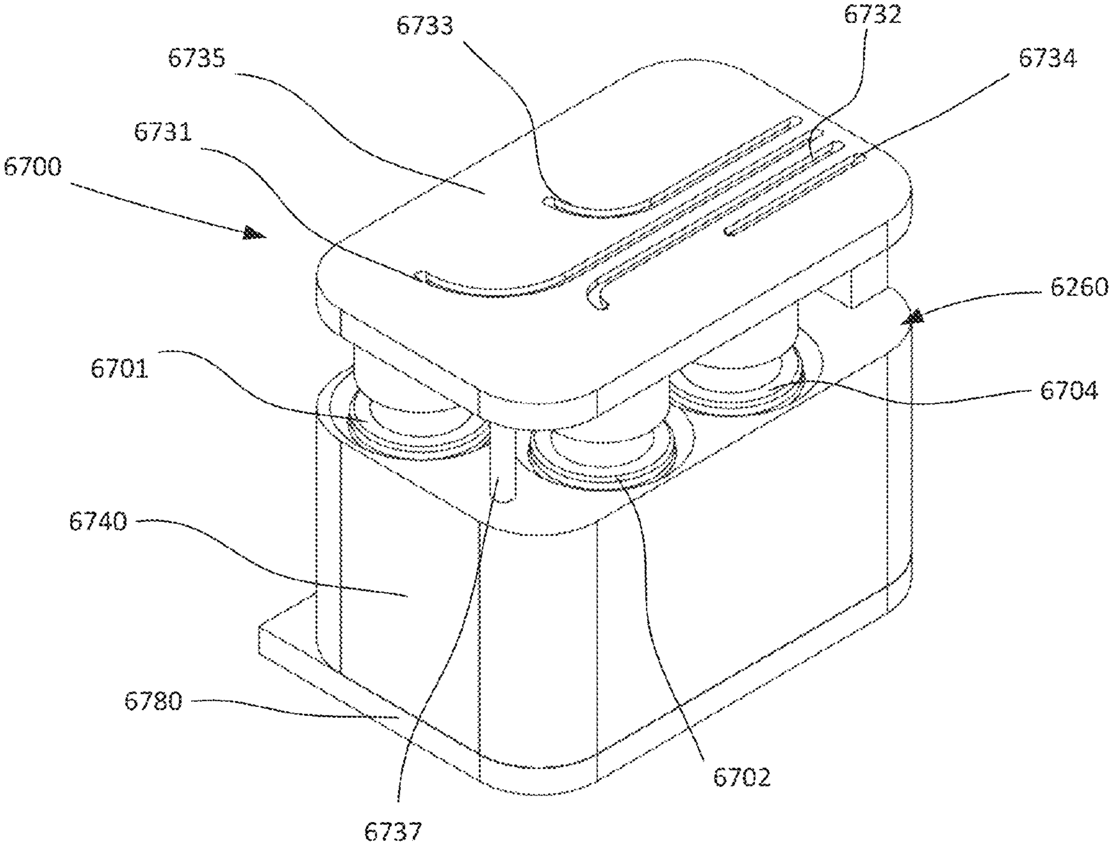
FIGS. 25 and 26 are a front perspective view and a rear perspective view, respectively, of an elution module and a reagent module of the molecular diagnostic test device shown in FIGS. 10 and 11.
Figure 26:
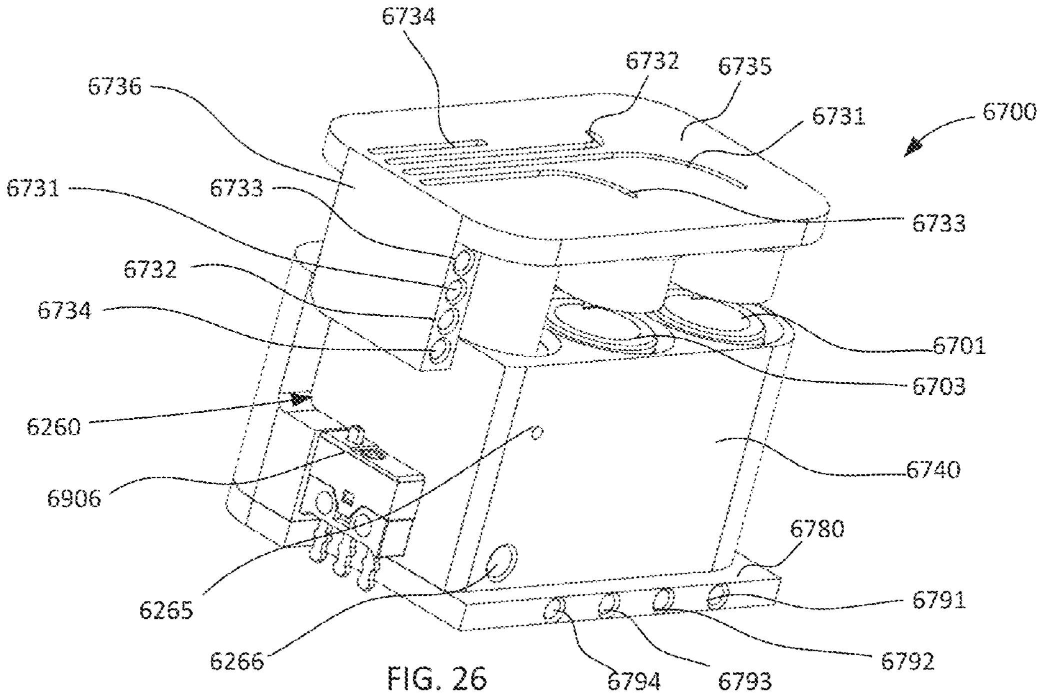

Referring to FIGS. 22-23, the wash module 6210 includes a piston 6220 and housing 6212 that defines a wash volume 6214. As shown by the dashed line in FIG. 23, the wash volume 6214 contains a first wash composition W1 and a second wash composition W2. More particularly, the first wash composition W1 is a gas (e.g., nitrogen, air, or another inert gas), and the second wash composition W2 is a liquid wash. In this manner, the wash operation can include an "air purge" of the filter assembly 6230, as described in more detail herein.

The piston 6220 is movably disposed within the sample wash volume 6214, and defines a wash output port 6216. The wash output port 6216 is fluidically coupled to the wash input port 6176 of the sample input module 6170. Moreover, the wash output port 6216 can include any suitable flow control devices, such as check valves, duck-bill valves, or the like to prevent flow back towards and/or into the wash volume 6214. The arrangement of the wash output port 6216 allows the wash compositions (e.g., W1 and W2) to be conveyed from the wash volume 6174 into the "dead volume" remaining of sample volume 6174 and towards the filter assembly 6230 when the wash actuator 6060 is actuated. More particularly, by including the wash output port 6216 on the piston 6220, movement of the piston 6220 downward will produce a serial flow of the first wash composition W1 followed by the second wash composition W2. By first including a gas (or air) wash (the first wash composition W1), the amount of liquid constituents from the input sample that has been conveyed to the filter assembly 6230 (indicated by the flow S2 in FIG. 9) can be reduced. Said another way, after delivery of the input sample to the filter assembly 6230 by actuation of the sample input module 6170, the filter assembly 6230 will retain the desired sample cells and some amount of residual liquid. By forcing the first, gaseous wash composition W1 through the filter (i.e., an "air wash"), the amount of residual liquid can be minimized. This arrangement can reduce the amount of liquid wash (e.g., the second wash composition W2) needed to sufficiently prepare the sample particles. Reducing the liquid volume contributes to the reduction size of the device 6000 and also reduces the likelihood of potentially harmful shearing stress when the liquid wash W2 is flowed through the filter assembly.

The wash module 6210 is actuated by the wash actuator (or button) 6060. The wash actuator 6060 is movably coupled to the wash portion 6025 of the lower housing 6030, and includes a side wall 6064 that defines an inner volume 6065 that can receive a portion of the wash module 6210. The wash actuator 6060 includes a protrusion 6066 that is aligned with and can move the piston 6220 when the wash module 6210 is actuated. The wash actuator 6060 further includes a lock tab 6067 that is fixedly received within the notch or opening 6035 to fix the wash actuator 6060 in its second or "actuated" position, as described above.

Figure 64:
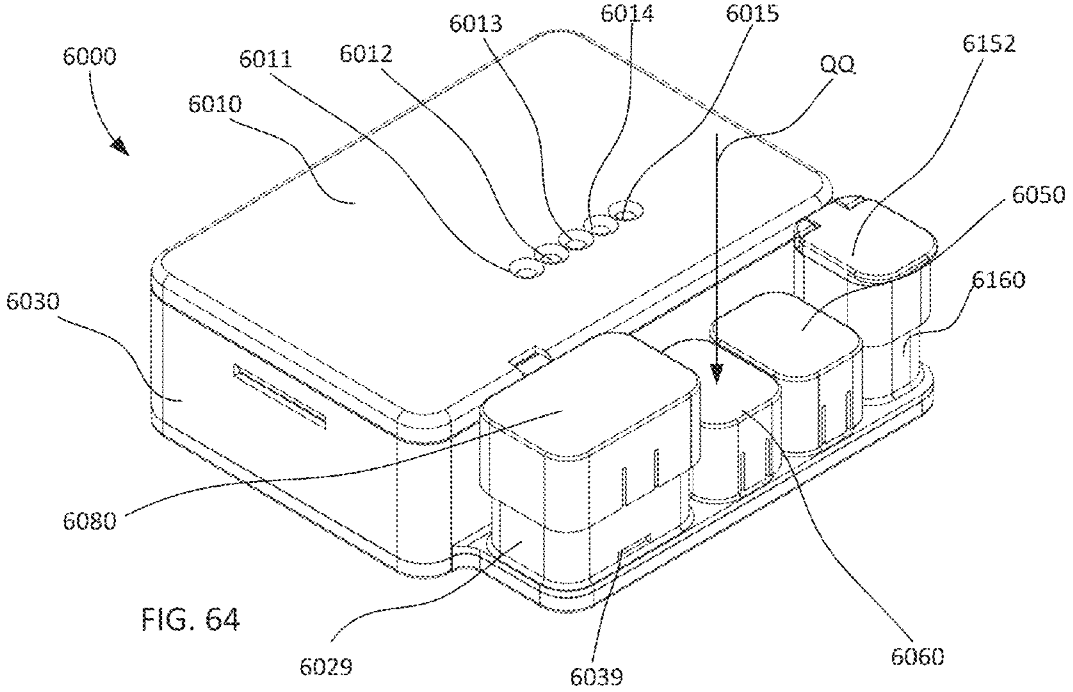
FIG. 64 is a perspective view of the molecular diagnostic test device shown in FIGS. 10 and 11 in a third (wash actuated) configuration.

In use, after the input sample S1 has been conveyed from the sample input module 6170 to the filter assembly (indicated by the arrow S2), the wash operation can be initiated by the downward movement of the wash actuator 6060 relative to the lower housing 6030 (this is shown by the arrow QQ in FIG. 64). Movement of the piston 6220 within the volume 6214 increases the internal pressure, and thus cause the first wash composition W1 and the second wash composition W2 to flow through the output port 6216 towards the sample input module 6170, as indicated by the arrow S3 in FIG. 9. The wash actuator 6060 is remains locked in its second or "actuated" position by the interface between the lock tab 6067 and the notch 6035.

As described above, as the piston 6220 moves downward, the first wash composition W1 (i.e., the air wash) flows through the "dead volume" remaining in the sample input module 6170, through the sample output port 6177, and towards the filter assembly 6230. The second wash composition W2 (i.e., the liquid wash) then flows through the "dead volume" remaining in the sample input module 6170, through the sample output port 6177, and towards the filter assembly 6230. The flow of the first and second wash is shown in FIG. 9 by the arrow S3 shown through the filter assembly 6230. The first wash composition W1, the second wash composition W2, and any other waste products that pass through the filter assembly 6230 are conveyed to the waste reservoir 6205. As described in more detail below, the filter assembly 6230 includes a valve 6280 that controls the flow of the sample and the wash through the filter assembly 6230.

In some embodiments, the wash actuator 6060 and/or the sample actuator 6050 can be interconnected or can otherwise include locking features that limit the movement of the actuators out of order. For example, in some embodiments the sample actuator 6050 can include a protrusion that contacts a portion of the lock protrusion 6067 of the wash actuator 6060, thereby preventing movement of the lock actuator 6060 when the sample actuator 6050 is in its first position. In this manner, the actuators can be configured to reduce the likelihood of being actuated out of order.

Although shown and described as including a first wash composition W1 (i.e., a gas) and a second wash composition W2 (i.e., a liquid), in other embodiments, the wash module 6210 can include only a single wash composition.

The filter assembly 6230 is shown in FIGS. 14, 15 and 32-35. The filter assembly 6230 includes a filter housing assembly 6250, a first valve plate 6233, a second valve plate 6243, and a valve body 6290. As described herein, the filter assembly 6230 is configured to filter and prepare the input sample (via the sample input operation and the sample wash operation), and to allow a back-flow elution operation to deliver captured particles from the filter membrane 6254 and deliver the eluted volume to the target destination (e.g., towards the amplification module 6600).

The filter housing assembly 6250 includes a first plate 6251, a second plate 6252, and a filter membrane 6254. The first plate 6251 defines an input/output port 6255 through which the sample and wash solutions flow (towards the waste reservoir 6205), as indicated by the arrow EE in FIG. 32, and through which the elution solution and sample particles flow (towards the inactivation chamber 6300), as indicated by the arrow FF in FIG. 34. The input/output port 6255 is selectively placed in fluid communication with the valve openings 6237 and 6238 to control the flow therethrough. The second plate 6252 defines an input/output port 6256 through which the sample and wash solutions flow (towards the waste reservoir 6205), as indicated by the arrow EE in FIG. 32, and through which the elution solution and sample particles flow (towards the inactivation chamber 6300), as indicated by the arrow FF in FIG. 34. The input/output port 6256 is selectively placed in fluid communication with the valve openings 6247 and 6248 to control the flow therethrough.

The filter membrane 6254 captures the target organism/entity while allowing the bulk of the liquid within the sample, the first wash composition W1, and the second wash composition W2 to flow through into the waste tank 6230. The filter membrane 6254 (and any of the filter membranes described herein) can be any suitable membrane and or combination of membranes. For example, in some embodiments, the filter membrane 6254 is a woven nylon filter membrane with a pore size of about 1 μm (e.g., 0.8 μm, 1.0 μm, 1.2 μm) enclosed between the first plate 6251 and the second plate 6252 such that there is minimal dead volume. In such embodiments, the particle capture can be achieved primarily through a binding event. Such pore sizes and filter construction can lead to reduced fluid pressure during the sample delivery, wash and the elution operations. Such designs, however, may also allow target organisms to flow through the filter membrane 6254, potentially resulting in lower efficiency of capture. Furthermore the target organism may be harder to remove on the elution step (e.g., the backwash) due to the nature of the binding. However the resulting eluent solution is "cleaner" as more of the unwanted material gets washed away through the filter membrane 6254. Thus, the filter member 6254 and size thereof can be selected to be complimentary to and/or consistent with the target organism. For example, the filter membrane 6254 can be constructed and/or formulated to capture target specimens through either size exclusion (where anything smaller than the target organism is allowed to flow through the membrane), or via binding the target to the filter membrane through a chemical interaction (and later removing the target from the membrane with the elution solution).

For example, in some embodiments, the filter membrane 6254 can be a cellulose acetate filters with a pore size of approximately 0.35 μm, and can be constructed to achieve particle capture by size exclusion. Such filter construction, however, can tend to clog more easily, thus generating higher pressures during sample delivery, wash and the elution operations. In some embodiments, the internal pressures can be reduced by altering the diameter of the filter membrane 6254 and/or reducing the total volume of sample to be conveyed through the filter assembly 6230.

The first valve plate 6233 defines a valve slot 6234 in fluid communication with the input/output port 6255. Thus, the first valve plate 6233 provides fluidic access to the filter membrane 6254 (via the valve body 6290). The second valve plate 6243 defines a valve slot 6244 in fluid communication with the input/output port 6256. Thus, the second valve plate 6244 provides fluidic access to the filter membrane 6254 (via the valve body 6290).

The valve body 6290 includes an actuation portion 6291, a first valve leg 6232, and a second valve leg 6242. The first valve leg 6232 and the second valve leg 6242 are coupled to the actuation portion 6291, such that the sliding movement of the actuation portion 6291 causes the first valve leg 6232 to slide within the slot 6243 and the second valve leg 6242 to slide within the slot 6244. The first valve leg 6232 includes the valve openings 6237 and 6238, and a pair of O-rings (not shown) that sealing surround each of the openings. The second valve leg 6242 includes the valve openings 6247 and 6248, and a pair of O-rings 6253 that sealing surround each of the openings. Thus, depending on the position of the valve body 6290 within the slots 6234, 6244, a pair of the openings can be selectively aligned with the opening 6255 of the second plate 6251 and the opening 6256 of the second plate 6252 to either block a particular flow path, or allow fluid flow therethrough. In this manner, the valve assembly 6230 can control the fluid flow during the sample flow, wash flow and elution flow operations.

Figure 32:
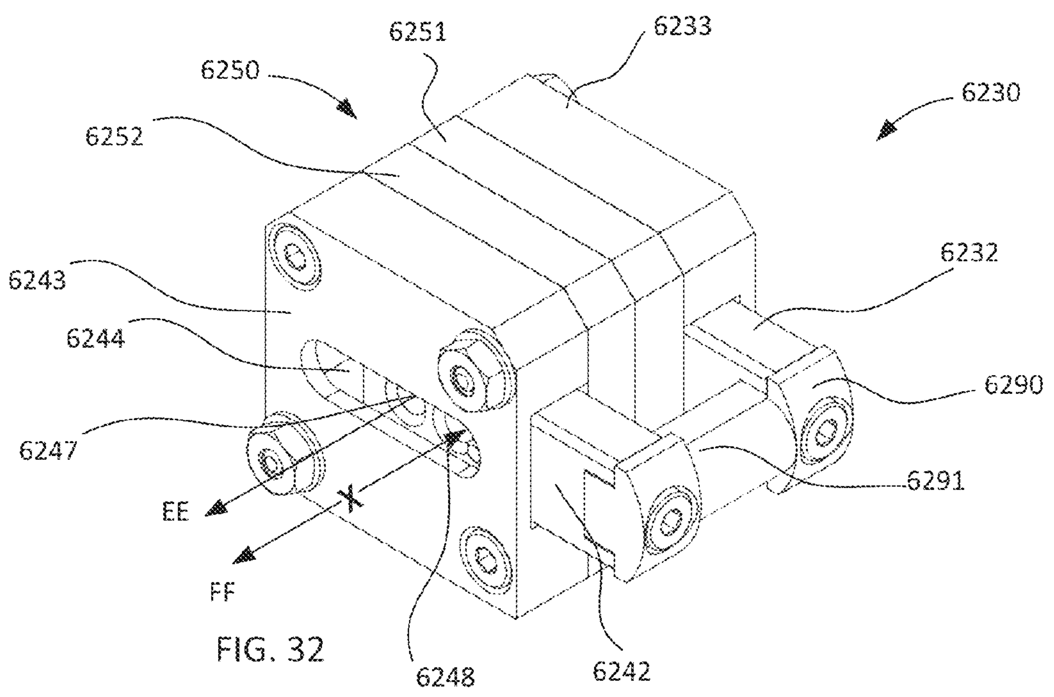
FIGS. 32 and 34 are front perspective views of a filter assembly of the molecular diagnostic test device shown in FIGS. 10 and 11, in a first (ready) configuration and a second (actuated) configuration, respectively.
Figure 33:
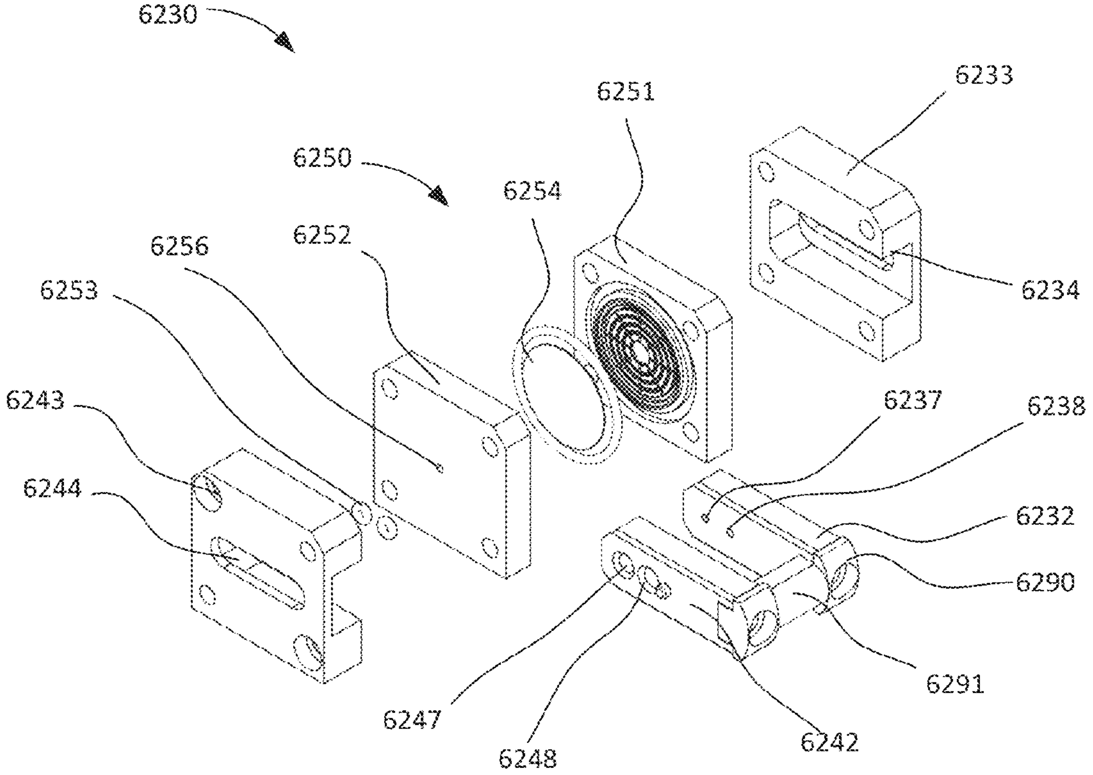
FIGS. 33 and 35 are a front exploded view and a rear exploded view, respectively, of the filter assembly shown in FIGS. 32 and 34.

FIG. 32 shows the filter assembly 6230 in its first (or "sample wash") configuration. When in the first configuration, the valve opening 6237 and the valve opening 6247 are both aligned with the input/output port 6255 and with the input/output port 6256. The valve opening 6237 receives flow of the sample from the sample output port 6177, and the valve opening 6247 is fluidically coupled to the waste reservoir 6205. Thus, when the filter assembly 6230 is in its first configuration, the sample S2 can be conveyed through the filter membrane 6254 (with the waste portion going to the waste reservoir 6205) as shown by the arrow EE. Further, the wash compositions S3 can be conveyed through the filter membrane 6254 (with the waste portion going to the waste reservoir 6205) as shown by the arrow EE. Moreover, the sample and or wash flows (S2 and S3, respectively) are prevented from flowing through the filter membrane 6254 and towards the elution module 6260 because the valve opening 6248 is sealed with the second valve leg 6242. This is depicted by the arrow FF in FIG. 32. The sample and or wash flows (S2 and S3, respectively) are also prevented from bypassing the filter membrane 6254 and flowing towards the inactivation chamber 6300 because the valve opening 6238 is sealed with the first valve leg 6232.

Figure 34:
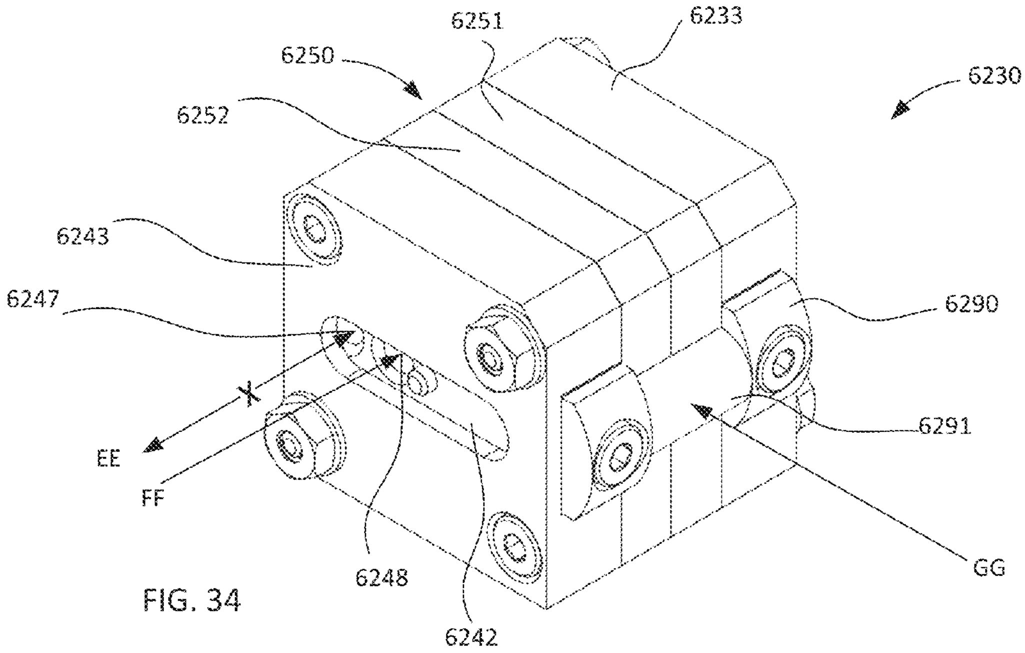
Figure 35:
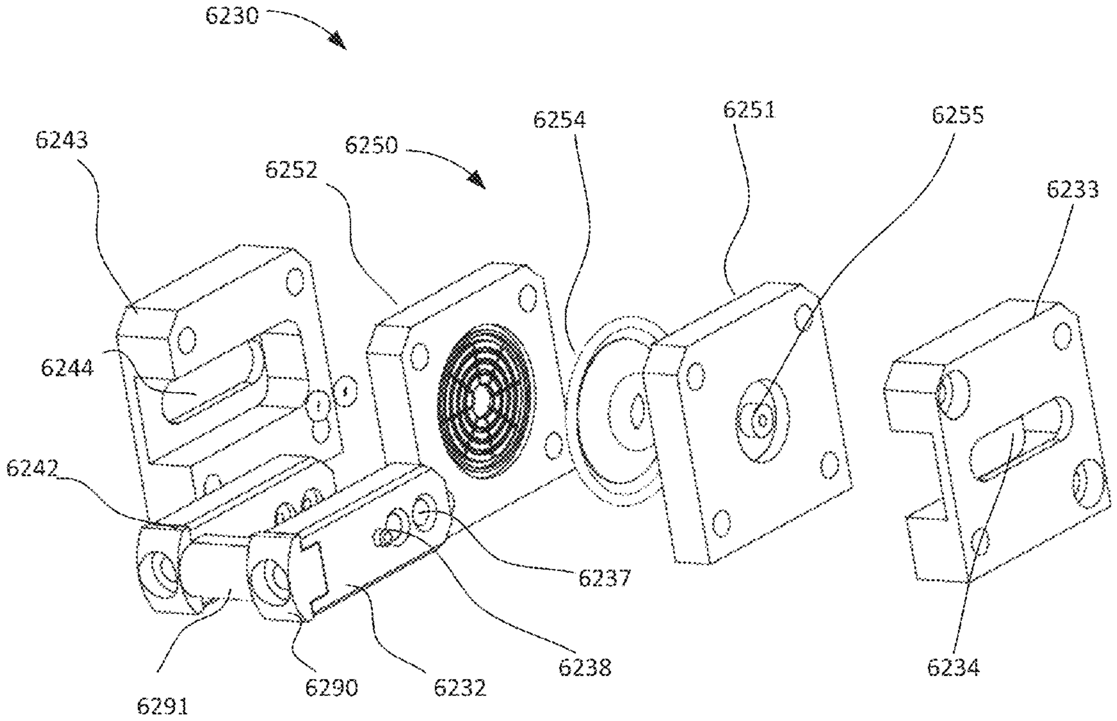

FIG. 34 shows the filter assembly 6230 in its second (or "elution") configuration. When in the second configuration, the valve opening 6238 and the valve opening 6248 are both aligned with the input/output port 6255 and with the input/output port 6256. The valve opening 6248 receives the elution flow from the elution module 6260 (described below), and the valve opening 6238 is fluidically coupled to the inactivation chamber 6300. Thus, when the filter assembly 6230 is in its second configuration, the elution flow (indicated by the arrow S4 in FIG. 9) can be conveyed back through the filter membrane 6254 as shown by the arrow FF. Moreover, the elution flow S4 is prevented from flowing through the filter membrane 6254 and towards the sample input module 6170 because the valve opening 6237 is sealed with the first valve leg 6232. This is depicted by the arrow EE in FIG. 34. The elution flow S4 is also prevented from bypassing the filter membrane 6254 and flowing towards the waste reservoir 6205 because the valve opening 6247 is sealed with the second valve leg 6242.

As described below, the valve body 6290 is actuated by movement of the reagent actuator 6080. In particular, the ramp 6088 defined by the protrusion 6086 of the reagent actuator 6080 contacts the actuation portion 6291 and moves the valve body 6290 inward, as shown by the arrow GG in FIG. 34 to move the filter assembly 6230 from its first configuration (FIG. 32) to its second configuration (FIG. 34).

The elution module (or assembly) 6260 of the sample preparation module 6200 is shown in FIGS. 25-28. The elution module 6260 is contained, along with the reagent module 6700, in the reagent portion 6029 of the housing. Moreover, the elution module 6260 and the initial actuation of the reagent module 6700 are both actuated by movement of a single, manual actuator (the reagent actuator 6080). The elution module 6260 is described immediately below, whereas the reagent module 6700 is described in more detail further below.

Figure 28:
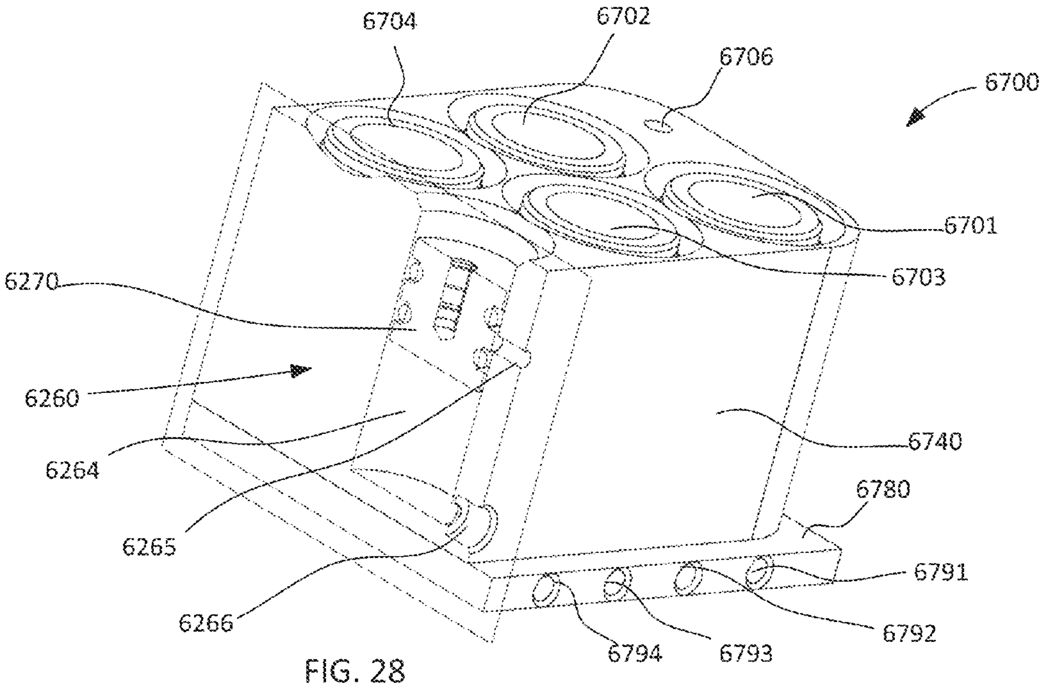
FIG. 28 is a perspective cross-sectional view of the elution module and the reagent module shown in FIGS. 25 and 26, with a top portion removed.

The elution module 6260 is contained within the reagent housing 6740 (also referred to as the "tank body" or the "reagent body"), and includes a piston 6270 (see FIG. 28). The reagent housing 6740 defines an elution volume 6264 within which an elution composition is stored. The elution composition can include proteinase K, which allows for the release of any bound cells and/or DNA from the filter membrane 6254. The reagent housing 6740 further defines an input (or fill) port 6265 and an elution output port 6266. The elution output port 6266 is fluidically coupled to the valve opening 6248 of the second valve leg 6242, and can be selectively placed in fluid communication with the filter assembly 6230, as described above. The elution output port 6266 can include any suitable flow control devices, such as check valves, duck-bill valves, or the like to prevent flow back towards and/or into the elution volume 6264.

Figure 30:
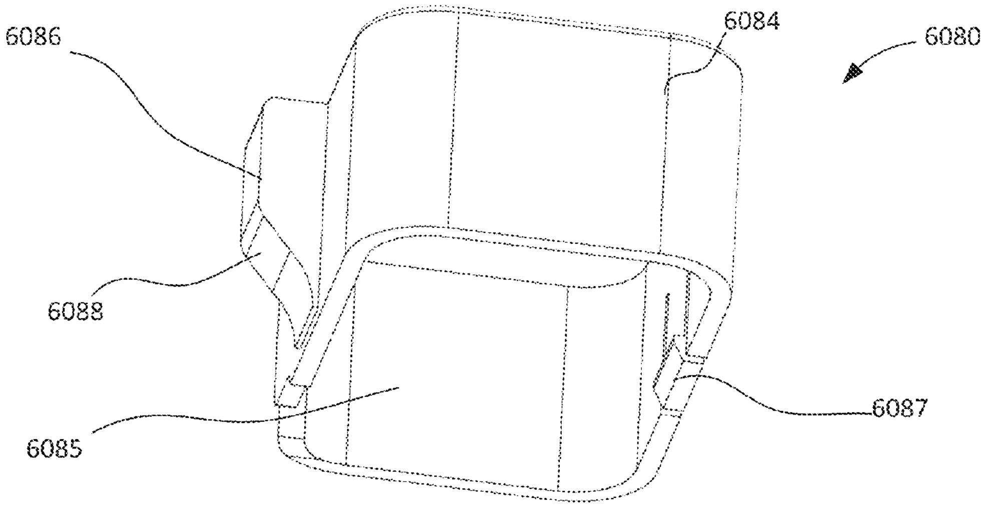
FIG. 30 is a side perspective view of an elution and reagent actuator of the molecular diagnostic test device shown in FIGS. 10 and 11.

The elution module 6210 is actuated by the reagent actuator (or button) 6080 (see FIG. 30). The reagent actuator 6080 is movably coupled to the reagent portion 6029 of the lower housing 6030, and includes a side wall 6084 that defines an inner volume 6065 that can receive a portion of the elution module 6260. The inner volume 6065 also receives the top member 6735 of the reagent module 6700, which includes a protrusion that is aligned with and can move the piston 6270 when the reagent actuator 6080 is moved. The reagent actuator 6080 further includes a lock tab 6087 that is fixedly received within the notch or opening 6039 to fix the reagent actuator 6080 in its second or "actuated" position, as described above.

In use, the filter assembly 6230 recovers the target organisms with a certain efficiency, from a given starting volume. The wash operation then removes undesired material, without removing the target organisms (which stay present on the filter membrane 6254). The elution operation then removes the target organism from the filter membrane 6254, diluting the total amount of captured organisms in the volume of the elution solution, thus comprising the eluent. By modifying the total output volume of eluent a higher or lower concentration of both target organism and any potential inhibiting matter can be achieved. In some embodiments, a further dilution can be achieved, if desired, by mixing the eluent solution with another reagent after the initial sample preparation. Given a known volume of eluent, and a known volume of diluent, a correct dilution factor can be achieved, through to maintain the reliability of the system very high dilution factors are avoided.

Reagent Module

As described herein, the detection method includes sequential delivery of the detection reagents (reagents R3-R6) and other substances within the device 6000. Further, the device 6000 is configured to be an "off-the-shelf" product for use in a point-of-care location (or other decentralized location), and is thus configured for long-term storage. In some embodiments, the molecular diagnostic test device 6000 is configured to be stored for up to about 36 months, up to about 32 months, up to about 26 months, up to about 24 months, up to about 20 months, up to about 18 months, or any values there between. Accordingly, the reagent storage module 6700 is configured for simple, non-empirical steps for the user to remove the reagents from their long term storage containers, and for removing all the reagents from their storage containers using a single user action. In some embodiments, the reagent storage module 6700 and the rotary selection valve 6340 (described below) are configured for allowing the reagents to be used in the detection module 6800, one at a time, without user intervention.

Specifically, the device 6000 is configured such that the last step of the initial user operation (i.e., the depressing of the reagent actuator 6080) results in dispensing the stored reagents. As described below, this action crushes and/or opens the sealed reagent containers present in the assembly and relocates the liquid for delivery. A rotary venting selector valve 6340 (see FIGS. 50-62) allows all of the reagent module 6700 to be vented for this step, and thus allows for opening of the reagent containers, but closes the vents to the tanks once this process is concluded. The reagents remain in the reagent module 6700 until needed in the detection module 6800. When a particular reagent is needed, the rotary valve 6340 opens the appropriate vent path to the reagent module 6700, and the fluidic drive module 6400 applies vacuum to the output port of the reagent module 6700 (via the detection module 6800), thus conveying the reagent from the reagent module 6700.

Figure 16:
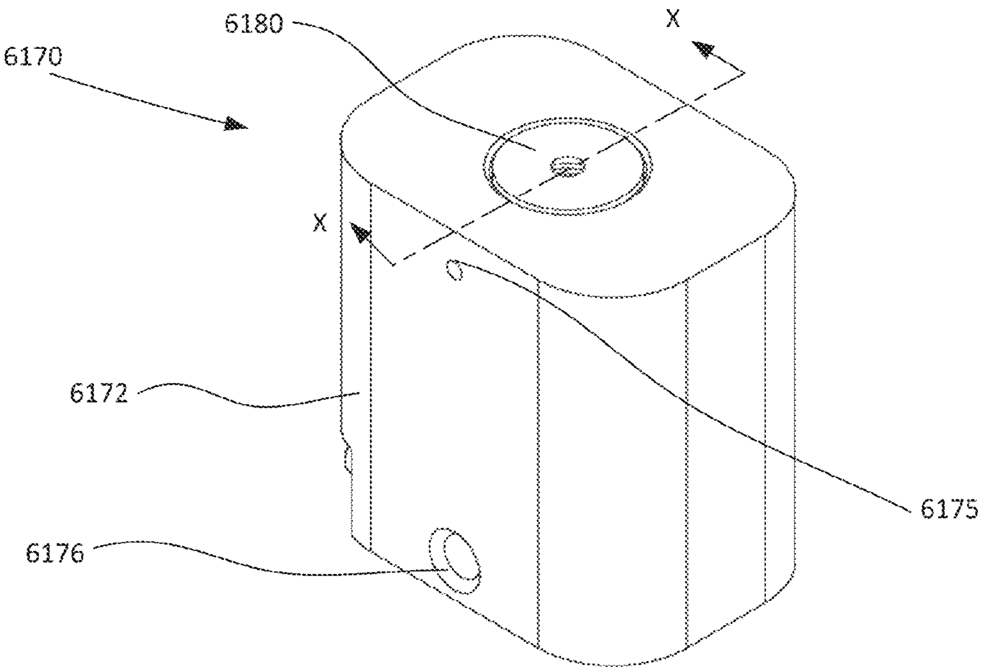
FIG. 16 is a front perspective view of a sample input module of the molecular diagnostic test device shown in FIGS. 10 and 11.
Figure 17:
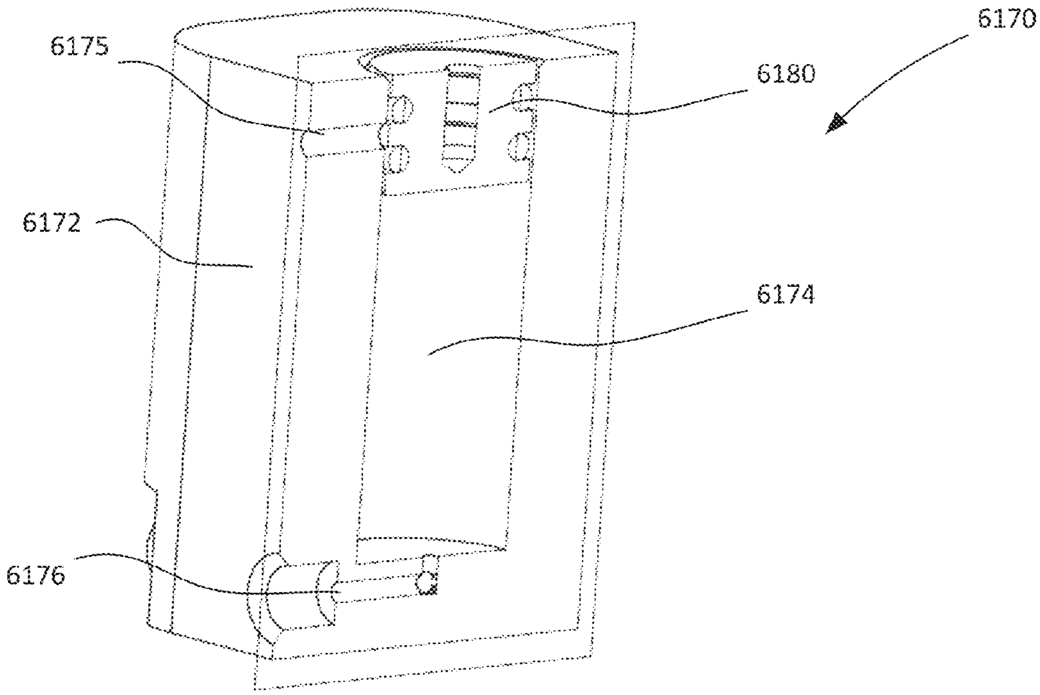
FIG. 17 is a perspective cross-sectional view of the sample input module shown in FIG. 16 taken along the line X-X in FIG. 16.
Figure 18:
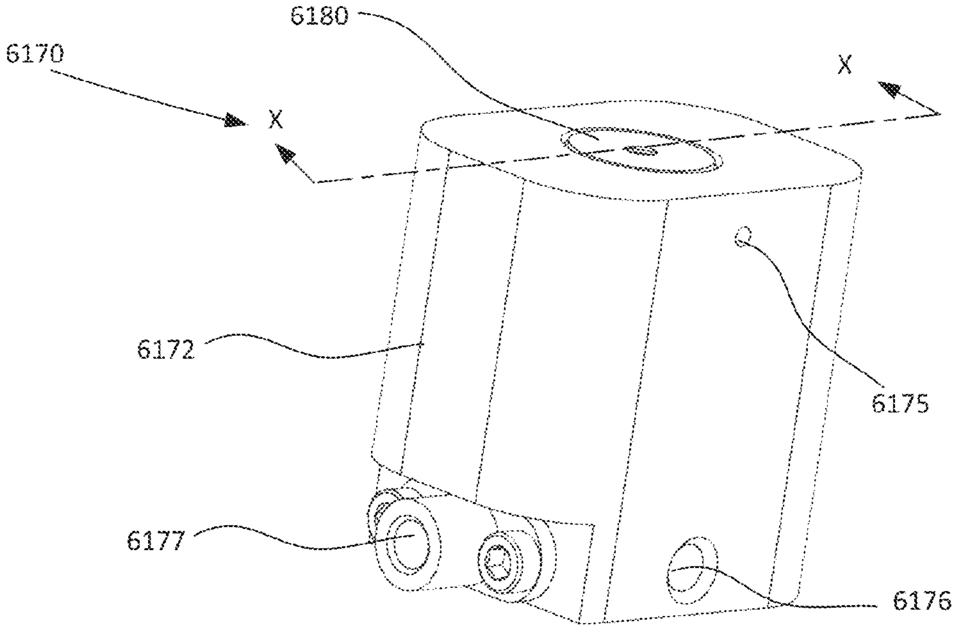
FIG. 18 is a side perspective view of the sample input module of the molecular diagnostic test device shown in FIGS. 10 and 11.
Figure 19:
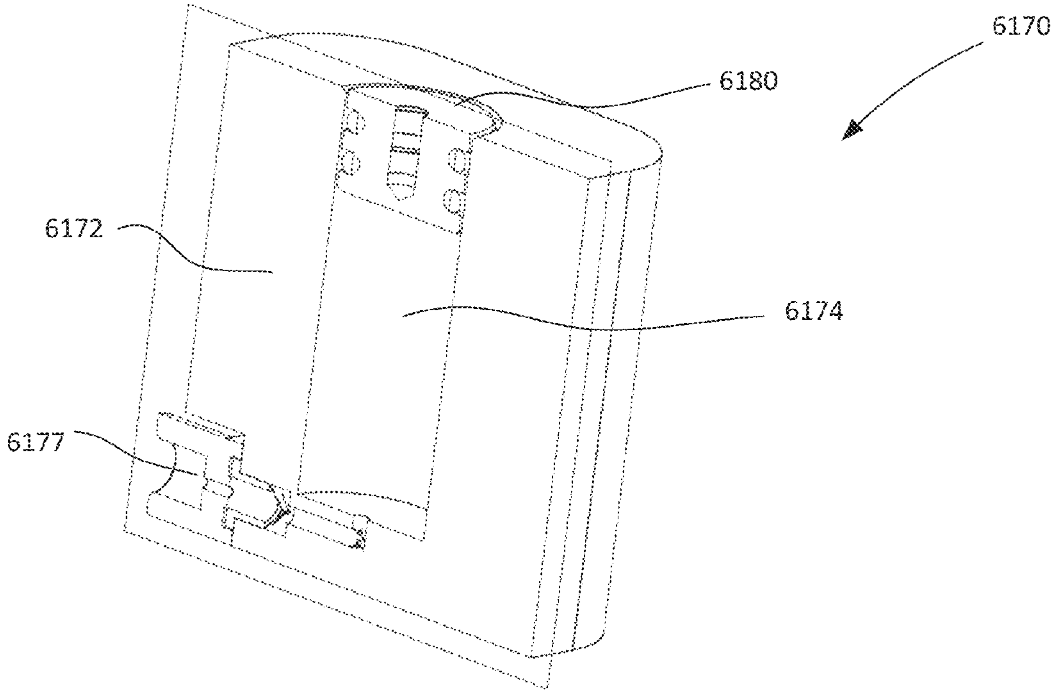
FIG. 19 is a perspective cross-sectional view of the sample input module shown in FIG. 18 taken along the line X-X in FIG. 18.

As illustrated in FIGS. 9 (schematically) and 25-31, the reagent storage module 6700 stores packaged reagents, identified herein as reagent R3 (a first wash solution), reagent R4 (an enzyme reagent), reagent R5 (a second wash solution), and reagent R6 (a substrate), and allows for easy un-packaging and use of these reagents in the detection module 6800. As shown in FIGS. 15-17, the reagent storage module 6700 includes a first reagent canister 6701 (containing the first reagent R3), a second reagent canister 6702 (containing the second reagent R4), and a fourth reagent canister 6704 (containing the fourth reagent R6), a reagent housing (or tank) 6740, a top member (or lid) 6735, and bottom (or outlet) member 6780. As described above, the reagent housing 6740 also contains and/or forms a portion of the elution module 6260.

Figure 29:
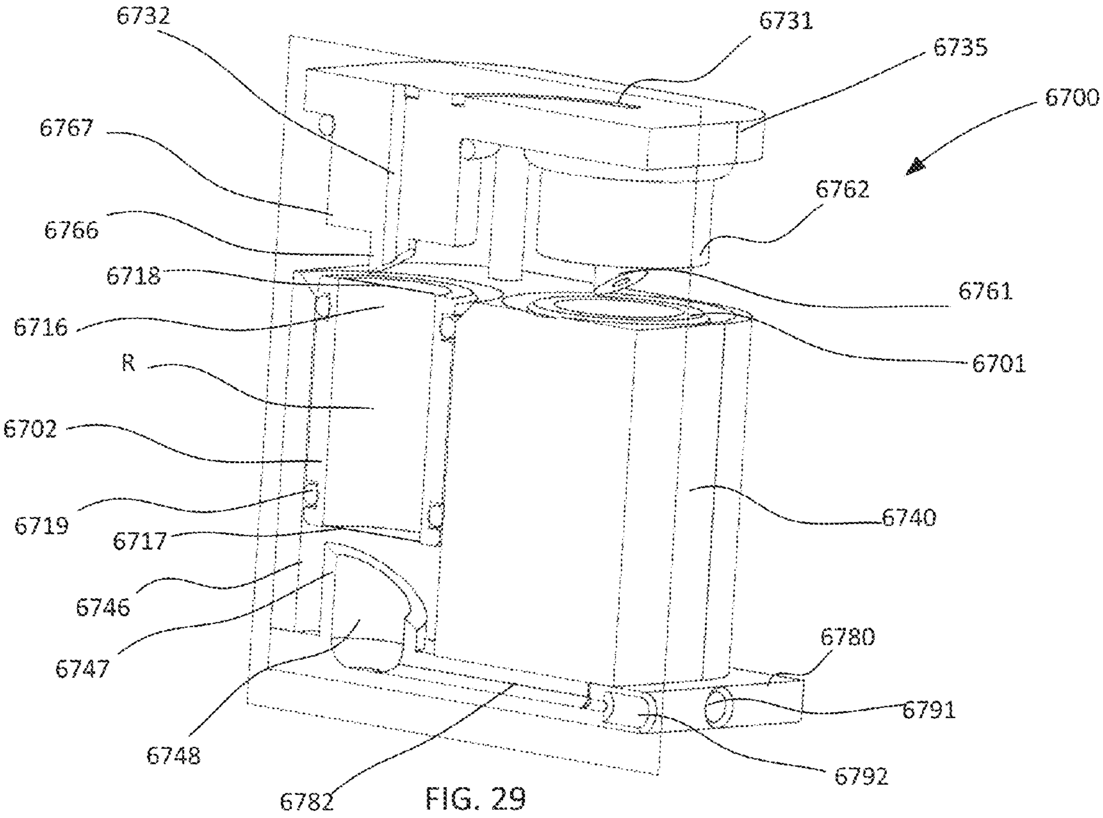
FIGS. 29 and 31 are perspective cross-sectional the reagent module shown in FIGS. 25 and 26, in a first (or ready) configuration and a second (or actuated) configuration, respectively.

Each of the reagent canisters includes frangible seals on the upper and lower ends thereof to define a sealed container suitable for long-term storage of the substance therein. For example, referring to FIG. 29, the second reagent canister 6702 includes a first (or top) frangible seal 6718 and a second (or lower) frangible seal 6717. As described below, the frangible seals are punctured upon actuation of the reagent module 6700 to configure or "ready" the reagent within each canister for use within the detection module 6800. The frangible seals can be, for example, a heat-sealed BOPP film (or any other suitable thermoplastic film). Such films have excellent barrier properties, which prevent interaction between the fluids within the canister and external humidity, but also have weak structural properties, allowing the films to be easily broken when needed. When the reagent canister is pushed into the crush feature or puncturers, as described below, the BOPP film breaks, allowing liquid within the canister to flow when vented. Each of the reagent canisters also includes two O-ring seals that fluidically isolate the canister within its bore of the reagent housing 6740. For example, as shown in FIG. 29, the second reagent canister 6702 includes a first (or upper) O-ring 6716 and a second (or lower) O-rings 6719. These O-rings seal the second reagent canister 6702 within the bore 6746 of the reagent housing 6740.

Figure 27:
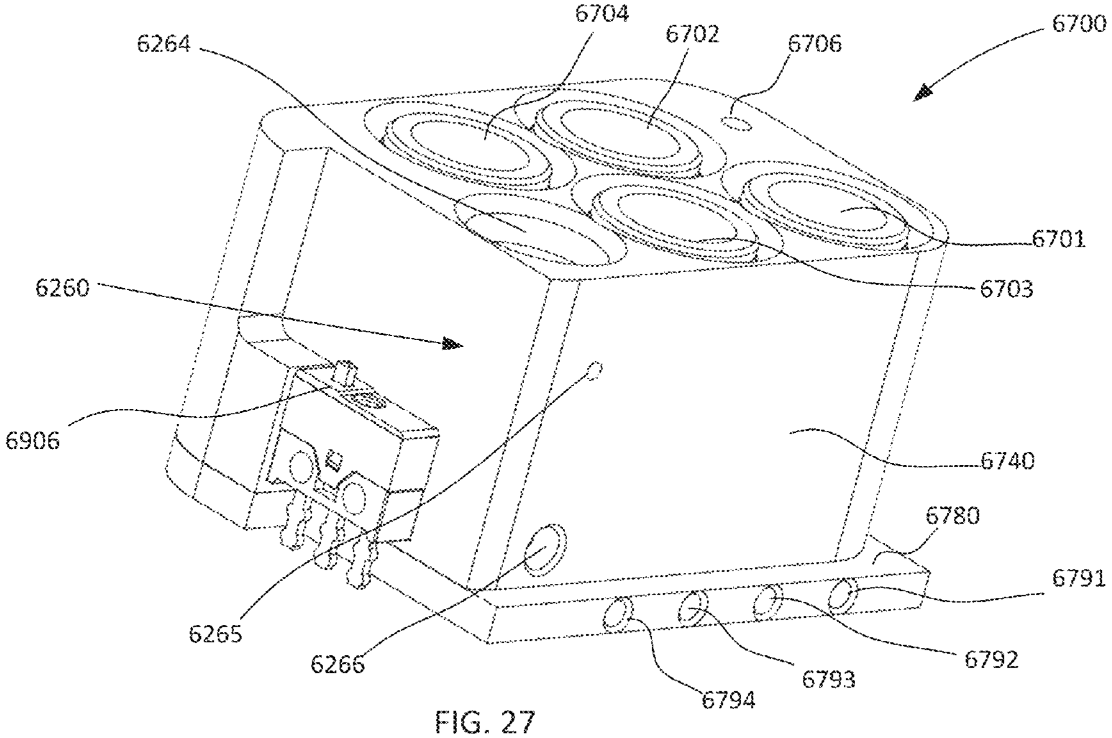
FIG. 27 is a rear perspective view of the elution module and the reagent module shown in FIGS. 25 and 26, with a top portion removed.

The reagent housing 6740 defines a set of cylindrical bores within which a corresponding reagent canister is movably contained. As shown in FIG. 27, a first bore contains the first reagent canister 6701, a second bore (which is identified as bore 6746 in FIG. 29) contains the second reagent canister 6702, a third bore contains the third reagent canister 6703, and a fourth bore contains the fourth reagent canister 6704. The reagent housing 6740 includes a puncturer in the bottom portion of each bore configured to pierce the second frangible seal of the respective canister when the canister is moved downward within the reagent housing 6740. Similarly stated, the reagent housing 6740 includes a set of puncturers that each pierce a corresponding frangible seal to open a reagent canister when the reagent module 6700 is actuated. Further, each puncturer defines a flow path that places the internal volume of the reagent canister in fluid communication with an outlet port of the reagent module 6700 after the frangible seal is punctured. For example, referring to FIGS. 29 and 31, the second bore 6746 includes a puncturer 6747 that defines a puncturer flow path 6748. The puncturer flow path 6748 is in fluid communication with the second outlet port 6792 via the passageway 6782.

The reagent housing 6740 also defines the elution volume 6264 (described above) and a guide bore 6706. The guide bore 6706 receives the corresponding pin or protrusion 6737 of the top member 6735 to guide movement of the top member 6735 relative to the reagent housing 6740.

The bottom member 6780 is coupled to the bottom portion of the reagent housing 6740 and defines the reagent outlet ports that are in fluid communication with each of the reagent bores. Specifically, the bottom member 6780 defines a first outlet port 6791 that is in fluid communication with the first bore, and through which the first reagent R3 can flow. The bottom member 6780 defines a second outlet port 6792 that is in fluid communication with the second bore 6746, and through which the second reagent R4 can flow (via the puncturer flow path 6748 and the passageway 6782, as shown in FIG. 29). The bottom member 6780 defines a third outlet port 6793 that is in fluid communication with the third bore, and through which the third reagent R5 can flow. The bottom member 6780 defines a fourth outlet port 6794 that is in fluid communication with the fourth bore, and through which the fourth reagent R6 can flow.

Figure 31:
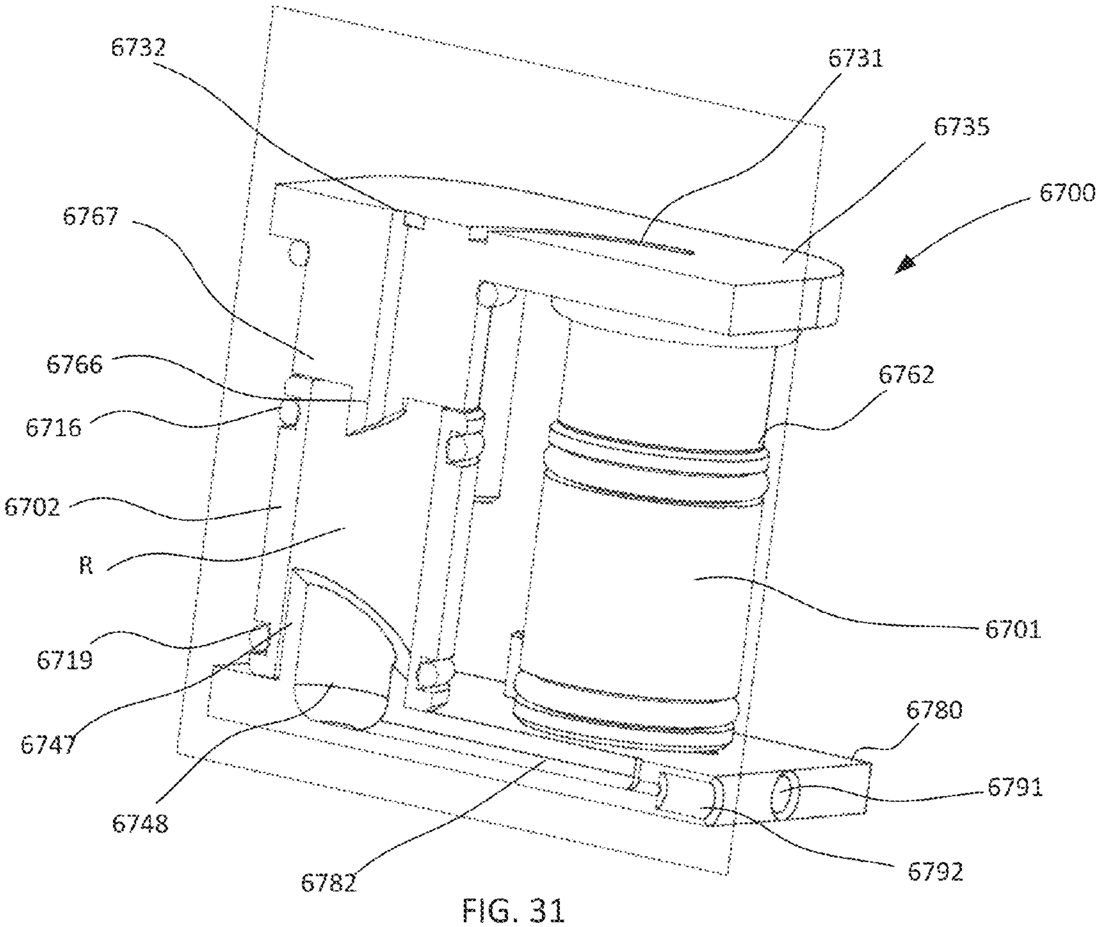

The top member 6735 is configured to move relative to the reagent housing 6740 when the reagent module 6700 is actuated. The top member 6735 includes a set of shoulders, each including a puncturer, and each of which corresponds to one of the reagent canisters. Similarly stated, the top member 6735 includes a set of shoulders, each including a puncturer, and each of which is aligned with and is configured to move at least partially within a corresponding bore defined by the reagent housing 6740. Referring to FIGS. 29 and 31, for example, the top member 6735 includes a first shoulder 6762 that corresponds to the first reagent canister 6701 (and the first bore) and a second shoulder 6767 that corresponds to the second reagent canister 6702 (and the second bore 6746). The first shoulder 6762 includes a first puncturer 6761 and the second shoulder 6767 includes a second puncturer 6766. Further, each puncturer of the top member 6735 defines a flow path that places the internal volume of the reagent canister in fluid communication with vent port of the reagent module 6700 after the top frangible seal is punctured. For example, referring to FIGS. 29 and 31, the second puncturer 6766 that defines a puncturer flow path 6732 that serves as the vent port 6732 (see the outlet vent ports in FIG. 26). Specifically, the first canister 6701 and/or first bore is vented via the first vent port 6731, the second canister 6702 and/or second bore 6746 is vented via the second vent port 6732, the third canister 6703 and/or third bore is vented via the third vent port 6733, and the fourth canister 6704 and/or fourth bore is vented via the fourth vent port 6734. As described below, each of the vent ports is fluidically coupled to the rotary valve 6340 to allow for selective and/or sequential venting of each canister to control the flow of the reagents to the detection module 6800.

The vent portion 6736 of the top member 6735 is also configured to engage with the switch 6906 to actuate the power and control module 6900 when the reagent module 6700 (and the elution module 6260) is actuated. The top member 6735 further includes the guide pin (or protrusion) 6737 that moves within the guide bore 6706 of the reagent housing 6740 during use.

When the reagent module 6700 is in its first (or storage) configuration (e.g., FIG. 29), the frangible seals 6717, 6718 fluidically isolate the interior volume of the second canister 6702, thus maintaining the reagent R2 in condition for storage. The reagent module 6700 is actuated when the top member 6735 is moved downward from its first position (FIG. 29) to its second position (FIG. 31). Specifically, the reagent module 6700 is actuated along with the elution module 6210 by the reagent actuator (or button) 6080 (see FIG. 30). The reagent actuator 6080 allows the user to manually actuate the system by depressing the actuator 6080 downward (see the arrow RR in FIG. 65).

As the reagent actuator 6080 and the top member 6735 move downward relative to the reagent housing 6740, the top puncturers pierce the top frangible seal of each of the reagent containers. Specifically, as shown in FIG. 31, the second puncturer 6768 pierces the top frangible seal 6718 thereby placing the interior volume of the second reagent canister 6702 in fluid communication with the vent port 6732. Further downward movement of the top member 6735 causes the shoulders of the top member 6735 to engage each respective canister and move the canister downward in its respective bore. This causes the lower puncturers (of the reagent housing 6740) to pierce the lower frangible seals. Specifically, as shown in FIG. 31, the shoulder 6767 pushes the second canister 6702 downward within the bore 6746, thus causing the puncturer 6747 to pierces the lower frangible seal 6717. This places the interior volume of the second reagent canister 6702 in fluid communication with the outlet port 6792.

When the reagent module 6700 is in the second configuration, the reagents are "readied" for use (i.e., they are released from the sealed canisters). The reagents, however remain within their respective canister and/or bore until such time as they are actuated by operation of the rotary valve assembly 6340, which selectively opens the vent ports 6731, 6732, 6733, and 6734 to allow the reagents to flow out of the reagent assembly 6700 via the outlet ports 6791, 6792, 6793 and 6794.

The reagent module 6700 and the rotary valve 6340 allows for the reagents to be prepared and sequentially conveyed into the detection module 6800 in a simple manner, and by a user with minimal (or no) scientific training, in accordance with methods that require little judgment. More particularly, the preparation of the reagents requires only the manual depression of a button (the reagent actuator 6080). The sequential addition of the reagents is controlled automatically by the rotary valve 6340. This arrangement contributes to the device 6000 being a CLIA-waived device and/or being operable in accordance with methods that are CLIA waived.

Inactivation Chamber

As shown by the arrow S4 in FIG. 9, the elution solution and the captured cells and/or organisms are conveyed during the elution operation back through the filter assembly 6230, and to the inactivation module (or "chamber") 6300. The inactivation module 6300 is configured to be fluidically coupled to and receive the eluted sample S4 from the sample preparation module 6200. In some embodiments, the inactivation module 6300 is configured for lysis of the received input fluid. In some embodiments, the inactivation module 6300 is configured for de-activating the enzymes present in input fluid after lysis occurs. In some embodiments, the inactivation module 6300 is configured for preventing cross-contamination between the output fluid and the input fluid.

Figure 36:
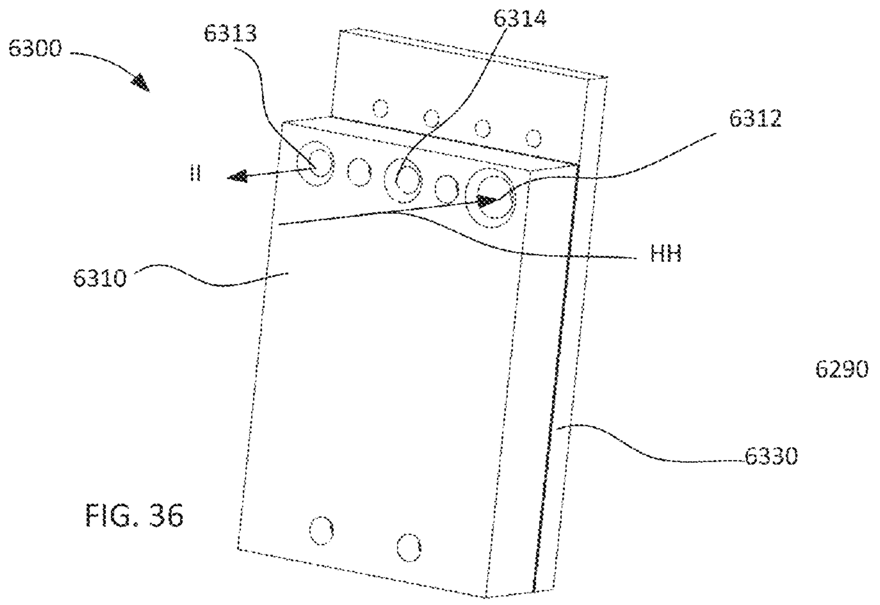
FIG. 36 is a side perspective view of an inactivation chamber of the molecular diagnostic test device shown in FIGS. 10 and 11.
Figure 37:
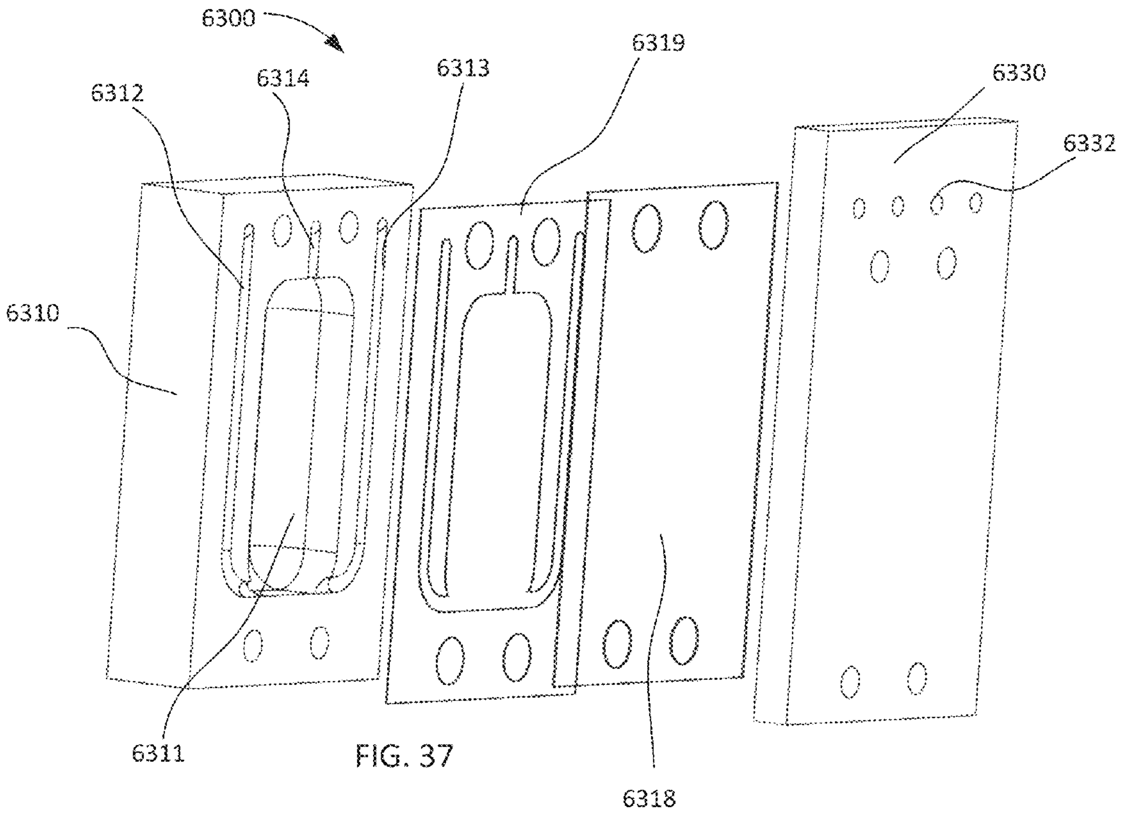
FIG. 37 is an exploded view of the inactivation chamber shown in FIG. 36.

Referring to FIGS. 36 and 37, the inactivation module 6280 includes a housing 6310, a lid 6318, a heater 6330, as well as fluidic and electrical interconnects (not shown) to other modules. The housing 6310 defines an inactivation chamber 6311, an input port 6212, an output port 6313, and a vent 6314. As shown in FIG. 37, the inactivation chamber 6311 is constructed to allow for being filled with the sample from the sample preparation module 6200, followed by heating the entirety of the liquid received. This is accomplished by making the input port 6212 and the output port 6313 have more arduous and/or tortuous flow paths than that of the vent port 6314. In this manner, when the liquid is manipulated, or when the liquid expands from being heated, the flow of liquid goes either towards or away from the vent port 63214, rather than into any of the conduits connected to the input port 6212 and/or the output port 6313.

As shown in FIG. 37, the lid 6318 (or cover) is coupled to the housing 6310 by an adhesive layer 6319. In other embodiments, the inactivation module 6300 can be constructed using any suitable mechanism.

The heater assembly 6330 can be any suitable heater construct, and can include electrical connections 6332 to electrically couple the heater 6330 to the controller 6950, power supply 6905 or the like. In some embodiments, the heater 6330 can integrate a simple heat spreader and a resistive heater layer with an integrated temperature sensor (not shown). The lid 6318 of the housing 6310 is constructed of a thin plastic membrane, and the heater assembly 6330 can be attached thereto by any suitable mechanism. This direct coupling arrangement allows for good thermal conduction from the heater assembly 6330 into the liquid inside the inactivation chamber 6311. The heater 6330 is controlled by the electronics module (e.g., the electronic controller 6950, or any other suitable controller) to control and/or maintain the heater 6330 at a certain temperature. Through characterization of the module, an offset from this control temperature is developed to the temperature of the liquid inside the inactivation chamber 6311.

In use, the sample is deposited in/transferred to the inactivation chamber 6311 from the sample preparation module 6200 via the input port 6312, as shown by the arrow HH. In some embodiments, the permanently open hydrophobic vent port 6314 allows the inactivation chamber 6311 to be filled passively; i.e., without need for intervention from a user (e.g., a manual operation) or control module (e.g., activating an addition piston pump). Once the fill is complete and the inactivation module 6300 is powered on, the heater assembly 6330 warms the liquid in the inactivation chamber 6311 to allow for the lysis reagents contained in the eluent to function at peak efficiency. This process lyses the target organism cells captured in the sample preparation module 6200 and releases the DNA present in the target. In some embodiments, the sample can be heated to about 56 C for about 1 minute. After an allotted amount of time, the heater 6330 heats the liquid to a high temperature to deactivate the lysis enzymes as well as any other enzymes present. In some embodiments, the sample can be heated to about 95 C for about 3 minutes. Liquid is then retained in the inactivation chamber 6311 until moved by the fluidic drive module 6400.

Mixing Module

As illustrated in FIGS. 9 (schematically), 38, and 39, the mixing module (also referred to as simply the mixing chamber) 6500 mixes the output of inactivation module 6300 with the reagents (e.g., R1 and R2) to conduct a successful PCR reaction. Similarly stated, the mixing module 6500 is configured to reconstitute the two reagent R1 and R2 in a given input volume, while ensuring even local concentrations of reagents in the entirety of the volume. In some embodiments, the mixing chamber module 6500 is configured to produce and/or convey a sufficient volume of liquid for the amplification module 6600 to provide sufficient volume output to the detection module 6800.

The mixing module 6500 includes a first housing 6520, a second housing (or cover) 6570, and a lyophilized reagent bead containing two reagents (identified as reagents R1 and R2). The mixing module 6500 also includes the tubing, interconnects and other components to couple the mixing module 6500 to the inactivation chamber 6300, the fluid drive module 6400, and the rotary valve assembly 6340. The first housing 6520 defines a mixing reservoir 6530, an inlet port 6540, an outlet port 6550 and a vent port 6556. The first housing 6520 also defines an opening 6523 within which the joining pin 6522 can be disposed to couple the first housing 6520 to the second housing 6570.

Figure 38:
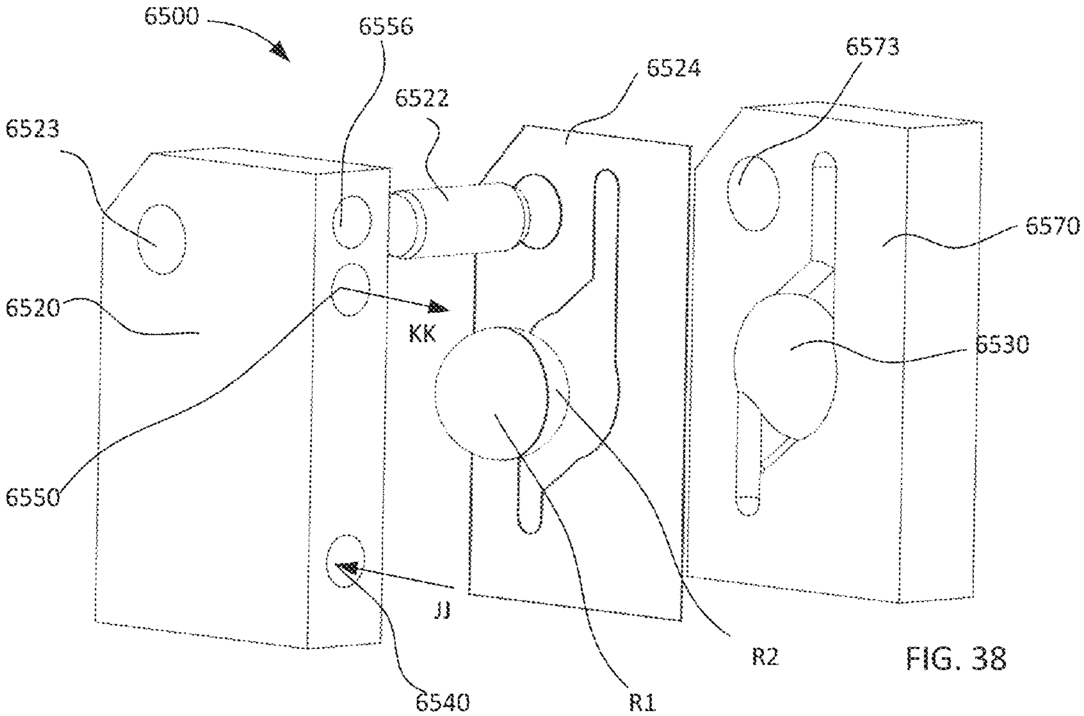
FIGS. 38 and 39 are a front exploded view and a rear exploded view, respectively, of a mixing assembly of the molecular diagnostic test device shown in FIGS. 10 and 11.
Figure 39:
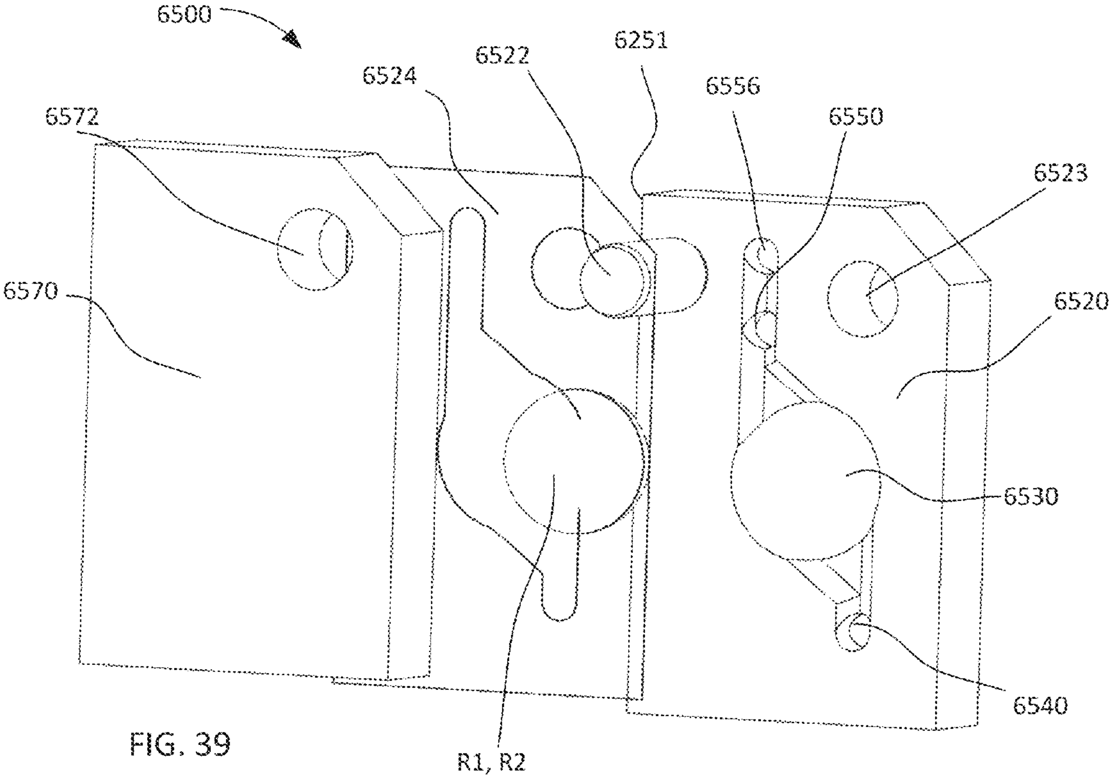

The input (or fill) port 6540 is fluidically coupled to the outlet port 6313 of the inactivation module 6300, and is configured to receive a flow from the inactivation module 6300 as shown by the arrow JJ in FIG. 38. The outlet port 6550 is fluidically coupled to the fluid transfer module 6400, and is configured to produce a flow to the fluidic drive module 6400 (and on to the amplification module 6600), as shown by the arrow KK in FIG. 38. The input port 6540 and the outlet port 6550 can include any suitable flow control devices, such as check valves, duck-bill valves, or the like to control the flow into and/or out of the mixing reservoir 6530. Although the mixing module 6500 is shown as being disposed upstream of the fluid transfer module 6400, in other embodiments, the mixing module 6500 can be disposed between the fluid transfer module 6400 and the amplification module 6500 (i.e., the mixing module 6500 can be downstream of the fluid transfer module 6400).

The second housing 6570 defines a portion of the mixing reservoir 6530, and is coupled to the first housing 6520 by the pin 6522 and any other sealing mechanism (such as the laminate 6524). Thus, together the first housing 6520 and the second housing 6570 define the mixing reservoir 6530 having the desired geometry to promote fluidic mixing, as described herein. Specifically, the mixing reservoir 6530 and/or other portions of the mixing module 6500 are configured to increase the effect of diffusion of the liquid by increasing the total contact area between segments of the liquid with areas of low and high local concentrations of reagents. This is accomplished by allowing the initial portion the liquid entering the chamber to contact the back of other portions of liquid and/or structure, and then maintaining the liquid in the mixing reservoir 6530 for sufficient time for diffusion to even out the concentration. In some embodiments, the first housing 6520 and/or the second housing 6570 can include on or more flow structures, vanes or the like (not shown) configured to influence, impact and/or change the fluid flow within the mixing reservoir 6520. Such flow structures and produce areas of recirculation, turbulent flow areas, and the like.

Although the mixing module 6500 is shown as being a passive module (i.e., relying solely on fluid flow to achieve the desired mixing and diffusion), in other embodiments, a mixing module can include an active mixing approach. For example, in some embodiments, the mixing module can include a stir rod or vibration mixer.

In use, when the fluid flows from the inactivation chamber 6300 (as a result of actuation of the fluid transfer module 6400), the initial (or first portion) of the liquid drawn into the mixing reservoir 6530 reconstitutes the lyophilized beads R1, R2 into the total volume of the mixing reservoir 6530. In some embodiments, the mixing reservoir can include structures that limit the fluid flow out of the mixing reservoir 6530 for a period of time until it is fully filled. In this manner, an overall concentration can be achieved and/or maintained prior to the sample being conveyed to the amplification module 6600. Structural features of the mixing reservoir 6530, combined with controlled stop/start flow from the fluid transfer module 6400 allow correct local concentrations to be achieved before the liquid flows out of the mixing chamber into the amplification module 6600.

The reagents R1 and R2 are each lyophilized pellets having a substantially hemispherical shape, and are disposed together in the spherical portion of the mixing reservoir 6530. This arrangement allows the two pellets to be hydrated together and/or substantially simultaneously when the flow of solution from the inactivate chamber 6300 is received within the mixing reservoir 6530. Similarly stated, the two lyophilized pellets are shaped to matingly fit together within the mixing reservoir 6530. In other embodiments, however, the two lyophilized pellets can each be spherically shaped, and can be placed within the mixing reservoir 6530.

The mixing module 6500 is also a storage location for the two lyophilized beads R1, R2, which, once reconstituted and mixed, form the master mix for the subsequent amplification step. The reagents R1 and R2 can be any suitable PCR reagents, such as the primers, nucleotides (e.g., dNTPs), and the DNA polymerase. In some embodiments, the reagent R1 and/or the reagent R2 can include the KAPA2G Fast DNA Polymerase, which includes a hot start function. This arrangement allows for very fast thermocycling and very little primer dimer formation. In some embodiments, the reagent R1 and/or the reagent R2 can include the PCR primers designed to target *Chlamydia trachomatis* (CT), *Neisseria gonorrhea* (NG) and *Trichomonas vaginalis* (TV). In addition, the reagent R1 and/or the reagent R2 can include a primer set for a non-target gram negative organism (*Aliivibrio fischeri*) to act as a positive control organism. All of the primers are designed with Tm values of approximately 60° C. In this manner, the PCR reaction conducted by the device is a multiplex reaction containing all four sets of primers. Specifically, in some embodiments, the primer set for *C. trachomatis* targets the 7.5 kb endogenous plasmid and produces a 101 by amplicon. In some embodiments, the primer set for *N. gonorrhoeae* targets the opa gene and produces a 70 bp amplicon. In some embodiments, the primer set for *T. vaginalis* targets a repetitive DNA fragment in the genome and produces a 65 bp amplicon. In some embodiments, the primer set for *A. fischeri* targets the hvnC locus and produces a 107 bp amplicon.

In some embodiments, the reagent R1 can contain the primers and raw base pairs for the reaction, and reagent R2 can include the enzymes necessary for PCR amplification. Moreover, because the device 6000 can be configured for single-use in a point-of-care setting, the reagents R1 and R2 can be formulated for and/or packaged within the mixing module 6500 to enhance long term storage. Accordingly, in some embodiments, the reagents R1 and R2 and/or the device 6000 can be configured to have a shelf life of up to about 36 months, up to about 32 months, up to about 26 months, up to about 24 months, up to about 20 months, up to about 18 months, or any values therebetween.

For example, by separating the two major constituents of the master mix solution (the primers and the enzymes) high shelf life and reagent stability can be achieved. In other embodiments, however, the mixing module 6500 can include any number of lyophilized pellets or beads, each containing any suitable reagents for the PCR reaction. Additionally, the first housing defines the vent port 6556, which fluidically coupled to a desiccated area of the device, and which is coupled to the vent line 6356 of the rotary valve assembly 6340. In this manner, moisture can be drawn away from the reagents R1, R2 during storage and shipping. Specifically, as described in more detail below, when the rotary valve assembly 6340 is in the "shipping" condition, the vent port 6556 is open to atmosphere, and the desiccant is in-line between the vent port 6556 and the valve assembly 6340. During use, the valve assembly 6340 closes the vent port 6556 to ensure proper fluid flow and mixing, as described above.

Fluidic Drive Module

Figure 40:
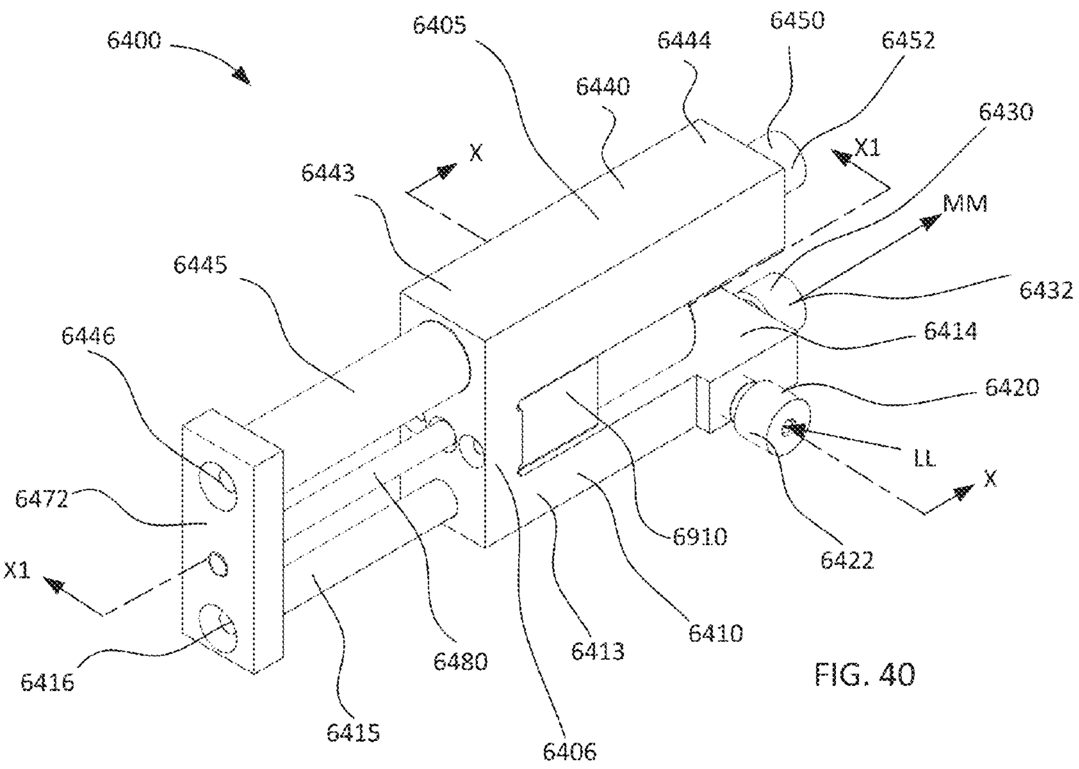
FIG. 40 is a front perspective view of a fluid transfer module of the molecular diagnostic test device shown in FIGS. 10 and 11.
Figure 41:
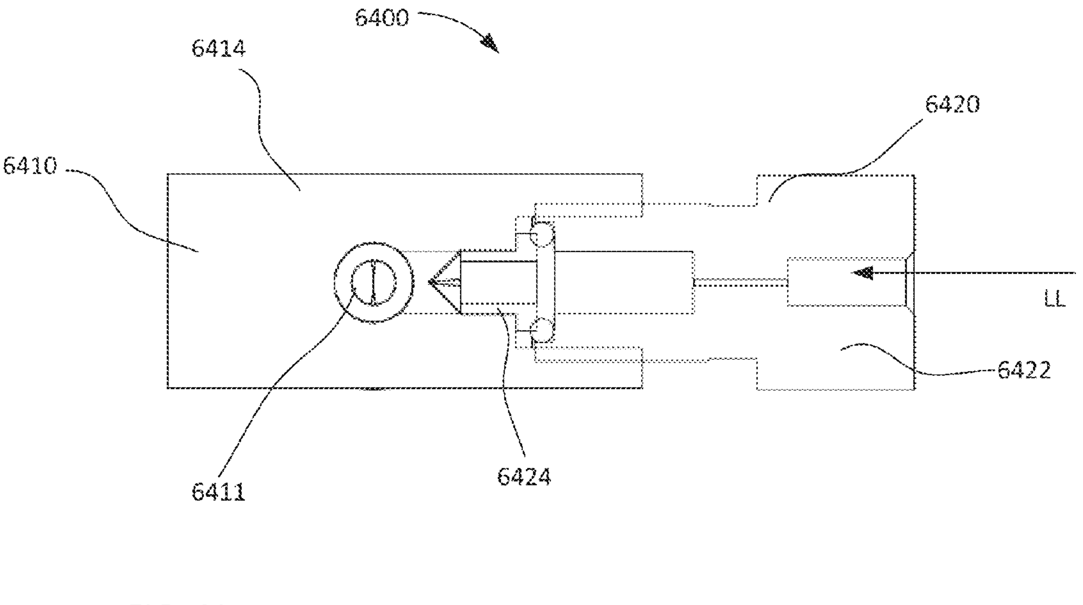
FIG. 41 is a cross-sectional view of the fluid transfer module shown in FIG. 40 taken along the line X-X in FIG. 40.
Figure 42:
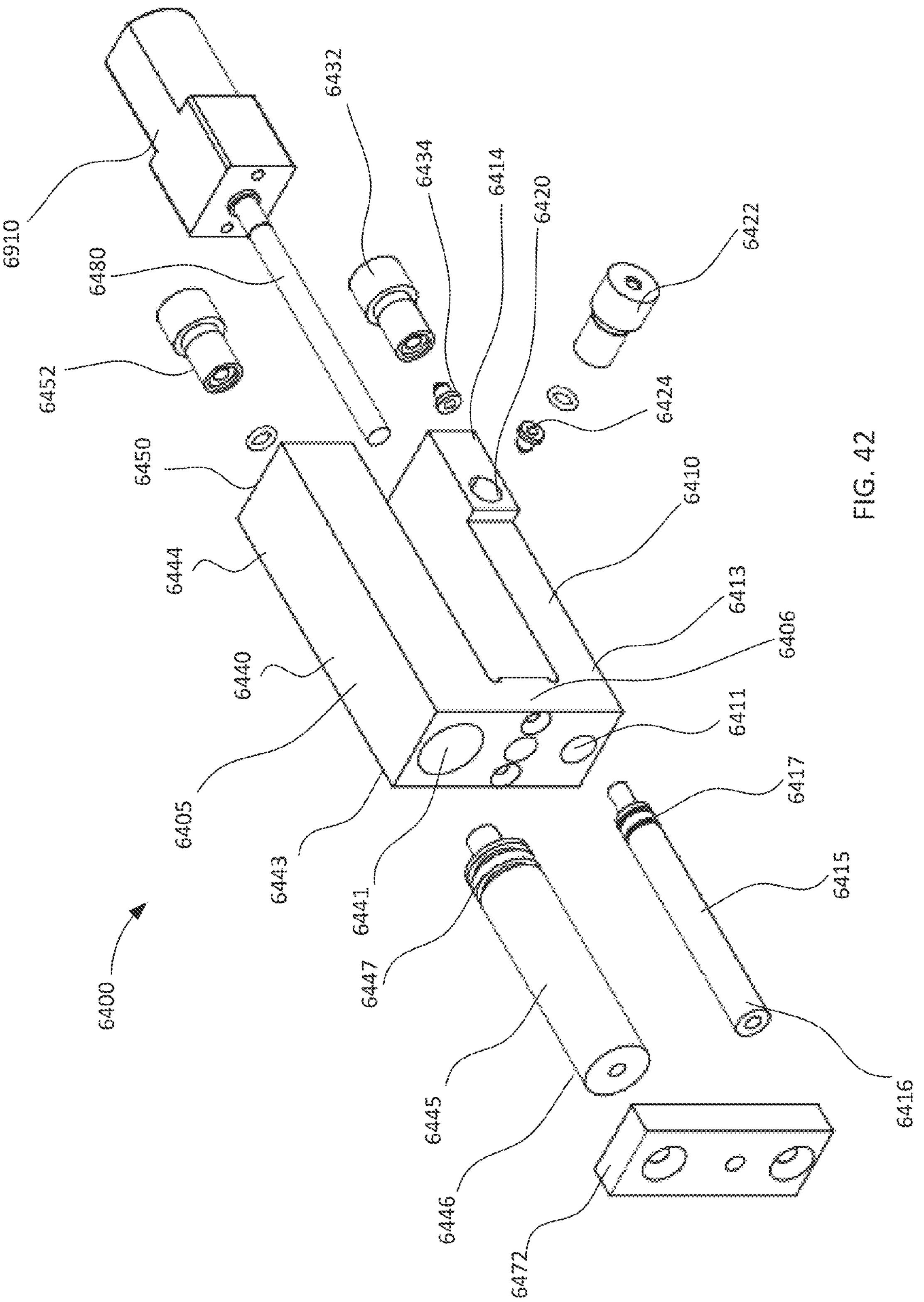
FIG. 42 is an exploded view of the fluid transfer module shown in FIG. 40.
Figure 43:
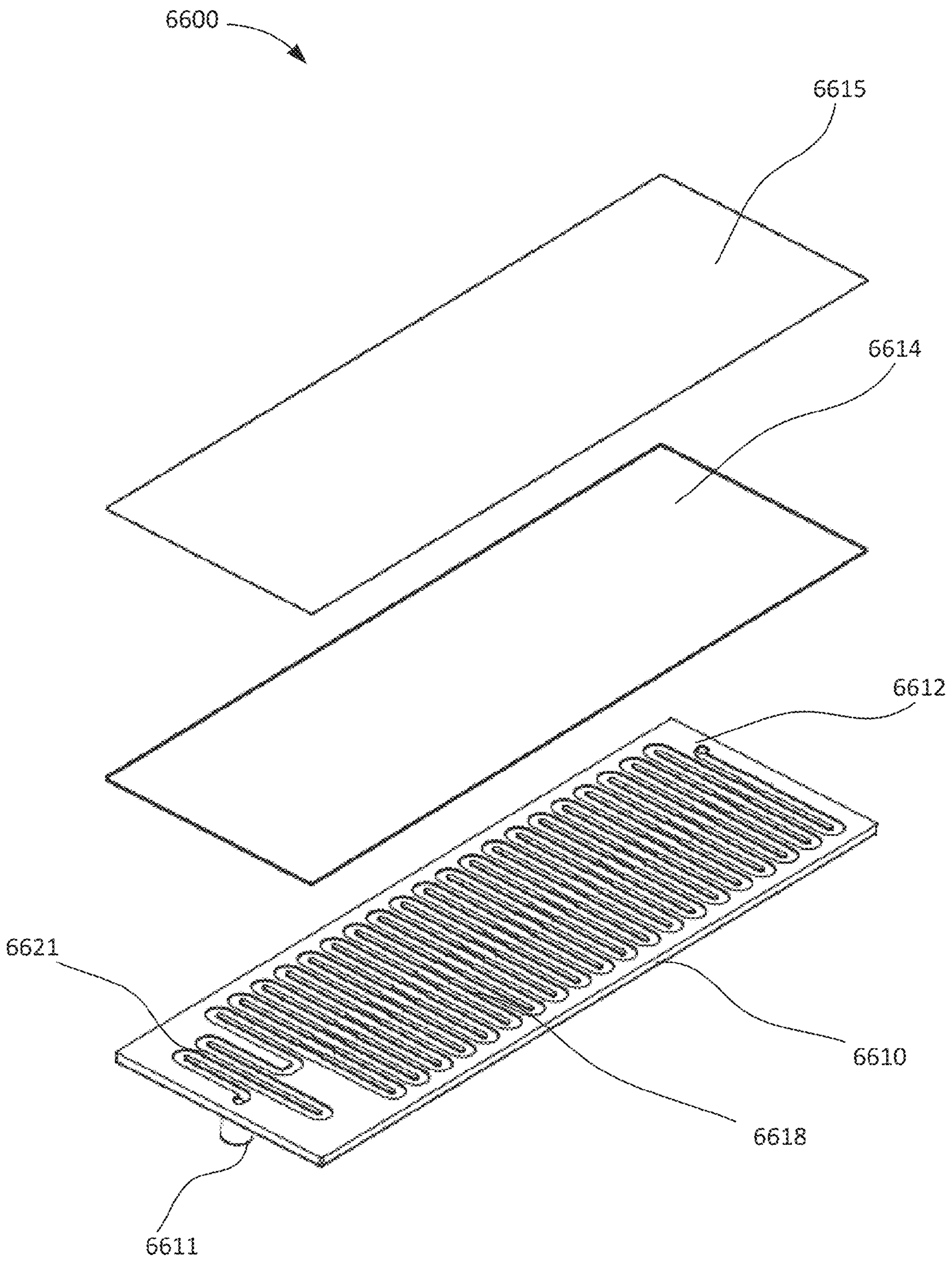
FIG. 43 is an exploded view of an amplification module of the molecular diagnostic test device shown in FIGS. 10 and 11.

FIGS. 40-42 show the fluidic drive module 6400 (also referred to as the fluid transfer module 6400). The fluid transfer module 6400 can be any suitable module for manipulating the sample within the device 6000. Similarly stated, the fluid transfer module 6400 is configured to generate fluid pressure, fluid flow and/or otherwise convey the input sample S1, and all of the reagents through the various modules of the device 6000. As described below, the fluid transfer module 6400 is configured to contact and/or receive the sample flow therein. Thus, in some embodiments, the device 6000 is specifically configured for a single-use to eliminate the likelihood that contamination of the fluid transfer module 6400 and/or the sample preparation module 6200 will become contaminated from previous runs, thereby negatively impacting the accuracy of the results.

As described herein, the fluid transfer module 6400 is configured to aspirate and dispense at constant rates with extremely high accuracy and precision in a small, lightweight, simply constructed, and inexpensively manufactured format. Moreover, the fluid transfer module 6400 is designed to be discarded after a single use, and allows for all of the components to be disposed of in ordinary waste streams throughout the world without the need to disassemble and remove specific components for special treatment after use. The basic design employs a series of individual piston pumps, each with a plunger and barrel assembly, driven by a common actuator composed of a frame, motor and lead screw, to move fluids into different modules within the diagnostic test cartridge. Each stroke, whether aspiration or dispense, combined with targeted positioning of passive valve elements, such as check valves of the flapper, umbrella or duckbill types, moves fluid so that no actuator motions go unused.

By selectively venting specific fluid paths total control over all fluid movement is achieved during power strokes. The advantages offered by using multiple pistons include the ability to address a wide range of fluid volumes, the use of a single stroke length for conveying a wide range of fluid volumes, the use of a single actuator to drive multiple pistons, the ability to provide flow via multiple fluid paths simultaneously, a reduction in the valves between fluid paths, the ability to produce complex differential and tunable pressure gradients within a single fluid circuit (e.g., by placing multiple pistons in fluid communication with each circuit).

As illustrated in FIG. 14, the fluid transfer module 6400 is disposed within the housing 6030 and is configured to manipulate the sample and any of the reagents described herein to convey, mix and otherwise transfer the fluids within the device 6000, as described herein. Referring to FIG. 40, the fluid transfer module 6400 includes a housing 6405 that includes a first barrel portion 6410 and a second barrel portion 6440. The fluid transfer module 6400 also includes a single drive motor 6910 and lead screw 6480 that is configured to actuate both of the barrel portions. The fluid transfer module 6400 also includes various fluidic conduits (e.g., tubes, lines, valves, etc.) connecting the fluid transfer module 6400 to the mixing module 6500, the amplification module 6600, the detection module 6800 and any other components within the device 6000.

The housing 6405 serves as the overall frame for the fluid transfer module 6400 to anchor all of the components therein to the housing 6030. The design of the housing 6405 (or frame) is "U" shaped, and includes the first barrel portion 6410 disposed spaced apart from the second barrel portion 6440, with the drive motor 6910 located therebetween. The housing 6405 includes a mounting portion 6406 in the center of the "U" shape that includes accommodations for seating a bearing assembly (not show) and a set of mounting holes for the mounting of the drive motor 6910. The mounting portion 6406 also defines an opening that provides passage for the lead screw 6480. The housing 6405 can be constructed from material that offers flexibility and compliance while being able to hold tight tolerances and maintain rigidity. Moreover, because the housing 6405 defines at least one bore (e.g., the lumen 6441 within which the sample is contained during transfer, the housing 6405 is also constructed from a biocompatible material. For example, in some embodiments, the housing 6405 can be constructed from polycarbonate, cyclic olefin copolymer (COC), or certain grades of polypropylene.

The first barrel portion 6410 (also referred to as the first barrel assembly) includes a first end portion 6413 and a second end portion 6414 and defines a lumen 6411 (or bore) therein. The bore 6411 has a defined length and an inner surface of defined diameter, and thus can define a "swept volume" for control of the flow of sample and/or reagents. The second end portion 6414 of the bore 6411 has a reduced diameter portion, and is in fluid communication with the inlet port 6420 and the outlet port 6430. The opposite end of the bore 6411 receives the sealing portion 6417 of the first piston plunger 6415. When the first piston plunger 6415 is inserted into the cylinder, an inner chamber of variable volume is formed which follows the formula:

$$V(z)=\pi r^2 z$$

where z is the linear distance traveled by the first piston plunger 6415 and r is the radius of the bore 6411.

The second end portion 6414 of the first barrel portion 6410 includes the inlet port 6420 and the outlet port 6430. The inlet port 6420 includes a fitting 6422, a valve 6424, and O-rings or seals. The inlet port 6420 is configured to receive fluid flow into the bore 6411 (e.g., from the mixing module 6500), as shown by the arrow LL in FIG. 40. The valve 6424 can be any suitable valve (e.g., duckbill valve, check valve or the like) that allows the inlet flow when the first piston plunger 6415 moves out of the bore 6411 (a negative pressure cycle, as shown in FIG. 40), but prevents fluid flow out when the first piston plunger 6415 moves into the bore 6411 (a positive pressure cycle). The outlet port 6430 includes a fitting 6432, a valve 6434, and O-rings or seals. The outlet port 6430 is configured to convey fluid flow out of the bore 6411 (e.g., to the amplification module 6600), as shown by the arrow MM in FIG. 40 (see also the arrow CC in FIG. 9, showing the flow to the amplification module 6600). The valve 6434 can be any suitable valve (e.g., duckbill valve, check valve or the like) that prevents any inlet (or reverse) flow when the first piston plunger 6415 moves out of the bore 6411 (a negative pressure cycle, as shown in FIG. 40), but allows fluid flow out when the first piston plunger 6415 moves into the bore 6411 (a positive pressure cycle).

Although the input port and the output port are shown as being two separate ports, in other embodiments, the first barrel assembly 6410 can be equipped with an integrated flow control module. Whether as separate ports (as shown) or as an integrated unit, the flow control (e.g., the inlet port 6420 and the outlet port 6430) are configured direct and/or control the fluid flow direction during a negative or positive pressure cycle. A secondary function of the inlet port 6420 and the outlet port 6430 is to limit dead volume by reducing captured air. As pressure is either increased or decreased on one side of a valve element relative to the opposite side, fluid is made to pass through the element or stay on a specified side of the element. Depending on the orientation of the valve element and its position in the inlet port 6420 or the outlet port 6430, it may either act as a stop flow valve during a pressure stroke or a pass through orifice.

The first barrel portion 6410 includes the first piston plunger 6415 that is movable disposed within the bore 6411. The first piston plunger 6415 has a long cylindrical shape, and includes a first end portion (or "head") 6416, a central portion (or "shaft"), and the second end portion (or "sealing tip") 6417. The basic body structure can be made from any formable material with the appropriate rigidity such as plastics or metals. The first end portion 6416 is coupled to the drive plate 6472 which in turn is attached to and/or driven by the lead screw 6480. In some embodiments, the first end portion 6416 has a larger diameter than that of the shaft and second end portion 6417. The shaft is smaller in diameter than the sealing tip and is smaller in dimension than the inner diameter of the bore 6411, to allow unrestricted passage. The fit of the shaft diameter to the piston barrel is an important parameter for properly guiding the plunger assembly during operation. The sealing tip 6417 is located opposite the head 6416, and is responsible for smoothly traversing the slightly drafted inner diameter of the bore 6411 while maintaining a seal capable of withstanding both negative and positive pressure conditions through its full stroke. The sealing tip 6417 includes an elastomeric material and has one or more surface that contact the inner diameter of the bore 6411 to form the seal. The shape of the sealing tip 6417 is design to mate with the inner surfaces of the first barrel assembly 6410 to provide minimal dead volume at end of stroke.

The second barrel portion 6440 (also referred to as the second barrel assembly) includes a first end portion 6443 and a second end portion 6444 and defines a lumen 6441 (or bore) therein. The bore 6441 has a defined length and an inner surface of defined diameter, and thus can define a "swept volume" for control of the flow of air, sample and/or reagents. The second end portion 6444 of the bore 6441 has a reduced diameter portion, and is in fluid communication with the flow port 6450. The opposite end of the bore 6441 receives the sealing portion 6447 of the second piston plunger 6445. When the second piston plunger 6445 is inserted into the bore 6441, an inner chamber of variable volume is formed which follows the formula:

$$V(z)=\pi r^2 z$$

where z is the linear distance traveled by the second piston plunger 6445 and r is the radius of the bore 6441.

The second end portion 6444 of the second barrel portion 6440 includes the flow port 6450. The flow port 6450 includes a fitting 6452 and O-rings or seals, and is configured to receive fluid flow into and convey fluid flow out of the bore 6441 (e.g., producing a vacuum within the detection module 6800). In some embodiments, The flow port 6450 can include any suitable valve (e.g., duckbill valve, check valve or the like) that controls the inlet flow when the second piston plunger 6445 moves out of the bore 6441 (a negative pressure cycle, as shown in FIG. 40), and the outlet fluid flow out when the second piston plunger 6445 moves into the bore 6441 (a positive pressure cycle).

Additionally, the inlet flow can be controlled by the vent line 6355, which can be selectively placed into fluid communication with the atmosphere via the rotary valve assembly 6340, as described below. In particular, the vent 6355 can opened thereby allowing any air or fluid within the bore 6441 to be exhausted to atmosphere during a positive pressure cycle, rather than flowing through the detection module 6800. The vent 6355 can be closed during the negative pressure cycle to pull a vacuum through the detection module 6800, as shown by the arrow DD in FIG. 9.

The second barrel portion 6440 includes the second piston plunger 6445 that is movable disposed within the bore 6441. The second piston plunger 6445 has a long cylindrical shape, and includes a first end portion (or "head") 6446, a central portion (or "shaft"), and the second end portion (or "sealing tip") 6447. The basic body structure can be made from any formable material with the appropriate rigidity such as plastics or metals. The first end portion 6446 is coupled to the drive plate 6472 which in turn is attached to and/or driven by the lead screw 6480. In some embodiments, the first end portion 6446 has a larger diameter than that of the shaft and second end portion 6447. The shaft is smaller in diameter than the sealing tip and is smaller in dimension than the inner diameter of the bore 6441, to allow unrestricted passage. The fit of the shaft diameter to the piston barrel is an important parameter for properly guiding the plunger assembly during operation. The sealing tip 6447 is located opposite the head 6446, and is responsible for smoothly traversing the slightly drafted inner diameter of the bore 6441 while maintaining a seal capable of withstanding both negative and positive pressure conditions through its full stroke. The sealing tip 6447 includes an elastomeric material and has one or more surface that contact the inner diameter of the bore 6441 to form the seal. The shape of the sealing tip 6447 is design to mate with the inner surfaces of the first barrel assembly 6440 to provide minimal dead volume at end of stroke.

The drive plate 6472 links the lead screw 6480 to the first piston plunger 6415 and the second piston plunger 6445. In some embodiments the drive plate 6572 can include a threaded bore or captive drive nut (not shown) in engagement with lead screw 6480. In this manner, the threaded bore or captive drive nut can convert the rotational motion of the lead screw 6480 into linear motion. The drive plate 6472 and any threaded portion or drive nut therein can be constructed from materials and/or machined to a tolerance in a way that minimize friction and binding during its transit. In some embodiments, a captive drive nut (not shown) can be configured for some rotational (or non-axial) motion to overcome the tendency to bind under asymmetric forces derived from uneven loading of the two pistons during operation.

The lead screw 6480 delivers the required thrust to translate the drive plate 6472 and displace the first piston plunger 6415 and the second piston plunger 6445. The lead screw is secured to, or part of, the motor 6910. In some embodiments, the distal end of the lead screw 6480 can include a mating feature concentric to the longitudinal axis of the screw and designed to provide constraint in both the axially and radial directions. Such a mating feature on the lead screw can cooperatively function with a bearing assembly (not shown). A variety of materials can be used to make the lead screw including plastics and plastics with filler materials to alter the bearing properties as well as various metals. The thread pitch is predetermined and sets the fluid flow rates of the fluid transfer module 6400.

In some embodiments, the fluid transfer module 6400 conveys fluid throughout the device 6000 according to a prescribed protocol that includes multiple parts. When initiated, the first part of the protocol (the "mixing method") signals the motor 6910 to move in a first direction that causes the first barrel assembly 6410 to develop negative pressure in the inlet port 6420 thereby drawing in fluid from the inactivation chamber 6300, which is at atmospheric pressure, and towards the mixing module 6500. The flow rate and/or dwell time of the sample within the mixing module 6500 can be controlled by changing the rotational speed of the motor 6910 and/or including periods of dwell during the movement of the motor 6910. In this manner, the desired fluid flow characteristics within the mixing module 6500 can be established or maintained to ensure the desired mixing. The mixing method includes continued movement of the motor 6910 in the first direction thereby drawing in fluid from the mixing module 6500, through the inlet port 6420, and into the bore 6411 of the first barrel assembly 6410. Fluid conveyance continues into the bore 6411 until it has been filled as prescribed. Once filled, the control module 6950 signals the motor 6910 to reverse rotational direction, causing the development of positive pressure within the bore 6411 (the "fluid delivery method"). The positive pressure acts on the valve 6424, effectively closing the inlet port 6420. As positive pressure builds, fluid flows through the outlet port 6430, through tubing and then onward to the amplification module 6600. This is shown schematically by the arrow CC in FIG. 9. Continued movement of the motor 6910 in the second direction pushes the sample through the amplification module 6600 at the desired flow rate, and into the detection module 6800. During this first part of the protocol (i.e., the mixing method and the fluid delivery method), the bore 6441 within the second barrel assembly 6440 is maintained at atmospheric pressure via the vent line 6355, which is controlled through a series of venting actions initiated by the control module 6950 and conducted by the rotary venting valve 6340.

The second part of the fluid transfer protocol (the "detection method") is initiated by an advancement of the rotary vent valve 6340, which effectively exchanges control over the fluid movements from the first barrel assembly 6410 to the second barrel assembly 6440. The "detection method" protocol reverses the motor direction for a second time (i.e., the motor 6910 begins rotating in the first direction). This causes the drive plate 6472 and thus, the second piston plunger 6445 to retract causing a negative pressure to develop within the chamber of the second barrel assembly 6440 (because the vent line 6355 is closed). The pressure drop created between the detection module 6800 and the bore 6441 results in a higher pressure on the inlet side of the detection module 6800 then on the outlet side of the detection module 6800 creating a preferred direction of flow into the bore 6441 of the second barrel assembly 6440. This is shown schematically by the arrow DD in FIG. 9. After the sample has been conveyed from the amplification module 6600 through the detection module 6800, continued retraction of the second piston plunger 6445 can be used, in conjunction with the valve assembly 6340, to sequentially flow detection reagents through the detection module 6800. The operation of the valve assembly 6340 is described below.

The motor 6910 can be any suitable variable direction motor to provide power to the fluid transfer module 6400 with adequate torque to drive the lead screw 6480. The pitch of the lead screw 6480 is also determined to provide the desired accuracy and flow rates. There are a multitude of factors and parameters requiring consideration and control to maintain a balanced load during extension and compression cycles, and to maintain the desired precision and accuracy. A balanced load around the drive train presents a significant challenge for a multi-piston system with a single drive motor (e.g., motor 6910) as there is a continually varying load due to changing head pressure (positive or negative) as fluid flows through elements of the circuitry. To achieve a balance in load, compression in the sealing tips within piston barrels must be controlled, along with the amount of surface area in contact with the barrel due to the compression. Additionally, the amount of draft or taper in the manufacturing of the piston barrels must be considered, as small and large diameter seals behave differently under increasing and decreasing compression conditions. Failure to consider the issue of load balancing results in a non-uniform fluid velocity profile which intern will result in inefficiencies during amplification and inconsistencies during detection.

Component sizing for flow rate control and chamber volume in a dual-piston fluid transfer module system are demonstrated in Tables 1-5 below. From the calculation in the tables, specifications for a motor and the control requirements for the motor 6910 are determined. For example, in some embodiments, consider that the first barrel assembly 6410 (also referred to as the "amplification piston" in Table 1 below) has a requirement to deliver fluid at a rates between 0.3 μl/sec and 0.5 μl/sec. Given the nominal diameter of 4.65 mm for the first bore 6411, a full stroke of 60 mm, and a lead screw pitch of 0.5 mm/rev, the motor 6910 is required to operate with sufficient torque between about 2.12 rpm and about 6.53 rpm. The second barrel assembly 6440 (also referred to as the "detection piston" in Table 1 below) has a requirement to deliver fluid at a rate between 15 μl/sec and 60 μl/sec. Given the nominal diameter of 8.5 mm for the second bore 6441, a full stroke of 60 mm, and a lead screw pitch of 0.5 mm/rev, the motor 6910 is required to operate with sufficient torque between about 61.7 rpm and about 63.44 rpm. The total range of speeds for a motor 6910 to meet the requirements specified is therefore about 2 rpm to about 64 rpm, with sufficient torque to overcome both the back pressure from the fluid and the drag due to the piston seals.

TABLE 1

| Amplification Piston 1 | | | Detection Piston 2 | | |
|---|---|---|---|---|---|
| 0.3 | flow rate (min) | ul/sec | 15 | flow rate (min) | ul/sec |
| 0.5 | flow rate (max) | ul/sec | 30 | flow rate (max) | ul/sec |
| 4.65 | barrel diameter | mm | 8.5 | barrel diameter | mm |
| 30 | piston stroke | mm | 30 | piston stroke | mm |
| 0.5 | lead screw pitch | mm/rev | 0.5 | lead screw pitch | mm/rev |
| 60 | Total Rev/ Stroke | | 60 | Total Rev/ Stroke | |
| Vol/Stroke | 509.47 | ul | Vol/Stroke | 1702.35 | ul |
| Vol/Rev | 8.49 | ul | Vol/Rev | 28.37 | ul |
| flow rate (min) | 0.04 | rev/sec | flow rate (min) | 0.53 | rev/sec |
| flow rate (min) | 2.12 | rev/min | flow rate (min) | 31.72 | rev/min |
| flow rate (max) | 0.06 | rev/sec | flow rate (max) | 1.06 | rev/sec |
| flow rate (max) | 3.53 | rev/min | flow rate (max) | 63.44 | rev/min |

The amount of torque that is sufficient to achieve the required flow rates can be determined through an evaluation of data tabulated during repeated measurements of the linear force needed to compress and extend the first piston plunger 6415 and the second piston plunger 6445, as indicated below in Tables 2-4.

TABLE 2

| Piston 1 Compression (Individual) | | | Piston 1 Extension (Individual) | | |
|---|---|---|---|---|---|
| Meas # | Crack (IbF) | Drive (IbF) | Meas # | Crack (IbF) | Drive (IbF) |
| 1 | 0.09 | 0.04 | 1 | 0.19 | 0.06 |
| 2 | 0.14 | 0.05 | 2 | 0.1 | 0.07 |
| 3 | 0.19 | 0.02 | 3 | 0.07 | 0.08 |
| 4 | 0.07 | 0.02 | 4 | 0.1 | 0.07 |
| 5 | 0.08 | 0.03 | 5 | 0.13 | 0.05 |
| 6 | 0.09 | 0.04 | 6 | 0.09 | 0.04 |
| Average | 0.11 | 0.03 | Average | 0.11 | 0.06 |

TABLE 3

| Piston 2 Compression (Individual) | | | Piston 2 Extension (Individual) | | |
|---|---|---|---|---|---|
| Meas # | Crack (IbF) | Drive (IbF) | Meas # | Crack (IbF) | Drive (IbF) |
| 1 | 0.34 | 0.11 | 1 | 0.21 | 0.14 |
| 2 | 0.4 | 0.09 | 2 | 0.15 | 0.13 |
| 3 | 0.48 | 0.04 | 3 | 0.19 | 0.15 |
| 4 | 0.33 | 0.05 | 4 | 0.19 | 0.04 |
| 5 | 0.32 | 0.16 | 5 | 0.23 | 0.11 |
| 6 | 0.34 | 0.11 | 6 | 0.17 | 0.14 |
| Average | 0.37 | 0.09 | Average | 0.19 | 0.12 |

TABLE 4

| Dual Piston Compression | | | Dual Piston Extension | | |
|---|---|---|---|---|---|
| Meas # | Crack (IbF) | Drive (IbF) | Meas # | Crack (IbF) | Drive (IbF) |
| 1 | 0.54 | 0.38 | 1 | 0.46 | 0.12 |
| 2 | 0.48 | 0.44 | 2 | 0.24 | 0.14 |
| 3 | 0.27 | 0.46 | 3 | 0.28 | 0.19 |
| 4 | 0.32 | 0.49 | 4 | 0.2 | 0.22 |
| 5 | 0.35 | 0.51 | 5 | 0.3 | 0.1 |
| 6 | 0.39 | 0.37 | 6 | 0.31 | 0.14 |
| Average | 0.39 | 0.44 | Average | 0.30 | 0.15 |

The motor torque required to achieve a specific linear drive force in the lead screw 6480 coupled system is a function of parameters including lead screw pitch and lead screw efficiency. Lead screw efficiency is itself a function of many factors including, rotation speed and material selection for both the threaded portion of the drive plate 6472 (and any drive nut therein) and lead screw 6480. The required motor torque can be represented using the formula:

$$\tau(F)=F(p/2\pi\eta)$$

In the formula, τ(F) is the torque as a function of the force, F is the measured force, p is the lead screw pitch, π is the constant "pi", and η is the lead screw efficiency. From the tabulated data the maximum torque required to carry out the fluid transfer function can be determined. Additionally, these calculated values are used to specify the motor 6910 such that it can handle the maximum required to load that will be experienced during both compression and extension strokes of the fluid transfer module 6400. For example, the maximum torque experienced during fluid transfer occurs during the compression stroke of the combined dual piston and its value is 0.211 oz-in (shown in Table 5).

TABLE 5

| Motor Torque Calculations | | | |
|---|---|---|---|
| 40% | lead screw efficiency | η | |
| 0.5 | lead screw pitch (mm) | p | |
| 3.14 | pi | π | |
| **Force (IbF)** | **Measurement Description** | **Torque (kg-cm)** | **Torque (oz-in)** |
| 0.02 | Piston 1 min. drive force-compression | 0.109 | 0.008 |
| 0.19 | Piston 1 max. crack force-compression | 1.032 | 0.074 |
| 0.04 | Piston 1 min. drive force-extension | 0.217 | 0.016 |
| 0.19 | Piston 1 max. crack force-extension | 1.032 | 0.074 |
| 0.04 | Piston 2 min. drive force-compression | 0.217 | 0.016 |
| 0.48 | Piston 2 max. crack force-compression | 2.608 | 0.188 |
| 0.04 | Piston 2 min. drive force-extension | 0.217 | 0.016 |
| 0.23 | Piston 2 max. crack force-extension | 1.250 | 0.090 |
| 0.54 | Dual Piston max. force-compression | 2.934 | 0.211 |
| 0.46 | Dual Piston max. force-extension | 2.499 | 0.180 |
| | max motor torque for fluid transfer | 2.934 | 0.211 |

Any suitable motor can be used to drive the fluid transfer module to achieve the desired flow rates and power consumption targets as described herein. For example, based on the maximum and minimum flow rates for the assay, a lead screw 6480 pitch can be selected and the maximum required torque is calculated. In embodiments, the motor 6910 can be the Pololu item #1596 (Source: https://www.pololu.com/category/60/micro-metal-gearmotors). This motor 6910 can deliver the desired performance (14 RPM, 70 oz-in stall torque, 986.41:1 gear ratio).

Amplification Module

As illustrated in FIGS. 9 (schematically) and 43-45, the amplification module 6600 is configured to perform a PCR reaction on an input of target DNA mixed with required reagents (from the mixing module 6500, described above). In some embodiments, the amplification module 6600 is configured to conduct rapid PCR amplification of an input target. In some embodiments, the amplification module 6600 is configured to generate an output copy number that reaches or exceeds the threshold of the sensitivity of the detection module 6800.

Figure 45:
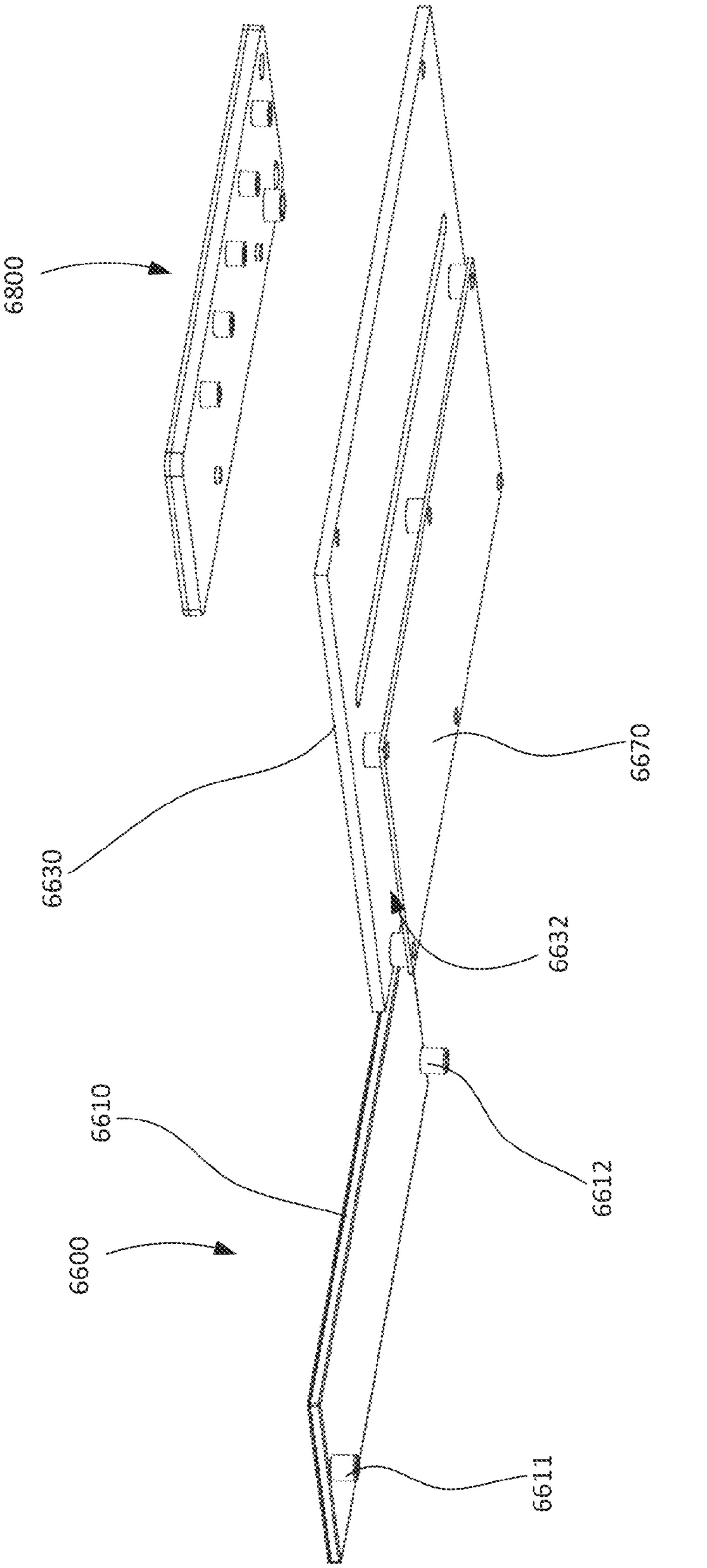
FIG. 45 is an exploded perspective view of the amplification module shown in FIG. 43 and a detection module of the molecular diagnostic test device shown in FIGS. 10 and 11.
Figure 46:
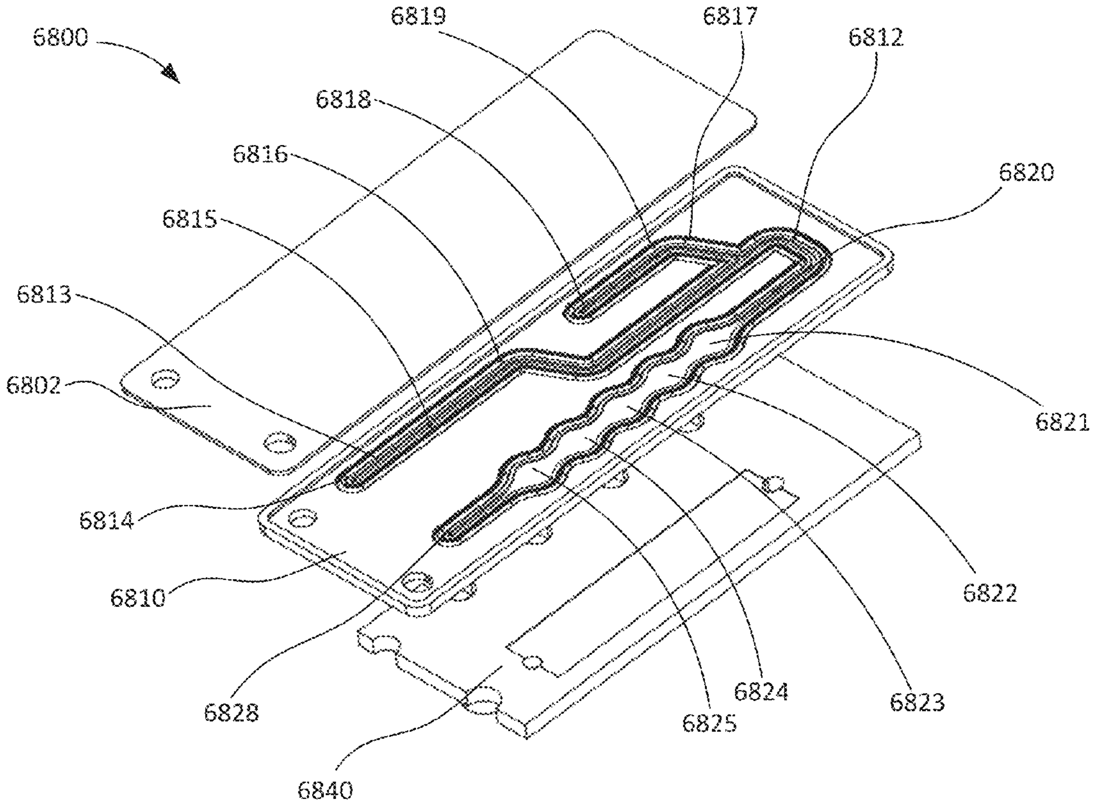
FIG. 46 is an exploded perspective view of the detection module of the molecular diagnostic test device shown in FIGS. 10 and 11.

The amplification module 6600 includes a flow member 6610, a substrate 6614 and a lid (or cover) 6615. As shown in FIG. 45, the amplification module also includes a heater assembly 6630 and electrical interconnects (not shown) to connect amplification module 6600 to the surrounding modules. The components of the amplification module 6600 can be coupled together by any suitable manner, such as, for example, by clamps, screws, adhesive or the like. In some embodiments, the flow member 6610 is fixedly coupled to the heater assembly 6630. Said another way, in some embodiments, the flow member 6610 is not designed to be removed and/or decoupled from the heater assembly 6630 during normal use. For example, in some embodiments, the heater assembly 6630 is coupled to the flow member 6610 by a series of clamps, fasteners and potting material. In other embodiments, the heater assembly 6630 is coupled to the flow member 6610 by an adhesive bond. This arrangement facilitates a single-use, disposable device 6000.

The flow member 6610 includes an inlet port 6611, and outlet port 6612, and defines an amplification flow path (or channel) 6618. As shown, the amplification flow path has a curved, switchback or serpentine pattern. More specifically, the flow member (or chip) 6610 has two serpentine pattern molded into it—the amplification pattern and the hot-start pattern 6621. The amplification pattern allows for PCR to occur while the hot-start pattern 6621 accommodates the hot-start conditions of the PCR enzyme.

Figure 44:
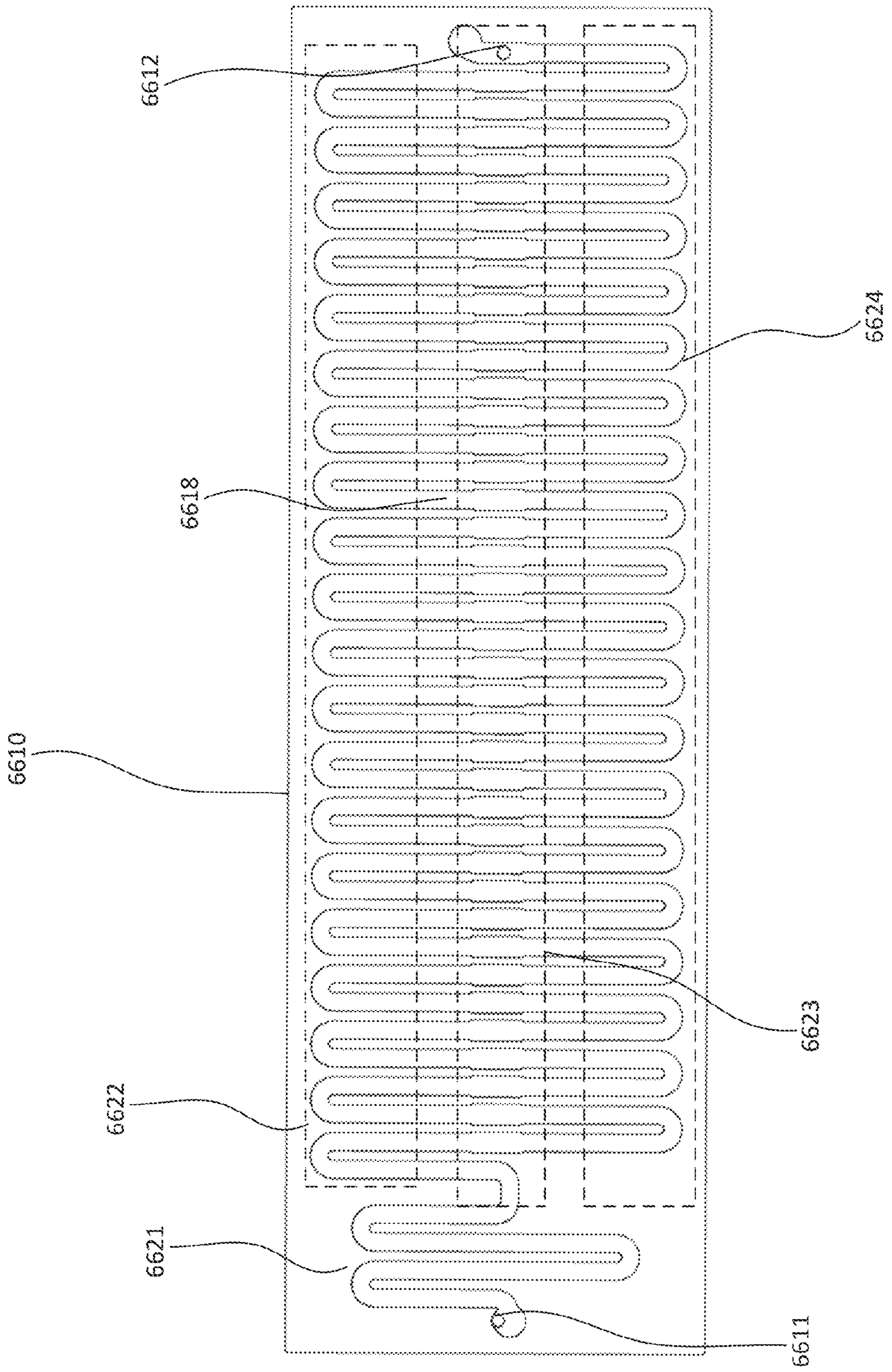
FIG. 44 is a top view of a flow member of the amplification module shown in FIG. 43.

The serpentine arrangement provides a high flow length while maintaining the overall size of the device within the desired limits. Moreover, the serpentine shape allows the flow path 6618 to intersect heater assembly 6630 at multiple locations. This arrangement can produce distinct "heating zones" throughout the flow path 6618, such that the amplification module 6600 can perform a "flow through" PCR when the sample flows through multiple different temperature regions. Specifically, as shown in FIG. 44, the heater assembly 6630 is coupled to the flow member 6610 to establish three temperature zones identified by the dashed lines: a first temperature zone 6622, a second (or central) temperature zone 6623, and a third temperature zone 6624. In use, the first temperature zone 6622 and the third temperature zone 6624 can be maintained at a temperature of about 60 degrees Celsius (and/or at a surface temperatures such that the fluid flowing therethrough reaches a temperature of about 60 degrees Celsius). The second temperature zone 6623 can be maintained at a temperature of about 90 degrees Celsius (and/or at a surface temperatures such that the fluid flowing therethrough reaches a temperature of about 90 degrees Celsius).

As shown, the serpentine pattern establishes 40 different zones of "cold to hot to cold;" or 40 amplification cycles. In other embodiments, however, the flow member 6610 (or any of the other flow members described herein) can define any suitable number of switchbacks or amplification cycles to ensure the desired test sensitivity. In some embodiments, the flow member can define at least 30 cycles, at least 34 cycles, at least 36 cycles, at least 38 cycles, or at least 40 cycles.

The dimensions of the flow channel 6618 in the flow member 6610 determine the temperature conditions of the PCR and dictate the overall dimensions of the chip, and thus impact the overall power consumption. For example, a deeper, narrower channel will develop a larger gradient in temperature from the side closest to the lid 6615 to the bottom (resulting in lower PCR efficiency). This arrangement, however, requires less overall space since the channels will take up less overall surface area facing the heater assembly 6630 (and thus require less energy to heat). The opposite holds true for a wide and shallow channel. In some embodiments, the depth of the flow channel 6618 is about 0.15 mm and the width of the flow channel 6618 is between about 1.1 mm and about 1.3 mm. More particularly, in some embodiments, the flow channel 6618 has a width of about 1.1 mm in the "narrow" sections (that are within the first temperature zone 6622 and the third temperature zone 6624) and about 1.3 mm in the "wide" section (that falls within the second temperature zone 6623). In some embodiments, the overall path length is about 960 mm (including both the amplification portion and the hot start portion 6621). In such embodiments, the total path length of the amplification portion is about 900 mm. This produces a total volume of the flow channel 6618 of about 160 μl (including the hot start portion 6621) and about 150 μl (without the hot start portion 6621). In some embodiments, the separation between each parallel path is between about 0.4 mm and about 0.6 mm.

As fluid passes through the serpentine flow channel 6618, it is inherently mixed due to the "u-turns" in the pattern. The liquid near the outside of the channel 6618 walls takes a long path of travel, while the liquid on the inside of the turn takes a shorter path. As flow moves towards the straight sections of the channel 6618, the two areas of liquid that were not previously adjacent can become mixed. This prevents localized depletion of reagents as well as homogenizing the concentrations of target DNA. If left completely unmanaged this effect can also cause a portion of the liquid to have a reduced cold dwell time—the liquid on the shorter path does not spend as much time in the cold zone.

Creating a cold zone dwell that allows even the inside path to maintain the minimum cold dwell is one solution to this problem. The other is to "pinch" the turn areas in an attempt to force all of the liquid to have the same distance to travel thus forcing all of the liquid to have the same cold dwell time.

The flow member 6610 can be constructed from any suitable material, and can have any suitable thickness. For example, in some embodiments, the flow member 6610 (and any of the flow members described herein) can be can be molded from COC (Cyclic Olefin Copolymer) plastic, which has inherent barrier properties and low chemical interactivity. In other embodiments, the flow member 6610 (and any of the flow members described herein) can be can be constructed from a graphite-based material (for improved thermal properties). The overall thickness of the flow member 6610 can be less than about 0.5 mm, less than about 0.4 mm, less than about 0.3 mm or less than about 0.2 mm.

The flow member 6610 is lidded with a thin plastic lid 6615 and a substrate 6614, which are attached with a pressure sensitive adhesive (not identified in the figure). The lid 6615 allows for easy flow of thermal energy from the heater assembly 6630. In some embodiments, the flow member 6610 also contains features to allow other parts of the assembly (e.g., the heater assembly 6630) to correctly align with the features on the flow member 6610, as well as features to allow the fluidic connections to be bonded correctly. The adhesive used to attach the lid 6615 is selected to be "PCR-safe" and is formulated to not deplete the reagent or target organism concentrations in the PCR reaction In some embodiments, the output volume from the amplification module 6600 is sufficient to fully fill the detection chamber in the detection module 6800.

The heater 6630 (and any of the heaters described herein) can be of any suitable design. For example, in some embodiments, the heater 6630 can be a resistance heater, a thermoelectric device (e.g. a Peltier device), or the like. In some embodiments, the heater assembly 6630 can include one or more linear "strip heaters" arranged such that the flow path 6618 crosses the heaters at multiple different points to define the temperature zones as described above.

In some embodiments, the heater assembly 6630 can include multiple different heater/sensor/heat spreader constructs (not shown). The configuration and mating alignment of these determines the areas of the temperature zones 6622, 6623 and 6624 on the flow member 6610. The individual heater constructs (or strip heaters) can be controlled to a predetermined set point by the electronics module 1950. In some embodiments, each construct can include a resistive heater with an integrated sensor element which, when connected to the electronics module 1950, allows for the temperature of the attached heat spreader to be regulated to the correct set point.

In some embodiments, the amplification module 6800 is configured to consume minimal power, thus allowing the device 6000 to be battery-powered by the power source 6905 (e.g., by a 9V battery). In some embodiments, for example, the power source 6905 is a battery having a nominal voltage of about 9 VDC and a capacity of less than about 1200 mAh.

In use, fluid is conveyed into the amplification module 6600 by the fluid transfer module 6400 as described above. The amplification is accomplished by the movement of the fluid through the serpentine flow path 6618 held in contact with the heater assembly 6630, during which the fluid inside the chip passes through alternating temperature zones. The flow rate and the temperature of the zones, as well as the layout of the amplification flow path 6618, can determine the intensity and the duration of the various temperature conditions as well as the total number of PCR cycles. After the flow path 6618 fills with liquid, any liquid emerging from the output side has undergone PCR (as long as the total volume of the liquid collected from the output is lower or equal to the "output" volume). The output of the module flows directly into the detection module 6800. In some embodiments, for example, the flow rate through the amplification path 6618 can be about 0.35 μl/second, and the temperature zones can fluctuation the temperature between about 95 C and about 60 C. The length and/or flow areas can be such that the sample is maintained at about 95 C for about 1.5 seconds, and can be maintained at about 60 C for about 7 seconds. In other embodiments, the flow rate through the amplification path 6618 can be at least 0.1 μl/second. In yet other embodiments, the flow rate through the amplification path 6618 can be at least 0.2 μl/second.

Detection Module

As illustrated in FIGS. 9 (schematically) and 46-49, the detection module 6800 is configured to receive output from the amplification module 6600 and reagents from the reagent module 6700 to produce a colorimetric change to indicate presence or absence of target organism in the initial input sample. The detection module 6800 also produces a colormetric signal to indicate the general correct operation of the test (positive control and negative control). As described herein, the detection module 6800 is configured for enzyme linked detection reaction resulting in a colorimetric change in the detection chamber. Thus, the outputs (e.g., OP1, OP2, OP3 shown in FIG. 66) are non-fluorescent signals. This arrangement allows the device 6000 to be devoid of a light source (e.g., lasers, light-emitting diodes or the like) and/or any light detectors (photomultiplier tube, photodiodes, CCD devices, or the like) to detect and/or amplify the output produced by the detection module. In some embodiments, color change induced by the reaction is easy to read and binary, with no requirement to interpret shade or hue.

In some embodiments, the readout of the detection module 6800 is easy to read and remains so for sufficient time. For example in some embodiments, the output signals OP1, OP2, and/or OP3 shown in FIG. 66 can remain present for at least about 30 minutes. Moreover, in some embodiments, the device 6000 (and any of the other devices shown and described herein) can be configured to produce the signals OP1, OP2, and/or OP3 in a time of less than about 25 minutes from when the sample S1 is received. In other embodiments, the device 6000 (and any of the other devices shown and described herein) can be configured to produce the signal OP1, OP2, and/or OP3 in a time of less than about 20 minutes from when the sample S1 is input, less than about 18 minutes from when the sample S1 is input, less than about 16 minutes from when the sample S1 is input, less than about 14 minutes from when the sample S1 is input, and all ranges therebetween.

Figure 47:
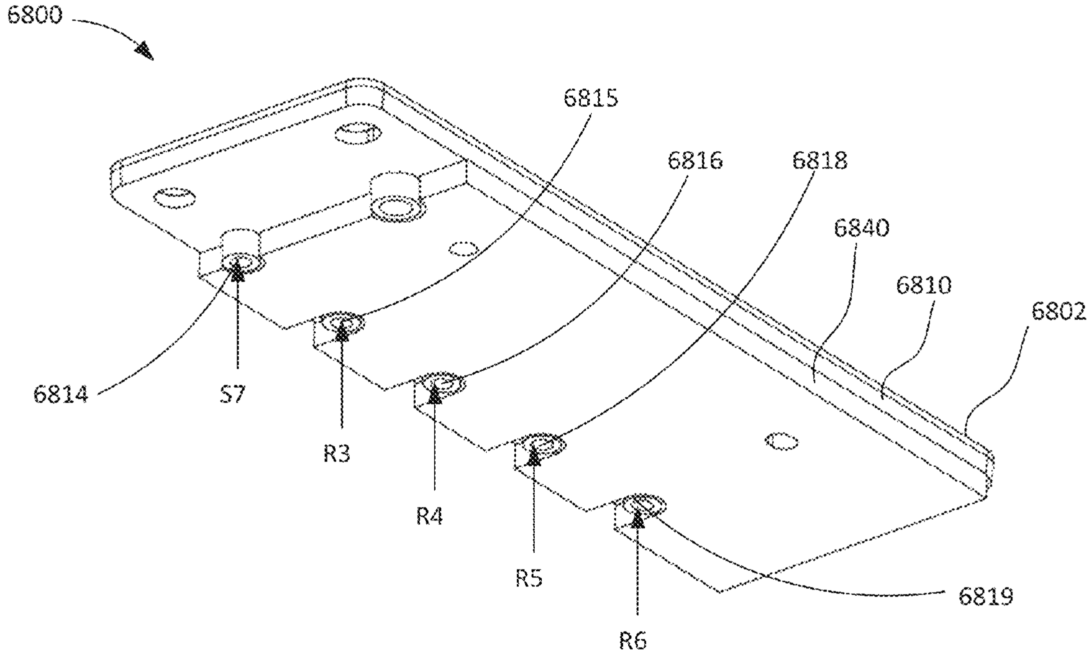
FIG. 47 is bottom perspective view of the detection module shown in FIG. 46.

The detection module 6600 includes a detection flow cell (or "housing") 6810, a viewing window (or lid) 6802, a heater/sensor assembly 6840, and fluidic and electrical interconnects (not shown). The detection flow cell 6810 defines a detection chamber/channel 6812 having a first inlet portion 6813, a second inlet portion 6817, a detection portion 6820 and an outlet portion 6828. The first inlet portion 6813 includes a first inlet port 6814, a second inlet port 6815 and a third inlet port 6815. The first inlet port 6814 is fluidically coupled to the outlet of the amplification module 6600 and receives the amplified sample (indicated by the arrow S7 in FIG. 47). The second inlet port 6815 is fluidically coupled to the reagent module 6700 and receives the first reagent, which is a first wash (indicated by the arrow R3 in FIG. 47). The third inlet port 6816 is fluidically coupled to the reagent module 6700 and receives the second reagent, which can be, for example, a horseradish peroxidase (HRP) enzyme with a streptavidin linker (indicated by the arrow R4 in FIG. 47).

The second inlet portion 6817 includes a fourth inlet port 6818, and a fifth inlet port 6819. The fourth inlet port 6818 is fluidically coupled to the reagent module 6700 and receives the third reagent, which is a second wash (indicated by the arrow R5 in FIG. 47). The fifth inlet port 6819 is fluidically coupled to the reagent module 6700 and receives the fourth reagent, which can be, for example, a substrate formulated to enhance, catalyze and/or promote the production of the signal from the detection reagent R4 (indicated by the arrow R6 in FIG. 47). In some embodiments, for example, the reagent R4 can be a tetramethylbenzidine (TMB) substrate. The second inlet portion 6817 is separate from the first inlet portion 6813 to ensure that any downstream area within the path 6810 into which the substrate (reagent R6) might flow has been thoroughly washed of enzyme (reagent R4). Similarly stated, the second inlet portion 6817 is separate from the first inlet portion 6813 to minimize interaction between the substrate and the enzyme. Undesired interaction could cause color change, and potentially false positives results.

The detection portion (or "read lane") 6820 of the detection channel 6812 is defined, at least in part by, and/or includes a detection surface. Specifically, the detection portion 6820 includes a first detection surface (or spot) 6821, a second detection surface (or spot) 6822, a third detection surface (or spot) 6823, a fourth detection surface (or spot) 6824, and a fifth detection surface (or spot) 6825. Each of the detection surfaces are chemically modified to contain hybridization probes (i.e., single stranded nucleic acid sequences that capture complementary strand of target nucleic acid.) to capture complementary strands of the amplified nucleic acid. The first detection surface 6821 includes a hybridization probe specific to *Neisseria gonorrhea* (NG). The second detection surface 6822 includes a hybridization probe specific to *Chlamydia trachomatis* (CT). The third detection surface 6823 includes a hybridization probe specific to *Trichomonas vaginalis* (TV). The fourth detection surface 6824 includes a hybridization probe for a positive control (*A. fischeri, N. subflava*, or the like). The fifth detection surface 6825 includes a non-target probe for a negative control.

The positive control surface 6824 includes any suitable organism, such as, for example, *Aliivibrio fischeri*. This organism is suitable because it is gram negative, nonpathogenic, bio safety level 1, not harmful to the environment, and is extremely unlikely to be found on a human. The positive control surface 6824 contains capture probes for both the control organism (e.g., *A. fischeri*) as well as each of the target organisms. This arrangement ensures that the positive control surface 6824 always produces color if the device functions correctly. If only the control organism were present, a very strong positive for one of the target organisms could "swamp out" or "outcompete" the amplification of the control organism during PCR. Under such circumstances, the positive control spot would not produce a color change which would be confusing for the user. This arrangement facilitates the detection method and the device 6000 being operated by a user with minimal (or no) scientific training, in accordance with methods that require little judgment.

The positive control portion of the assay is designed to be sensitive to inhibition. More particularly, this is accomplished by optimizing the number of control organisms added to the system (e.g., via the lyophilized reagents or other suitable delivery vehicle), as well as the concentration of the primers used to amplify the control organism. In this manner, the control organism should not be amplified if there is enough PCR inhibition to prevent a target organism from amplification. If a weak positive signal for one of the target organisms has been inhibited then the system should register an "Invalid" run (due to no signal from the positive control spot) rather than being read as a false negative. The ordering of the capture probe surfaces ensures that a positive control signal is valid because the target spots must first have been exposed to the same reagents.

The negative control surface 6825 includes a non-target probe and should always appear white (no color). The placement of the negative control surface 6825 as the last spot is preferred because this arrangement shows whether the reagent volumes, fluidic movement, and wash steps were working properly.

The area of the spots on the detection surfaces (and thus the width of the detection surfaces within the flow channel 6812) is selected based on ease of manipulation as the area has little effect on the visibility of the spot (to a certain lower limit at which creating the spot becomes an issue). The volume of the liquid above the spot (i.e., the depth of the flow channel 6812), however, does affect the intensity of the color generated. A larger volume (or depth) will generate a deeper color, while a lower volume will generate a paler color. After the flow of sample and reagents, diffusion can take place, and color from the spots can migrate into areas outside the designated spot. The total amount of time required for color from one spot to migrate and make the neighboring spot appear positive affects the maximum read period of the test. A larger volume flow cell, with more intense colors also makes the migrating colors more intense. Since larger volume also makes the amplification module take more time to complete its process, a lower volume flow channel is preferable. In some embodiments, the depth of the detection portion 6820 is between about 0.135 mm and about 0.165 mm.

The lid (or "viewing window") 6802 allows the spot locations within the flow channel 6812 be seen through the main housing 6010 of the device 6000. Specifically, as shown in FIG. 66, each of the detection surfaces is aligned with and/or is viewable through the corresponding detection openings defined by the top housing member 6010. The viewing window 6802 is a simple colored piece of plastic providing contrast to the spot locations on the detection surfaces and obscuring any non-spot location in the detection channel 6812. The viewing window 6820 can have a simple molded plastic optic to allow the viewer to see the spot from any angle, and to make the result easier to read.

Figure 48:
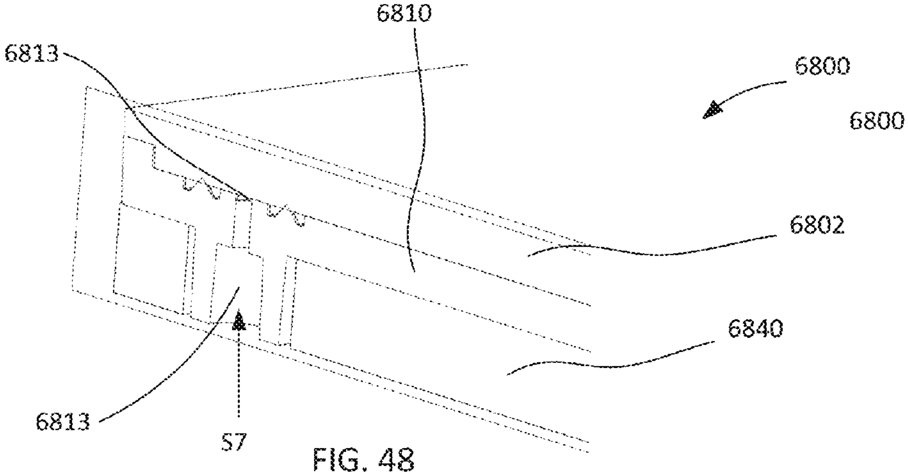
FIG. 48 is a side cross-sectional view of a portion of the detection module shown in FIG. 46.

The flow cell 6810 can be constructed from any suitable material. For example, in some embodiments, the flow cell 6810 can be molded in COC plastic, then coupled to the lid 6802 to form flow channel 6812. COC plastic is used for the construction of the detection flow cell due to its barrier and chemical properties. The barrier properties are necessary to maintain the chemistry stored on the surface of the part over time. COC plastic is sufficiently chemically active to accept the chemical modification necessary to spot the detection zones, but not active enough to induce non-specific binding of the reagents. In some embodiments, the molded flow cell 6810 can include flash traps or other geometric constructs to facilitate mounting of the lid 6802 to the flow cell 6810 (see e.g., FIG. 48). Moreover, the detection channel 6812 is shaped to allow liquid to fill it evenly and without forming air bubbles as liquid is introduced to the chamber.

The heater construct 6840 is a resistive heater with an integrated sensor. The heater 6840 is attached to the detection flow cell 6810 to allow for easy flow of thermal energy into the fluid contained in the channel 6812. The heater 6840 is electrically connected to the electronics module to allow it to control to desired set temperatures.

In use, the post-amplification solution is flowed into the detection flow cell 6810 from the amplification module 6600. After the sample is in the flow cell 6810, DNA strands in the post-amplification solution bind to complimentary pre-spotted zones on the detection surfaces 6821, 6822, 6823, 6824, and 6825. The pre-spotted zones are configured and/or formulated to bind only their specific DNA targets, which are different for each zone based on the target organism that the zone represents. Once sufficient amount of time has passed, the amplicon solution is flushed from the flow cell 6810 with a wash solution (reagent R3), and an enzyme solution (reagent R4) is flowed into and maintained within the flow channel 6812. During the dwell time, the enzyme binds to any DNA strands still remaining in the flow cell (which are now attached to specific detection surfaces 6821, 6822, 6823, 6824, and 6825). After the enzyme binding has occurred the flow cell 6810 is flushed with a second wash (reagent R5), and is then refilled with a substrate solution (reagent R6). The enzymes (also attached to the specific detection surfaces 6821, 6822, 6823, 6824, and 6825) interact with the substrate, which causes the substrate to change color. Because enzymes are bound locally to only some areas, the color change is also localized to the specific detection surfaces 6821, 6822, 6823, 6824, and 6825. The viewing window 6802 and/or the detection openings of the top housing 6010 limit the view of the user to only show the specific detection surfaces 6821, 6822, 6823, 6824, and 6825 highlighting the results of the test. The heater construct 6840 mediates the temperature in the flow cell to allow for higher enzyme activity levels, and thus lower requisite dwell times.

Rotary Valve

As described herein, the detection method includes sequential delivery of the detection reagents (reagents R3-R6) and other substances within the device 6000. Further, the device 6000 is configured to be an "off-the-shelf" product for use in a point-of-care location (or other decentralized location), and is thus configured for long-term storage. In some embodiments, the molecular diagnostic test device 6000 is configured to be stored for up to about 36 months, up to about 32 months, up to about 26 months, up to about 24 months, up to about 20 months, up to about 18 months, or any values there between. Accordingly, the reagent storage module 6700 is configured for simple, non-empirical steps for the user to remove the reagents from their long term storage container, and for removing all the reagents from their storage containers using a single user action. In some embodiments, the reagent storage module 6700 is configured for allowing the reagents to be used in the detection module, one at a time, without user intervention.

The sequential addition of the detection reagents and/or wash (including the amount each respective reagent and the timing of addition of each reagent) is controlled automatically by the rotary vent valve 6340. In this manner, the detection method and the device 6000 can be operated by a user with minimal (or no) scientific training, in accordance with methods that require little judgment.

Figure 51:
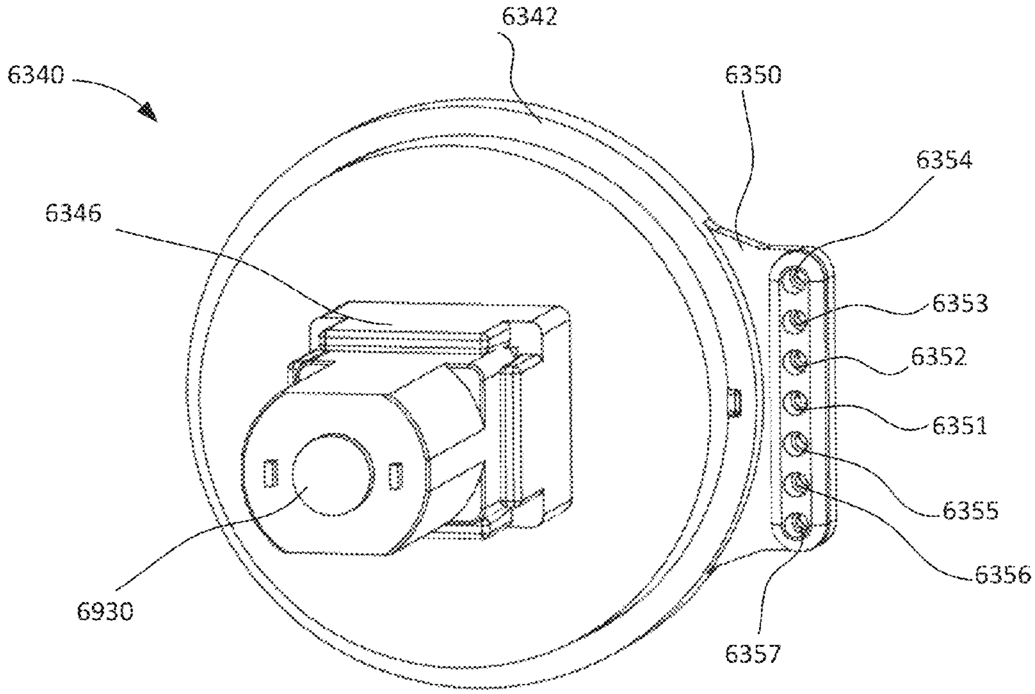
Figure 52:
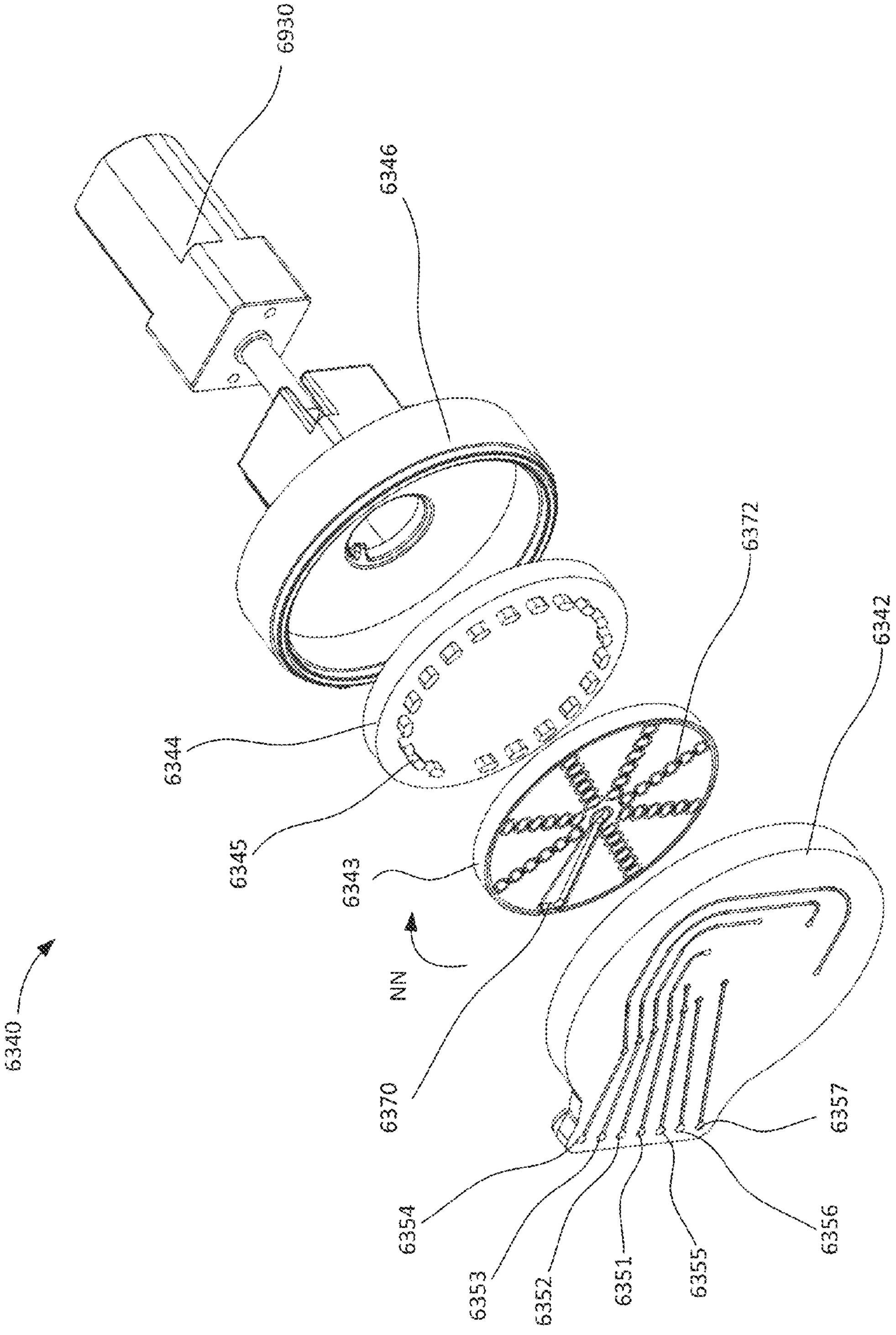
FIGS. 52 and 53 are a front exploded view and a rear exploded view, respectively, of the rotary valve assembly shown in FIGS. 50 and 51.

The rotary vent valve 6340 is shown in FIGS. 9 (schematically) and 50-53. FIGS. 54-61 show the rotary vent valve 6340 in each of eight different operational configurations. The rotary vent valve 6340 includes a vent housing 6342, a valve body (or disk) 6343, a drive member 6344, a retainer 6345 and a motor 6930. The vent housing 6342 defines a valve pocket 6358 within which the valve disk 6343 is rotatably disposed. The vent housing 6342 includes a flow path portion 6360 that defines seven vent flow paths. The flow path portion 6360 is shown with the end cover removed so that each of the vent paths can be easily seen. A description of each vent path follow: the vent path 6357 is fluidically coupled to the atmosphere). The vent path 6356 is fluidically coupled to the vent port 6556 of the mixing module 6500. The vent path 6355 is fluidically coupled to the outlet port 6828 of the detection module 6800 and/or the outlet port 6450 of the fluid transfer module 6400. The vent path 6354 is associated with the fourth reagent R6, and is fluidically coupled to the reagent vent port 6734 of the reagent module 6700. The vent path 6353 is associated with the third reagent R5, and is fluidically coupled to the reagent vent port 6733 of the reagent module 6700. The vent path 6352 is associated with the second reagent R4, and is fluidically coupled to the reagent vent port 6732 of the reagent module 6700. The vent path 6351 is associated with the first reagent R3, and is fluidically coupled to the reagent vent port 6731 of the reagent module 6700. As shown in FIG. 51, the vent housing 6342 includes a flow path portion 6350 that includes connection portions where each of the vent paths can be coupled to the respective modules via tubing, interconnects and the like (not shown).

Figure 53:
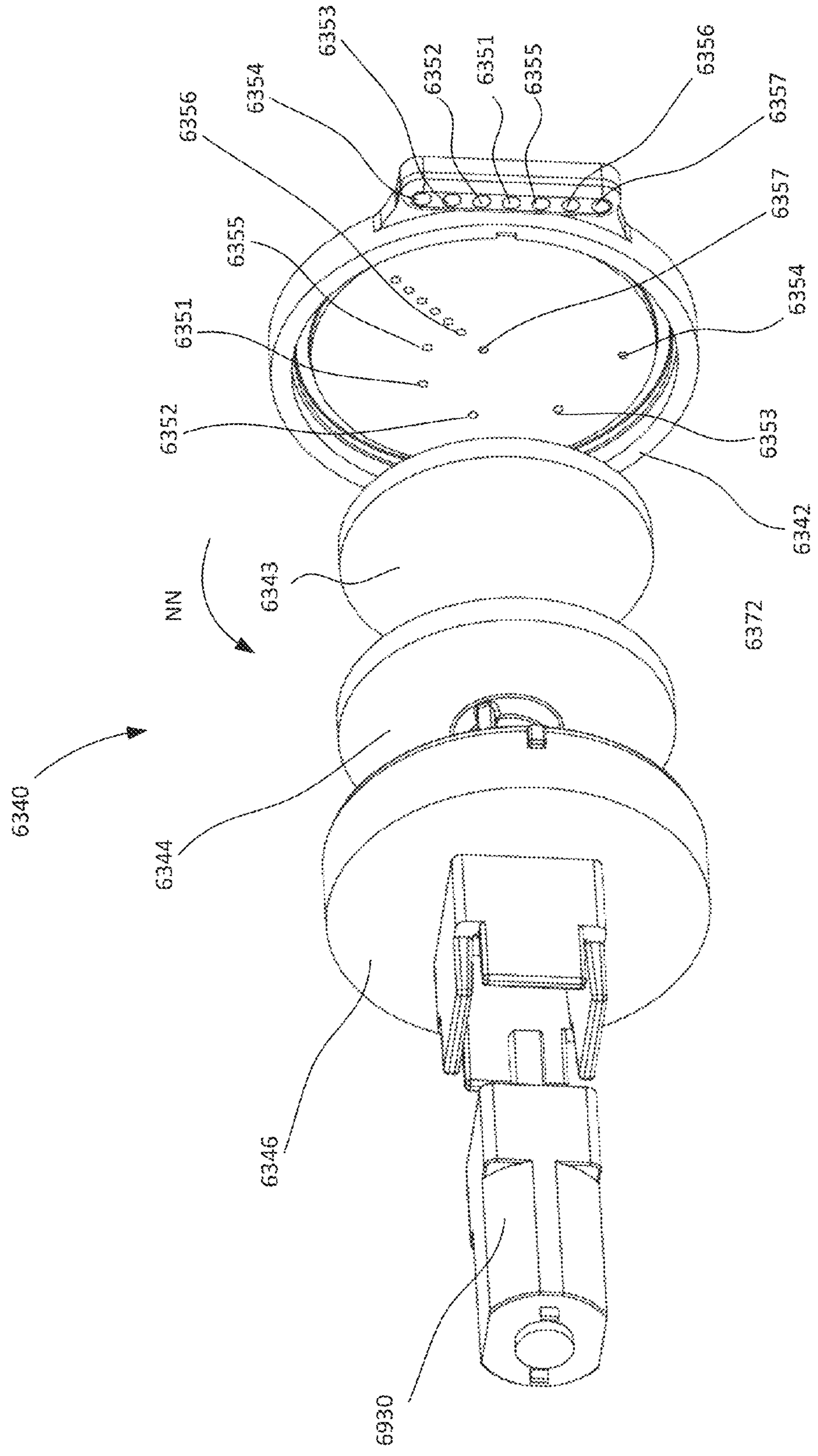

As shown in FIG. 53, each of the vents ports described above opens into the valve pocket 6358. Specifically, each of the vent ports has an opening within the valve pocket 6358 that is spaced apart from the center of the valve pocket 6358 by a specific radius and also at a different angular position.

Specifically, the vent path 6357 (to atmosphere) is located at the center. In this manner, when the valve body 6343 rotates around the center of the valve pocket 6358 (as shown by the arrow NN), the slot channel 6370 of the valve body 6343 can connect the central port, atmospheric vent path 6357 to the other ports depending on their radial and angular position. The use of multiple radii allows not only a single port, but multiple ports at once to be vented depending on the configuration.

The valve body 6343 includes the slot channel 6370 and a series of seals 6372. The slot channel 6370 is tapered, and thus has a wide angular tolerance, allowing the valve to be operated in a low-precision regiment. The seals 6372 are aligned with the vent path openings within the valve pocket 6358 to maintain the seal when those vents are not selected. The valve body 6343 is pressed into the valve pocket 6358 by the retainer 6346, and is coupled to the drive motor 6930 by the drive member 6344, which includes a series of lugs 6345.

Figure 54:
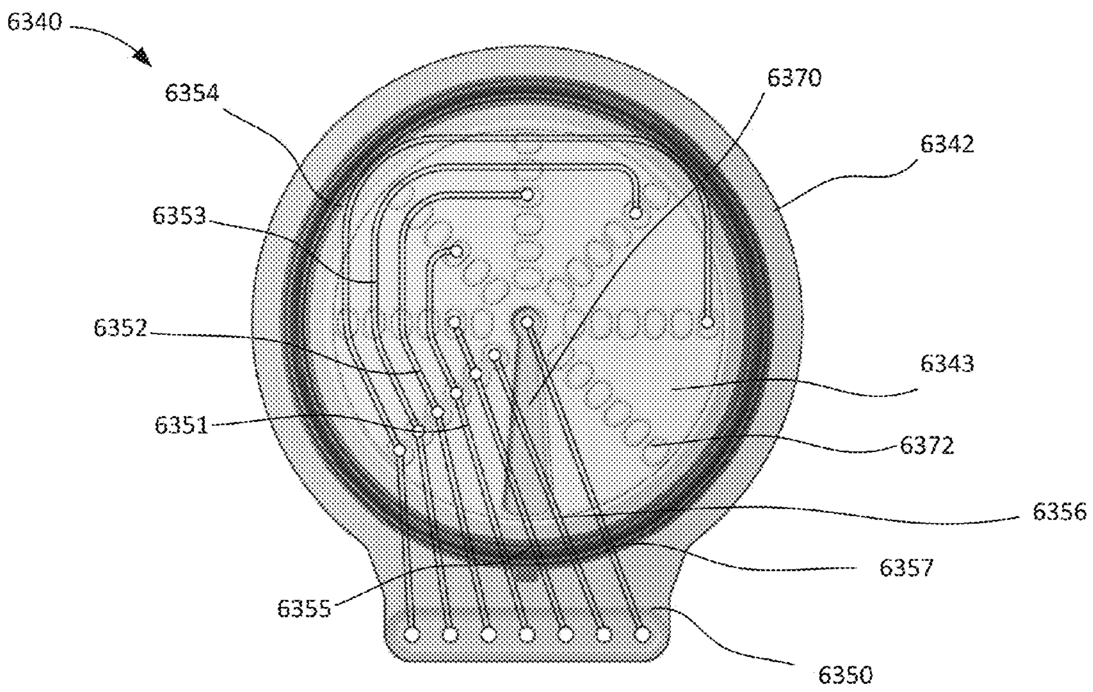
FIGS. 54 through 61 are front views of the rotary valve assembly shown in FIGS. 50 and 51 in each of eight different operational configuration.
Figure 55:
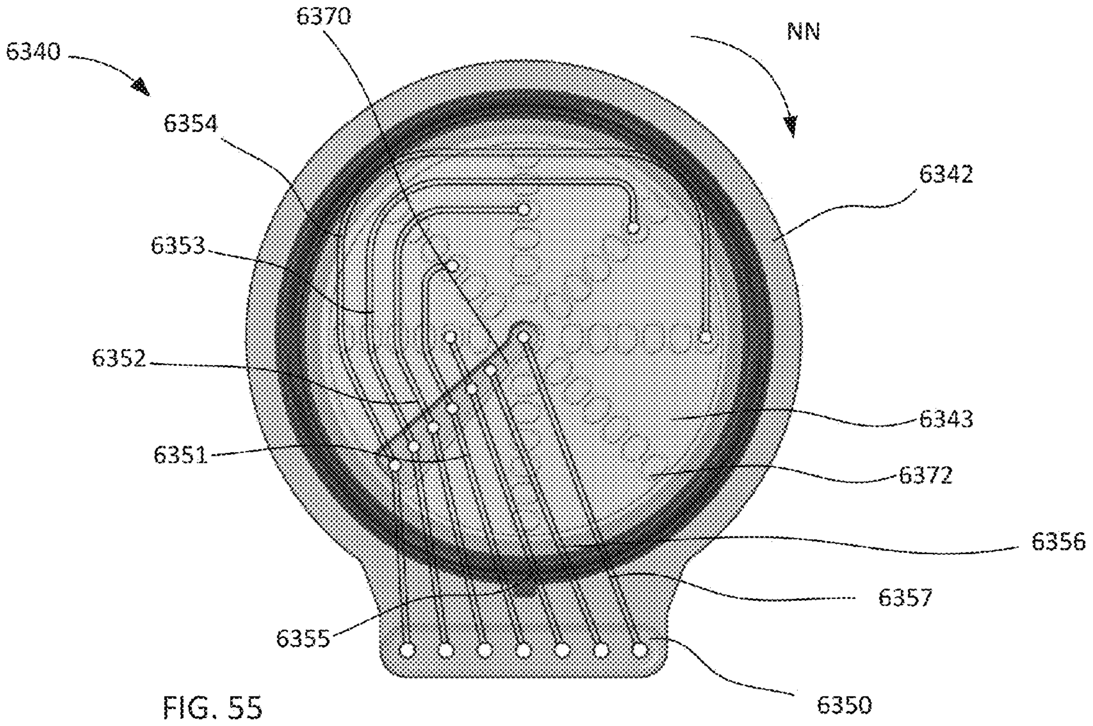

The valve assembly 6340 can be moved between eight different configurations, depending on the angular position of the valve body 6343 within the valve pocket 6358. FIG. 54 shows the assembly in the first configuration (with the valve body 6343 in "position 0"). In the zeroth configuration, no vents are open, and the valve body 6343 rests against a hard stop. The zeroth configuration is used for homing the valve only. FIG. 55 shows the assembly in the first configuration (with the valve body 6343 in "position 1"). In the first configuration, all vents are open, and thus, the reagent actuator 6080 can be manually depressed allowing the reagent canisters to be punctured, as described above. The first configuration also allows for the dry reagents (e.g., the reagents R1 and R2 within the mixing chamber 6500) to be properly desiccated. The first configuration is the "shipping" and storage configuration.

Figure 56:
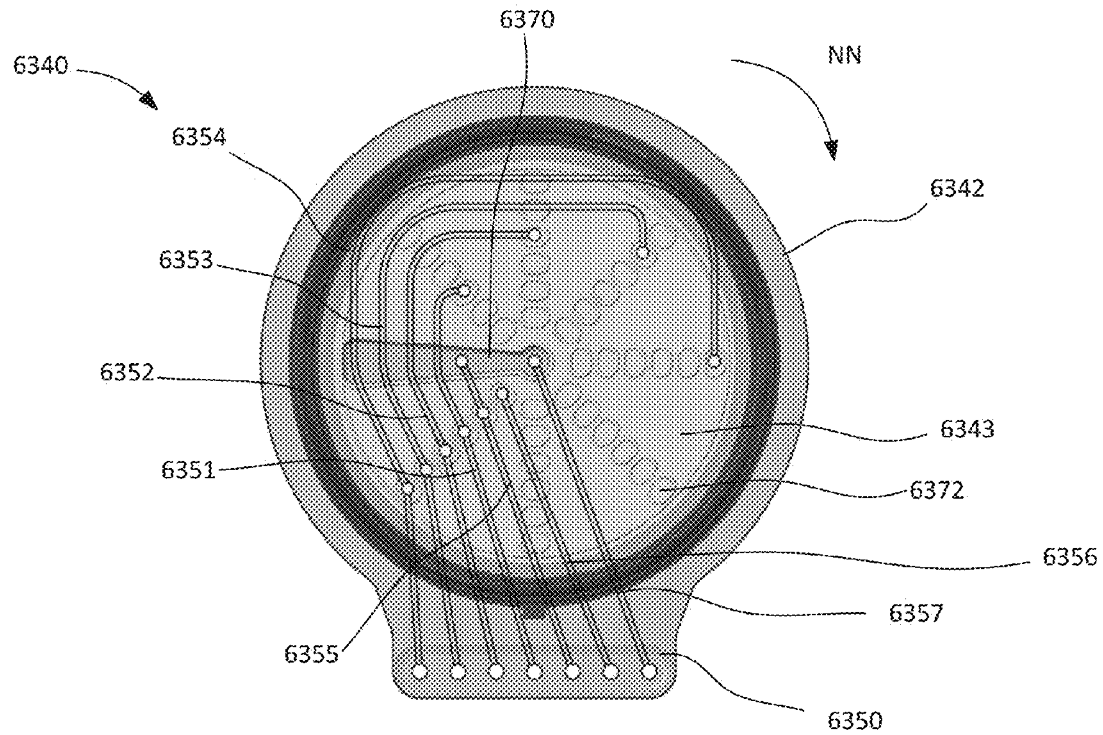
Figure 57:
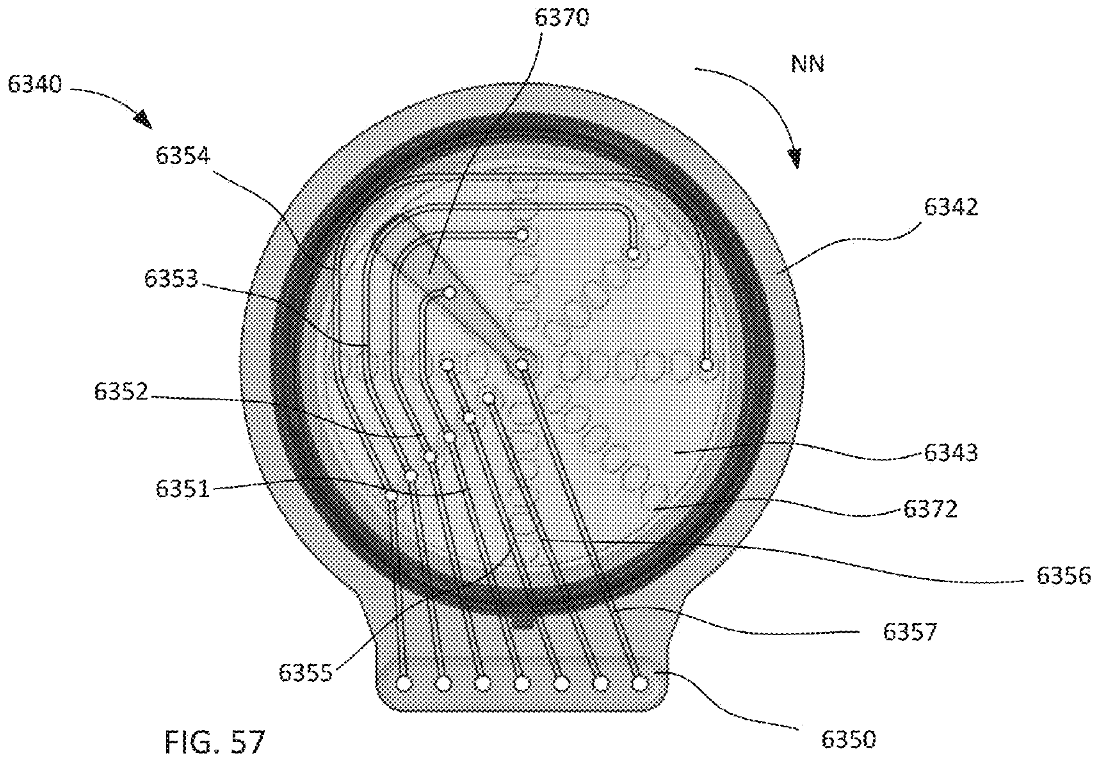

After the device 6000 is "powered-on" by actuation of the switch 6906 when the reagent actuator 6080 is depressed, the power and control module 6900 can incrementally move the valve body 6343. FIG. 56 shows the assembly in the second configuration (with the valve body 6343 in "position 2"). In the second configuration, the vent 6355 (to outlet port 6828 of the detection module 6800 and/or the outlet port 6450 of the fluid transfer module 6400) is open. Further the vent 6356 to the mixing module 6500 is closed. Thus, the inactivation chamber 6311 and the mixing module 6500 can be emptied and filled as described above. The sample can also be conveyed via the fluid transfer module 6400 into the PCR module 6600. FIG. 57 shows the assembly in the third configuration (with the valve body 6343 in "position 3"). In the third configuration, the vent 6351 (to the first reagent R3) is open. Thus, when the fluid transfer module 6400 produces a vacuum through the detection module 6800, the first reagent R3 (the wash) can move freely through the detection module 6800 when the assembly is in the third configuration. Because the other reagent vent ports are sealed, the remaining reagents R4, R5 and R6 are not conveyed through the detection module 6800 when the valve assembly 6340 is in the third configuration.

Figure 58:
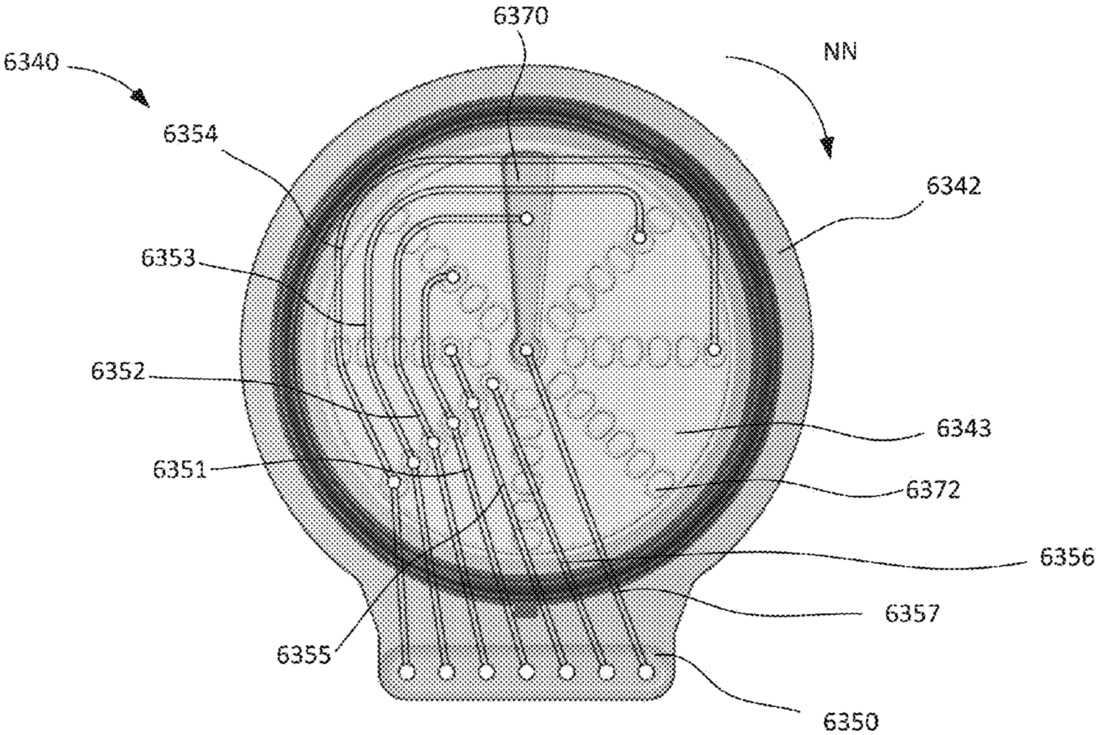

FIG. 58 shows the assembly in the fourth configuration (with the valve body 6343 in "position 4"). In the fourth configuration, the vent 6352 (to the second reagent R4) is open. Thus, when the fluid transfer module 6400 produces a vacuum through the detection module 6800, the second reagent R4 (the enzyme) can move freely through the detection module 6800 when the assembly is in the fourth configuration. Because the other reagent vent ports are sealed, the remaining reagents R3, R5 and R6 are not conveyed through the detection module 6800 when the valve assembly 6340 is in the fourth configuration.

Figure 59:
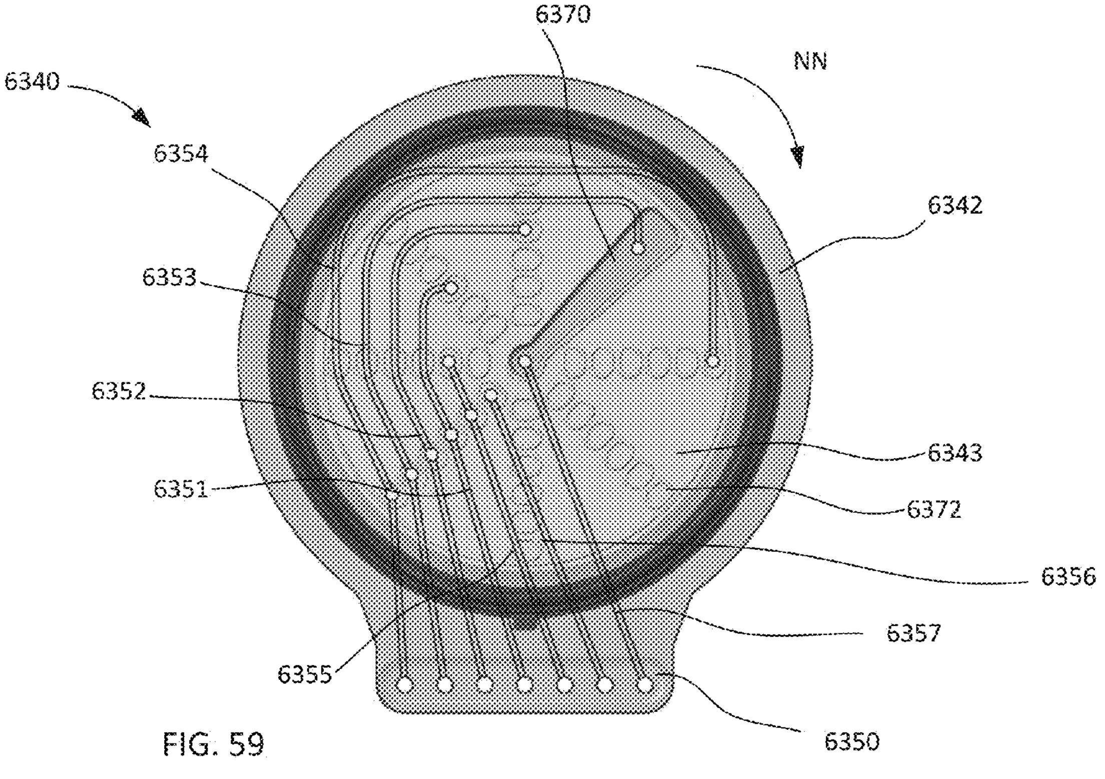

FIG. 59 shows the assembly in the fifth configuration (with the valve body 6343 in "position 5"). In the fifth configuration, the vent 6352 (to the third reagent R5) is open. Thus, when the fluid transfer module 6400 produces a vacuum through the detection module 6800, the third reagent R5 (the second wash) can move freely through the detection module 6800 when the assembly is in the fifth configuration. Because the other reagent vent ports are sealed, the remaining reagents R3, R4 and R6 are not conveyed through the detection module 6800 when the valve assembly 6340 is in the fifth configuration.

Figure 60:
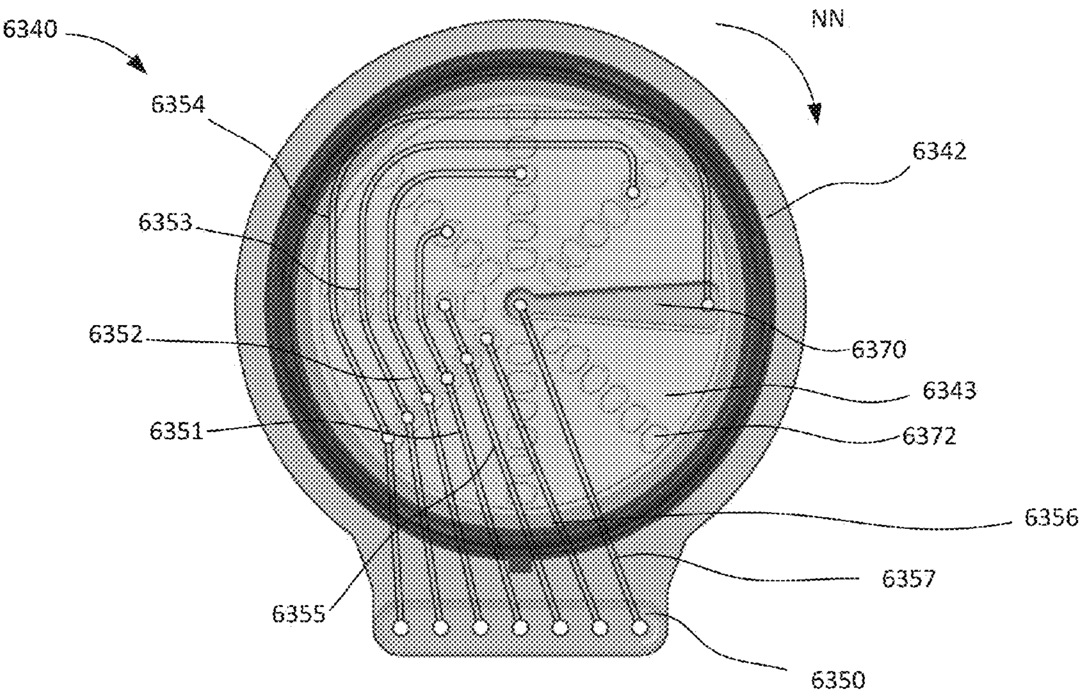

FIG. 60 shows the assembly in the sixth configuration (with the valve body 6343 in "position 6"). In the sixth configuration, the vent 6352 (to the fourth reagent R6) is open. Thus, when the fluid transfer module 6400 produces a vacuum through the detection module 6800, the fourth reagent R6 (the substrate) can move freely through the detection module 6800 when the assembly is in the sixth configuration. Because the other reagent vent ports are sealed, the remaining reagents R3, R4 and R5 are not conveyed through the detection module 6800 when the valve assembly 6340 is in the sixth configuration.

Figure 61:
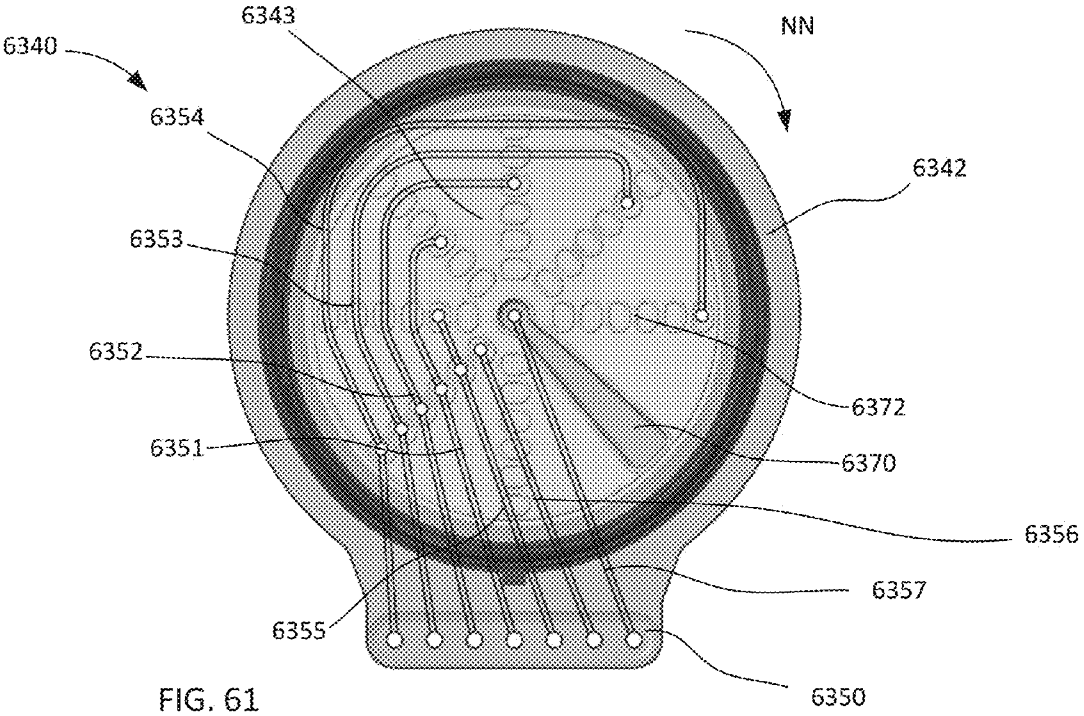

FIG. 61 shows the assembly in the seventh configuration (with the valve body 6343 in "position 7"). In the seventh configuration, all vents are closed. This is the disposal configuration.

By including a vent valve to control the reagent flow, the number of moving parts is minimized, and thus the simplicity of the device 6000 is improved. Moreover, this approach eliminates the possibility of valve contamination because only air, and no fluid, ever passes through the valve.

Power Management and Control

The system 6000 (or any other systems shown and described herein) includes a control module 6900 that includes a power source 6905, a processor (which can be similar to the processor 4950 shown and described above), and an electronic circuit system. The electronic circuit system (not shown) can include any suitable electronic components, such as, for example, printed circuit boards, switches, resistors, capacitors, diodes, memory chips or the like arranged in a manner to control the operation of the device 6000, as described herein.

The power source 6905 can be any suitable power source that provides power to the electronic circuit system (including the processor) and any of the modules (e.g., heaters, motors, and the like) within the device 6000. Specifically, the power source 6905 can provide power to the amplification module 6600 and/or the heater 6630 to facilitate the completion of the PCR on the input sample S1. In some embodiments, the power source 6905 can be one or more DC batteries, such as, for example, multiple 1.5 VDC cells (e.g., AAA or AA alkaline batteries). In other embodiments, the power source 6905 can be a 9 VDC battery having a capacity of less than about 1200 mAh. In some embodiments, the power source 6905 can be an alkaline battery (e.g. a 9 VDC alkaline battery), which exhibits a high energy density at a low cost. This arrangement facilitates the device 6000 being a hand-held, disposable, single-use diagnostic test. These energy sources are considered depleted when terminal voltages drop below 5V, a common logic level voltage. By regulating the digital controller signal directly from the battery, a stable control voltage throughout the lifetime of the battery is possible.

The primary consumer of power in the system 6000 will be the resistive heaters shown and described above (e.g., for the inactivation module 6300, the amplification module 6600, and the detection module 6800). By specifying the resistance of the inactivation heater and detection heater to be low enough such that the required power density can be obtained from a nearly depleted battery, these heaters can be powered from the unregulated battery source.

The processor used to control the device 6000 (and any of the processors shown herein) can be a commercially-available processing device dedicated to performing one or more specific tasks. For example, in some embodiments, the device 6000 can include and be controlled by an 8-bit PIC microcontroller, which will control the power delivered to various components of the system. This microcontroller can also contain code for and/or be configured to minimize the instantaneous power requirements on the battery. The highest power consumption occurs when amplification heater 6630, the inactivation heater 6330, and detection heater 6840 are being raised to temperature. By scheduling these warmup times during periods of low power consumption, the power requirements on the battery 6905 are reduced at the expense of increased energy consumption. With the high energy density of the alkaline battery, this is a favorable tradeoff. When multiple loads require power simultaneously, the controller contain code for and/or be configured to ensure that each load receives the necessary average power while minimizing the time in which multiple loads are powered simultaneously. This is achieved by interleaving the PWM signals to each load such that the periods in which both signals are in an on state is kept to a minimum.

Figure 67:
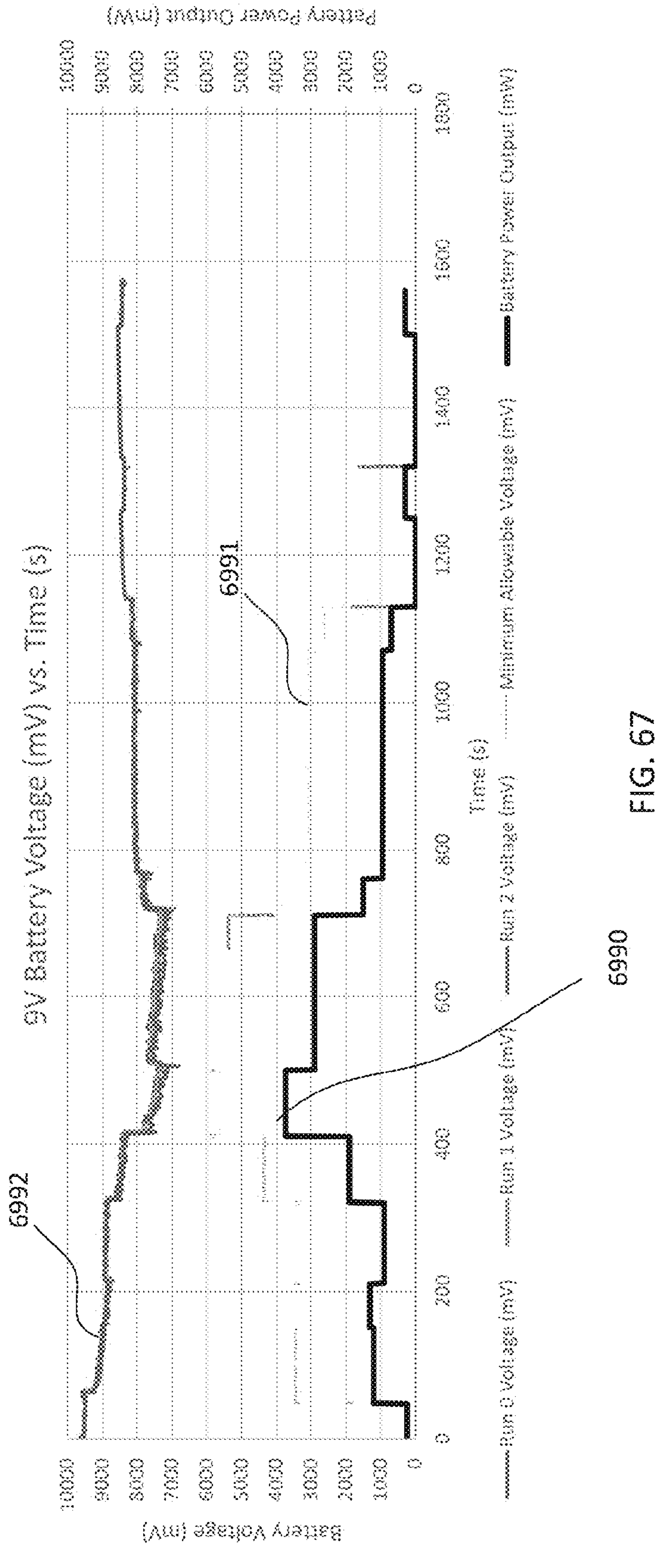
FIG. 67 is a graph of power usage and power source voltage when the device shown in FIGS. 10 and 11 is used to conduct a test protocol according to an embodiment.

For example, in some embodiments, the control and power module 6900 can regulate the modules within the device 6000 to perform within a power budget that is sufficient to allow the device to be powered by the power source 6905 that is a 9 VDC battery having a capacity of about 1200 mAh. FIG. 67 shows a graph of a power budget as a function of elapsed time for the device 6000 running a test protocol according to an embodiment. As shown, the line identified as 6990 indicates the power output of the power source 6905 (i.e., the 9 VDC battery) in mW. The line identified as 6991 indicates a threshold of the minimum allowable voltage (in mV) of the battery 6905. The line identified as 6992 indicates voltage drawn (in mV) during three test runs. As shown, because the voltage drawn does not drop below the minimum allowable voltage (line 6991), the tests were successfully completed using the 9 VDC battery as the power source 6905.

In some embodiments, the total electric charge consumed by one cycle of operation can be about 550 mAh. In such embodiments, the device 6000 can include as the power source 6905 a 9 VDC battery having a capacity of less than about 1200 mAh, which can allow for a margin of safety of about 650 mAh. In particular, Table 6 lists the approximate charge consumption for each major operation in the detection process.

TABLE 6

| Module/Operation | Approx Charge Consumed (mAh) |
|---|---|
| Sample prep | 100 |
| Amplification | 300 |
| Detection | 50 |
| Motors/microcontroller | 100 |
| TOTAL | 550 |

Although the system 6000 is shown and described as including a 9 volt alkaline battery 6905, in other embodiments, the device 6000 can include multiple power sources and/or energy storage devices. For example the power and control module 6900 can include supercapacitors in parallel with the battery 6905 to deliver additional power. In such embodiments, the capacitor will be charging continuously during periods of low power consumption and will assist the battery 6905 in delivering power throughout the run. Increasing this capacitance increases the stored energy and, hence, the time during which the system can operate at elevated power levels. Supercapacitors require large inrush currents, so this capacitor will be current limited to prevent the battery voltage from dropping below the required logic level voltage while the capacitor is charging, resulting in a reset of the microcontroller.

As described above, the system 6000 requires control of brushed DC motors 6910 and 6930, which is can be accomplished, in some embodiments, using rotary encoders (not shown). In other embodiments, the processor can include code to and/or be configured to implement a closed loop method of tracking motor position by monitoring the current draw of motors 6910 and 6930. More particularly, due to the reactive nature of motor coils, the current draw by a brushed DC motor is not constant. By monitoring current through a low impedance shunt resistor, the processor can detect a DC component superimposed with an AC component. The DC component represents the power required to actuate the motor under its current load and the AC component is due to the self-inductance of each motor coil, the mutual inductance between motor coils, and the changing resistance of the rotor windings as the brushes move across the armature windings during rotation. This changing resistance is the primary contributor to this alternating current and is directly related to the angular position of the motor.

In some embodiments, the electronic circuit system and/or processor can determine and isolate this small AC component, filter this component, and then amplify it to a logic level signal. The processor can include a motor control module that keeps track of the time between each pulse. These time values can be filtered (e.g., using a single pole IIR digital filter) and then used as an input for a PID controller within the motor control module. The PID controller controls the input power to the motor, regulating the power such that the time between motor pulses maintains a predetermined value based on the desired flowrate. By counting the number of pulses coming from this feedback circuit, a brushed DC motor can aspirate or dispense a known volume from the drive syringe or move the rotary valve to known positions.

As described herein, the device 6000 (and any of the other devices shown and described herein) can be configured to produce the signals OP1, OP2, and/or OP3 in a time of less than about 25 minutes from when the sample S1 is received. In other embodiments, the device 6000 (and any of the other devices shown and described herein) can be configured to produce the signal OP1, OP2, and/or OP3 in a time of less than about 20 minutes from when the sample S1 is input, less than about 18 minutes from when the sample S1 is input, less than about 16 minutes from when the sample S1 is input, less than about 14 minutes from when the sample S1 is input, and all ranges therebetween.

More particularly, the device 6000, the control module 6900 and the other modules within the device 6000 are collectively configured to produce sample flow rates and overall sample volumes in amounts and in a manner to achieve the power consumption and delivery time specifications set forth herein. In this manner, the device 6000 can be operated in a sufficiently simple manner, and can produce results with sufficient accuracy to pose a limited likelihood of misuse and/or to pose a limited risk of harm if used improperly. For example, in some embodiments, the device 6000 is configured to produce the volumes at each operation as set forth in Table 6 below. The nominal time for each operation is also included in Table 7.

TABLE 7

| Step | Task | Initial vol. (ml) | Resulting vol. (ml) | Yield | Time (min) |
|---|---|---|---|---|---|
| 1 | Add sample | 0.5-1.0 | — | | |
| 2 | Wash filter | 0.5 | — | | 0.1 |
| 3 | Back-flush/elution | 0.2 | 0.2 | 0.5 | 0.1 |
| 4 | Inactivation (37° C.) | 0.15 | 0.15 | | 1 |
| 5 | Inactivation (95° C.) | 0.15 | 0.15 | 0.2 | 5 |
| 6 | Master mix and sample prep eluent | 0.085 | 0.085 | | 0.16 |
| 7 | 40 cycle PCR | 0.085 | 0.085 | $10^{10}$ | 8 |
| 8 | Ready for Detection | | | | |
| 9 | Flow amplicon | 0.075 | 0.075 | n/a | 0.5 |
| 10 | Amplicon hybridization | 0.075 | 0.075 | $10^{-3}$ | 3 |
| 11 | First wash | 0.5 | 0.5 | n/a | 0.5 |
| 12 | Flow enzyme and incubate | 0.1 | 0.1 | 80 | 2 |
| 13 | Second wash | 0.5 | 0.5 | n/a | 0.5 |
| 14 | Flow substrate and incubate | 0.1 | 0.1 | $1.2 \times 10^5$ | 3 |
| 15 | Ready to read | | | | |

Methods of Use

Figure 68A:
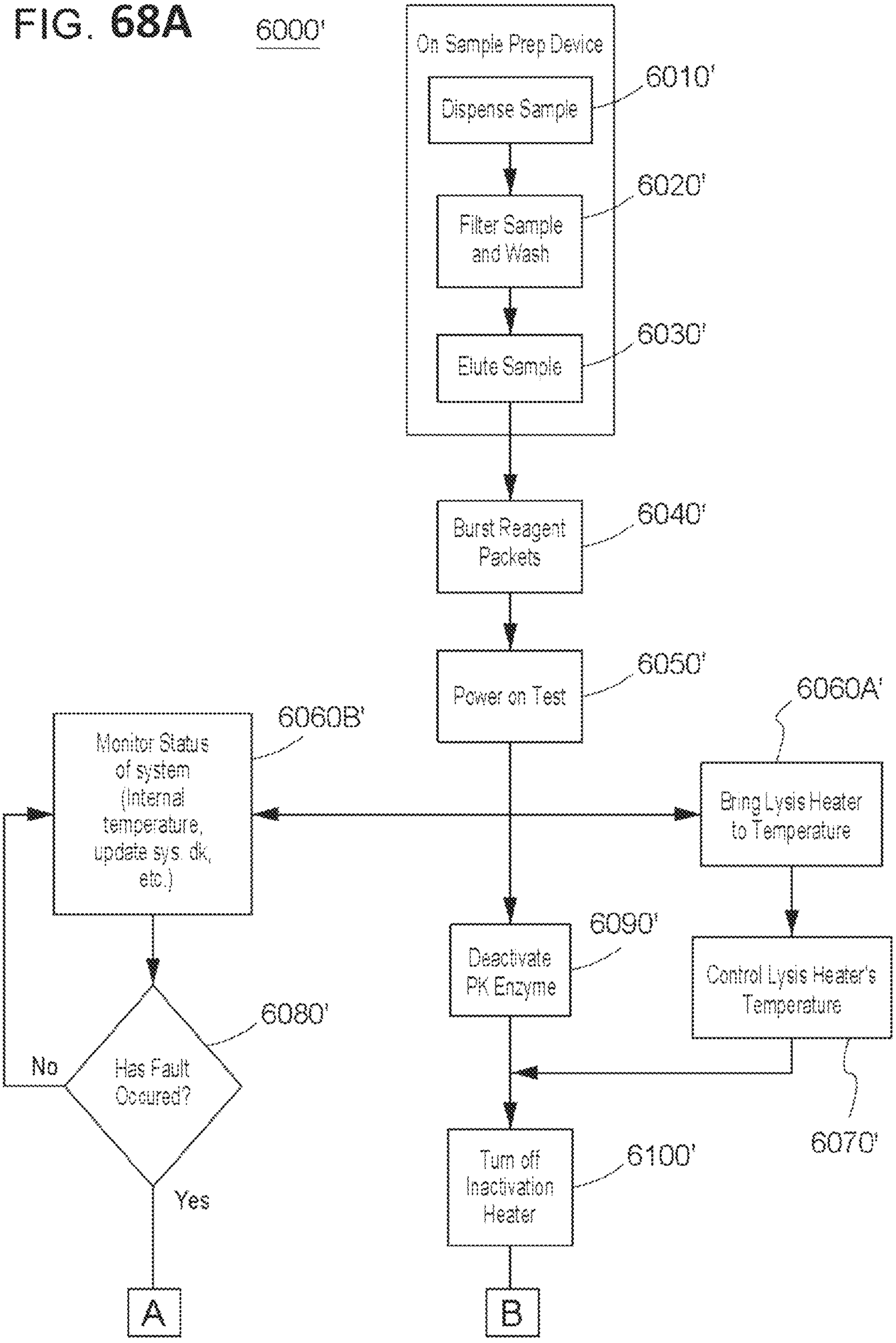
FIGS. 68A-68C show a flow chart of a test process flow for a diagnostic test, according to an embodiment.
Figure 68B:
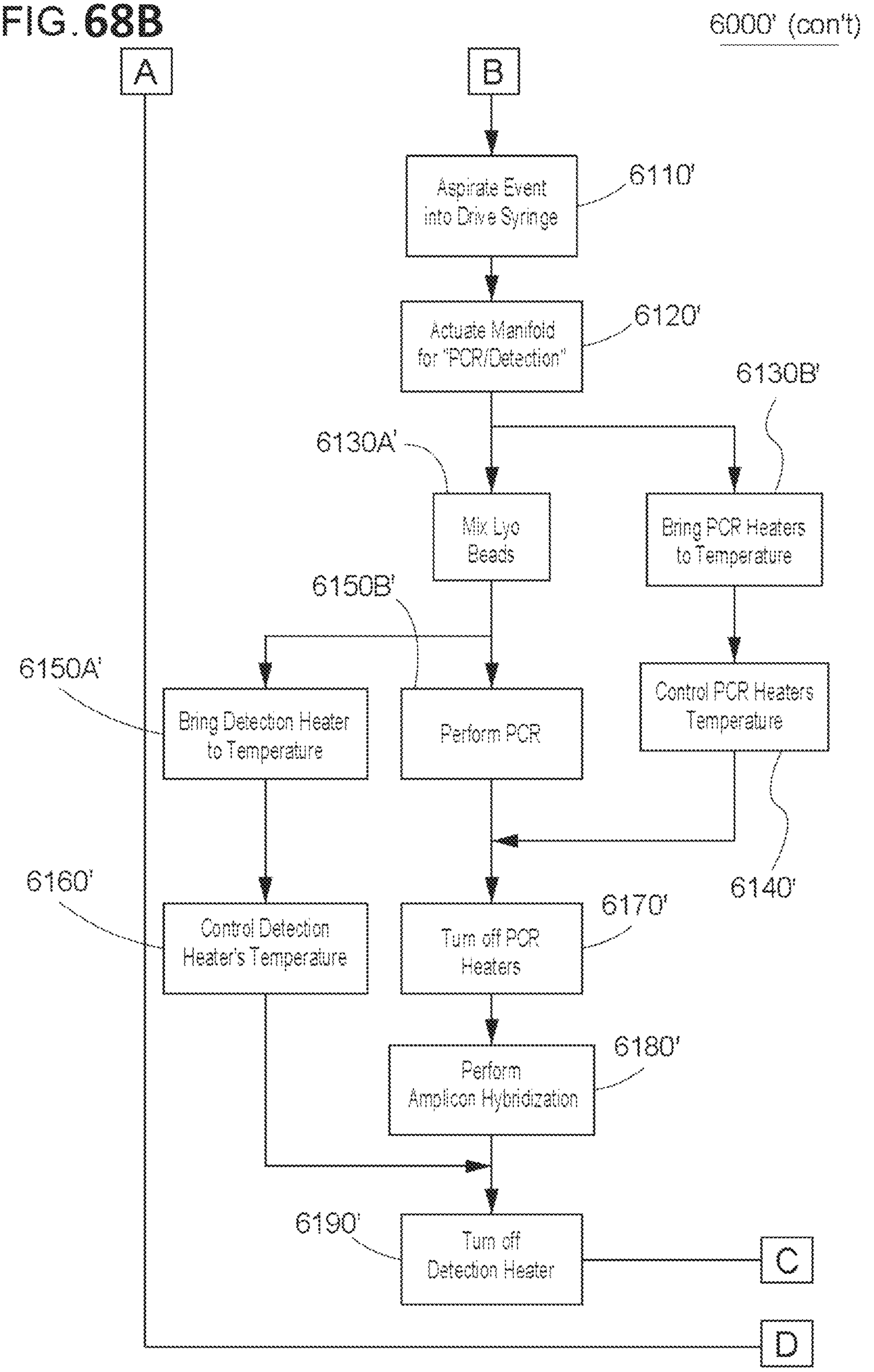
Figure 68C:
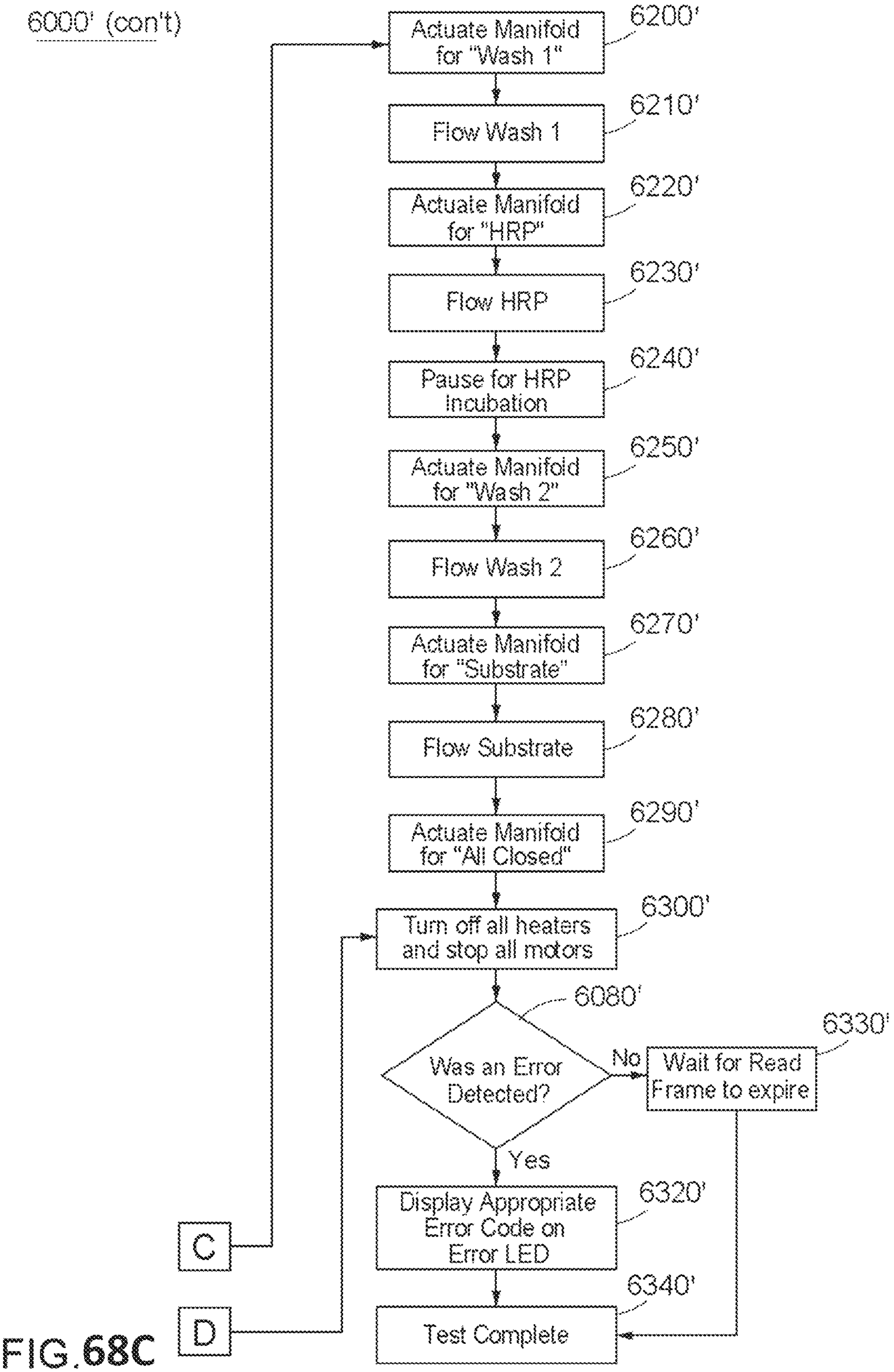

FIGS. 68A-C illustrate a detailed process flow chart of a method 6000' for a diagnostic test according to an embodiment, such as one executed/run by the diagnostic test device 6000 (or any other system described herein). At step 6010', the method 6000' includes dispensing a sample into an input port of the test system. The input port is capped and the sample is pushed through a filter, followed by a wash buffer, at step 6020'. In some embodiments, this button as a last action opens a valve to allow elution of the sample from the filter at step 6030'. At step 6040', an elution lysing buffer is pushed through the filter to backflush the contents off the filter, filling an inactivation chamber. In some embodiments, the method 6000' further includes, at the step 6040', opening a series of reagent tanks for use later in the method. At step 6050', the method includes powering on/activating electronics and heaters contained within the test system, such as, for example, by an operator attaching a battery pack to the test system. In some embodiments, the power on operation can be performed automatically and/or in conjunction with a reagent opening step (e.g., operation 6040'). Alternatively, if the battery is stored within the cartridge/system, in some embodiments, the operator can push a power button to start electronics and heaters contained in the test system. In some embodiments, a light indicator on the test system lights to notify the operator that the test is operating.

At step 6060A', once the test is powered on, the inactivation and/or lysis heater is powered and allowed to rise to its set-point temperature. This heater is controlled by a digital circuit (e.g., similar to the electronic control module 6900 described above) to ensure that the set-point temperature or temperatures is held within tolerance, at step 6070'. Substantially simultaneously, at step 6060B', control electronics continually monitor the test system to ensure that a fault condition has not occurred. A fault condition might include, for example, an out-of-temperature condition, out-of-voltage condition, out-of-pressure condition, etc. If a fault condition is detected at step 6080', in some embodiments, an indicator light changes state to notify the operator, and the method proceeds to step 6300' (described later). In some embodiments, the presence of a fault condition will render the device inoperable (e.g., will cause the cartridge/system to cease operations), thereby minimizing the risk that a user will receive an inaccurate result.

Once the inactivation chamber temperature set-point(s) have been achieved, the elution lysing volume, which has now undergone cell lysis, is incubated to inactivate the PK enzyme/lysing reagent at step 6090'. This incubation time, in some embodiments, can be on the order of about 5 minutes. Once this incubation has been completed, the inactivation heater is turned off at 6100', and at 6110', a syringe pump is activated to aspirate the eluent ready for dispense to a mixing chamber. At step 6120', the rotary valve is actuated to vent the PCR fluidic circuit and detection flow channel. In this manner, the fluidic pathways are prepared to allow transfer of the desired fluids therethrough, as described below. At step 6130A', the syringe pump reverses direction to dispense the eluent into a mixing chamber where it hydrates a lyophilized pellet/bead holding the primers and enzymes necessary for PCR. In some embodiments, this hydration occurs over about 2 minutes to allow complete mixing of reagents. In some embodiments, the mixing operation can occur before and/or upstream of the syringe pump.

At step 6130B', PCR heaters are turned on and raised to their set-point temperatures. In some embodiments, the PCR heaters can be activated at substantially the same time as when the syringe pump dispenses the eluent into the mixing chamber. At step 6140', control electronics ensure that the PCR heaters are controlled to within their set-point tolerances. At steps 6150A' and 6160', the detection heater is turned on and allowed to warm up for subsequent use. Substantially simultaneously, at step 6150B', the syringe pump continues to push fluid from the mixing chamber to the PCR fluidic circuit, where the mixed lysed sample and polymerase are thermally cycled between about 59 degree C. and about 95 degree C. for 40 cycles. When the desired amplified volume is produced, the heaters are shut off to conserve power at step 6170. The syringe pump continues to push fluid from the PCR module to the detection module. At step 6180', the amplicon is incubated in a flow channel for about 6-5 minutes to perform amplicon hybridization. The flow channel is heated to about 65 degree C. for this incubation step. At step 6190', the detection heater is turned off.

The rotary valve of the test system is actuated to the first wash position at step 6200'. The rotary valve can be any suitable rotary valve, such as those described herein. The syringe pump reverses direction and a vacuum is pulled on the wash reagent, and at step 6210', the unbound amplicon is washed from the channel followed by a volume of air. At step 6220', the rotary valve is actuated to the HRP enzyme position. At step 6230', HRP enzyme is conveyed within the flow channel and, at step 6240, is incubated for 6-5 minutes. The enzyme is removed followed by an air slug. At step 6250', the rotary valve is actuated to the wash 2 position. At step 6260', wash buffer is pulled over the flow channel to wash away unbound enzyme followed by a volume of air. At step 6270', the rotary valve is actuated to the substrate position. At step 6280', substrate is pulled into the flow channel and parked. At step 6290', the rotary valve is actuated to the "all ports closed" position. In some embodiments, a light indicator is illuminated to notify the operator the test results are ready. At step 6300', all heaters and motors are stopped and/or shut down.

At step 6310', it is determined if an error was detected such as, for example, if a fault occurs at step 6080'. If a fault is detected, the appropriate error code is indicated on error LEDs of the test system at 6320'. If no error is detected, then at step 6330, when the read frame expires after approximately 20 minutes, the "test ready" light indicator is shut off to indicate the read frame has elapsed and testing is complete at step 6340'.

The operations described above can be performed by the diagnostic test system 6000 (or any other system described herein). In some embodiments, the test system (or unit) can include a series of modules configured to interact with the other modules to manipulate the sample to produce a diagnostic test.

Figure 69:
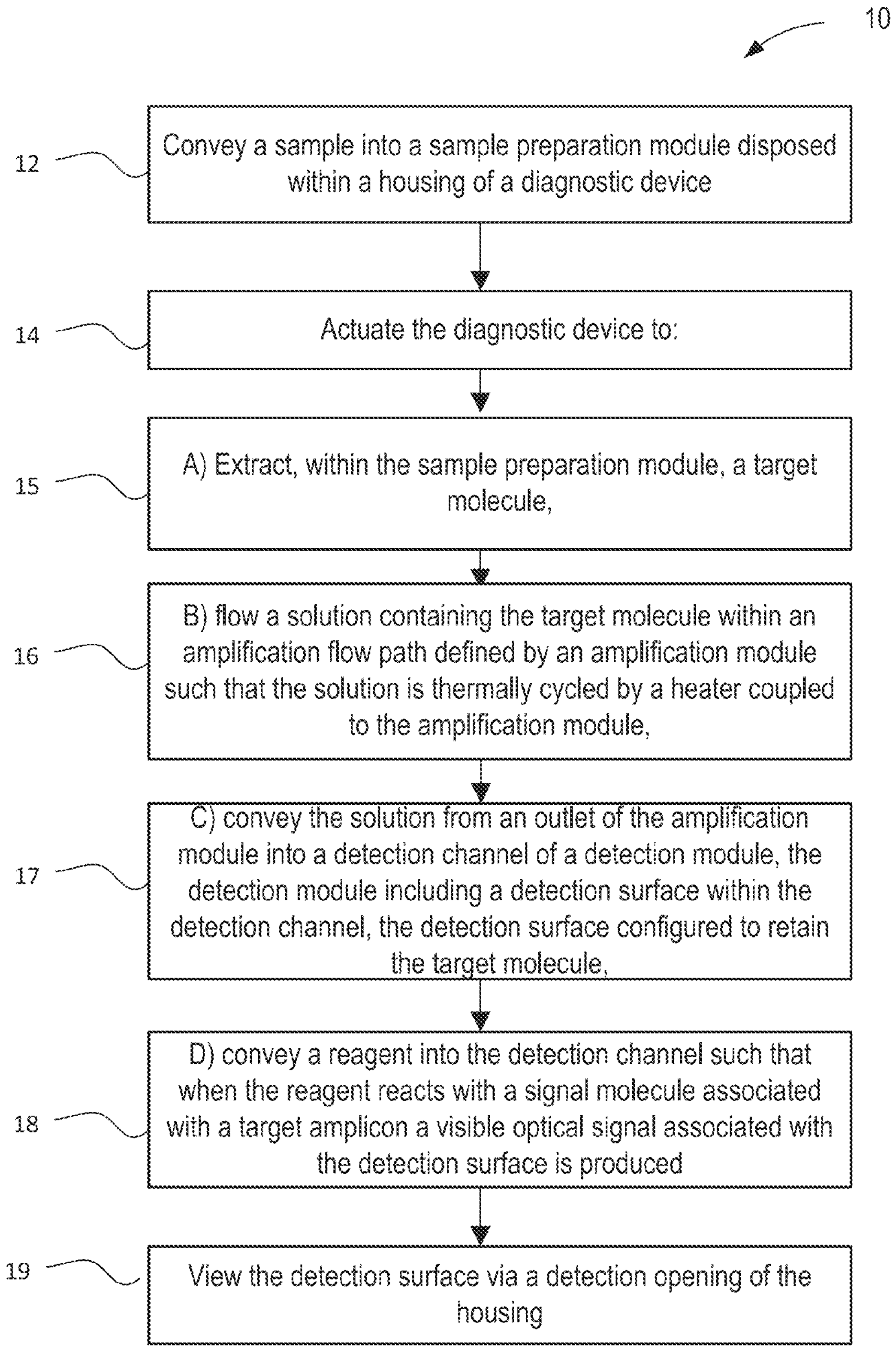
FIG. 69 shows a flow chart of a method of diagnostic testing, according to an embodiment.

FIG. 69 is a flowchart of a method 10 of molecular diagnostic testing, according to an embodiment. The method 10 can be conducted on the device 6000 or any other device and/or system shown and described herein. The method includes conveying a sample into a sample preparation module disposed within a housing of a diagnostic device, at 12. The sample can be any sample as described herein, and can be conveyed into the device using any method as described herein (e.g., using a transfer device such as the device 6100). The method then includes actuating the device, at 14, to: A) extract, within the sample preparation module, a target molecule (at 15); B) flow a solution containing the target molecule within an amplification flow path defined by an amplification module such that the solution is thermally cycled by a heater coupled to the amplification module (at 16); C) convey the solution from an outlet of the amplification module into a detection channel of a detection module, the detection module including a detection surface within the detection channel, the detection surface configured to retain the target molecule (at 17); and D) convey a reagent into the detection channel such that when the reagent reacts with a signal molecule associated with a target amplicon a visible optical signal associated with the detection surface is produced (at 18). The method includes viewing the detection surface via a detection opening of the housing, at 19.

Applications

The diagnostic test/test system 6000 (and all other devices and systems described herein) is a platform for detection of infectious disease from biological fluids. In some embodiments, the diagnostic system detects targeted infectious agents (e.g., bacteria and viruses) by changing the types of primers inside the consumable platform to amplify and detect the desired nucleic acid sequence of interest. While the diagnostic system 6000 has been designed for sample collection of either urine or swab sample and detection of a 4-plex STI panel (i.e., a 3-plex plus a positive control), in other embodiments, the diagnostic system 6000 (or any of the other devices shown and described herein) can easily be extended to other diagnostic panels. For example, consider a urinary tract infection panel which allows detection of *E. coli, Staphylococcus saprophyticus, Enterococcus faecalis, Klebsiella pneumoniae, Proteus*, and *P. aeruginosa*. The sample prep module has been shown to isolate the desired pathogen and lyse these organisms with the addition of reagents (e.g., lysozyme and proteinase K) and heat. Subsequently, pathogen specific primers would need to be added to the mixing chamber to allow amplification of these target pathogen gene sequences. Finally, the hybridizing probe bound to the read lane in the detection module would need to change to bind these new specific amplified targets. All other aspects of the test cartridge can remain unchanged.

In some embodiments, a device (such as the device 6000, or any of the other devices shown and described herein) can be configured to detect a universal reagent immunoabsorbent assay (URI). In some embodiments, a device (such as the device 6000, or any of the other devices shown and described herein) can be configured to detect a hemagglutination inhibition test (HAI).

For viral targets, the sample preparation module 6200 (and any of the sample preparation modules described herein) can be modified in any suitable manner. For example, in some embodiments, a sample preparation module can be configured to isolate viruses from biological fluids using a solid phase material such as a filter of specific chemisorbent material with a pore size conducive to flow and capture of viral particles. The captured viral particle are washed and eluted from the filter into a heated chamber where the viral particles are lysed and any PCR inhibitors are neutralized. Pathogen specific primers and master mix are added to the viral nucleic acid for amplification. For viral RNA targets, reverse transcription takes place in the heating chamber prior to PCR). After PCR amplification, the amplicons are captured by sequence specific hybridizing probes in the read lane for detection.

Figure 70:
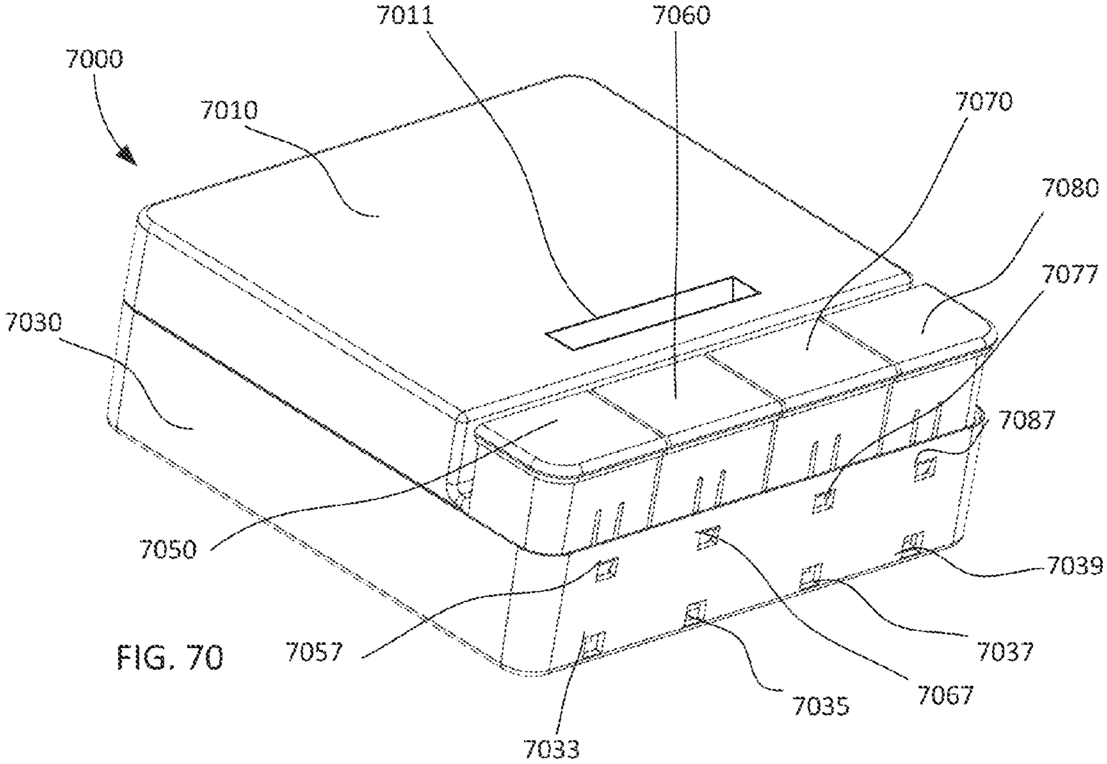
FIG. 70 is a perspective view of a molecular diagnostic test device, according to an embodiment.
Figure 71:
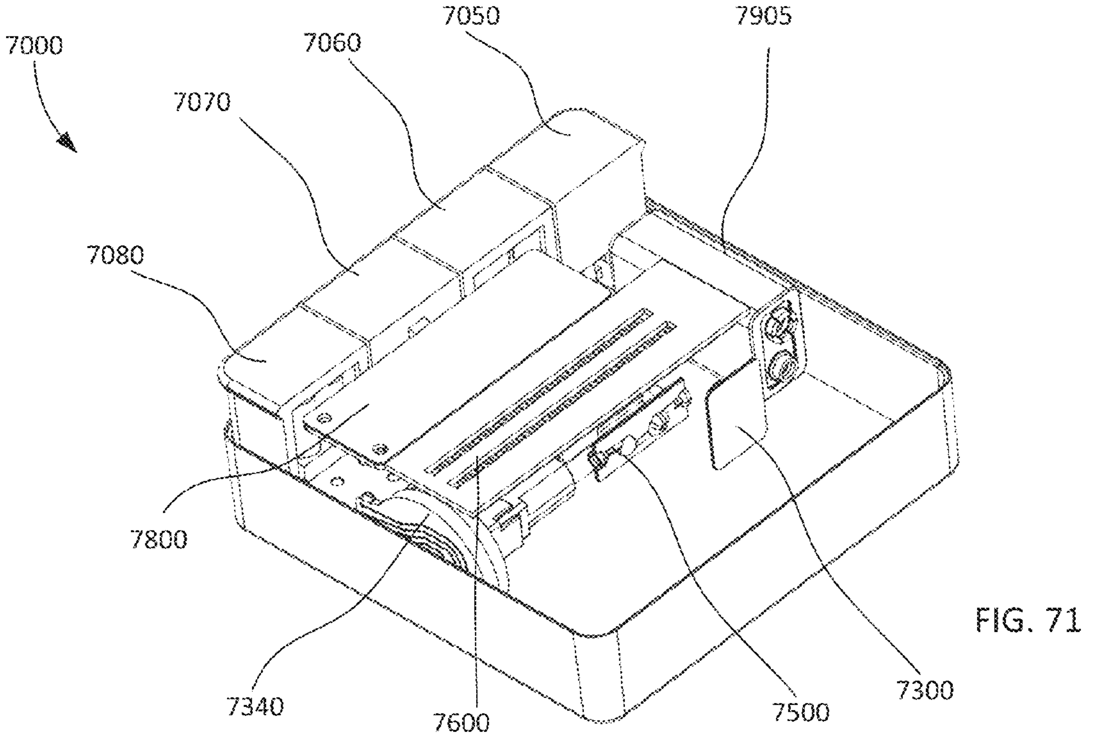
FIG. 71 is a perspective view of the molecular diagnostic test device shown in FIG. 70, with the top portion of the housing removed to show the internal components.
Figure 72:
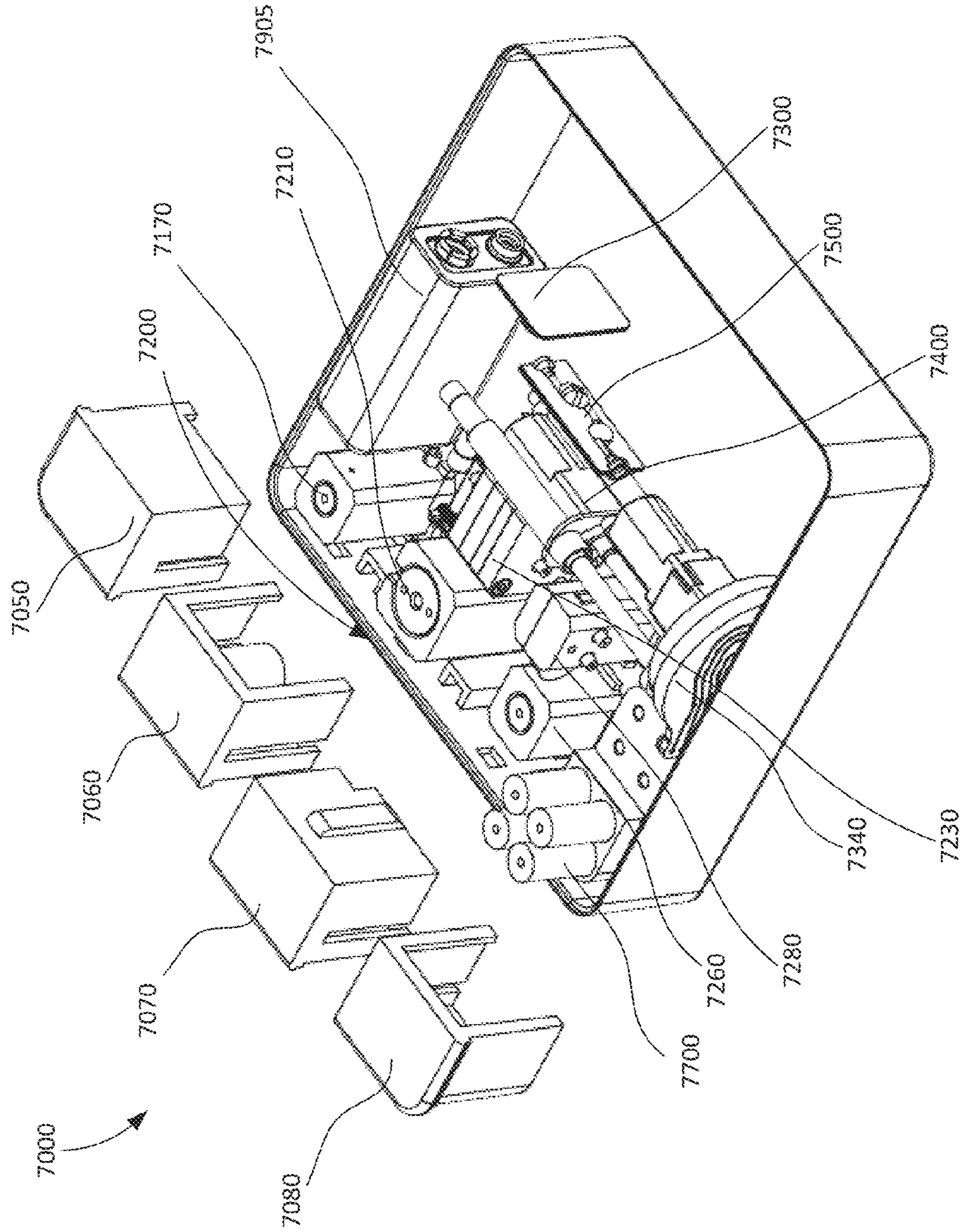
FIG. 72 is a perspective view of the molecular diagnostic test device shown in FIG. 70, with the top portion of the housing, the amplification module, and the detection module removed to show the internal components.

Although the molecular diagnostic system 6000 is shown and described above as including certain modules disposed within a housing in a particular arrangement, in other embodiments, a device need not include all of the modules identified in the device 6000. Moreover, in some embodiments, the functions described as being performed by two modules can be performed by a single device and/or structure. For example, in some embodiments a device need not include a separate mixing module, but instead can perform the mixing operation described above with respect to the mixing module 6500 within another module (such as the inactivation module or the fluid transfer module). Moreover, in other embodiments, a device can include the modules disposed within a housing in any suitable arrangement. For example, FIGS. 70-72 show perspective views of a molecular diagnostic test device 7000 according to an embodiment. The diagnostic test device 7000 includes a housing (including a top portion 7010 and a bottom portion 7030), within which a variety of modules are contained. Specifically, the device 7000 includes a sample preparation module 7200, an inactivation module 7300, a fluidic drive (or fluid transfer) module 7400, a mixing chamber 7500, an amplification module 7600, a detection module 7800, a reagent storage module 7700, a rotary venting valve 7340, and a power and control module 7900. The device 7000 can be similar to the device 6000, and thus the internal components and functionality is not described in detail herein.

FIG. 71 shows the device 7000 with the top housing 7010 removed so that the placement of the modules can be seen. FIG. 72 shows the device 7000 with the top housing 7010, the actuation buttons, the amplification module 7600, and the detection module 7800 removed so that underlying modules can be seen. As shown, the device 7000 is includes a top housing 7010 and a lower housing 7030. The top housing 7010 defines a detection (or "status") opening 7011 that allows the user to visually inspect the output signal(s) produced by the device 7000. When the top housing 7010 is coupled to the lower housing 7030, the detection opening 7011 is aligned with the corresponding detection surfaces of the detection module 7800 such that the signal produced by and/or on each detection surface is visible through the corresponding detection opening.

In some embodiments, the top housing 7010 and/or the portion of the top housing 7010 surrounding the detection opening 7011 is opaque (or semi-opaque), thereby “framing” or accentuating the detection openings. In some embodiments, for example, the top housing 7010 can include markings (e.g., thick lines, colors or the like) to highlight the detection openings. For example, in some embodiments, the top housing 7010 can include indicia identifying the detection opening to a particular disease (e.g., *Chlamydia trachomatis* (CT), *Neisseria gonorrhea* (NG) and *Trichomonas vaginalis* (TV)) or control.

The lower housing 7030 defines a volume within which the modules and or components of the device 7000 are disposed. For example, the sample preparation portion receives at least a portion of the sample input module 7170. The sample input module 7170 is actuated by the sample actuator (or button) 7050. The housing defines a notch or opening 7033 that receives a lock tab 7057 of the sample actuator 7050 after the actuator 7050 has been moved to begin the sample preparation operation. In this manner, the sample actuator 7050 is configured to prevent the user from reusing the device after an initial use has been attempted and/or completed.

The wash portion of the housing receives at least a portion of the wash module 7210. The wash module 7210 is actuated by the wash actuator (or button) 7060. The housing defines a notch or opening 7035 that receives a lock tab 7067 of the wash actuator 7060 after the actuator 7060 has been moved to begin the wash operation. In this manner, the wash actuator 7060 is configured to prevent the user from reusing the device after an initial use has been attempted and/or completed.

The elution portion of the housing receives at least a portion of the elution module 7260. The elution module 7260 is actuated by the elution actuator (or button) 7070. The housing defines a notch or opening 7037 that receives a lock tab 7077 of the elution actuator 7070 after the actuator 7070 has been moved to begin the wash operation. In this manner, the elution actuator 7070 is configured to prevent the user from reusing the device after an initial use has been attempted and/or completed.

The reagent portion of the housing receives at least a portion of the reagent module 7700. The housing defines a notch or opening 7039 that receives a lock tab 7087 of the reagent actuator 7080 after the actuator 7080 has been moved to begin the reagent opening operation. In this manner, the reagent actuator 7080 is configured to prevent the user from reusing the device after an initial use has been attempted and/or completed. By including such lock-out mechanisms, the device 7000 is specifically configured for a single-use operation, and poses a limited risk of misuse.

Figure 73:
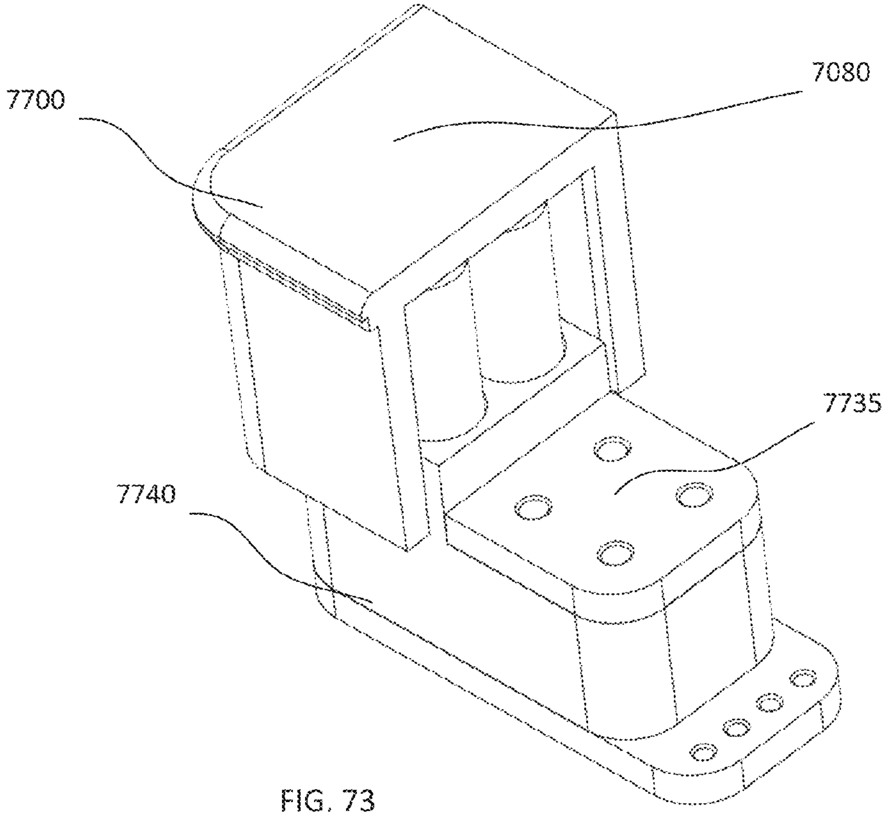
FIGS. 73 and 74 are perspective views of a reagent module of the molecular diagnostic test device shown in FIG. 70.
Figure 74:
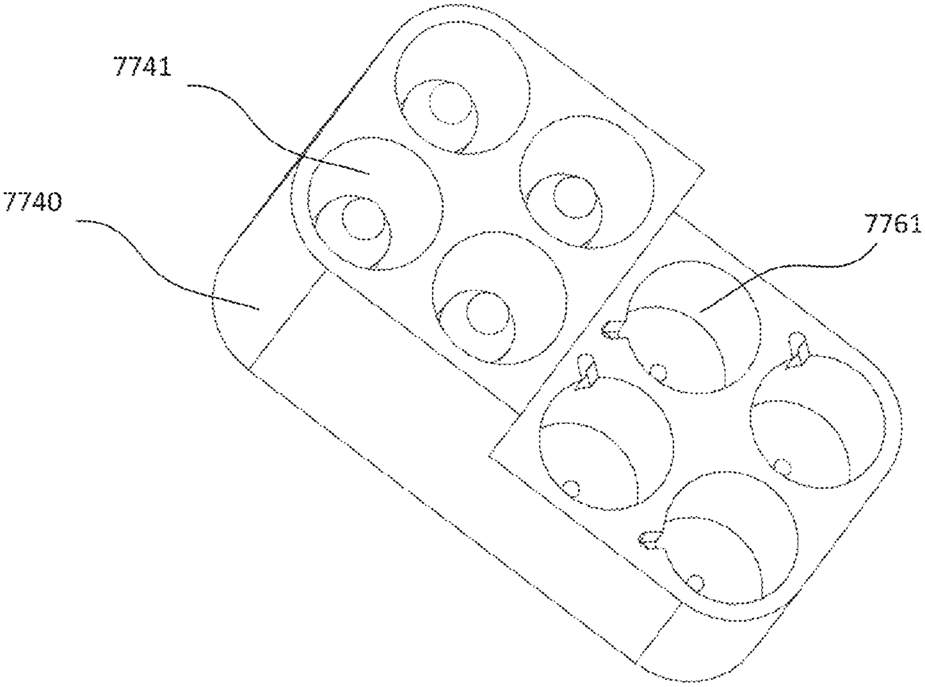

As shown in FIGS. 73 and 74, the reagent module 7700 can include a holding tank 7740 that defines a series of bores 7741 within which the reagent canisters are stored, and also a series of holding reservoirs 7761 to which the reagents flow upon actuations. The reagent module includes a top member 7735 that includes a series of vent ports that function similar to the vent ports described above with respect to the reagent module 6700.

Figure 75:
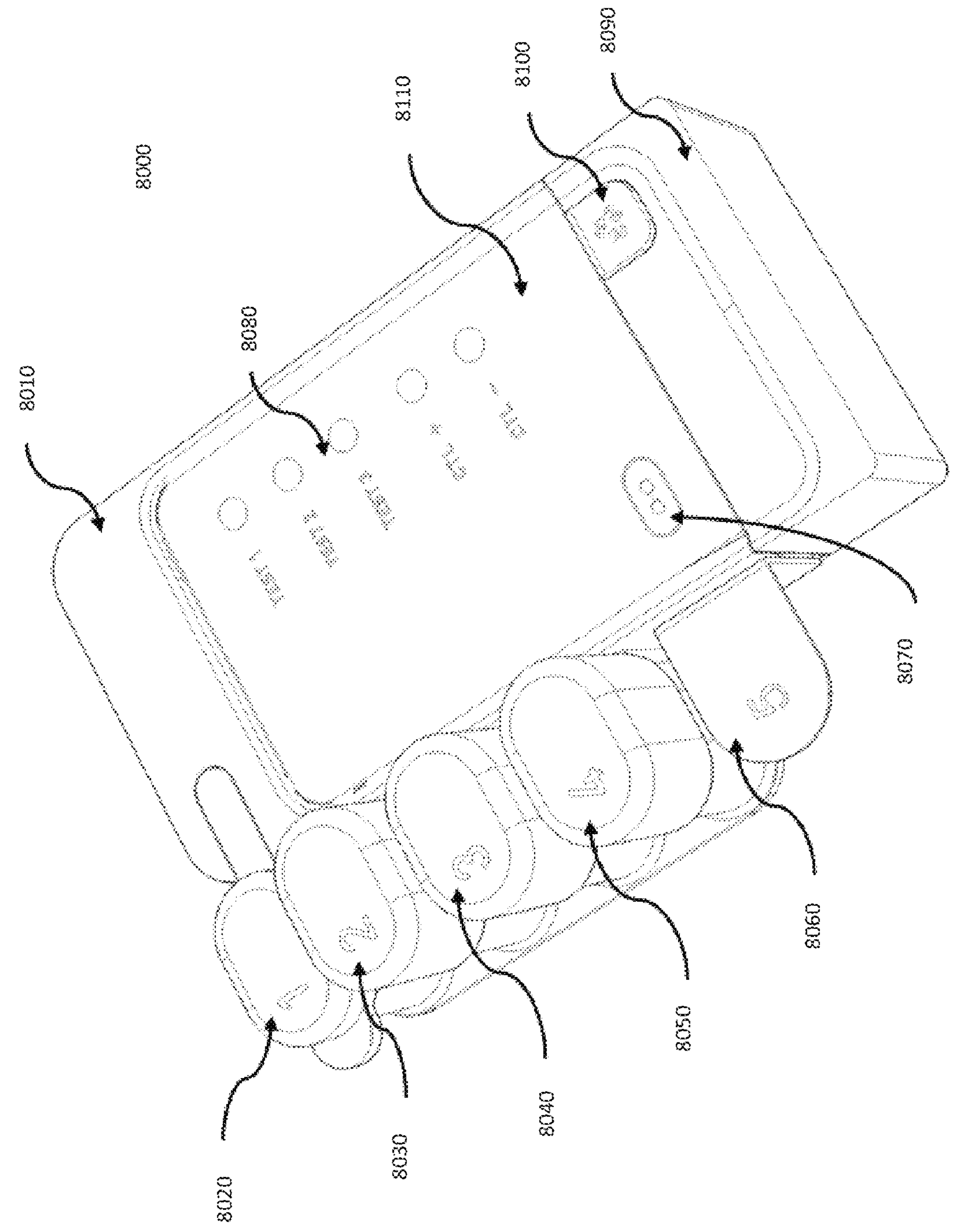
FIG. 75 is a perspective view of an apparatus for diagnostic testing, according to an embodiment.

FIGS. 75-82 illustrate an embodiment of an apparatus 8000 for diagnostic testing that can be structurally and/or functionally similar to the apparatus 6000 and/or the apparatus 7000. As best illustrated in FIG. 75, the apparatus 8000 includes a housing 8010, a sample input port 8020 (including a cap), three plungers 8030/4040/4050, a pull tab 8060, status indicators/lights 8070, a read lane (and/or detection openings) 8080, a battery housing 8090, and a label 8110.

Figure 77:
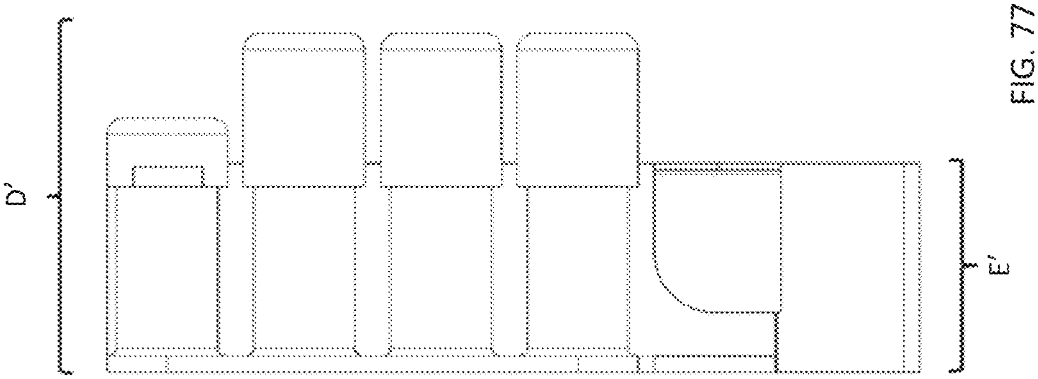
FIG. 77 is a side view of the apparatus of FIG. 75.
Figure 76:
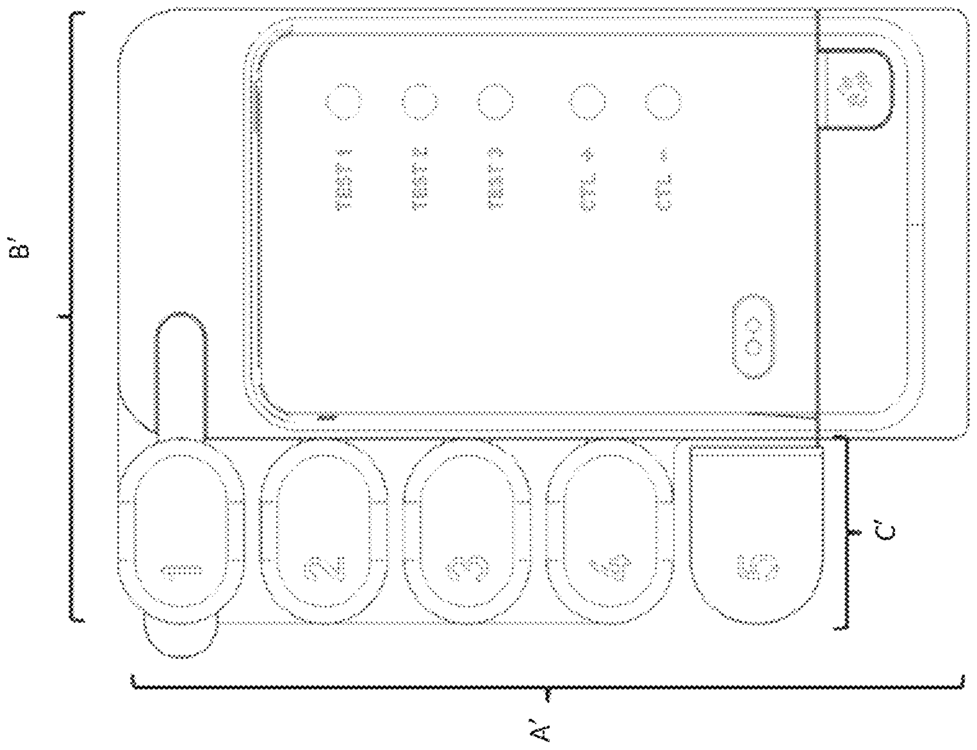
FIG. 76 is a top view of the apparatus of FIG. 75.

As illustrated in FIG. 76, in some embodiments, the overall dimensions of the apparatus 8000 in a front view can be about 101 mm (dimension A')×about 73 mm (dimension B'), or any suitably scaled value. One dimension of the plungers 8030, 8040, 8050, and the tab 8060 can be about 22 mm (dimension C'), or any suitable scaled value relative to the rest of the apparatus 8000. As best illustrated in FIG. 77, in some embodiments, the dimensions of the apparatus 8000 in a side view can be about 82 mm (dimension D')×about 26 mm (dimension E'), or any suitably scaled value. In some embodiments, the housing 8010 includes a clear top surface for ease of viewing by the user. In some embodiments (not shown), the housing 8010 can include a prepare module and a read module. The prepare module (not shown) is configured to intuitively guide the user in preparing a sample for analysis/testing, while the read module (not shown) is configured to intuitively guide the user in reading out the test results.

In some embodiments, as illustrated, the input port 8020, the plungers 8030/4040/4050, and the pull tab 8060 have indicators “1”, “2”, etc., to guide a user in the correct sequence of steps for use of the apparatus 8000. In some embodiments, during use, the sample input port 8020 is configured to receive a sample, such as a patient sample (see FIG. 78). In some embodiments, the cap is tethered to the port and/or any other part of the apparatus 8000 to prevent it from being misplaced. In some embodiments, the port 8020 is configured for use with standard pipettes. In some embodiments, the port 8020 can hold up to about 700 μL of sample. In some embodiments, the port and cap structure can withstand up to 50 psi of pressure. In some embodiments (not shown), the port 8020 includes one or more visual indicators (e.g., LEDs) to verify the correct volume has been dispensed.

Figure 79:
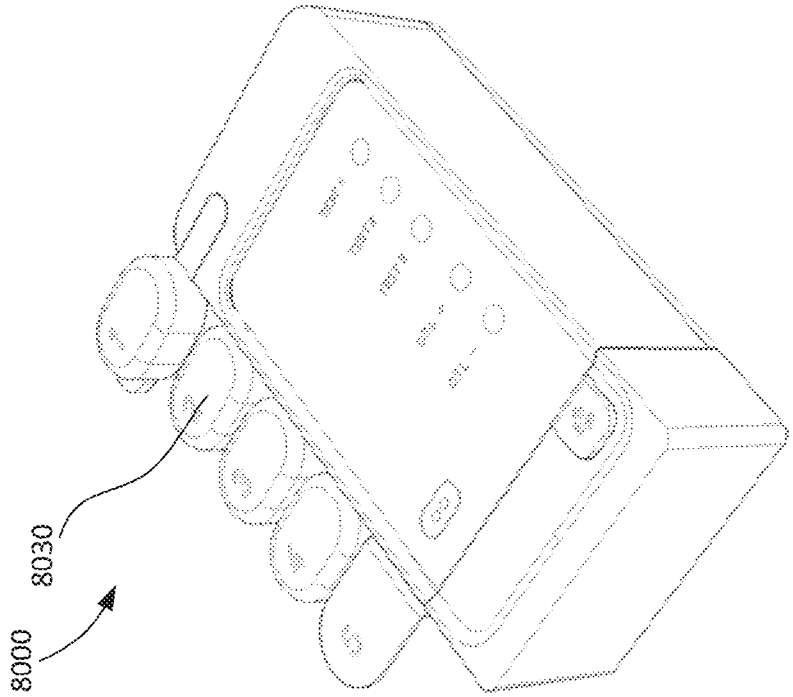
FIG. 79 is an illustration of use of plungers of the apparatus of FIG. 75.
Figure 78:
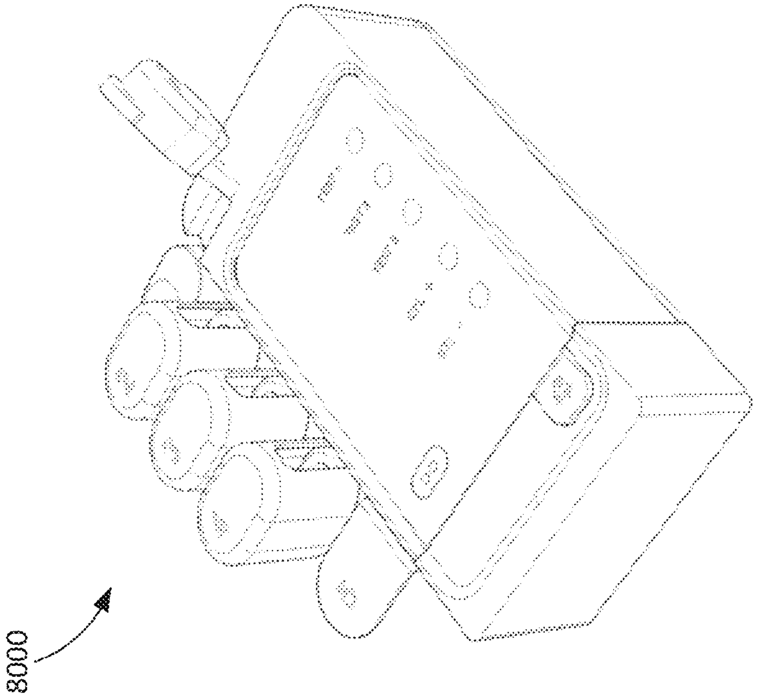
FIG. 78 is an illustration of use of a sample input port of the apparatus of FIG. 75.

In some embodiments, as best illustrated in FIG. 79, the plunger 8030 is configured to push the sample in the port 8020 through a filter, similar to the operation of the sample preparation module 6200 described earlier. The plunger 8030 is also configured to convey a volume of air, followed by a wash buffer, through the filter. In some embodiments, the plunger 8030 locks into place once the user depresses it substantially completely. In some embodiments, the locking of the plunger 8030 is irreversible.

In some embodiments, the plunger 8040 is configured to flush the filter with eluent, similar to the operation of the sample preparation module 1200 described earlier. The plunger 8040 is also configured to push eluent into the inactivation chamber. In some embodiments, the plunger 8040 locks into place once the user depresses it substantially completely. In some embodiments, the locking of the plunger 8040 is irreversible.

In some embodiments, the plunger 8050 “bursts” the reagent tank, or releases reagents from the reagent tank, similar to the operation of the reagent module 6700 described earlier. In some embodiments, the plunger 8050 locks into place once the user depresses it substantially completely. In some embodiments, the locking of the plunger 8060 is irreversible.

Figure 80:
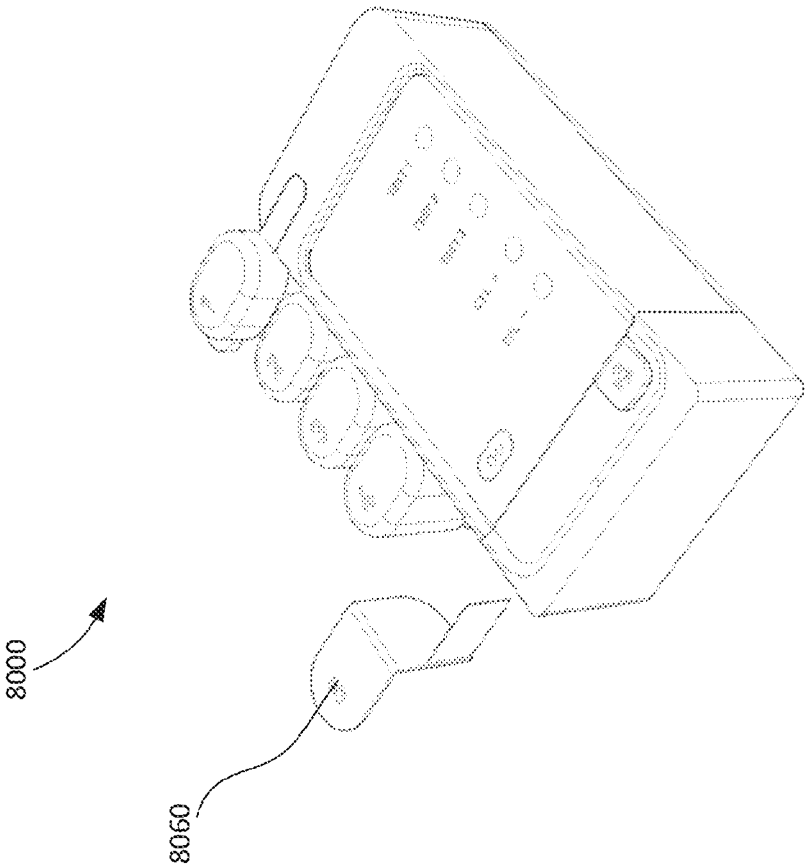
FIG. 80 is an illustration of use of a pull-out tab of the apparatus of FIG. 75.

In some embodiments, as best illustrated in FIG. 80, the tab 8060 is configured such that, when pulled by the user, an internal electrical circuit is completed, which begins one or more diagnostic tests on the sample, such as by, for example, initiating operation of the amplification module (which can be similar to the amplification module 6600. In some embodiments, the tab 8060 is detachable and disposable, such that a user can dispose the tab 8060 after removal from the apparatus 8000.

In some embodiments, the input port 8020, the plungers 8030/4040/4050, and the pull tab 8060 are configured for irreversible operation. Said another way, each of these elements is configured to "lock" and/or disable reversal once properly deployed by the user. In this manner, a user is prevented from improperly using the device. In some embodiments, the input port 8020, the plungers 8030/4040/4050, and the pull tab 8060 include one or more lock out mechanisms to prevent the user from completing steps/using the apparatus 8000 out of order.

In some embodiments, the status lights 8070 are visual indicators, such as LED lights, that are configured for providing feedback to the user on one or more states of the apparatus 8000 including, but not limited to, when the tab 8060 is removed, when the diagnostic test is processing (after the tab 8060 is pulled), when the diagnostic test is ready for the user to review, when an error state is present, and/or the like. For example, in some embodiments, some variation in number of lit LEDs, the pattern of lighting of LEDs, the duration of lighting of LEDs, and/or the color of the lit LEDs, can be employed to represent each state of the apparatus 8000.

In some embodiments, the read lane and/or detection opening 8080 is configured to permit interpretation of the test results by the user. In some embodiments, the read lane 8080 includes a substrate that produces a color indicator, in accordance with the methods described herein (e.g., the enzymatic reaction described above with reference to FIG. 8). In other embodiments, the read lane 8080 includes color strip or absorbent paper configured to produce a colormetric output associated with a target. In some embodiments, the housing 8010 partially masks the read lane 8080. In this manner, housing 8010 can be labeled for the convenience of the user. In some embodiments, as seen in FIG. 75, the read lane 8080 can include one or more dots or "spots." In some embodiments, some dots are configured to indicate test results, while some dots are configured to indicate control results. FIG. 75 illustrates an example scenario with three dots as a test panel and two dots as a control panel for user analysis.

Figure 81:
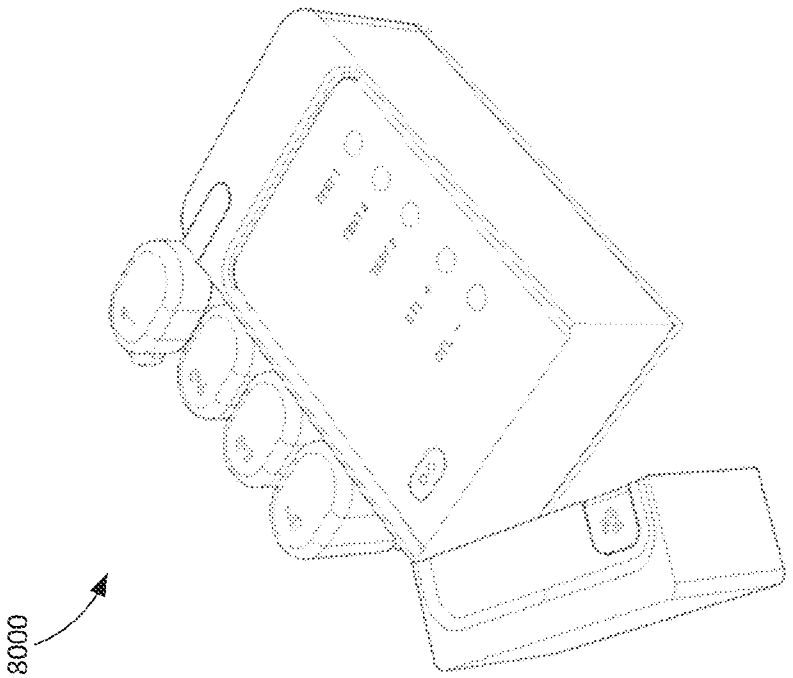
FIG. 81 is an illustration of a detachable battery of the apparatus of FIG. 75.
Figure 82:
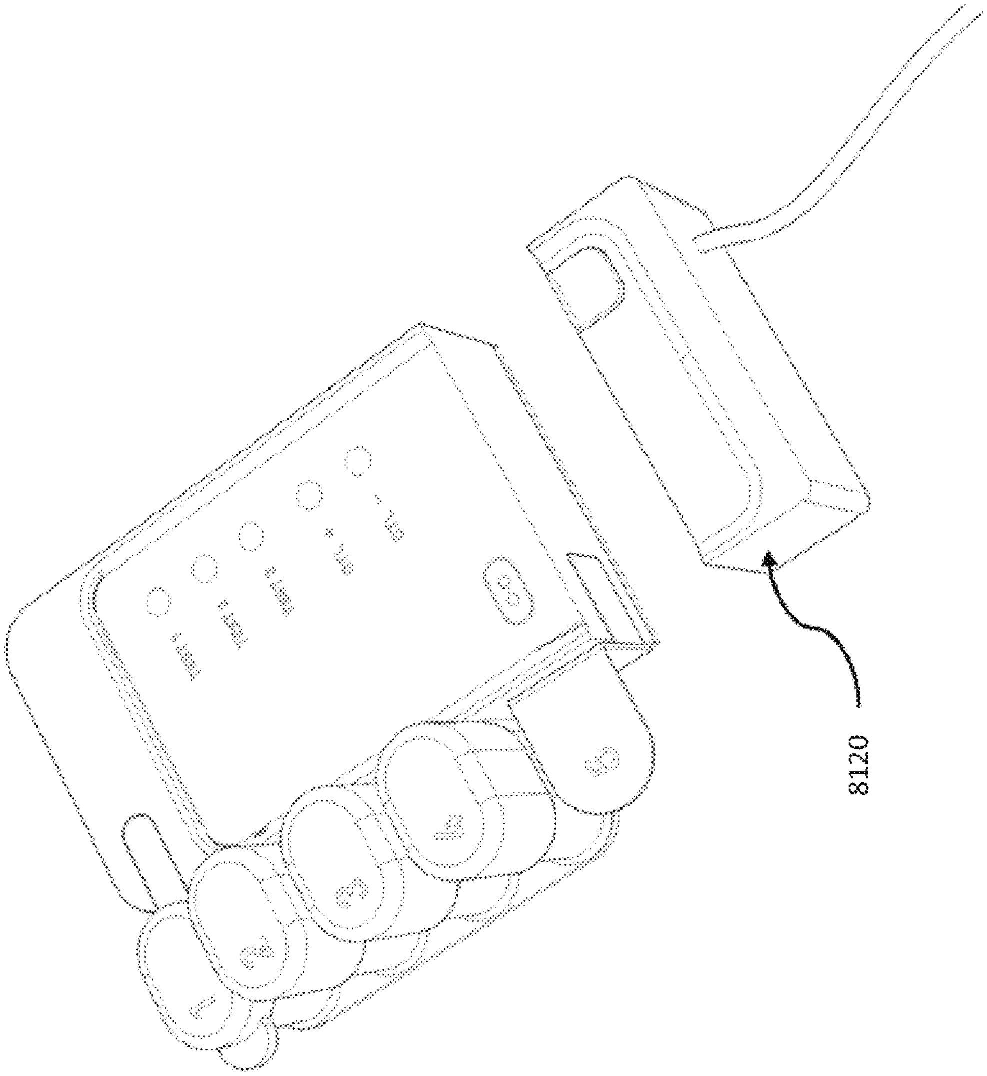
FIG. 82 is an illustration of a rechargeable battery of the apparatus of FIG. 75.

As best illustrated in FIGS. 75 and 81, the battery housing 8090 is configured to hold a battery source, such as, for example, a 9V battery, for powering the apparatus 8000. A button 8100 is configured to permit a user to removably detach an attached battery, such as, for example, for replacement and/or disposal. As best illustrated in FIG. 82, in some embodiments, the apparatus 8000 can be configured for use with a rechargeable battery unit 8120. In this manner, instead of disposing the entire apparatus 8000 after use, the user retains the battery unit 8120 for recharging and reuse with a new cartridge (i.e., where a "cartridge," for purposes of this example embodiment, is the apparatus 8000 without the battery unit 8120).

In other embodiments, the power source in any of the devices shown and described herein can be any suitable energy storage/conversion member, such as a capacitor a magnetic storage systems, a fuel cell or the like. In yet other embodiments, any of the devices shown and described herein, including the device 6000, can be configured to operate on AC power. Thus, in some embodiments, a device can include a plug configured to be disposed within an AC outlet. In such embodiments, the power and control module (e.g., the module 6900) can include the necessary voltage and/or power converters to supply the appropriate power to each of the modules therein. In some embodiments, the AC plug can also serve as a mechanism to ensure that the device is properly oriented (e.g., in a level and flat orientation) during use.

Although the device 6000 is shown as including a separate fluid transfer device 6110, in other embodiments, a device can include a sample transfer device that engages with and/or is removably coupled to the overall housing. For example, FIGS. 83-87 show a molecular diagnostic test device 9000 according to an embodiment. The diagnostic test device 9000 is contained with a housing 9010, and includes a variety of modules. Specifically, the device 9000 includes a sample preparation module (similar to the sample preparation module 6200), an inactivation module (similar to the inactivation module 6300), a fluidic drive (or fluid transfer) module (similar to the fluid transfer module 6400), a mixing chamber (similar to the mixing module 6500), an amplification module (similar to the amplification module 6600), a detection module (similar to the detection module 6800), a reagent storage module (similar to the reagent module 6700), a valve module (similar to the valve module 6340), and a power and control module (similar to the power and control module 6900). The device 9000 can be similar to the device 6000, and thus the internal components and functionality is not described in detail herein. The device 9000 differs from the device 6000, however, in that the device 9000 includes an interlocking transfer member 9110, as described below.

Figure 83:
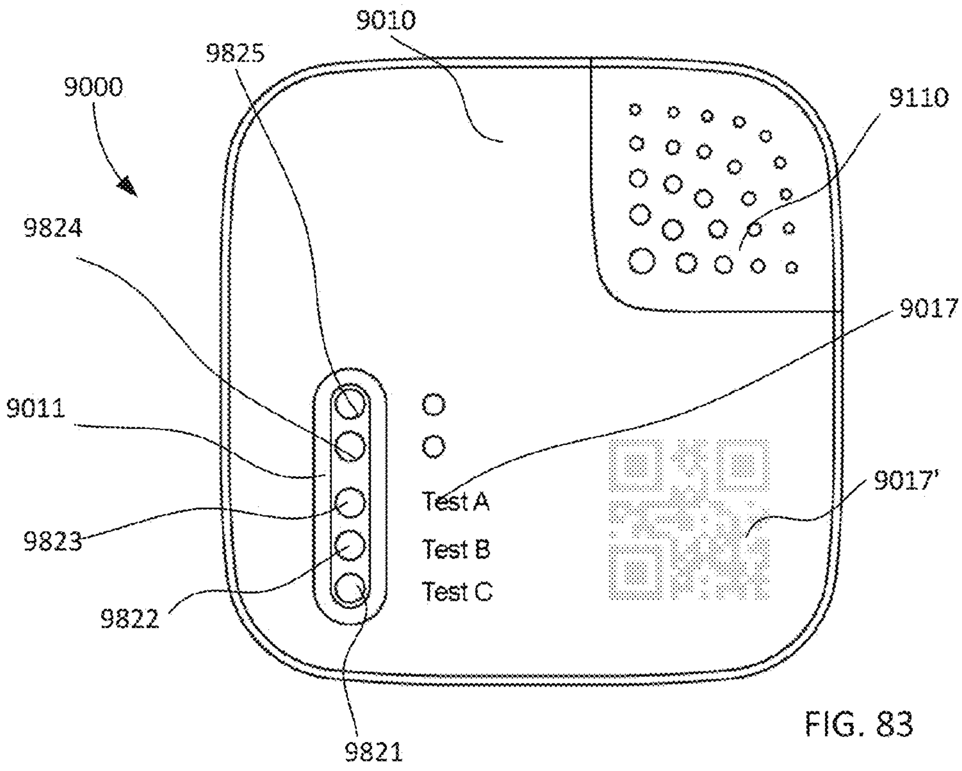
FIG. 83 is a top view of a molecular diagnostic test device, according to an embodiment.

FIG. 83 shows a top view of the device 9000, and illustrates the housing 9010 and the sample transfer device 9110 coupled to and/or disposed within the housing 9010. The housing 9010 defines a detection (or "status") opening 9011 that allows the user to visually inspect the output signal(s) produced by the device 9000. The opening 9011 is aligned with and allows viewing of five detection surfaces of the detection module contained therein. In particular the opening 9011 allows viewing of a signal produced by a first detection surface 9821, a second detection surface 9822, a third detection surface 9823, a fourth detection surface 9824, and a fifth detection surface 9825. These detection surfaces can produce signals for detection of a disease in a similar manner as described above with respect to the detection module 6800.

The housing 9010 and/or the portion of the housing 9010 surrounding the detection opening 9011 is opaque (or semi-opaque), thereby "framing" or accentuating the detection openings. In some embodiments, the housing 9010 can include markings (e.g., thick lines, colors or the like) to highlight the detection openings. Additionally, the housing 9010 can include indicia 9017 identifying the detection opening to a particular disease (e.g., *Chlamydia trachomatis* (CT), *Neisseria gonorrhea* (NG) and *Trichomonas vaginalis* (TV)) or control. The housing 9010 also includes a bar code 9017'.

Figure 84:
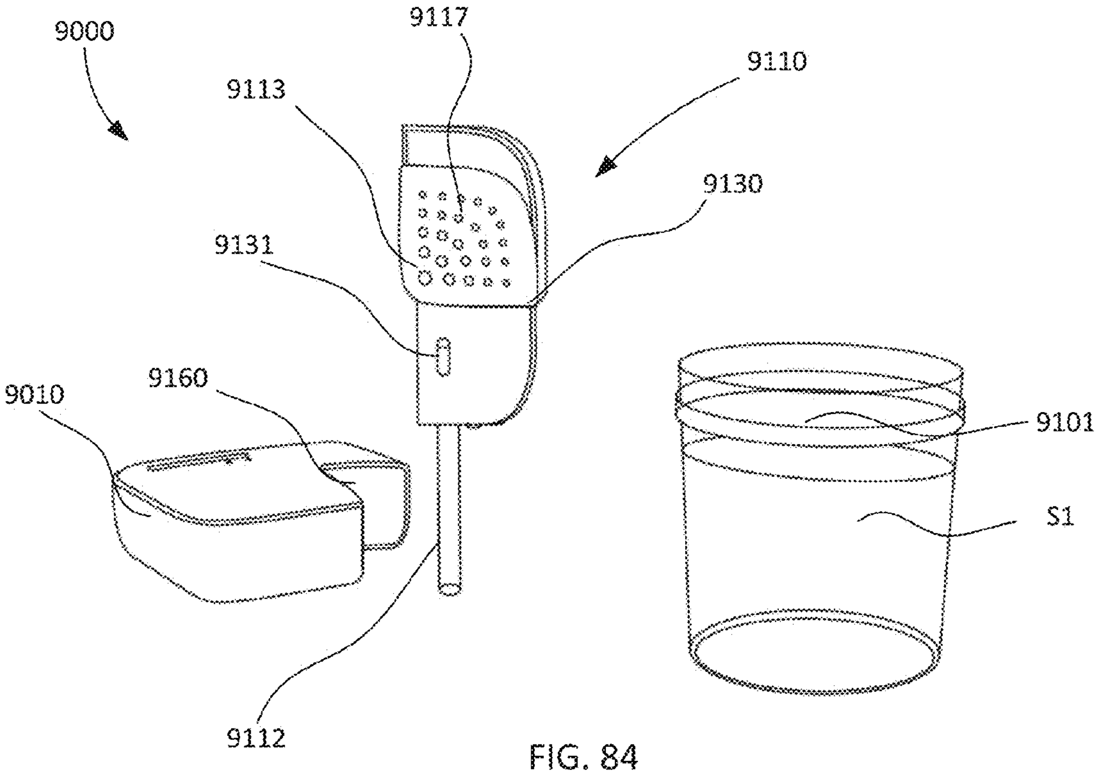
FIG. 84 is a perspective view of the molecular diagnostic test devices shown in FIG. 83, in an unpackaged configuration.
Figure 85:
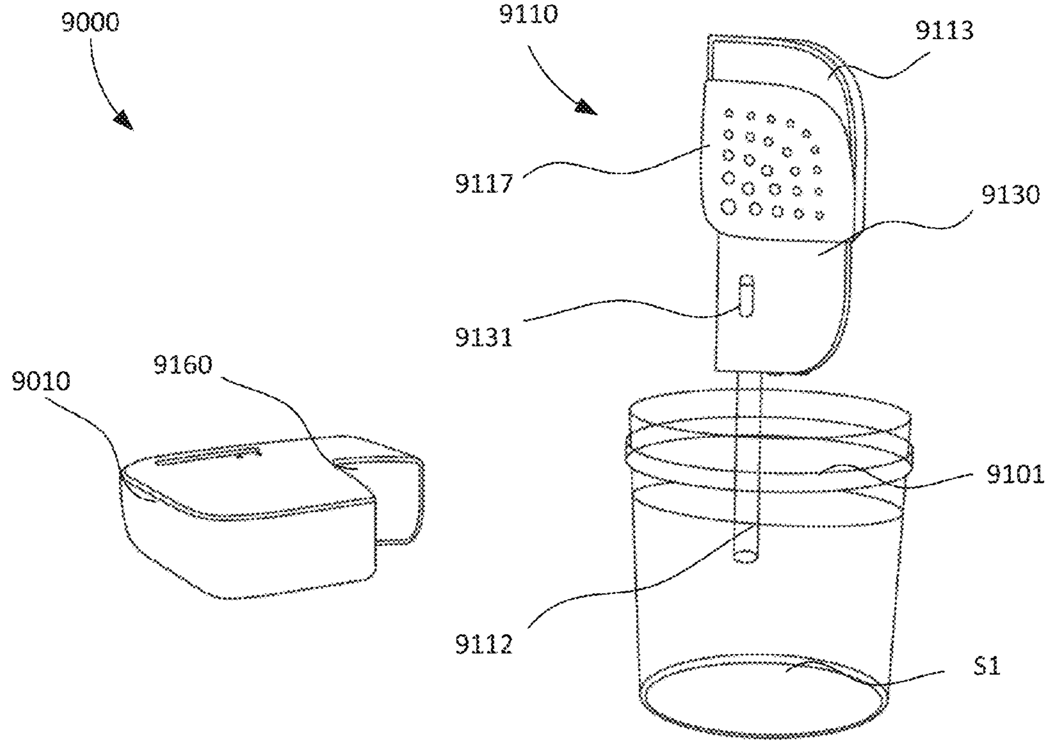
FIGS. 85-87 are various views of the molecular diagnostic test devices shown in FIG. 83, in various stages of operation.

The device 9000 is packaged along with and/or includes a sample transport device 9110 configured to convey a sample S1 into the device 9000 and/or the sample preparation module therein. As shown in FIG. 84, the sample transfer device 9110 includes a distal end portion 9112 and a proximal end portion 9113, and can be used to aspirate or withdraw a sample S1 from a sample cup 9101. The sample transfer device 9110 then delivers a desired amount of the sample S1 to an input portion 9160 of the device 9000. Specifically, the distal end portion 9112 includes a dip tube portion, and in some embodiments, can define a reservoir having a desired and/or predetermined volume.

The proximal end portion 9113 includes a housing 9130 and an actuator 9117. The actuator 9117 can be manipulated by the user to draw the sample into the distal end portion 9112. The housing 9130 includes a status window 9131 or opening through which the user can visually check to see that adequate volume has been aspirated. In some embodiments, the sample transport device 9110 includes an overflow reservoir that receives excess flow of the sample during the aspiration step. The overflow reservoir includes a valve member that prevents the overflow amount from being conveyed out of the transfer device 9110 when the actuator 9117 is manipulated to deposit the sample into the input portion 9160 of the device 9000. This arrangement, ensures that the desired sample volume is delivered to the device 9000. Moreover, by including a "valved" sample transfer device 9110, the likelihood of misuse during sample input is limited. This arrangement also requires minimal (or no) scientific training and/or little judgment of the user to properly deliver the sample into the device.

Figure 86:
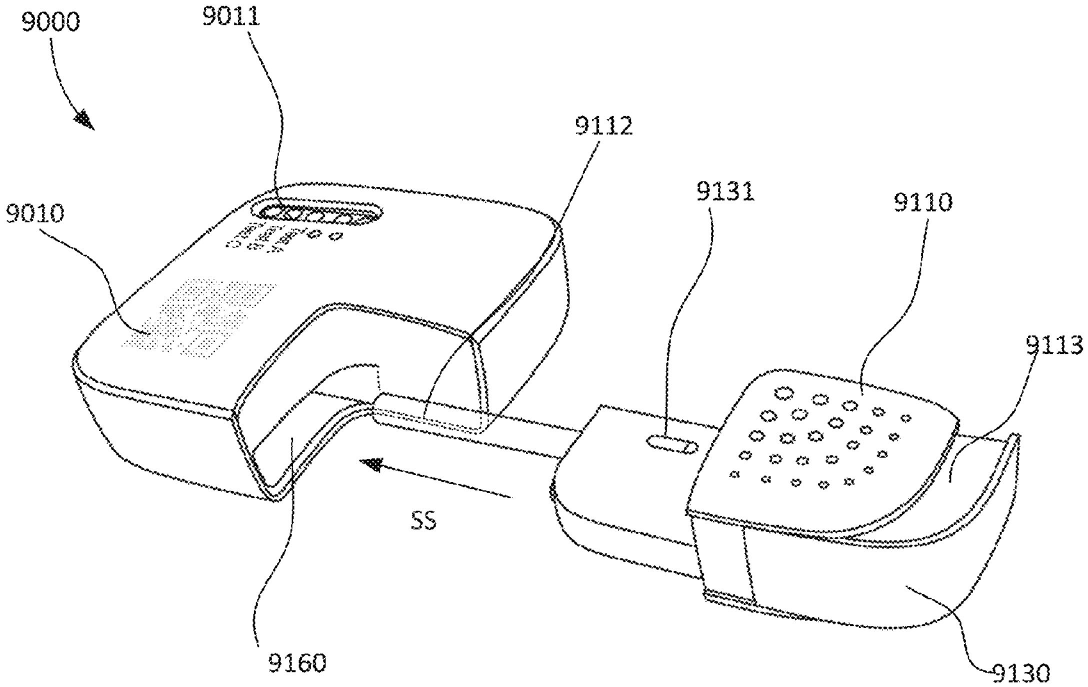

In use, the sample transfer device 9110 is removed from the housing 9010 and the distal end portion 9112 is disposed within the sample cup 9101. The actuator 9117 is manipulated to withdraw a portion of the sample S1 into the sample transfer device 9110. During use, the operator can inspect the status window 9131 to ensure that the sample S1 is visible, thereby indicating that the sample aspiration operation was successful. As shown in FIG. 86, the sample transfer device 9110 is then placed into the receiving portion 9160 of the housing 9010, as indicated by the arrow SS. In some embodiments, the sample transfer device 9110, the housing 9130 and/or the housing 9010 can include locking mechanisms, such as mating protrusions, recesses and the like that prevent removal of the sample transfer device 9110 after it has been locked in place.

Figure 87:
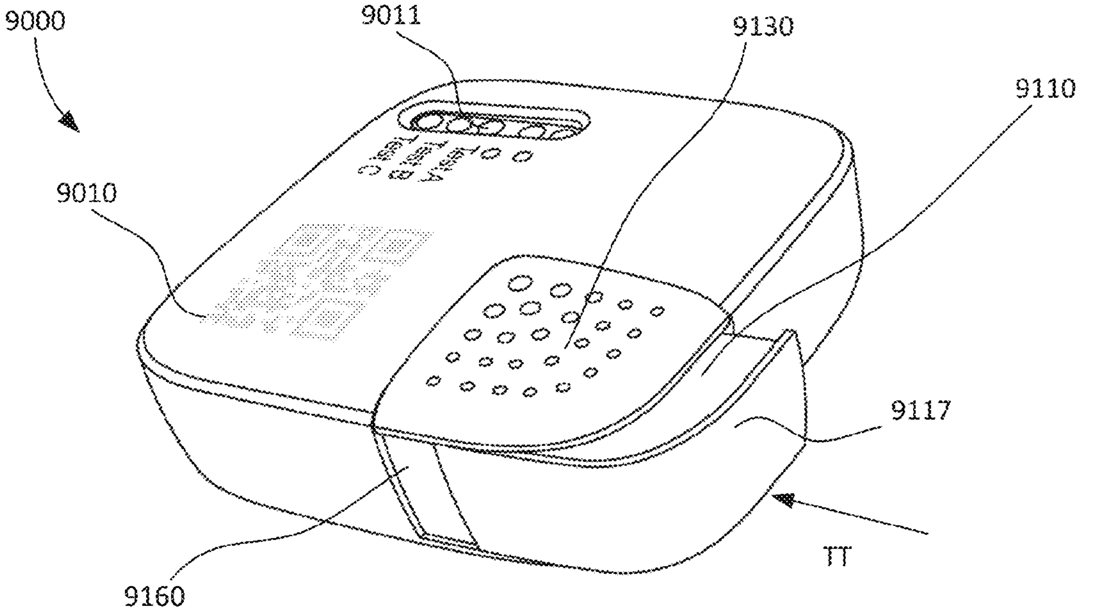

To initiate a test, the actuator 9117 is the moved as shown by the arrow TT in FIG. 87, to push the sample into the sample preparation module of the device 9000.

Figure 88:
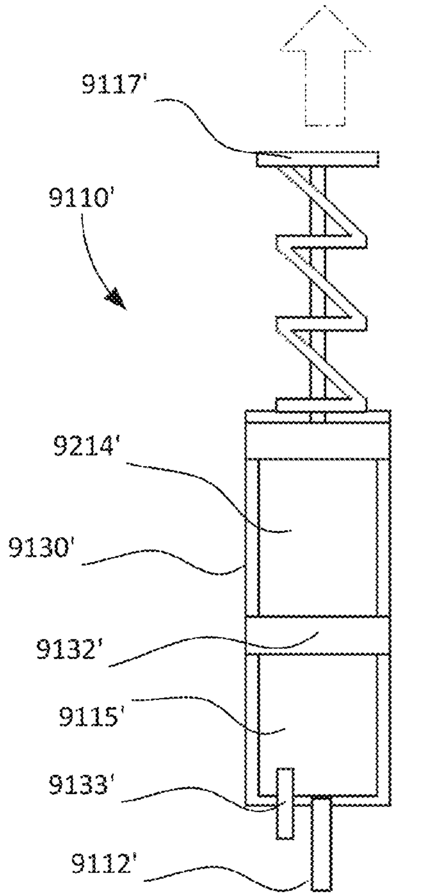
FIGS. 88-89 are schematic illustrations of a sample transfer device according to an embodiment, in a first configuration and a second configuration, respectively.
Figure 89:
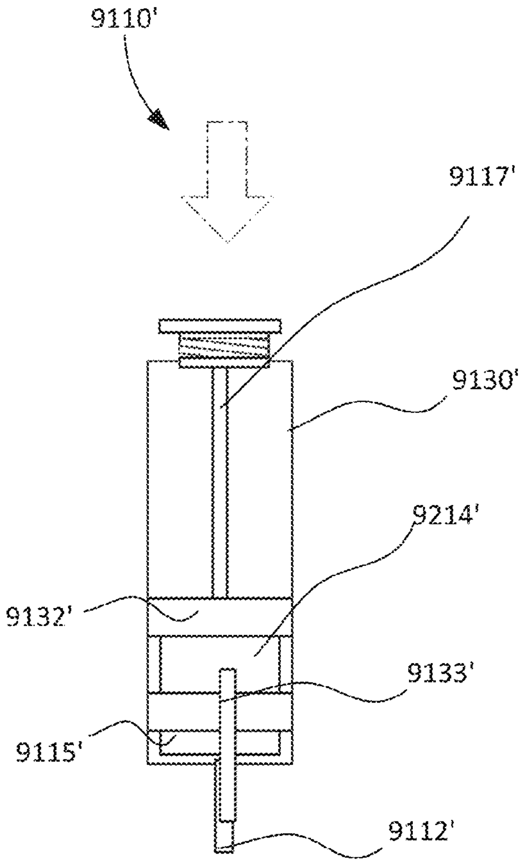

Although the device 6000 is shown as including a wash module 6210 that is included within the housing, and that is separate from the sample transfer device 6110, in other embodiments, a device can include a sample transfer device that includes the wash therein. In such embodiments, movement of an actuator to deliver the sample (e.g., to convey the sample through a filter within the device) can also be used to convey a wash solution (including an air wash) contained within the sample transfer device through the filter. For example, FIGS. 88 and 89 are schematic illustrations of a sample transfer device 9110' according to an embodiment. The sample transfer device 9110' can be used in conjunction with any of the molecular diagnostic test devices shown and described herein.

The sample transfer device 9110' includes a housing 9130' having distal end portion and a proximal end portion, and can be used to aspirate or withdraw a sample from a sample cup (not shown). The sample transfer device 9110' then delivers a desired amount of the sample to an input portion of a molecular diagnostic test device of the types shown and described herein. The housing 9130' defines a sample reservoir 9115' (for receiving a sample), and a wash reservoir 9214' (that contains a wash solution). The sample reservoir 9115' and the wash reservoir 9214' are separated by (and or fluidically isolated from each other by) a septum (or elastomeric stopper) 9132'.

The distal end portion of the housing includes a dip tube 9112'. The proximal end portion of the housing includes an actuator 9117'. In use, the actuator 9117' is moved and/or manipulated by the user to draw the sample through the dip tube 9112' and into the sample reservoir 9115'. To transfer the sample to the device (not shown), the dip tube 9112' and/or a portion of the housing 9130' is placed into and/or adjacent the device, and the actuator 9117' is moved distally (as indicated by the arrow in FIG. 89). Movement of the actuator 9117' pushes the sample out of the dip tube 9112', and also moves the septum 9132' down towards the puncture 9133'. After the sample has been dispensed, the puncture 9133' pierces the septum 9132' thereby allowing the wash solution to flow from the wash reservoir 9214' to the sample reservoir 9115' and/or out of the dip tube 9112'.

Figure 90:
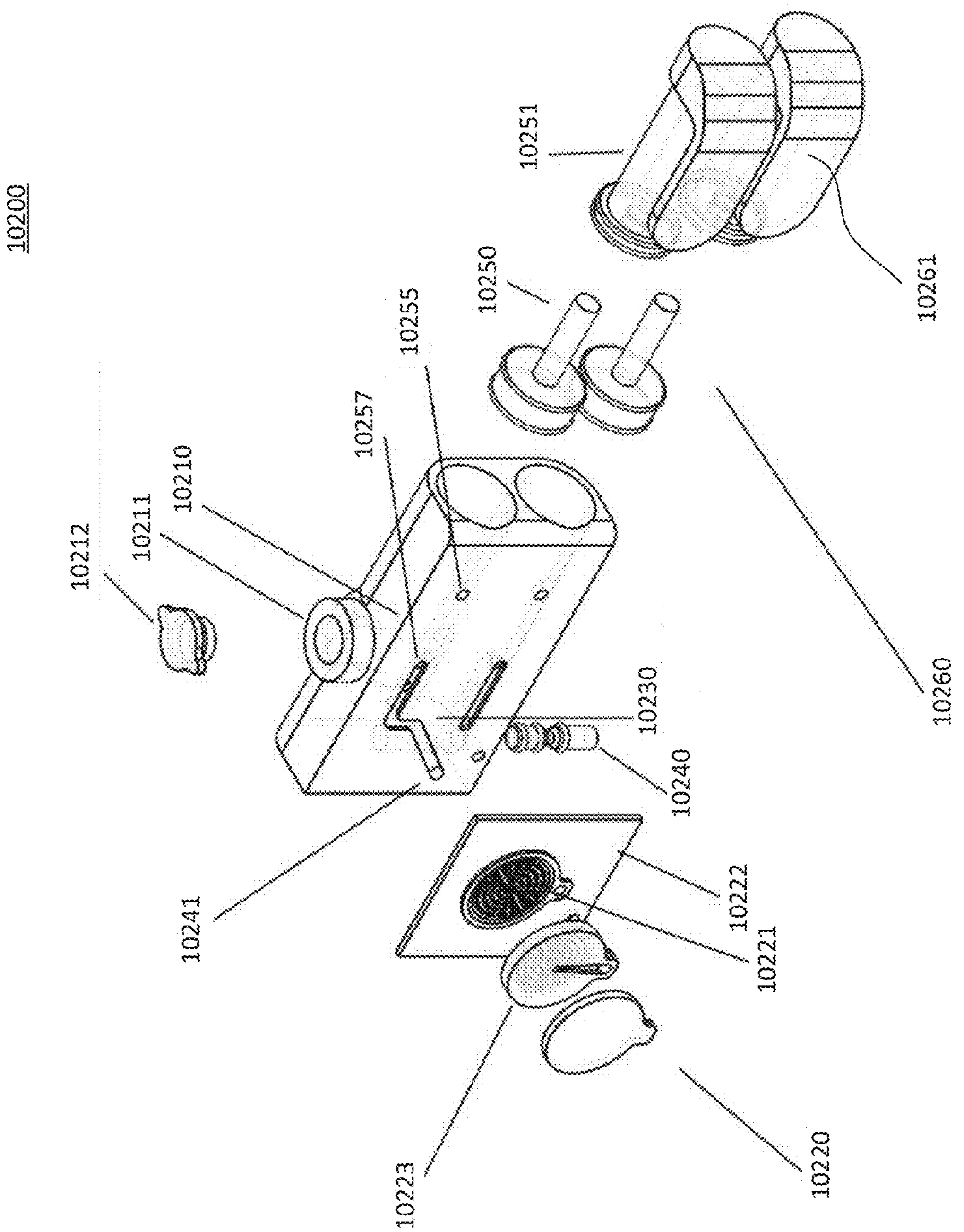
FIG. 90 is a perspective exploded view of components of a sample preparation module, according to an embodiment.
Figure 91:
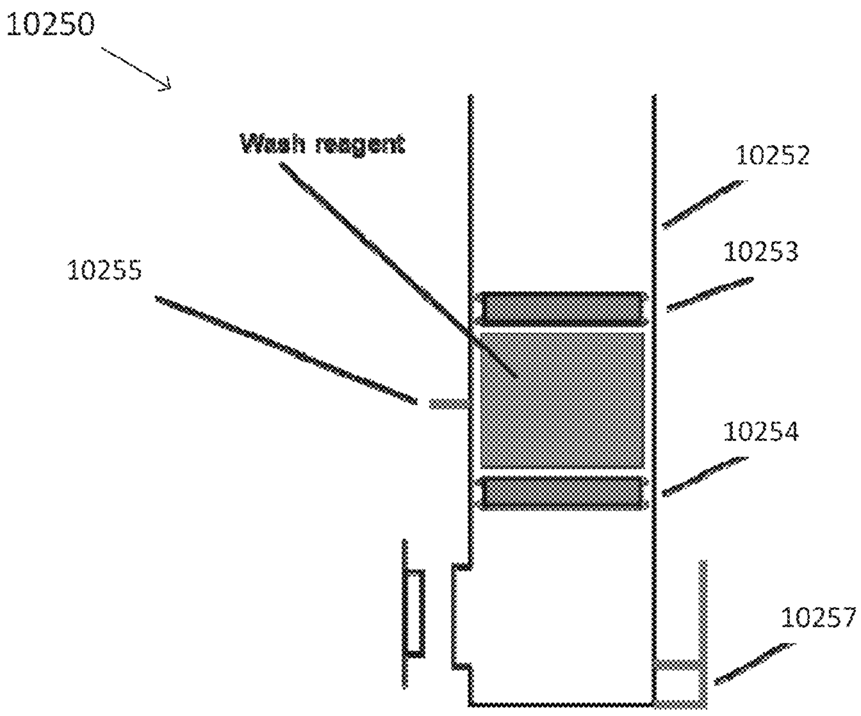
FIG. 91 is a schematic illustration of the wash reagent storage and dispensing assembly shown in FIG. 90.
Figure 92:
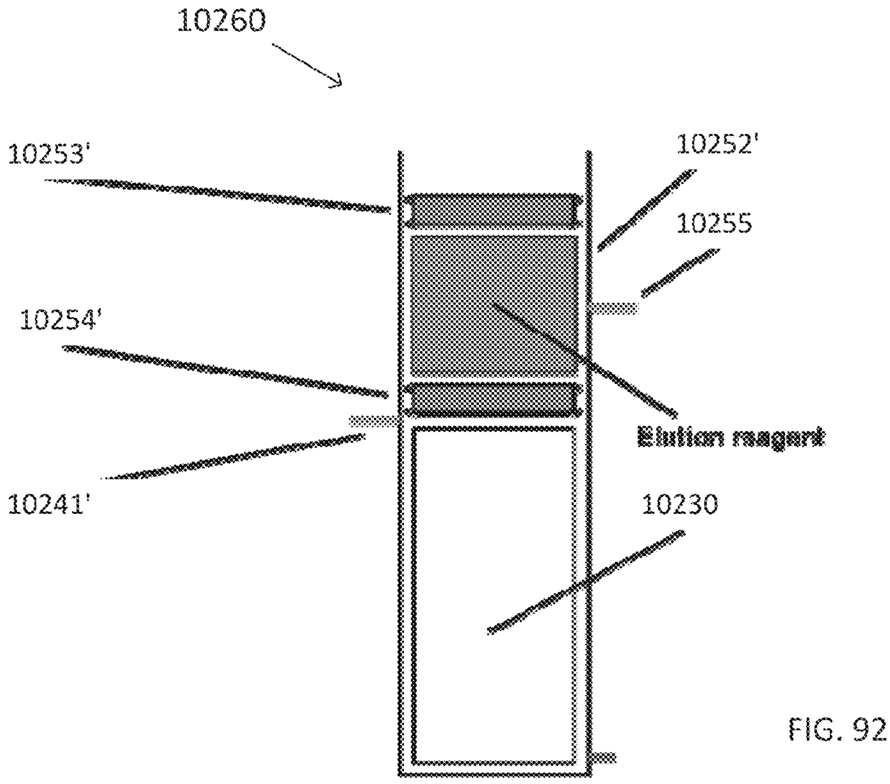
FIG. 92 is a schematic illustration of the elution reagent storage and dispensing assembly shown in FIG. 90.

Although the device 6000 is shown and described as including a wash module 6210 that is separate from (and/or in a different housing from) the elution module 6260, in other embodiments, any of the sample transfer, sample input, wash and/or elution modules described herein can be constructed together as integral units, or maintained as distinct components. Similarly stated, any of the components in any of the sample preparation modules described herein can be in any suitable form. For example, in some embodiments Individual components can include modifications and changes. For example, in some embodiments a sample preparation module can include a sample delivery portion, a wash portion, an elution portion and a filter portion e (including a flow valve assembly) within a common housing. FIGS. 90-92 show a sample preparation module 10200 according to an embodiment. As illustrated in FIG. 90, the sample preparation module 10200 is configured to receive an input sample in connection with any suitable device (such as the diagnostic test devices 6000, 7000, 8000, 9000 or any other devices shown and described herein), and process the sample for use in the subsequent modules. The sample preparation module 10200 includes a reservoir 10210 for receiving and containing the sample, a filter assembly 10220, waste tank 10230, a normally closed valve 10240, two storage and dispensing assemblies (10250 and 10260, see also FIGS. 91 and 92, respectively), and various fluidic conduits (e.g., the output conduit 10241) connecting the various components.

In some embodiments, the sample preparation module 10200 is configured to accept and allow for spill proof containment of a volume of liquid from the sample transfer module (not shown). In some embodiments, the sample preparation module 10200 is configured for onboard storage of wash solution, elution solution, and a positive control. The positive control may be stored in liquid form in the wash solution or stored as a lyophilized bead that is subsequently hydrated by the wash solution. In some embodiments, the sample preparation module 10200 is configured for dispensing the bulk of the sample liquid (~80%) through a filter, while storing the generated waste in a secure manner. In some embodiments, the sample preparation module 10200 is configured for following the sample dispense with a wash dispense, thereby dispensing the bulk of the stored liquid (e.g., about 80%). In some embodiments, the sample preparation module 10200 is configured for back-flow elution to occur off the filter membrane and deliver the bulk (e.g., about 80%) of the eluted volume to the target destination. In some embodiments, the sample preparation module 10200 is configured so as not cause the output solution to be contaminated by previous reagents (e.g., like the sample or wash). In some embodiments, the sample preparation module 10200 is configured for ease of operation by a lay user, requiring few, simple, non-empirical steps, and for a low amount of actuation force.

The sample preparation module 10200 first accepts an input sample through input port 10211. A sample input port cap 10212 is placed over the input port 10211 to contain the sample in its reservoir 10210, to disallow spillage, and to allow accurate manipulation. In some embodiments, the input port cap 10212 can include an irreversible lock to prevent reuse of the device and/or the additional of supplemental sample fluids. In this manner, the sample preparation module 10200 and/or the device within which the module is included can be suitably used by untrained individuals.

To actuate the sample preparation module 10200, the end user pushes down on a handle 10251, which is portion of a wash reagent storage and dispensing assembly 10250. The assembly 10250 moves the entire plunger assembly towards the bottom of the sample reservoir 10210 and thus forces the sample through a series of conduits into a filter assembly 10220. A filter membrane 10221 captures the target organism/entity while allowing the remaining liquid to flow through into the waste tank 10230. Once substantially all of the sample is emptied from the sample reservoir 10210, the wash solution is flowed through the filter assembly 10220 by the continuing motion of the storage and dispensing assembly 10250. The wash solution removes as much as possible of the remaining non-target material from the filter membrane 10221 and flows into the waste tank 10230. After the completion of the wash, a push-valve 10240 is actuated to open an output conduit 10241. The second storage and dispensing assembly 10260 is then actuated using the handle 10261. The initial motion closes the conduit connecting the filter assembly 10220 to the waste tank 10230, and the continuing motion flows the elution solution through the filter 10220 and removes the target organism from the filter membrane 10221, outputting the solution into an output conduit 10241 connected to a subsequent module (e.g., an inactivation module, not shown).

Referring to FIGS. 90 and 91, in some embodiments, the wash reagent storage and dispensing assembly 10250 includes two seal disks 10253 (top seal disk), 10254 (bottom seal disk) housed in a cylindrical bore 10252 to form a sealed reservoir. An opening formed as a fill port 10255 in the side of the bore between the two seals allows the reservoir to be filled. The opening/port 10255 is sealed with a heat seal film (not shown) after the reservoir is filled. Another opening formed as an output port 10257 below the seal disks 10253, 10254 serves as the output for the stored reagent. A handle 10251 is placed on top of the top seal disk 10253, so that when the handle 10251 is actuated downward both of the seals 10253, 10254 (and the liquid trapped between them) are moved downward in a bore 10252 due to the incompressibility of the liquid. Once the bottom seal disk 10254 moves past the output port 10257, however, a new path for the liquid to escape is opened, and instead of the whole assembly moving downward, the top seal disk 10253 is moved, thus compressing the liquid reservoir, and forcing the liquid into the output port 10257.

Referring to FIGS. 90 and 92, the eluent reagent storage and dispensing assembly 10260 contains at least some of the same components as the wash reagent storage and dispensing assembly 10250, but differs at least in the sense that the assembly 10260 stores the eluent reagent downstream of the filter assembly 10220. The lower disk seal (10254' on the elution side of the assembly 10260 also acts as a normally open valve for the filter to waste fluidic conduit. Once this lower seal is moved past the output port 10241' in its bore 10252', it serves to segregate the fluidic path between the output conduit and the waste location further in the bore.

Through manipulation of the initial starting positions of the disk seals (10253', 10254'), the total volume of each of the reagent reservoirs can be modified. Manipulation of the fill volume for each of the reagents, and of the volume transferred by the sample preparation module can also allow for either minimizing or maximizing the volume of air in the reservoir. Combined with the orientation of the module during operation, this can be used to create an "air purge" of the filter 10221 at any desired step, or be used to substantially eliminate air interaction with the filter 10221.

In some embodiments, the module 10200 can be operated with the fill opening/sample input port 10211 facing upward, so that any air remaining in the sample input reservoir 10210 is trapped in the top of the input cavity when the module is operated. The volume of reagents dispensed into the storage reservoirs can be calibrated to leave as little air volume in those chambers as possible. In this manner the sample preparation module 10200 can be used in a manner to minimize air volume.

In other embodiments (e.g., those directed to maximizing air volume), the module 10200 can be used with the operating handles 10251 facing upward (sample can still be input from any orientation). With the volumes involved, this would force the air to the top of each of the reagent reservoirs, and thus allow for substantially all of the reagent to be dispensed first before an air slug would be pushed through. For the stored reagents, the fill volume would be adjusted to leave an appropriate amount of air volume in the reservoir.

Referring to FIG. 90, the filter assembly 10220 includes any suitable membrane 10221. The membrane can be any suitable membrane material, and can be constructed in any manner as described here. In some embodiments, the housings 10222, 10223 can be ultrasonically welded together to correctly tension the filter membrane 10221. The housings 10222, 10223 are also configured to spread the liquid out over the whole area of the filter membrane 10221, rather than allowing the liquid to flow directly through the center. The upper housing 10223 includes a conduit (not shown) to return the liquid back to the plane of the lower housing upon passing through the filter membrane 10221.

Figure 93:
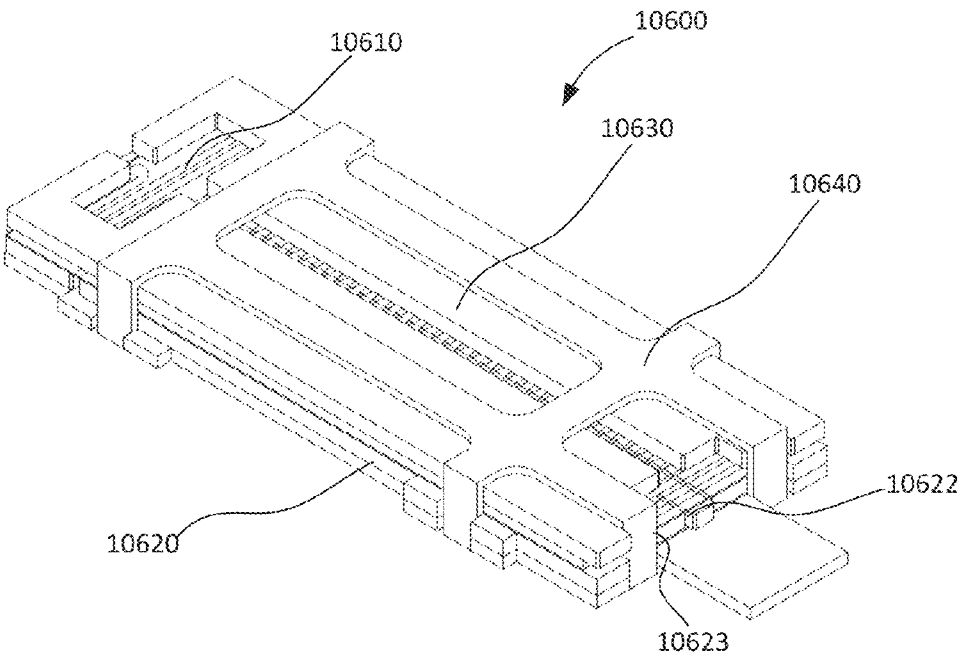
FIG. 93 is perspective view of an amplification module, according to an embodiment.
Figure 94:
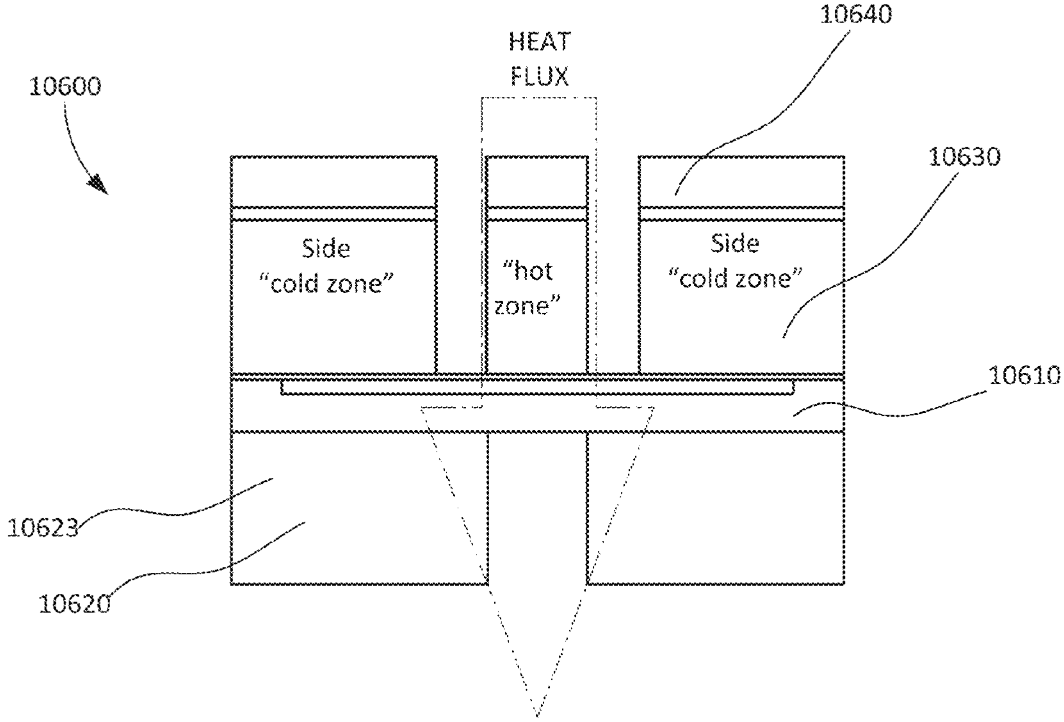
FIG. 94 is a schematic illustration of a heat sink of the amplification module shown in FIG. 93.
Figure 95:
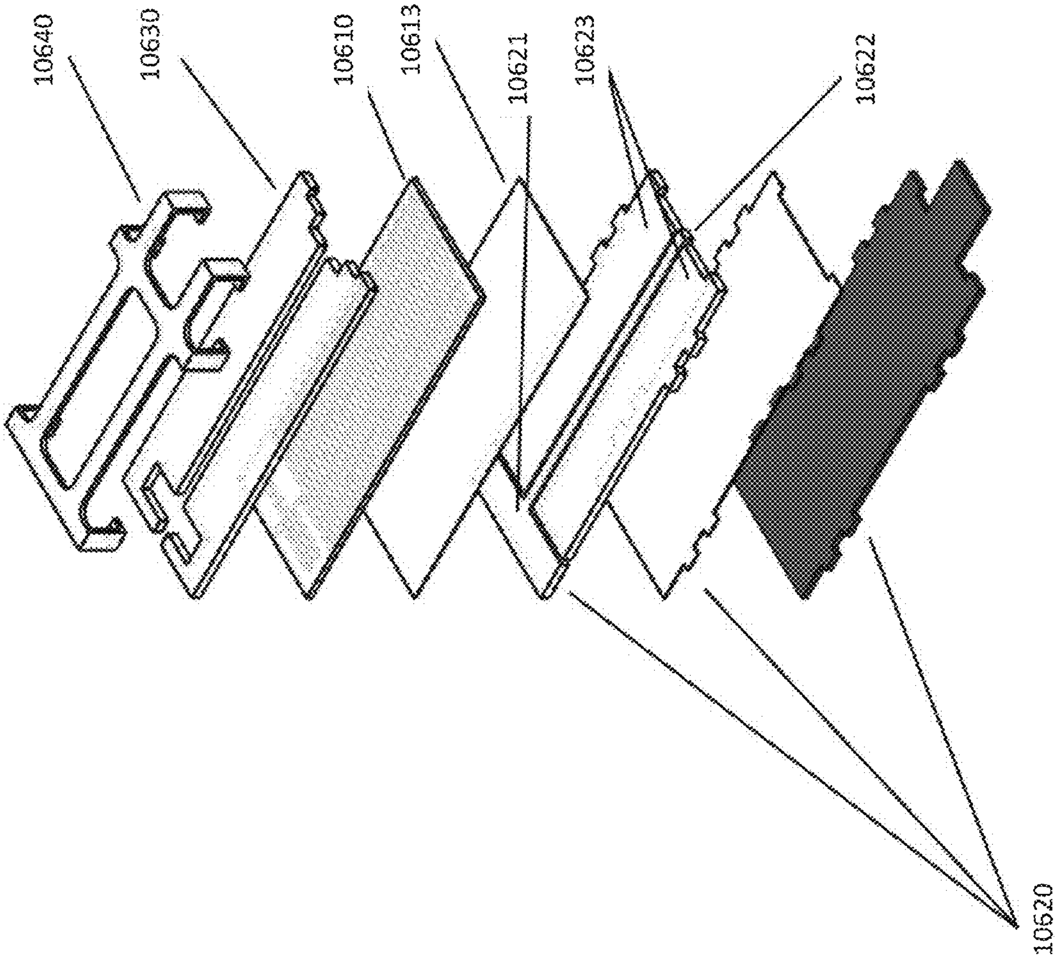
FIG. 95 is an exploded view of components of the amplification module shown in FIG. 93.
Figure 96:
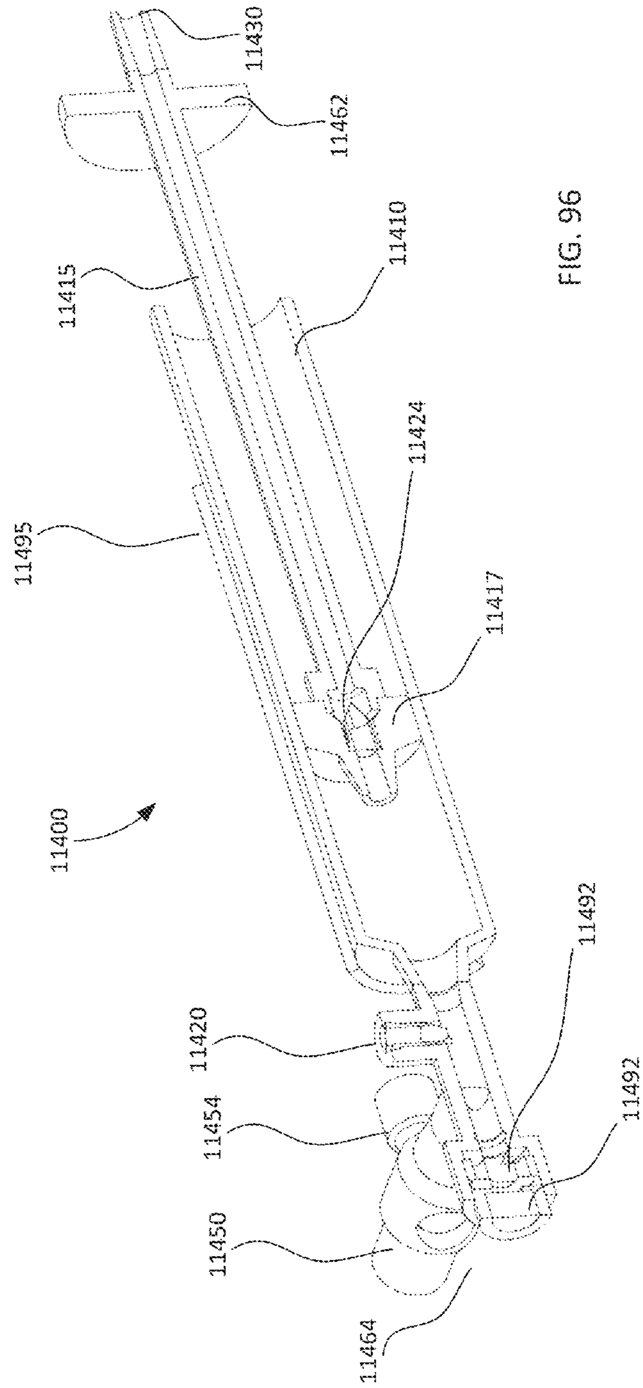
FIG. 96 is perspective cross-sectional view of a fluid transfer module, according to an embodiment.
Figure 97:
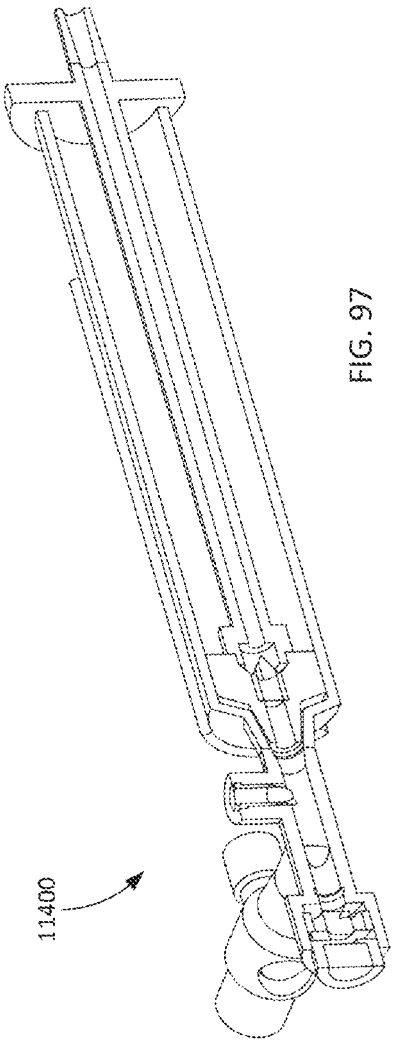
FIGS. 97-99 are perspective cross-sectional views of the fluid transfer module shown in FIG. 96, in various stages of operation.
Figure 98:
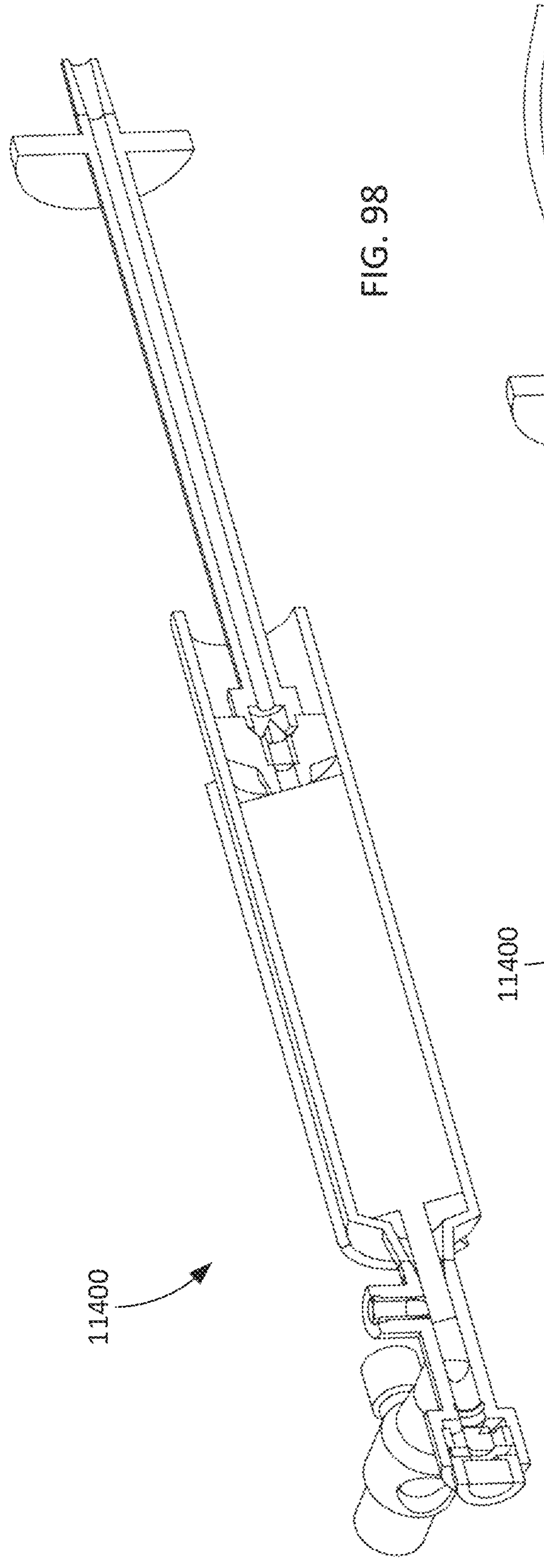
Figure 99:
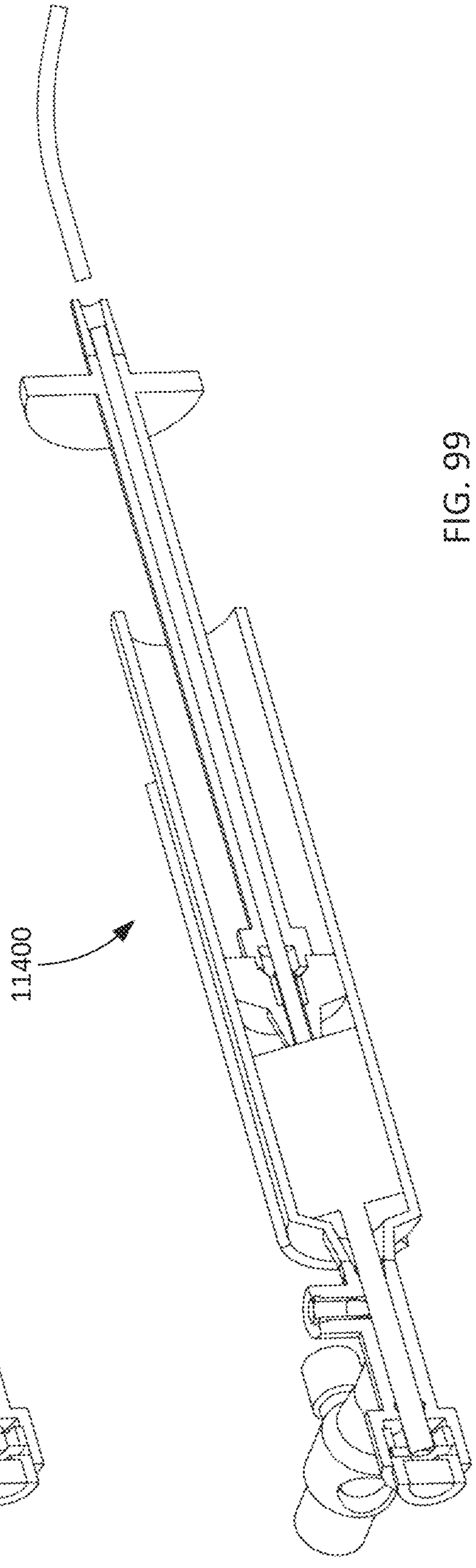

Although the heater assembly 6630 of the amplification module 6600 is described above a including a single member or construct (that can include any number heating elements to produce the desired heating zones as described above), in other embodiments, a heater assembly can be constructed of multiple heaters, clamps, heat spreaders, fasteners or the like. For example, FIGS. 93-95 show an amplification module 10600 according to an embodiment. The amplification module 10600 can receive an input sample in connection with any suitable device (such as the diagnostic test devices 6000, 7000, 8000, 9000 or any other devices shown and described herein), and amplify the sample for use in the subsequent modules.

As illustrated in FIGS. 93-95, the amplification module 10600 is configured to perform a PCR reaction on an input of target DNA mixed with required reagents. The amplification module 10600 includes a serpentine pattern fluidic chip 10610, a hot plate construct 10620, a heat sink construct 10630, support and clamping structure 10640 to mount all the components, and fluidic and electrical interconnects (not shown) to connect to the surrounding modules.

In some embodiments, the amplification module 10600 is configured to conduct rapid PCR amplification of an input target. In some embodiments, the amplification module 10500 is configured to generate an output copy number that reaches or exceeds the threshold of the sensitivity of the detection module 10600, as described herein. In some embodiments, the output volume is sufficient to fully fill the detection chamber in the detection module 10600. In some embodiments, the amplification module 10600 employs a constant set point control scheme—for example, heaters are powered on to control to a set point and set point does not change through the process. Amplification is conducted as long as the reagents are present and the input flow rate is correct. In some embodiments, the amplification module 10600 consumes minimal power, allowing the overall device 10000 to be battery powered (e.g., by a 9V battery), similar to the device 6000 described above.

In use, amplification is accomplished by the movement of the fluid through a serpentine fluidic chip 10610 held in contact with a hot plate construct 10620 during which the fluid inside the chip passes through alternating temperature zones. In some embodiments, the serpentine fluidic chip 10610 is in fixed contact with the hot plate construct 10620, while in other embodiments, the serpentine fluidic chip 10610 is in removable contact with the hot plate construct 10620.

The hot plate construct 10620 heats the zones to the correct temperatures, while the heat sink construct 10630 draws thermal energy away from the areas next to the hot zones, thus allowing the liquid to cool upon exit. Once the chip 10610 fills with liquid, any liquid emerging from the output side has undergone PCR (as long as the total volume of the liquid collected from the output is lower or equal to the "output" volume). The output of the module flows directly into the detection module (e.g., the detection module 6800 described above).

As with the flow member 6610 described above, the serpentine fluidic chip 10610 has two serpentine pattern molded into it—the amplification pattern and the hot-start pattern. The chip 10610 is lidded with a thin plastic lid 10613 ("serpentine chip lid") which is attached with a pressure sensitive adhesive (not identified in the figure). The lid 10613 allows for easy flow of thermal energy from the hot plate 10620. The chip 10610 also contains features to allow other parts of the assembly (like the hot plate) to correctly align with the features on the chip, as well as features to allow the fluidic connections to be bonded correctly.

The hot plate assembly 10620 is made up from four different heater/sensor/heat spreader constructs 10621 (one construct), 10622 (one construct), 10623 (two constructs). The configuration and mating alignment of these determines the areas of the temperature zones on the fluidic chip 10610. The individual heater constructs are controlled to a predetermined set point by the electronics module. Each construct has a resistive heater with an integrated sensor element which, when connected to the electronics module, allows for the temperature of the attached heat spreader to be regulated to the correct set point. There are two "hot" constructs—the hot start zone construct 10621, and the center zone construct 10622, and two "cold" constructs—the two identical side zones constructs 10623.

The heat sink construct 10630 includes pieces of conductive material bonded to the side of the serpentine chip opposite the hot plate. As best illustrated in the schematic illustration of FIG. 94, these allow for some of the thermal energy that the liquid carries from the center hot zone to be dissipated, thus allowing the temperature in the "side cold" zones to be regulated.

Although the fluid transfer module 6400 is shown and described above as including two barrel portions within a monolithically constructed housing, in other embodiments, a fluid transfer module can include two separately constructed barrel assemblies that are coupled together via a frame member. In yet other embodiments, a fluid transfer module can include a single barrel design, in which the single barrel functions to move the sample through the mixing and amplification modules, and also functions to draw the vacuum through the detection module (as described above). For example, FIGS. 96-99 show a fluid transfer module 11400 according to an embodiment. The fluid transfer module 11400 operates to aspirate a fluid sample, store the fluid during a heated incubation period, remove residual gas from the syringe barrel, and then dispense the fluid (e.g., to an amplification module) at a constant rate against varying head pressure.

In use, a linear actuator is connected to the plunger 11415 or the flange 11462 to drive the "piston" in and out of the barrel 11410. The sequence of actions for using the device is as follows: Initially, the piston 11415 is disposed into the syringe barrel 11410. When the piston 11415 retracted, a vacuum is created inside the syringe barrel 11410 causing fluid to enter through the sample inlet port 11420 from a mixing chamber, an inactivation chamber, a filter or any other upstream portion of the sample preparation module. Once the piston 11415 is fully retracted (see FIG. 98) and the barrel 11410 is filled with sample, motion stops. In some embodiments, the chamber heater 11495 brings the sample to 95C effectively inactivating the lysing enzyme. After incubation, the heat is turned off and the linear actuator (not show) changes direction and the piston 11415 moves back into the syringe barrel 11410. The plunger head 11417 pushes on the fluid in the barrel 11410 and any trapped gas therein is forced through a low cracking pressure flapper type check valve 11491 and exits through a hydrophobic vent filter 11492 mounted in the filter valve housing 11464. As soon as fluid enters the filter 11492, the hydrophobic nature of the material prevents the liquid from passing though and effectively becomes blocked. As the piston 11415 is driven further into the barrel 11410 (see FIG. 99), all of the gas within the sample is pushed out and liquid sample is now forced through the higher cracking pressure duckbill check valve 11424 mounted inside of the plunger head 11417, and exits the syringe through the hollow piston drive shaft 11415 and into the PCR tube connector 11430 and on to the amplification module (not shown).

Following the PCR dispense cycle, the fluid transfer module 11400 is again used to produce a vacuum directed at moving fluids through the detection module (not shown), in a similar manner as described above. To redirect the vacuum to the detection module, the normally closed dog-bone slide valve 11454 is opened at the vacuum inlet port 11450. This port stays open for the remainder of the test. As described above, a valve system (e.g., the valve system 6340) can sequentially apply the vacuum to the reagents to produce the desired flow through the detection module.

While various embodiments have been described above, it should be understood that they have been presented by way of example only, and not limitation. Where methods and/or schematics described above indicate certain events and/or flow patterns occurring in certain order, the ordering of certain events and/or flow patterns may be modified. While the embodiments have been particularly shown and described, it will be understood that various changes in form and details may be made.

The devices and methods described herein are not limited to performing a molecular diagnostic test on human samples. In some embodiments, any of the devices and methods described herein can be used with veterinary samples, food samples, and/or environmental samples.

Although the fluid transfer assemblies are shown and described herein as including a piston pump (or syringe), in other embodiments, any suitable pump can be used. For example, in some embodiments any of the fluid transfer assemblies described herein can include any suitable positive-displacement fluid transfer device, such as a gear pump, a vane pump, and/or the like.

Although the filter assembly 6230 shown and described above includes an integral control valve (e.g., including the valve arm 6290), in other embodiments, a device can include a filter assembly and a valve assembly that are separately constructed and/or are spaced apart.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices.

Examples of computer code include, but are not limited to, micro-code or microinstructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

The positive control organism can be stored in any suitable portion of any of the devices shown and described herein. For example, referring to the device 6000, in some embodiments, the positive control organism can be a lyophilized bead that is located in the sample volume 6174 and rehydrated as sample is added. In such embodiments, the control organism is not used to verify sample adequacy. Rather, the sample adequacy would be checked visually by the user verifying the volume of sample in the transfer pipette 1110, as described above. In other embodiments, the positive control organism pellet can be located in a fluidic path that leads out of the sample volume 6174 at a specific location. In such embodiments, if more than a desired amount of sample (e.g., about 300 μL) is present then a portion of sample will rehydrate the control pellet properly. If, however, less than the desired amount of sample (e.g., about 300 μL) is present then the control pellet will not be rehydrated and will result in an invalid signal (no color on the positive control spot) at the end of the run (unless one of the target organisms is detected). In this manner, the location of the control organism can verify sample volume adequacy. In yet other embodiments, the control organism pellet can be located in a sample transfer device (e.g., the device 1100) in such a manner or position that if less than a desired amount of sample (e.g., about 300 μL) is transferred the pellet will not be sufficiently rehydrated. This arrangement will also result in an invalid signal (no color on the positive control spot) at the end of the run (unless one of the target organisms is detected).

Although various embodiments have been described as having particular features and/or combinations of components, other embodiments are possible having a combination of any features and/or components from any of embodiments as discussed above.

For example, any of the devices shown and described herein can include a processor (such as the processor 4950 shown and described above), and can include a memory device configured to receive and store information, such as a series of instructions, processor-readable code, a digitized signal, or the like. The memory device can include one or more types of memory. For example, the memory device can include a read only memory (ROM) component and a random access memory (RAM) component. The memory device can also include other types of memory suitable for storing data in a form retrievable by the processor, for example, electronically-programmable read only memory (EPROM), erasable electronically-programmable read only memory (EEPROM), or flash memory.

As another example, any of the devices shown and described herein can include an indicator light, such as the LED indicator light shown and described above with respect to the device 8000. The light indicator can include, for example, two LEDs (a green and a red) that illuminate to indicate various operations, including a successful "power on" event, notification that the test is in process; notification that the test is complete and/or that the device can be read; and/or an error message.

What is claimed is:

1. A molecular diagnostic test device, comprising:

a housing;

a sample preparation module including a sample input module and a filter assembly disposed within the housing, the sample input module including an inlet port and an outlet port, the inlet port configured to receive an input sample;

a sample actuator operatively coupled to the sample input module, the sample actuator configured to apply a force to the sample input module to convey the input sample from the outlet port through the filter assembly when the sample actuator is moved from a first position to a second position, the sample actuator including a tab configured to irreversibly engage a portion of the housing when the sample actuator is moved to the second position to maintain the sample actuator in the second position;

an amplification module configured to receive the input sample from the sample preparation module, the amplification module defining a reaction volume and including a heater such that the amplification module can perform a polymerase chain reaction (PCR) on the input sample; and a detection module defining a detection channel configured to receive an output from the amplification module and a reagent formulated to produce a signal that indicates a presence of a target amplicon within the input sample, wherein the amplification module, the sample preparation module, and the detection module are integrated within the housing.

2. The molecular diagnostic test device of claim 1, wherein the signal is a non-fluorescent signal.

3. The molecular diagnostic test device of claim 1, wherein:

the signal is a visible signal characterized by a color associated with the presence of the target amplicon; and the detection module includes a detection surface from which the visible signal is produced, the detection surface visible via a detection opening defined by the housing.

4. The molecular diagnostic test device of claim 1, wherein the signal is a visible signal characterized by a color associated with the presence of the target amplicon, the reagent formulated such that the visible signal remains present for at least about 30 minutes.

5. The molecular diagnostic test device of claim 1, further comprising:

a power source disposed within the housing and configured to supply power to the amplification module, the power source including a DC battery having a nominal voltage of 9V, the power source having a capacity of less than about 1200 mAh.

6. The molecular diagnostic test device of claim 1, wherein the sample actuator is in a fixed position relative to at least one of the amplification module or the detection module when the sample actuator is in the second position.

7. The molecular diagnostic test device of claim 1, wherein the sample actuator is a non-electronic actuator.

8. The molecular diagnostic test device of claim 1, wherein the molecular diagnostic test device is configured for one and only one use and is disposable.

9. A method of detecting a target amplicon using a disposable molecular diagnostic test device, comprising:

conveying a sample into a sample preparation module, the sample preparation module including a sample input module and a filter assembly within a housing of the disposable molecular diagnostic test device, the sample being conveyed via an input port of the same input module;

moving a sample actuator operably coupled to the sample input module from a first position to a second position to actuate the sample input module to convey the sample from an outlet port of the sample input module and through a filter assembly, a tab of the sample actuator irreversibly engaging a portion of the housing to maintain the sample actuator in the second position;

actuating the molecular diagnostic test device to:

convey the sample from the sample preparation module to an amplification module, the amplification module within the housing of the disposable molecular diagnostic test device, the amplification module defining a reaction volume and including a heater;

perform, within the reaction volume of the amplification module, a polymerase chain reaction (PCR) on the sample; and convey into a detecting channel defined by a detection module each of A) the sample from the amplification module and B) a reagent formulated to produce a visible signal characterized by a color that indicates a presence of a target amplicon within the sample, the detection module including a detection surface configured to retain the target amplicon to produce the visible signal from the detection surface; and viewing, via a detection opening defined by the housing, the visible signal from the detection surface; and discarding, after the viewing, the disposable molecular test device.

10. The method of claim 9, wherein the discarding includes placing the disposable molecular test device in a waste receptacle after a single use.

11. The method of claim 9, wherein the discarding includes placing the disposable molecular test device in a waste receptacle after a single use of the disposable molecular test device and while the sample preparation module and the amplification module are within the housing.

12. The method of claim 9, wherein the detection opening is defined by an outer surface of the housing, the outer surface of the housing including an indicator characterized by the color.

13. The method of claim 9, wherein the detection opening is defined by an outer surface of the housing, the outer surface of the housing including a mask portion surrounding at least a portion of the detection opening, the mask portion including an indicator characterized by the color.

14. The method of claim 9, wherein the actuating the molecular diagnostic test device includes moving a reagent actuator such that a first portion of the reagent actuator exerts a puncture force on a reagent container within the housing and a second portion of the reagent actuator engages a switch to actuate the molecular diagnostic test device.

15. The method of claim 9, wherein the visible signal is produced from the detection surface in less than about 25 minutes after the actuating the molecular diagnostic test device.

16. The method of claim 9, wherein:

the detection surface is a first detection surface that includes a first hybridization probe specific to the target amplicon;

the detection module includes a second detection surface, the second detection surface being visible via the detection opening of the housing, the second detection surface including a second hybridization probe specific to a control; and the viewing the visible signal includes viewing the visible signal from the first detection surface and the second detection surface.

17. The method of claim 9, wherein:

the sample actuator is a non-electronic actuator.

* * * * *